US011685929B2

(12) United States Patent
Bovet et al.

(10) Patent No.: US 11,685,929 B2
(45) Date of Patent: Jun. 27, 2023

(54) PLANTS WITH SHORTENED TIME TO FLOWERING

(71) Applicant: PHILIP MORRIS PRODUCTS S.A., Neuchatel (CH)

(72) Inventors: Lucien Bovet, La Chaux-de-Fonds (CH); Simon Goepfert, Lausanne (CH); Helene Laparra, Neuchatel (CH)

(73) Assignee: Philip Morris Products S.A., Neuchatel (CH)

( * ) Notice: Subject to any disclaimer, the term of this patent is extended or adjusted under 35 U.S.C. 154(b) by 0 days.

(21) Appl. No.: 16/470,741

(22) PCT Filed: Dec. 15, 2017

(86) PCT No.: PCT/EP2017/082961

§ 371 (c)(1),
(2) Date: Jun. 18, 2019

(87) PCT Pub. No.: WO2018/114641

PCT Pub. Date: Jun. 28, 2018

(65) Prior Publication Data

US 2020/0208164 A1 Jul. 2, 2020

(30) Foreign Application Priority Data

Dec. 20, 2016 (EP) .................................... 16205377

(51) Int. Cl.

*C12N 15/82* (2006.01)
*C07K 14/415* (2006.01)
*C12Q 1/6895* (2018.01)

(52) U.S. Cl.

CPC .......... *C12N 15/827* (2013.01); *C07K 14/415* (2013.01); *C12N 15/8218* (2013.01); *C12Q 1/6895* (2013.01); *C12N 2310/14* (2013.01); *C12Q 2600/13* (2013.01)

(58) Field of Classification Search

None
See application file for complete search history.

(56) References Cited

U.S. PATENT DOCUMENTS

| | | | | |
|---|---|---|---|---|
| 7,208,653 | B2 | 4/2007 | Kotoda | |
| 7,767,884 | B2 | 8/2010 | Nielsen | |
| 2006/0070141 | A1 * | 3/2006 | Nielsen ................ | C12N 15/827 800/287 |

FOREIGN PATENT DOCUMENTS

| | | |
|---|---|---|
| WO | WO 2004/067723 | 8/2004 |
| WO | WO 2006/091194 | 8/2006 |
| WO | WO 2008/070274 | 6/2008 |
| WO | WO 2009/064771 | 5/2009 |
| WO | WO 2009/074325 | 6/2009 |
| WO | WO 2011/088180 | 7/2011 |
| WO | WO 2012/028309 | 3/2012 |
| WO | WO 2013/149941 | 10/2013 |
| WO | WO 2014/081730 | 5/2014 |

OTHER PUBLICATIONS

Ahn JH, Miller D, Winter VJ, Banfield MJ, Lee JH, Yoo SY, Henz SR, Brady RL, Weigel D. (2006) A divergent external loop confers antagonistic activity on floral regulators FT and TFL1. EMBO J. 25: 605-414.

Alvarez et al., "Terminal Flower: A Gene Affecting Inflorescence Development in *Arabidopsis thaliana*", The Plant Journal, vol. 2, No. 1, Jan. 1992, pp. 103-116.

Amaya et al., "Expression of Centroradialis (CEN) and CEN-like Genes in Tobacco Reveals a Conserved Mechanism Controlling Phase Change in Diverse Species", The Plant Cell, American Society of Plant Biologists, US, vol. 11, No. 8, Aug. 1, 1999 (pp. 1405-1417.

Bouché F, D'Aloia M, Tocquin P, Lobet G, Detry N, Périlleux C. (2016) Integrating roots into a whole plant network of flowering time genes in *Arabidopsis thaliana*. Sci Rep. 6: 29042.

Cao K, Cui L, Zhou X, Ye L, Zou Z and Deng S (2016) Four Tomato Flowering Locus T-Like Proteins Act Antagonistically to Regulate Floral Initiation. Front. Plant Sci. 6: 1213.

Carmel-Goren L, Liu YS, Lifschitz E, Zamir D. (2003) The Self-Pruning gene family in tomato. Plant Mol Biol. 52:1215-1522.

Chun-Miao et al, "A Novel Approach Obtaining Intron-Containing Hairpin RNA Constructs", *Bioscience, Biotechnology, and Biochemistry* (2008) 72, 2, 615-617.

Cultivar Development. Crop Species. W. H. Fehr (ed.), MacMillan Publishing Co, Inc., New York, N.Y 761 pp.

Dey et al., "Structure and Promoter/Leader Deletion Analysis of Mirabilis Mosaic Virus (MMV) Full-Length Transcript Promoter in Transgenic Plants", *Plant Mol Biol.* (1999) 40: 771-82.

Fagerland, M. W. (2012). "t-tests, non-parametric tests, and large studies—a paradox of statistical practice?". BioMed Central Medical Research Methodology. 12: 78.

(Continued)

*Primary Examiner* — Elizabeth F McElwain
(74) *Attorney, Agent, or Firm* — Mueting Raasch Group

(57) ABSTRACT

There is described herein a mutant, non-naturally occurring or transgenic plant or part thereof having reduced expression of the gene encoding Terminal Flower 1 (TFL1) or reduced activity of the protein encoded by TFL1, said TFL1 comprising, consisting or consisting essentially of (i) a polynucleotide sequence comprising, consisting or consisting essentially of a sequence having at least 72% sequence identity to SEQ ID NO:7 or SEQ ID NO:8 or SEQ ID NO:10 or SEQ ID NO:11 or SEQ ID NO:19 or SEQ ID NO:20; or (ii) a polypeptide encoded by the polynucleotide set forth in (i); or (iii) a polypeptide having at least 72% sequence identity to SEQ ID NO:9 or SEQ ID NO:12 or SEQ ID NO:21; wherein the expression or activity of the polynucleotide or the polypeptide set forth in (i), (ii) or (iii) is reduced as compared to a control plant in which the expression or activity of the polynucleotide or the polypeptide set forth in (i), (ii) or (iii) has not been reduced.

20 Claims, 9 Drawing Sheets

Specification includes a Sequence Listing.

(56) References Cited

OTHER PUBLICATIONS

Flachowsky et al., "The MdTFL1 gene of apple (*Malus* x *domestica* Borkh.) reduced Vegetative Growth and Generation Time", Three Physiology, vol. 32, No. 10, Sep. 28, 2012, pp. 1288-1301.
Genbank Accession No. AJM13331.
Genbank Accession No. AVA62740.
Genbank Accession No. JQ071508.
Genbank Accession No. L22344.
Genbank Accession No. S78780.
Harig L, Beinecke FA, Oltmanns J, Muth J, Müller O, Rüping B, Twyman RM, Fischer R, Prüfer D, Noll GA. (2012) Proteins from the Flowering Locus T-like subclade of the PEBP family act antagonistically to regulate floral initiation in tobacco. Plant J. 72: 908-21.
Horsch et al, "Transgenic Plants," Cold Spring Harb Symp Quant Biol. (1985) 50: 433-437.
International Search Report and Written Opinion for PCT/EP2017/082961 dated Mar. 15, 2018 (13 pages).
Li C, Zhang Y, Zhang K, Guo D, Cui B, Wang X, Huang X. (2015) Promoting flowering, lateral shoot outgrowth, leaf development, and flower abscission in tobacco plants overexpressing cotton Flowering Locus T (FT)-like gene GhFT1. Front. Plant Sci. 6: 454.
Li, C., Luo, L., Fu, Q. et al. (2015) Identification and Characterization of the FT/TFL1 Gene Family in the Biofuel Plant *Jatropha curcas* Plant Mol Biol Rep 33: 326.
Lifschitz E and Eshed Y. (2006) Universal florigenic signals triggered by FT homologues regulate growth and flowering cycles in perennial day-neutral tomato, J. Exp. Bot. 57, 13: 3405-3414.
McCallum et al., (2000) Nat Biotechnol 18: 455-457.
McGarry RC, Ayre BG. (2012) Manipulating plant architecture with members of the CETS gene family. Plant Sci. 188-189: 71-81.
Office Action issued in Europe for Application No. 16205377.1 dated May 16, 2017 (8 pages).
Ratcliffe et al., "A Common Mechanism Controls the Life Cycle and Architecture of Plants," *Development* (1998) 125: 1609-1615.
Ratcliffe et al., "Separation of Shoot and Floral Identity in *Arabidopsis*", Development, The Company of Biologists Ltd., GB, vol. 126, Mar. 1, 1999, pp. 1109-1120.
Shannon et al., "A Mutation in the *Arabidopsis* TFL 1 Gene Affects Inflorescence Meristem Development", The Plant Cell, vol. 3, Sep. 1991, pp. 877-892.
Sierro et al., "The Tobacco Genome Sequence and its Comparison with Those of Tomato and Potato," *Nat Commun*. (2014) 5: 3833.
Sierro N, Battey JN, Ouadi S, Bovet L, Goepfert S, Bakaher N, Peitsch MC, Ivanov NV. (2013). Reference genomes and transcriptomes of Nicotiana sylvestris and Nicotiana tomentosiformis. Genome Biol. 14: R60.
Smith et al., "Total Silencing by Intron-Spliced Hairpin RNAs," (2000) *Nature*, 407, 319-320.
Stemple, "Tilling—A High-Throughout Harvest for Functional Genomics", (2004) *Nat Rev Genet* 5(2): 145-50.
Thompson et al., "CLUSTAL W: Improving the Sensitivity of Progressive Multiple Sequence Alignment Through Sequence Weighting, Position-Specific Gap Penalties and Weight Matrix Choice," *Nucleic Acids Research* (1994) 22, 4673-4680.
Thompson et al., "The CLUSTAL_X Windows Interface: Flexible Strategies for Multiple Sequence Alignment Aided by Quality Analysis Tools," *Nucleic Acids Research* (1997), 24, 4876-4882.
Welch, B. L. (1947). "The generalization of "Student's" problem when several different population variances are involved". Biometrika. 34 (1-2): 28-35.
Wernsman, E. A, and Rufty, R. C. 1987. Chapter Seventeen. Tobacco. pp. 669-698.
Wesley et al. (2001) Plant J., 27, 581-590.
Yamagishi N, Kishigami R, Yoshikawa N. (2014) Reduced generation time of apple seedlings to within a year by means of a plant virus vector: a new plant-breeding technique with no transmission of genetic modification to the next generation. Plant Biotechnol J. 12(1): 60-8.
Yoo et al, "Brother of FT and TFL1 (BFT) has TFL1-like Activity and Functions Reductantly with TFL1 in Inflorescence Meristem Development in *Arabidopsis*", *The Plant Journal* (2010) 63: 241-253.
Yoo SY, Kardailsky I, Lee JS, Weigel D, Ahn JH. (2004) Acceleration of flowering by overexpression of MFT (Mother of FT and TFL1). Mol Cells 17: 95-101.
Office Action issued in China for Application No. 201780072118.7 dated Nov. 1, 2022 (21 pages). English translation included.
Genbank Database Accession No. XP_016490483.1; Predicted: Protein Self-Pruning-like isoform X1 [Nicotiana Tabacum].

* cited by examiner

TFL1-2T-P131S

Mutation: T instead of C
→ Ser (TCT) instead of Pro (CCT)

TFL1-2T-P131S

```
   1 : MetSerValThrTyrAsnSerSerLysHisValTyrAsnGlyHisGluLeuPheProSerSe :   21 SEQ ID NO: 42
       |||||||||||||||||||||||||||||||||||||||||||||||||||||||||||||
       MetSerValThrTyrAsnSerSerLysHisValTyrAsnGlyHisGluLeuPheProSerSe
   1 : ATGTCTGTTACTTATAACAGCAGCAAGCATGTCTATAATGGACATGAACTCTTTCCTTCCTC :   61 SEQ ID NO: 43

  22 : rValThrSerLysProArgValGluValHisGlyGlyAspLeuArgSerPhePheThrLeu  :   42
       |||||||||||||||||||||||||||||||||||||||||||||||||||||||||||||
       rValThrSerLysProArgValGluValHisGlyGlyAspLeuArgSerPhePheThrLeu+
  62 : AGTCACCTCTAAACCTAGGGTTGAAGTTCATGGAGGTGATTTGAGATCTTTCTTTACACTGg :  124

  43 :  >>>> Target Intron 1 >>>>  IleMetIleAspProAspValProGlyProSerA :   53 SEQ ID NO: 44
                 237 bp           |||||||||||||||||||||||||||||||||
       +                        ++IleMetIleAspProAspValProGlyProSerA
 125 : t........................agATCATGATAGACCCAGATGTTCCTGGTCCTAGTG :  394 SEQ ID NO: 45

  54 : spProTyrLeuArgGluHisLeuHis{Tr}  >>>> Target Intron 2 >>>>  {p} :   62
       ||||||||||||||||||||||||||{||}           1079 bp          {|}
       spProTyrLeuArgGluHisLeuHis{Tr}++                        ++{p}
 395 : ATCCATATCTCAGGGAACATCTACAC{TG}gt........................ag{G} : 1502

  63 : IleValThrAspIleProGlyThrThrAspCysSerPhe{G}  >>>> Target Intron :   76 SEQ ID NO: 46
       |||||||||||||||||||||||||||||||||||||||{|}           317 bp
       IleValThrAspIleProGlyThrThrAspCysSerPhe{G}++
1503 : ATTGTCACAGACATTCCAGGCACTACAGATTGCTCGTTT{G}gt.................. : 1545 SEQ ID NO: 47

  77 :  3 >>>>  {ly}ArgGluIleValGlyTyrGluMetProArgProAsnIleGlyIleHisA :   93 SEQ ID NO: 48
                {||}|||||||||||||||||||||||||||||||||||||||||||||||||
              ++{ly}ArgGluIleValGlyTyrGluMetProArgProAsnIleGlyIleHisA
1546 : .......ag{GG}AGAGAAATAGTTGGGTATGAAATGCCAAGGCCAAATATTGGAATCCACA : 1910 SEQ ID NO: 49

  94 : rgPheValPheLeuLeuPheLysGlnLysLysArgGlnThrLeuLeuSerAlaProLeuSer :  113
       ||||||||||||||||||||||||||||||||||||||||||||||||||||||||||||||
       rgPheValPheLeuLeuPheLysGlnLysLysArgGlnThrLeuLeuSerAlaProLeuSer
1911 : GGTTTGTATTTCTGCTGTTCAAGCAGAAGAAGAGGCAAACATTATTGAGTGCACCTCTCTCC : 1970

 114 : ArgAspArgPheAsnThrArgLysPheSerGluGluAsnGluLeuGlySerProValAlaAl :  134
       ||||||||||||||||||||||||||||||||||||||||||||||||||||||||||||||
       ArgAspArgPheAsnThrArgLysPheSerGluGluAsnGluLeuGlySerProValAlaAl
1971 : AGGGATCGATTTAATACGCGCAAATTCTCAGAAGAAAATGAGCTTGGGTCTCCTGTTGCAGC : 2033

 135 : aAlaPhePheAsnCysGlnArgGluThrAlaAlaArgArgArg :  148
       |||||||||||||||||||||||||||||||||||||||||||
       aAlaPhePheAsnCysGlnArgGluThrAlaAlaArgArgArg
2034 : AGCTTTCTTCAATTGCCAGAGGGAAACCGCTGCCAGAAGGCGT : 2077
```

FIG. 4 (continued)

TFL1-4T-P110L

Mutation: T instead of C
→ Leu (CTA) instead of Pro (CCA)

TFL1-4T-P110L

```
   1 : MetAlaArgSerLeuGluProLeuIleValGlyArgValValGlyAspValLeuAspSerPh :   21   SEQ ID NO: 50
       |||||||||||||||||||||||||||||||||||||||||||||||||||||||||||||||
       MetAlaArgSerLeuGluProLeuIleValGlyArgValValGlyAspValLeuAspSerPh
   1 : ATGGCAAGAAGTTTGGAGCCTCTAATAGTTGGGAGAGTAGTAGGAGATGTTCTTGATTCATT :   61   SEQ ID NO: 51

  22 : eSerProIleValLysMetThrIleThrTyrAsnAsnLysLeuValCysAsnGlyHisGluP :   42
       |||||||||||||||||||||||||||||||||||||||||||||||||||||||||||||||
       eSerProIleValLysMetThrIleThrTyrAsnAsnLysLeuValCysAsnGlyHisGluP
  62 : TAGTCCTATAGTGAAAATGACAATTACTTATAACAACAAATTAGTGTGCAATGGTCATGAAT :  124

  43 : hePheProSerIleValThrSerArgProLysValGluValGlnGlyGlyAspLeuArgThr :   62
       |||||||||||||||||||||||||||||||||||||||||||||||||||||||||||||||
       hePheProSerIleValThrSerArgProLysValGluValGlnGlyGlyAspLeuArgThr
 125 : TCTTTCCTTCTATTGTCACTTCTAGACCTAAGGTTGAAGTTCAAGGAGGAGATTTGAGAACT :  184

  63 : PhePheThrLeu  >>>> Target Intron 1 >>>>  ValMetThrAspProAspVal :   73   SEQ ID NO: 52
       ||||||||||||           423 bp           |||||||||||||||||||||
       PhePheThrLeu++                        ++ValMetThrAspProAspVal
 185 : TTCTTCACACTGgt.......................agGTCATGACAGACCCTGATGTT :  640   SEQ ID NO: 53

  74 : ProGlyProSerAspProTyrLeuArgGluHisLeuHis{Tr}  >>>> Target Intro :   87
       |||||||||||||||||||||||||||||||||||||||{||}           311 bp
       ProGlyProSerAspProTyrLeuArgGluHisLeuHis{Tr}++
 641 : CCCGGCCCTAGTGATCCTTATCTACGAGAGCATCTCCAC{TG}gt................ :  686

  88 : n 2 >>>>  {p}IleValThrAspIleProGlyThrThrAspAlaThrPhe{G}  >>>>  :  101   SEQ ID NO: 54
                 {|}||||||||||||||||||||||||||||||||||||||||{|}
               ++{p}IleValThrAspIleProGlyThrThrAspAlaThrPhe{G}++
 687 : ........ag{G}ATAGTAACTGACATTCCAGGTACCACTGATGCTACTTTT{G}gt..... : 1038   SEQ ID NO: 55

 102 : Target Intron 3 >>>>  {ly}ArgGluLeuValSerTyrGluIleProArgProAsn :  113   SEQ ID NO: 56
           1400 bp           {||}|||||||||||||||||||||||||||||||||||
                           ++{ly}ArgGluLeuValSerTyrGluIleProArgProAsn
1039 : ...................ag{GA}AGAGAATTGGTTAGCTATGAGATTCCAAGGCCAAAT : 2471   SEQ ID NO: 57

 114 : IleGlyIleHisArgPheValPheValLeuPheLysGlnArgArgArgGlnSerValSerPr :  134
       |||||||||||||||||||||||||||||||||||||||||||||||||||||||||||||||
       IleGlyIleHisArgPheValPheValLeuPheLysGlnArgArgArgGlnSerValSerPr
2472 : ATTGGAATCCATAGGTTTGTATTTGTACTTTTCAAGCAAAGACGAAGACAATCAGTTAGCCC : 2534

 135 : oProThrSerArgGluAsnPheAsnThrArgAsnPheAlaGluGluAsnAspLeuSerGlnP :  155
       |||||||||||||||||||||||||||||||||||||||||||||||||||||||||||||||
       oProThrSerArgGluAsnPheAsnThrArgAsnPheAlaGluGluAsnAspLeuSerGlnP
2535 : TCCTACTTCAAGGGAAAACTTCAACACTAGAAATTTTGCCGAAGAAAATGATCTTAGCCAAC : 2597

 156 : roValAlaAlaValPhePheAsnAlaGlnArgGluThrAlaAlaArgArgArg :  172
       ||||||||||||||||||||||||||||||||||||||||||||||||||||||
       roValAlaAlaValPhePheAsnAlaGlnArgGluThrAlaAlaArgArgArg
2598 : CTGTTGCTGCTGTTTTCTTCAATGCACAGCGAGAAACCGCCGCGCGAAGACGC : 2650
```

FIG. 6 (continued)

PLANTS WITH SHORTENED TIME TO FLOWERING

This application is a U.S. National Stage Application of International Application No. PCT/EP2017/082961 filed Dec. 15, 2017, which was published in English on Jun. 28, 2018, as International Publication No. WO 2018/114641 A1. International Application No. PCT/EP2017/082961 claims priority to European Application No. 16205377.1 filed Dec. 20, 2016.

FIELD OF THE INVENTION

The present invention discloses the polynucleotide sequences of genes encoding Terminal Flower 1 (TFL1) from *Nicotiana tabacum* and variants, homologues and fragments thereof. The polypeptide sequences encoded thereby and variants, homologues and fragments thereof are also disclosed. The modification of the expression of the one or more genes or the activity of the protein(s) encoded thereby to modulate time to flowering in a plant is also disclosed. In one embodiment, the expression of the one or more genes or the activity of the protein(s) encoded thereby is reduced in order to shorten time to flowering. Plants, plant material and the like with altered time to flowering are also described.

BACKGROUND OF THE INVENTION

Flowering time is a strictly controlled mechanism in plants that has a direct impact on survival and reproduction. Floral transition is also directly related to crop yield. Plants have developed specialised signalling pathways that lead to the formation of reproductive structures instead of leaves. Flowering Locus T (FT) and TFL1 are phosphatidylethanolamine-binding protein (PEBP) family members that are similar to mammalian PEBPs and function as transcription factors. TFL1 acts antagonistically by delaying floral commitment. The FT protein interacts with the Flowering Locus D (FD) bZIP transcription factor at the shoot apical meristem to promote flowering. The TFL1 protein also binds to FD in order to repress downstream genes such as LEAFY (LFY) and APETALA1 (AP1). Upon floral transition, TFL1 is up-regulated to counterbalance FT activity.

There is a general need in the art to develop plants that have shortened time to flowering as this can result in a number of advantages especially related to the commercial production of plants. For example, it can provide a shorter time period from seeding/planting to harvest which can shorten the growth season. It can enable the faster introduction of new traits by crossing. This can result in cost savings for commercial plant production. The present invention seeks to address this need.

SUMMARY OF THE INVENTION

Seven TFL-1 genes have been identified in *Nicotiana tabacum* called TFL1-1S (SEQ ID NO: 1 or 2), TFL1-1T (SEQ ID NO: 4 or 5), TFL1-2S (SEQ ID NO: 7 or 8), TFL1-2T (SEQ ID NO: 10 or 11), TFL1-3T (SEQ ID NO: 13 or 14), TFL1-4S (SEQ ID NO: 16 or 17) and TFL1-4T (SEQ ID NO: 19 or 20). Suprisingly, the inventors found that when the expression of each of these genes is disrupted (for example, reduced) only TFL1-2S (SEQ ID NO: 7 or 8) and TFL1-2T (SEQ ID NO: 10 or 11) and TFL1-4T (SEQ ID NO: 19 or 20) impact time to flowering by altering (for example, accelerating) flower development and thus changing (for example, shortening) the time to flowering. Unexpectedly, TFL1-1S (SEQ ID NO: 1 or 2) and TFL1-1T (SEQ ID NO: 4 or 5), TFL1-3T (SEQ ID NO: 13 or 14) and TFL1-4S (SEQ ID NO: 16 or 17) had almost no impact on time to flowering. Certain motifs within TFL1-2S (SEQ ID NO: 7 or 8) and TFL1-2T (SEQ ID NO: 10 or 11) and TFL1-4T (SEQ ID NO: 19 or 20) have been identified that can be targeted for gene disruption (for example, RNAi knock out, mutagenesis and the like, as described herein) to alter time to flowering (see, for example, Example 4). These motifs can be used as target regions to alter their respective gene expression to develop stable lines that flower earlier or later. Without wishing to be bound by theory, it is believed that disrupting the expression of one or more TFL1 genes that are responsible for the maintenance of the vegetative state will favor the interaction of FT genes with floral gene promoters, thus shortening time to flowering.

Aspects and Embodiments of the Invention

Aspects and embodiments of the present invention are set forth in the accompanying claims. In a first aspect there is provided a mutant, non-naturally occurring or transgenic plant or part thereof having reduced expression of the gene encoding Terminal Flower 1 (TFL1) or reduced activity of the protein encoded by TFL1, said TFL1 comprising, consisting or consisting essentially of: (i) a polynucleotide sequence comprising, consisting or consisting essentially of a sequence having at least 72% sequence identity to SEQ ID NO:7 or SEQ ID NO:8 or SEQ ID NO:10 or SEQ ID NO:11 or SEQ ID NO:19 or SEQ ID NO:20; or (ii) a polypeptide encoded by the polynucleotide set forth in (i); or (iii) a polypeptide having at least 72% sequence identity to SEQ ID NO:9 or SEQ ID NO:12 or SEQ ID NO:21; wherein the expression or activity of the polynucleotide or the polypeptide set forth in (i), (ii) or (iii) is reduced as compared to a control plant in which the expression or activity of the polynucleotide or the polypeptide set forth in (i), (ii) or (iii) has not been reduced.

Suitably, the reduced expression of the polynucleotide or the reduced activity of the polypeptide shortens the time to flowering as compared to the control plant, suitably, wherein the time to flowering is shortened by at least 8% or at least 20%, or at least 28% or at least 30%.

Suitably, the leaf number is reduced by at least 16% or at least 22%.

Suitably, the plant height is reduced by at least 13% or at least 23% or is about the same.

Suitably, the plant comprises at least one genetic alteration in the polynucleotide sequence encoding TFL1.

Suitably, the plant comprises at least one mutation in the polynucleotide sequence encoding TFL1.

Suitably, the at least one mutation is selected from the group consisting: a mutation at position T143 or G129 in SEQ ID NO: 9; or a mutation at position R120 or G129 or P131 in SEQ ID NO: 12; or a mutation at position P110 or H86 in SEQ ID NO: 21 or a combination of two or more thereof; suitably, wherein the mutation is T143I or G129R or G129E or H84STOP in SEQ ID NO: 9; or wherein the mutation is R1200 or G129E or P131S in SEQ ID NO: 12; or wherein the mutation is P110L or H86STOP in SEQ ID NO: 21 or a combination of two or more thereof.

Suitably, the plant comprises at least one mutation at position P131 in SEQ ID NO: 12, suitably wherein the mutation is P131S.

Suitably, the plant comprises at least one mutation at position P110 in SEQ ID NO: 21, suitably, wherein the mutation is P110L. Suitably, the plant is or is derived from the genus *Nicotiana*, suitably, wherein the plant is *Nicotiana tabacum.*

In a further aspect, there is provided plant material derived or derivable from the plant described herein.

In a further aspect, there is provided a plant product comprising at least a part of the plant of or the plant material described herein In a further aspect, there is provided a method of shortening the time to flowering in a plant comprising modifying the plant by reducing the expression of at least one TFL1 gene or the activity of at least one protein encoded thereby in said plant.

Suitably, the method comprises: (a) providing a plant or part thereof comprising: (i) a polynucleotide sequence comprising, consisting or consisting essentially of a sequence having at least 72% sequence identity to SEQ ID NO:7 or SEQ ID NO:8 or SEQ ID NO:10 or SEQ ID NO:11 or SEQ ID NO:19 or SEQ ID NO:20; or (ii) a polypeptide encoded by the polynucleotide set forth in (i); or (iii) a polypeptide having at least 72% sequence identity to SEQ ID NO:9 or SEQ ID NO:12 or SEQ ID NO:21; and (b) reducing the expression of the TFL1 gene or the activity of the TFL1 protein in the plant; and (c) obtaining a plant with a shortened time to flowering as compared to a control plant in which the expression of the TFL1 gene or the activity of the TFL1 protein has not been reduced.

In a further aspect there is provided the use of reduced expression of at least one TFL1 gene or the activity of at least one protein encoded thereby for shortening the time to flowering in a plant.

Suitably, the expression of TFL1 or the activity of TFL1 is reduced by a method selected from the group consisting of: a) mutating the TFL1 gene in the plant; b) expressing an exogenous polynucleotide or polypeptide in the plant; and c) eliminating the TFL1 gene in the plant, or a combination of one or more thereof.

Suitably, the at least one mutation is selected from the group consisting of: a mutation at position T143 or G129 in SEQ ID NO: 9; or a mutation at position R120 or G129 or P131 in SEQ ID NO: 12; or a mutation at position P110 or H86 in SEQ ID NO: 21 or a combination of two or more thereof; suitably, wherein the mutation is T143I or G129R or G129E or H84STOP in SEQ ID NO: 9; or wherein the mutation is R1200 or G129E or P131S in SEQ ID NO: 12; or wherein the mutation is P110L or H86STOP in SEQ ID NO: 21 or a combination of two or more thereof.

Suitably, the at least one mutation is a mutation at position P131 in SEQ ID NO: 12, suitably wherein the mutation is P131S.

Suitably, the at least one mutation is a mutation at position P110 in SEQ ID NO: 21, suitably, wherein the mutation is P110L. Suitably, the mutation is a mutation at position P131 in SEQ ID NO: 12, suitably wherein the mutation is P131S, and a mutation at position P110 in SEQ ID NO: 21, suitably, wherein the mutation is P110L.

In a further aspect, there is provided a method for producing plant material with a shortened time to flowering as compared to a control plant, said method comprising: (a) providing the plant or the plant material as described herein; (b) harvesting plant material from the plant; (c) optionally curing or drying the plant material for a period of time; and (d) obtaining plant material that has a shortened time to flowering as compared to the control plant.

In a further aspect, there is provided plant material obtained or obtainable by the method or the use as described herein.

In a further aspect, there is provided an isolated polynucleotide sequence comprising, consisting or consisting essentially of a sequence having at least 72% sequence identity to SEQ ID NO:7 or SEQ ID NO:8 or SEQ ID NO:10 or SEQ ID NO:11 or SEQ ID NO:19 or SEQ ID NO:20.

In a further aspect, there is provided an isolated polypeptide encoded by the polynucleotide of claim 16 or a polypeptide having at least 72% sequence identity to SEQ ID NO:9 or SEQ ID NO:12 or SEQ ID NO:21.

Suitably, in the isolated polypeptide at least one mutation is selected from the group consisting of: a mutation at position T143 or G129 in SEQ ID NO: 9; or a mutation at position R120 or G129 or P131 in SEQ ID NO: 12; or a mutation at position P110 or H86 in SEQ ID NO: 21 or a combination of two or more thereof; suitably, wherein the mutation is T143I or G129R or G129E or H84STOP in SEQ ID NO: 9; or wherein the mutation is R1200 or G129E or P131S in SEQ ID NO: 12; or wherein the mutation is P110L or H86STOP in SEQ ID NO: 21 or a combination of two or more thereof.

Suitably, the at least one mutation is a mutation at position P131 in SEQ ID NO: 12, suitably wherein the mutation is P131S.

Suitably, the at least one mutation is a mutation at position P110 in SEQ ID NO: 21, suitably, wherein the mutation is P110L. Suitably, the mutation is a mutation at position P131 in SEQ ID NO: 12, suitably wherein the mutation is P131S, and a mutation at position P110 in SEQ ID NO: 21, suitably, wherein the mutation is P110L.

In a further aspect, there is provided an antibody that specifically binds to the isolated polypeptide described herein.

In a further aspect, there is provided a construct, vector or expression vector comprising the isolated polynucleotide described herein.

In a further aspect, there is provided a plant or plant material or a plant cell comprising the construct, vector or expression vector described herein.

In a further aspect, there is provided a plant cell derived or derivable from the plant or the plant material described herein.

In a further aspect, there is provided plant material comprising the cell described herein.

In a further aspect, there is provided a tobacco product or a smoking article comprising the plant material described herein.

In a further aspect, there is provided an RNAi construct for inhibiting expression of a TFL-1 gene, comprising a sequence that hybridizes to a target sequence on an mRNA of the TFL-1 gene and inhibits the expression of the TFL-1 gene through an RNA interference mechanism, wherein said target sequence is selected from the group consisting of: SEQ ID NOs: 7, 8, 10, 11, 19 and/or 20.

In a further aspect, there is provided a double-stranded RNA comprising at least two sequences that are at least partially complementary to each other and wherein a sense strand comprises a first sequence and an antisense strand comprises a second sequence and wherein at least one of the sequences comprises at least 10 contiguous nucleotides of TFL1 RNA, suitably, wherein at least one of the sequences comprises 21 to 23 contiguous nucleotides of TFL1 RNA.

Suitably, the double-stranded RNA comprises a first sequence having at least 10 nucleotides of TFL1, suitably 21 to 23 nucleotides of TFL-1; a second sequence; and a third sequence having a reverse complementary sequence of the first sequence, positioned in the same orientation as the first sequence, wherein the second sequence is positioned between the first sequence and the third sequence, and the second sequence is operably-linked to the first sequence and to the third sequence.

Suitably, the first sequence is selected from the group consisting of: SEQ ID NO:7 or SEQ ID NO:8 or SEQ ID NO:10 or SEQ ID NO:11 or SEQ ID NO:19 or SEQ ID NO:20 and/or wherein the third sequence is the reverse complement of the corresponding sequence to SEQ ID NO:7 or SEQ ID NO:8 or SEQ ID NO:10 or SEQ ID NO:11 or SEQ ID NO:19 or SEQ ID NO:20.

Suitably, the first sequence comprises or consists of SEQ ID NO: 22 and the third sequence comprises or consists of SEQ ID NO: 23; or the first sequence comprises or consists of SEQ ID NO: 25 and the third sequence comprises or consists of SEQ ID NO: 26; or the first sequence comprises or consists of SEQ ID NO: 27 and the third sequence comprises or consists of SEQ ID NO: 28; or the first sequence comprises or consists of SEQ ID NO: 29 and the third sequence comprises or consists of SEQ ID NO: 30; or the first sequence comprises or consists of SEQ ID NO: 32 and the third sequence comprises or consists of SEQ ID NO: 33; or the first sequence comprises or consists of SEQ ID NO: 34 and the third sequence comprises or consists of SEQ ID NO: 35; or the first sequence comprises or consists of SEQ ID NO: 36 and the third sequence comprises or consists of SEQ ID NO: 37; or the first sequence comprises or consists of SEQ ID NO: 39 and the third sequence comprises or consists of SEQ ID NO: 40.

Suitably, the double-stranded RNA comprises or consists of the sequences selected from the group consisting of: SEQ ID NO: 24, SEQ ID NO: 35, SEQ ID NO: 31, SEQ ID NO: 38 and SEQ ID NO: 41.

In a further aspect, there is provided an isolated polynucleotide sequence comprising, consisting or consisting essentially of a sequence having at least 21 contiguous nucleotides of SEQ ID NO:22, SEQ ID NO:23, SEQ ID NO:25, SEQ ID NO:26, SEQ ID NO:27, SEQ ID NO:28, SEQ ID NO:29, SEQ ID NO:30, SEQ ID NO:32, SEQ ID NO:33, SEQ ID NO:34, SEQ ID NO:35, SEQ ID NO:36, SEQ ID NO:37, SEQ ID NO:39 or SEQ ID NO:40, suitably wherein the sequence comprises, consists or consists essentially of at least 21 to 23 contiguous nucleotides.

In a further aspect, there is provided a method of identifying a molecule that modulates activity or expression of a TFL1 polynucleotide or a TFL1 polypeptide, the method comprising: (a) placing the molecule in contact with a plant comprising the polynucleotide or the polypeptide as described herein—such as a polynucleotide sequence comprising, consisting or consisting essentially of a sequence having at least 72% sequence identity to SEQ ID NO:7 or SEQ ID NO:8 or SEQ ID NO:10 or SEQ ID NO:11 or SEQ ID NO:19 or SEQ ID NO:20 or a polypeptide encoded by the polynucleotide or a polypeptide having at least 72% sequence identity to SEQ ID NO:9 or SEQ ID NO:12 or SEQ ID NO:21; (b) monitoring one or more of: (i) the expression level of the TFL1 polynucleotide in the plant; (ii) the expression level of the TFL1 polypeptide in the plant; (iii) modulation of an activity of the TFL1 polypeptide in the plant; or (iv) modulation of an activity of the TFL1 polynucleotide in the plant; and (c) identifying a molecule that modulates the activity or expression of the TFL1 polynucleotide or the TFL1 polypeptide.

Combinations of one or more of the embodiments set forth is also disclosed.

Some Advantages

A fast flowering trait can enable the breeding of late flowering plant varieties.

A fast flowering trait can enable the generation of commercial plant varieties adapted to climate conditions.

Controlling flowering time can allow increased seed or fruit productivity, as well as flower extract productivity.

Controlling flowering time can avoid the need for maturation treatment.

A fast flowering trait can enable a shorter time period from seeding/planting to harvest which can shorten the growth season.

A fast flowering trait can enable faster introduction of new traits by crossing.

A shorter plant lifecycle could lead to multiple crops of the plant per year which could result in more sustainable production.

A fast flowering trait can enable cutting of flowers earlier which could result in higher quality plant products.

It is advantageous to develop non-genetically modified organism (non-GMO) approaches to shorten time to flowering in plants through the use of gene inactivation. Due to the difficulties of growing and commercialising genetically modified crops in some countries, including Europe, it can be desirable to work with mutants featuring single nucleotide polymorphisms obtained by treatment with ethyl methanesulfonate (EMS) or the like rather than through the use of genetic engineering techniques. Mutants are not considered as GMOs even when the mutations are induced artificially. In the EU for example, there are no special regulations for plants derived from mutation breeding. Up to now, the only known solution for shortening time to flowering is to overexpress FT genes which might not be suitable in a non-GMO environment. Knocking-out TFL1 genes by, for example, selecting EMS/radiation lines or using a selection based on natural variants of TFL1 from different *Nicotiana tabacum* varieties or introgression form from other *Nicotiana* species is a suitable non-GMO solution. Alternatively, any gene editing technology can also be considered but regulation of such technical approaches is still unclear. Having TFL1 variants allows fast breeding by DNA testing, without waiting for flowering and requiring tedious selfing steps.

DEFINITIONS

Figure 1:
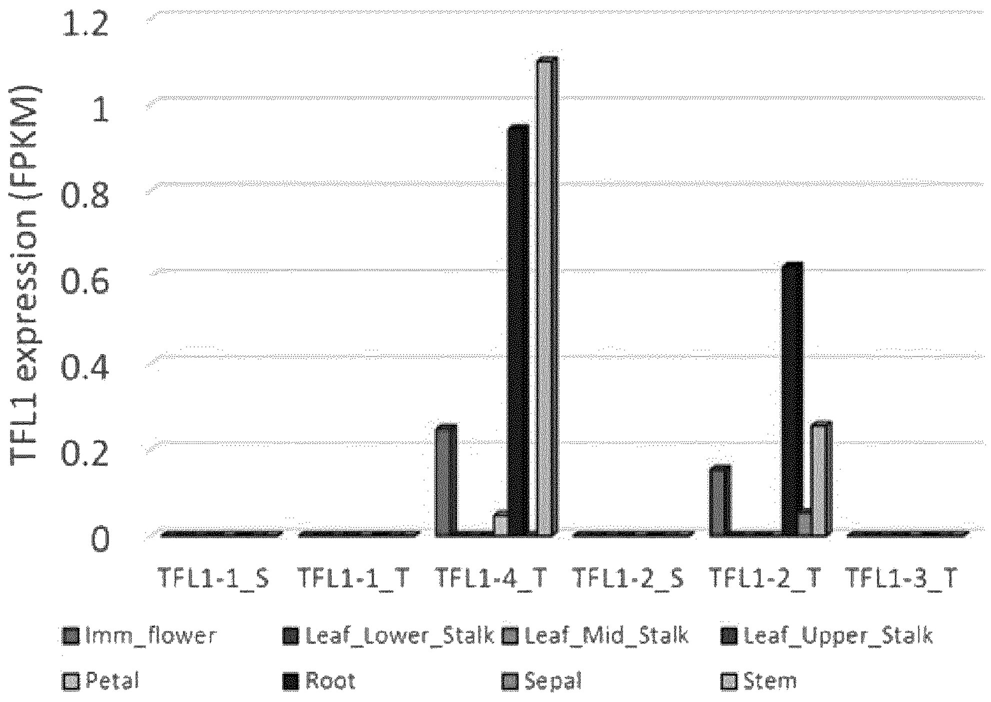
FIG. 1. TFL1 and FT expression in leaves of *N. tabacum* (TN90) flowering plants in the field. Transcript data is obtained by Fragments Per Kilobase Of Exon Per Million Fragments Mapped (FPKM) (see *Nat Biotechnol.* 2010 28(5):511-5). TFL1 and FT expression is determined by RNA-sequence analyses in immature flowers, lower stalk leaves, mid stalk leaves, upper stalk leaves, petals, roots, sepals and stem.

The technical terms and expressions used within the scope of this application are generally to be given the meaning commonly applied to them in the pertinent art of plant and molecular biology. All of the following term definitions apply to the complete content of this application. The word "comprising" does not exclude other elements or steps, and the indefinite article "a" or "an" does not exclude a plurality. A single step may fulfil the functions of several features recited in the claims. The terms "about", "essentially" and "approximately" in the context of a given numerate value or range refers to a value or range that is within 20%, within 10%, or within 5%, 4%, 3%, 2% or 1% of the given value or range.

The term "shortened time to flowering" or equivalents thereof means a shortened time period from seeding to the flowering of first flowers as compared to a control plant. The time may be shorterend by at least about 5%, 6%, 7%, 8%, 9% 10%, 20%, 28%, 30%, 40%, 50%, 60%, 70%, 80% or 90% or more as compared to the control plant.

The term "lengthened time to flowering" or equivalents thereof means a longer time period from seeding to the flowering of first flowers as compared to a control plant. The time may be lengthened by at least about 5%, 6%, 7%, 8%, 9% 10%, 20%, 30%, 40%, 50%, 60%, 70%, 80% or 90% or more as compared to the control plant.

The term "isolated" refers to any entity that is taken from its natural milieu, but the term does not connote any degree of purification.

An "expression vector" is a nucleic acid vehicle that comprises a combination of nucleic acid components for enabling the expression of nucleic acid. Suitable expression vectors include episomes capable of extra-chromosomal replication such as circular, double-stranded nucleic acid plasmids; linearized double-stranded nucleic acid plasmids; and other functionally equivalent expression vectors of any origin. An expression vector comprises at least a promoter positioned upstream and operably-linked to a nucleic acid, nucleic acid constructs or nucleic acid conjugate, as defined below.

The term "construct" refers to a double-stranded, recombinant nucleic acid fragment comprising one or more polynucleotides. The construct comprises a "template strand" base-paired with a complementary "sense or coding strand." A given construct can be inserted into a vector in two possible orientations, either in the same (or sense) orientation or in the reverse (or anti-sense) orientation with respect to the orientation of a promoter positioned within a vector—such as an expression vector.

A "vector" refers to a nucleic acid vehicle that comprises a combination of nucleic acid components for enabling the transport of nucleic acid, nucleic acid constructs and nucleic acid conjugates and the like. Suitable vectors include episomes capable of extra-chromosomal replication such as circular, double-stranded nucleic acid plasmids; linearized double-stranded nucleic acid plasmids; and other vectors of any origin.

A "promoter" refers to a nucleic acid element/sequence, typically positioned upstream and operably-linked to a double-stranded DNA fragment. Promoters can be derived entirely from regions proximate to a native gene of interest, or can be composed of different elements derived from different native promoters or synthetic DNA segments.

The terms "homology, identity or similarity" refer to the degree of sequence similarity between two polypeptides or between two nucleic acid molecules compared by sequence alignment. Suitably, the terms "homology, identity or similarity" refer to the degree of sequence similarity between the complete sequence, for example, the full length sequence, of two polypeptides or between two nucleic acid molecules. The degree of identity between two discrete nucleic acid sequences being compared is a function of the number of identical, or matching, nucleotides at comparable positions. The percent identity may be determined by visual inspection and mathematical calculation. Alternatively, the percent identity of two nucleic acid sequences may be determined by comparing sequence information using a computer program such as—ClustalW, BLAST, FASTA or Smith-Waterman. The percentage identity for two sequences may take different values depending on: (i) the method used to align the sequences, for example, ClustalW, BLAST, FASTA, Smith-Waterman (implemented in different programs), or structural alignment from 3D comparison; and (ii) the parameters used by the alignment method, for example, local vs global alignment, the pair-score matrix used (for example, BLOSUM62, PAM250, Gonnet etc.), and gap-penalty, for example, functional form and constants. Having made the alignment, there are different ways of calculating percentage identity between the two sequences. For example, one may divide the number of identities by: (i) the length of shortest sequence; (ii) the length of alignment; (iii) the mean length of sequence; (iv) the number of non-gap positions; or (iv) the number of equivalenced positions excluding overhangs. Furthermore, it will be appreciated that percentage identity is also strongly length dependent. Therefore, the shorter a pair of sequences is, the higher the sequence identity one may expect to occur by chance. The popular multiple alignment program ClustalW (*Nucleic Acids Research* (1994) 22, 4673-4680*; Nucleic Acids Research* (1997), 24, 4876-4882) is a suitable way for generating multiple alignments of polypeptides or polynucleotides. Suitable parameters for ClustalW maybe as follows: For polynucleotide alignments: Gap Open Penalty=15.0, Gap Extension Penalty=6.66, and Matrix=Identity. For polypeptide alignments: Gap Open Penalty=10. o, Gap Extension Penalty=0.2, and Matrix=Gonnet. For DNA and Protein alignments: ENDGAP=−1, and GAPDIST=4. Those skilled in the art will be aware that it may be necessary to vary these and other parameters for optimal sequence alignment. Suitably, calculation of percentage identities is then calculated from such an alignment as (N/T), where N is the number of positions at which the sequences share an identical residue, and T is the total number of positions compared including gaps but excluding overhangs.

A "variant" means a substantially similar sequence. A variant can have a similar function or substantially similar function as a wild-type sequence. For TFL1, a similar function is at least about 50%, 60%, 70%, 80% or 90% of wild-type function under the same conditions. For TFL1, a substantially similar function is at least about 90%, 95%, 96%, 97%, 98% or 99% of wild-type function under the same conditions. The variants can have one or more favourable mutations that result in a reduced level of TFL1 activity as compared to the wild-type polypeptide. The variants can have one or more favourable mutations that result in TFL1 activity being knocked out (ie. a 100% inhibition, and thus a non-functional polypeptide).

The term "plant" refers to any plant or part of a plant at any stage of its life cycle or development, and its progenies. In one embodiment, the plant is a "tobacco plant", which refers to a plant belonging to the genus *Nicotiana*. Preferred species of tobacco plant are described herein. Suitably, the plant is a mutant, non-naturally occurring or transgenic plant in which the expression of one or more genes or the activity of one or more proteins is modulated as compared to a control plant. Suitably, the alteration that renders the plant a mutant, non-naturally occurring or transgenic plant results in the modulation of the expression of one or more TFL1 genes or the modulation of the activity of one or more TFL1 proteins. In certain embodiments, the alteration is a genetic alternation or a genetic modification. Examples of mutations that can be incorporated into the plants to shorten time to flowering are described herein.

"Plant parts" include plant cells, plant protoplasts, plant cell tissue cultures from which a whole plant can be regenerated, plant calli, plant clumps and plant cells that are intact in plants or parts of plants such as embryos, pollen, anthers, ovules, seeds, leaves, flowers, stems, branches, fruit, roots, root tips and the like. Progeny, variants and mutants of regenerated plants are also included within the scope of the disclosure, provided that they comprise the introduced polynucleotides described herein. Leaves of plants are particularly preferred for use in the present disclosure.

A "plant cell" refers to a structural and physiological unit of a plant. The plant cell may be in the form of a protoplast without a cell wall, an isolated single cell or a cultured cell, or as a part of higher organized unit such as but not limited to, plant tissue, a plant organ, or a whole plant.

The term "plant material" refers to any solid, liquid or gaseous composition, or a combination thereof, obtainable from a plant, including biomass, leaves, stems, roots, flowers or flower parts, fruits, pollen, egg cells, zygotes, seeds, cuttings, secretions, extracts, cell or tissue cultures, or any other parts or products of a plant. In one embodiment, the plant material comprises or consists of biomass, stem, seed or leaves. In another embodiment, the plant material comprises or consists of leaves.

The term "variety" refers to a population of plants that share constant characteristics which separate them from other plants of the same species. While possessing one or more distinctive traits, a variety is further characterized by a very small overall variation between individuals within that variety. A variety is often sold commercially.

The term "line" or "breeding line" as used herein denotes a group of plants that are used during plant breeding. A line is distinguishable from a variety as it displays little variation between individuals for one or more traits of interest, although there may be some variation between individuals for other traits.

The term 'non-naturally occurring' as used herein describes an entity (for example, a polynucleotide, a genetic mutation, a polypeptide, a plant, and a plant cell and plant material) that is not formed by nature or that does not exist in nature. Such non-naturally occurring entities or artificial entities may be made, synthesized, initiated, modified, intervened, or manipulated by methods described herein or that are known in the art. Such non-naturally occurring entities or artificial entities may be made, synthesized, initiated, modified, intervened, or manipulated by man. Thus, by way of example, a non-naturally occurring plant, a non-naturally occurring plant cell or non-naturally occurring plant material may be made using genetic manipulation technologies—such as antisense RNA, interfering RNA, meganuclease and the like. By way of further example, a non-naturally occurring plant, a non-naturally occurring plant cell or non-naturally occurring plant material may be made by introgression of or by transferring one or more genetic mutations (for example one or more polymorphisms) from a first plant or plant cell into a second plant or plant cell (which may itself be naturally occurring), such that the resulting plant, plant cell or plant material or the progeny thereof comprises a genetic constitution (for example, a genome, a chromosome or a segment thereof) that is not formed by nature or that does not exist in nature. The resulting plant, plant cell or plant material is thus artificial or non-naturally occurring. Accordingly, an artificial or non-naturally occurring plant or plant cell may be made by modifying a genetic sequence in a first naturally occurring plant or plant cell, even if the resulting genetic sequence occurs naturally in a second plant or plant cell that comprises a different genetic background from the first plant or plant cell.

The term "modulating" may refer to reducing, inhibiting, increasing or otherwise affecting the expression or activity of a polypeptide. The term may also refer to reducing, inhibiting, increasing or otherwise affecting the activity of a gene encoding a polypeptide which can include, but is not limited to, modulating transcriptional activity. The term "modulating" may also refer to shortening or lengthening the time to flowering.

The term "reduce" or "reduced" or "decrease" or decreased as used herein, refers to a reduction of from about 10% to about 99%, or a reduction of at least 10%, at least 20%, at least 25% or 28%, at least 30%, at least 40%, at least 50%, at least 60%, at least 70%, at least 75%, at least 80%, at least 90%, at least 95%, at least 98%, at least 99%, or at least 100% or more of a quantity or an activity, such as but not limited to polypeptide activity, transcriptional activity and protein expression.

The term "inhibit" or "inhibited" as used herein, refers to a reduction of from about 98% to about 100%, or a reduction of at least 98%, at least 99%, but particularly of 100%, of a quantity or an activity, such as but not limited to polypeptide activity, transcriptional activity and protein expression.

Transformation of a cell may be stable or transient. The term "transient transformation" or "transiently transformed" or variations thereof refers to the introduction of one or more exogenous polynucleotides into a cell in the absence of integration of the exogenous polynucleotide into the host cell's genome. In contrast, the term "stable transformation" or "stably transformed" refers to the introduction and integration of one or more exogenous polynucleotides into the genome of a cell. The term "stable transformant" refers to a cell which has stably integrated one or more exogenous polynucleotides into the genomic or organellar DNA. It is to be understood that an organism or its cell transformed with the nucleic acids, constructs and/or vectors of the present disclosure can be transiently as well as stably transformed. In certain embodiments, stable transformation is preferred.

The term "increase" or "increased" as used herein, refers to an increase of from about 5% to about 99%, or an increase of at least 5%, at least 10%, at least 20%, at least 25%, at least 30%, at least 40%, at least 50%, at least 60%, at least 70%, at least 75%, at least 80%, at least 90%, at least 95%, at least 98%, at least 99%, or at least 100% or more of a quantity or an activity, such as but not limited to polypeptide activity, transcriptional activity and protein expression.

The term "substantially" as used herein and when used in the context of an amount means that the amount is at least about 10%, at least about 9%, at least about 8%, at least about 7%, at least about 6%, at least about 5%, at least about 4%, at least about 3%, at least about 2%, at least about 1%, or at least about 0.1% of the amount that it is being compared to.

The term "control" in the context of a control plant or control plant cell and the like means a plant or plant cell in which the expression or activity of the gene or protein of interest has not been modulated and so it can provide a comparison or reference with a plant or plant cell in which expression or activity has been modified. Thus, in the context of the present invention, the control will not include the at least one modification or genetic alteration which reduces the expression or activity of TFL1. The control plant or pant cell may comprise an empty vector. The control plant or plant cell may correspond to a wild-type plant or wild-type plant cell and the like. In all such cases, the subject plant and the control plant are cultured and harvested using the same protocols for comparative purposes. Changes in levels, ratios, activity, or distribution of the genes or polypeptides described herein, or changes in plant phenotype can be measured by comparing a subject plant to the control plant, suitably, where the subject plant and the control plant have been cultured and/or harvested using the same protocols. The control plant can provide a reference point for measuring changes in phenotype of the subject plant. The measurement of changes in phenotype can be measured at any time in a plant, including during plant development, senescence, or after curing. Measurement of changes in phenotype can be measured in plants grown under any conditions, including from plants grown in growth chamber, greenhouse, or in a field.

DETAILED DESCRIPTION

In one embodiment, there is provided an isolated polynucleotide comprising, consisting or consisting essentially of a polynucleotide sequence having at least 72% sequence identity to any of the sequences described herein, including any of polynucleotides shown in the sequence listing. Suitably, the isolated polynucleotide comprises, consists or consists essentially of a sequence having at least 72%, 73%, 74%, 75%, 78%, 80%, 85%, 87%, 88%, 89%, 90%, 91%, 92%, 93%, 94%, 95% 96%, 97%, 98%, 99% or 100% sequence identity thereto.

In another embodiment, there is provided an isolated polynucleotide comprising, consisting or consisting essentially of a polynucleotide sequence having at least 72%, 73%, 74%, 75%, 78%, 80%, 85%, 87%, 88%, 89%, 90%, 91%, 92%, 93%, 94%, 95% 96%, 97%, 98%, 99% or 100% sequence identity to SEQ ID NO:1 or SEQ ID NO:2 or SEQ ID NO:4 or SEQ ID NO:5 or SEQ ID NO:7 or SEQ ID NO:8 or SEQ ID NO: 10 or SEQ ID NO: 11 or SEQ ID NO: 13 or SEQ ID NO: 14 or SEQ ID NO: 16 or SEQ ID NO: 17 or SEQ ID NO: 19 or SEQ ID NO: 20 or any of SEQ ID NOs: 22 to 41.

In another embodiment, there is provided an isolated polynucleotide comprising, consisting or consisting essentially of a polynucleotide sequence having at least 72%, 73%, 74%, 75%, 78%, 80%, 85%, 87%, 88%, 89%, 90%, 91%, 92%, 93%, 94%, 95% 96%, 97%, 98%, 99% or 100% sequence identity to SEQ ID NO:2 or SEQ ID NO:5 or SEQ ID NO:8 or SEQ ID NO: 11 or SEQ ID NO: 14 or SEQ ID NO: 17 or SEQ ID NO: 20.

In another embodiment, there is provided an isolated polynucleotide comprising, consisting or consisting essentially of a polynucleotide sequence having at least 72%, 73%, 74%, 75%, 78%, 80%, 85%, 87%, 88%, 89%, 90%, 91%, 92%, 93%, 94%, 95% 96%, 97%, 98%, 99% or 100% sequence identity to SEQ ID NO: 7 or SEQ ID NO:8 or SEQ ID NO: 10 or SEQ ID NO: 11 or SEQ ID NO: 13 or SEQ ID NO: 14 or SEQ ID NO: 19 or SEQ ID NO: 20.

In another embodiment, there is provided an isolated polynucleotide comprising, consisting or consisting essentially of a polynucleotide sequence having at least 72%, 73%, 74%, 75%, 78%, 80%, 85%, 87%, 88%, 89%, 90%, 91%, 92%, 93%, 94%, 95% 96%, 97%, 98%, 99% or 100% sequence identity to SEQ ID NO:8 or SEQ ID NO: 11 or SEQ ID NO: 20.

In another embodiment, there is provided polynucleotide variants that have at least about 72%, 75%, 73%, 74%, 75%, 78%, 80%, 85%, 87%, 88%, 89%, 90%, 91%, 92%, 93%, 94%, 95% 96%, 97%, 98%, 99%, 99.1%, 99.2%, 99.3%, 99.4%, 99.5%, 99.6%, 99.7%, 99.8% or 99.9% sequence identity to the sequence of SEQ ID NO:1 or SEQ ID NO:2 or SEQ ID NO:4 or SEQ ID NO:5 or SEQ ID NO:7 or SEQ ID NO:8 or SEQ ID NO: 10 or SEQ ID NO: 11 or SEQ ID NO: 13 or SEQ ID NO: 14 or SEQ ID NO: 16 or SEQ ID NO: 17 or SEQ ID NO: 19 or SEQ ID NO: 20 or any of SEQ ID NOs: 22 to 41.

In another embodiment, there is provided polynucleotide variants that have at least about 72%, 73%, 74%, 75%, 78%, 80%, 85%, 87%, 88%, 89%, 90%, 91%, 92%, 93%, 94%, 95% 96%, 97%, 98%, 99%, 99.1%, 99.2%, 99.3%, 99.4%, 99.5%, 99.6%, 99.7%, 99.8% or 99.9% sequence identity to the sequence of SEQ ID NO:2 or SEQ ID NO:5 or SEQ ID NO:8 or SEQ ID NO: 11 or SEQ ID NO: 14 or SEQ ID NO: 17 or SEQ ID NO: 20.

In another embodiment, there is provided polynucleotide variants that have at least about 72%, 73%, 74%, 75%, 78%, 80%, 85%, 87%, 88%, 89%, 90%, 91%, 92%, 93%, 94%, 95% 96%, 97%, 98%, 99%, 99.1%, 99.2%, 99.3%, 99.4%, 99.5%, 99.6%, 99.7%, 99.8% or 99.9% sequence identity to the sequence of SEQ ID NO:8 or SEQ ID NO: 11 or SEQ ID NO: 20.

In another embodiment, there is provided fragments of SEQ ID NO:1 or SEQ ID NO:2 or SEQ ID NO:4 or SEQ ID NO:5 or SEQ ID NO:7 or SEQ ID NO:8 or SEQ ID NO: 10 or SEQ ID NO: 11 or SEQ ID NO: 13 or SEQ ID NO: 14 or SEQ ID NO: 16 or SEQ ID NO: 17 or SEQ ID NO: 19 or SEQ ID NO: 20 or any of SEQ ID NOs: 22 to 41 with substantial homology (that is, sequence similarity) or substantial identity thereto that have at least about 72%, 73%, 74%, 75%, 80%, 85%, 87%, 88%, 89%, 90%, 91%, 92%, 93%, 94%, 95% 96%, 97%, 98%, 99%, 99.1%, 99.2%, 99.3%, 99.4%, 99.5%, 99.6%, 99.7%, 99.8%, 99.9% or 100% sequence identity to the corresponding fragments of SEQ ID NO:1 or SEQ ID NO:2 or SEQ ID NO:4 or SEQ ID NO:5 or SEQ ID NO:7 or SEQ ID NO:8 or SEQ ID NO: 10 or SEQ ID NO: 11 or SEQ ID NO: 13 or SEQ ID NO: 14 or SEQ ID NO: 16 or SEQ ID NO: 17 or SEQ ID NO: 19 or SEQ ID NO: 20 or any of SEQ ID NOs: 22 to 41. In certain embodiments, the fragments can be 21 to 23 contiguous nucleotides in length. In certain embodiments, the fragments can be at least about 10, 11, 12, 13, 14, 15, 16, 17, 18, 19 or 20 or more contiguous nucleotides in length. In certain embodiments, the fragments can be at least about 10, 15, 20, 30, 40, 50 or 60 or more contiguous nucleotides in length.

In another embodiment, there is provided fragments of SEQ ID NO:2 or SEQ ID NO:5 or SEQ ID NO:8 or SEQ ID NO: 11 or SEQ ID NO: 14 or SEQ ID NO: 17 or SEQ ID NO: 20 with substantial homology (that is, sequence similarity) or substantial identity thereto that have at least about 72%, 73%, 74%, 75%, 80%, 85%, 87%, 88%, 89%, 90%, 91%, 92%, 93%, 94%, 95% 96%, 97%, 98%, 99%, 99.1%, 99.2%, 99.3%, 99.4%, 99.5%, 99.6%, 99.7%, 99.8%, 99.9% or 100% sequence identity to the corresponding fragments of SEQ ID NO:2 or SEQ ID NO:5 or SEQ ID NO:8 or SEQ ID NO: 11 or SEQ ID NO: 14 or SEQ ID NO: 17 or SEQ ID NO: 20.

In another embodiment, there is provided fragments of SEQ ID NO:8 or SEQ ID NO: 11 or SEQ ID NO: 20 with substantial homology (that is, sequence similarity) or substantial identity thereto that have at least about 72%, 73%, 74%, 75%, 80%, 85%, 87%, 88%, 89%, 90%, 91%, 92%, 93%, 94%, 95% 96%, 97%, 98%, 99%, 99.1%, 99.2%, 99.3%, 99.4%, 99.5%, 99.6%, 99.7%, 99.8%, 99.9% or 100% sequence identity to the corresponding fragments of SEQ ID NO:8 or SEQ ID NO: 11 or SEQ ID NO: 20.

In another embodiment, there is provided polynucleotides comprising a sufficient or substantial degree of identity or similarity to SEQ ID NO:1 or SEQ ID NO:2 or SEQ ID NO:4 or SEQ ID NO:5 or SEQ ID NO:7 or SEQ ID NO:8 or SEQ ID NO: 10 or SEQ ID NO: 11 or SEQ ID NO: 13 or SEQ ID NO: 14 or SEQ ID NO: 16 or SEQ ID NO: 17 or SEQ ID NO: 19 or SEQ ID NO: 20 that encodes a polypeptide that functions as a Terminal Flower 1 protein.

In another embodiment, there is provided polynucleotides comprising a sufficient or substantial degree of identity or similarity to SEQ ID NO:2 or SEQ ID NO:5 or SEQ ID NO:8 or SEQ ID NO: 11 or SEQ ID NO: 14 or SEQ ID NO: 17 or SEQ ID NO: 20 that encodes a polypeptide that functions as a Terminal Flower 1 protein.

In another embodiment, there is provided polynucleotides comprising a sufficient or substantial degree of identity or similarity to SEQ ID NO:8 or SEQ ID NO: 11 or SEQ ID NO: 20 that encodes a polypeptide that functions as a Terminal Flower 1 protein.

In another embodiment, there is provided polynucleotide(s) that encode a protein with Terminal Flower 1 protein activity that is at least about 72%, 73%, 74%, 75%, 80%, 90%, 95%, 96%, 97%, 98%, 99% or 100% or more of the activity of the protein set forth in SEQ ID NO:1 or SEQ ID NO:2 or SEQ ID NO:4 or SEQ ID NO:5 or SEQ ID NO:7 or SEQ ID NO:8 or SEQ ID NO: 10 or SEQ ID NO: 11 or SEQ ID NO: 13 or SEQ ID NO: 14 or SEQ ID NO: 16 or SEQ ID NO: 17 or SEQ ID NO: 19 or SEQ ID NO: 20.

In another embodiment, there is provided polynucleotide(s) that encode a protein with Terminal Flower 1 protein activity that is at least about 72%, 73%, 74%, 75%, 80%, 90%, 95%, 96%, 97%, 98%, 99% or 100% or more of the activity of the protein set forth in SEQ ID NO: 3 or SEQ ID NO:9 or SEQ ID NO:12 or SEQ ID NO:15 or SEQ ID NO:18 or SEQ ID NO:21.

In another embodiment, there is provided polynucleotide(s) described herein encode a protein with Terminal Flower 1 protein activity that is at least about 72%, 73%, 74%, 75%, 80%, 90%, 95%, 96%, 97%, 98%, 99% or 100% or more of the activity of the protein set forth in SEQ ID NO:9 or SEQ ID NO:12 or SEQ ID NO:21.

To determine if a polypeptide is a functional Terminal Flower 1 protein, BLAST analyses (Basic Local Alignment Search Tool) can be used to find regions of similarity between biological sequences. The program can be used to compare nucleotide or protein sequences to sequence databases and calculates the statistical significance. The activity of the TFL1 transcription factor can be determined by the ability of TFL1 to have increased or decreased binding function—such as increased or decreased binding function to other proteins (for example, transcription factors) or increased or decreased binding to one or more nucleic acids. Transcriptional activity of TFL1 can be determined either biochemically by defining binding properties or by surveying the result of the activity of the transcription factor—such as increased or decreased expression of a target gene which responds to the activity of the transcription factor. For example, in *Arabidopsis thaliana*, TFL1 acts by repressing LFY and AP1 gene activity (Development (1998) 125: 1609-1615; Development (1999) 126: 1109-1120). The transcriptional activity of TFL1 can therefore be determined by measuring LFY and/or AP1 gene activity in the presence and absence of TFL1. The final event is decreased flowering time such that the major biological activity of TFL1 can be defined as the repression of flowering. The biological role of TFL1/FT in flower development can be tested by using gain-of-function and loss-of-function of the corresponding alleles (see The Plant Journal (2010) 63: 241-253). A polynucleotide as described herein can include a polymer of nucleotides, which may be unmodified or modified deoxyribonucleic acid (DNA) or ribonucleic acid (RNA). Accordingly, a polynucleotide can be, without limitation, a genomic DNA, complementary DNA (cDNA), mRNA, or antisense RNA or a fragment(s) thereof. Moreover, a polynucleotide can be single-stranded or double-stranded DNA, DNA that is a mixture of single-stranded and double-stranded regions, a hybrid molecule comprising DNA and RNA, or a hybrid molecule with a mixture of single-stranded and double-stranded regions or a fragment(s) thereof. In addition, the polynucleotide can be composed of triple-stranded regions comprising DNA, RNA, or both or a fragment(s) thereof. A polynucleotide can contain one or more modified bases, such as phosphothioates, and can be a peptide nucleic acid. Generally, polynucleotides can be assembled from isolated or cloned fragments of cDNA, genomic DNA, oligonucleotides, or individual nucleotides, or a combination of the foregoing. Although the polynucleotide sequences described herein are shown as DNA sequences, the sequences include their corresponding RNA sequences, and their complementary (for example, completely complementary) DNA or RNA sequences, including the reverse complements thereof. The polynucleotides described herein may comprise one or more substitution modifications. The polynucleotides described herein may comprise one or more labels.

A polynucleotide as described herein will generally contain phosphodiester bonds, although in some cases, polynucleotide analogues are included that may have alternate backbones, comprising, for example, phosphoramidate, phosphorothioate, phosphorodithioate, or O-methylphophoroamidite linkages; and peptide polynucleotide backbones and linkages. Other analogue polynucleotides include those with positive backbones; non-ionic backbones, and non-ribose backbones. Modifications of the ribose-phosphate backbone may be done for a variety of reasons, for example, to increase the stability and half-life of such molecules in physiological environments or as probes on a biochip. Mixtures of naturally occurring polynucleotides and analogues can be made; alternatively, mixtures of different polynucleotide analogues, and mixtures of naturally occurring polynucleotides and analogues may be made.

A variety of polynucleotide analogues are known, including, for example, phosphoramidate, phosphorothioate, phosphorodithioate, O-methylphophoroamidite linkages and peptide polynucleotide backbones and linkages. Other analogue polynucleotides include those with positive backbones, non-ionic backbones and non-ribose backbones. Polynucleotides containing one or more carbocyclic sugars are also included.

Other analogues include peptide polynucleotides which are peptide polynucleotide analogues. These backbones are substantially non-ionic under neutral conditions, in contrast to the highly charged phosphodiester backbone of naturally occurring polynucleotides. This may result in advantages. First, the peptide polynucleotide backbone may exhibit improved hybridization kinetics. Peptide polynucleotides have larger changes in the melting temperature for mismatched versus perfectly matched base pairs. DNA and RNA typically exhibit a 2-4° C. drop in melting temperature for an internal mismatch. With the non-ionic peptide polynucleotide backbone, the drop is closer to 7-9° C. Similarly, due to their non-ionic nature, hybridization of the bases attached to these backbones is relatively insensitive to salt concentration. In addition, peptide polynucleotides may not be degraded or degraded to a lesser extent by cellular enzymes, and thus may be more stable.

Among the uses of the disclosed polynucleotides, and fragments thereof, is the use of fragments as probes in nucleic acid hybridisation assays or primers for use in nucleic acid amplification assays. Such fragments generally comprise at least about 10, 11, 12, 13, 14, 15, 16, 17, 18, 19 or 20 or more contiguous nucleotides of a DNA sequence. In other embodiments, a DNA fragment comprises at least about 10, 15, 20, 30, 40, 50 or 60 or more contiguous nucleotides of a DNA sequence. Such fragments generally comprise at least about 10, 11, 12, 13, 14, 15, 16, 17, 18, 19 or 20 or more contiguous nucleotides of SEQ ID NO:1 or SEQ ID NO:2 or SEQ ID NO:4 or SEQ ID NO:5 or SEQ ID NO:7 or SEQ ID NO:8 or SEQ ID NO: 10 or SEQ ID NO: 11 or SEQ ID NO: 13 or SEQ ID NO: 14 or SEQ ID NO: 16 or SEQ ID NO: 17 or SEQ ID NO: 19 or SEQ ID NO: 20. In other embodiments, a DNA fragment comprises at least about 10, 15, 20, 30, 40, 50 or 60 or more contiguous nucleotides of SEQ ID NO:1 or SEQ ID NO:2 or SEQ ID NO:4 or SEQ ID NO:5 or SEQ ID NO:7 or SEQ ID NO:8 or SEQ ID NO: 10 or SEQ ID NO: 11 or SEQ ID NO: 13 or SEQ ID NO: 14 or SEQ ID NO: 16 or SEQ ID NO: 17 or SEQ ID NO: 19 or SEQ ID NO: 20. Such fragments generally comprise at least about 10, 11, 12, 13, 14, 15, 16, 17, 18, 19 or 20 or more contiguous nucleotides of SEQ ID NO:2 or SEQ ID NO:5 or SEQ ID NO:8 or SEQ ID NO: 11 or SEQ ID NO: 14 or SEQ ID NO: 17 or SEQ ID NO: 20. In other embodiments, a DNA fragment comprises at least about 10, 15, 20, 30, 40, 50 or 60 or more contiguous nucleotides of SEQ ID NO:2 or SEQ ID NO:5 or SEQ ID NO:8 or SEQ ID NO: 11 or SEQ ID NO: 14 or SEQ ID NO: 17 or SEQ ID NO: 20. Such fragments generally comprise at least about 10, 11, 12, 13, 14, 15, 16, 17, 18, 19 or 20 or more contiguous nucleotides of SEQ ID NO:8 or SEQ ID NO: 11 or SEQ ID NO: 20. In other embodiments, a DNA fragment comprises at least about 10, 15, 20, 30, 40, 50 or 60 or more contiguous nucleotides of SEQ ID NO:8 or SEQ ID NO: 11 or SEQ ID NO: 20.

The basic parameters affecting the choice of hybridization conditions for polynucleotides and guidance for devising suitable conditions are described by Sambrook, J., E. F. Fritsch, and T. Maniatis (1989, Molecular Cloning: A Laboratory Manual, Cold Spring Harbor Laboratory Press, Cold Spring Harbor, N.Y.). Using knowledge of the genetic code in combination with the amino acid sequences described herein, sets of degenerate oligonucleotides can be prepared. Such oligonucleotides are useful as primers, for example, in polymerase chain reactions (PCR), whereby DNA fragments are isolated and amplified. In certain embodiments, degenerate primers can be used as probes for genetic libraries. Such libraries would include but are not limited to cDNA libraries, genomic libraries, and even electronic express sequence tag or DNA libraries. Homologous sequences identified by this method would then be used as probes to identify homologues of the sequences identified herein.

Also of potential use are polynucleotides and oligonucleotides (for example, primers or probes) that hybridize under reduced stringency conditions, typically moderately stringent conditions, and commonly highly stringent conditions to the polynucleotide(s) as described herein. The basic parameters affecting the choice of hybridization conditions and guidance for devising suitable conditions can be readily determined by those having ordinary skill in the art based on, for example, the length or base composition of the polynucleotide. One way of achieving moderately stringent conditions involves the use of a prewashing solution containing 5× Standard Sodium Citrate, 0.5% Sodium Dodecyl Sulphate, 1.0 mM Ethylenediaminetetraacetic acid (pH 8.0), hybridization buffer of about 50% formamide, 6× Standard Sodium Citrate, and a hybridization temperature of about 55° C. (or other similar hybridization solutions, such as one containing about 50% formamide, with a hybridization temperature of about 42° C.), and washing conditions of about 60° C., in 0.5× Standard Sodium Citrate, 0.1% Sodium Dodecyl Sulphate. Generally, highly stringent conditions are defined as hybridization conditions as above, but with washing at approximately 68° C., 0.2× Standard Sodium Citrate, 0.1% Sodium Dodecyl Sulphate. SSPE (1×SSPE is 0.15 M sodium chloride, 10 mM sodium phosphate, and 1.25 mM Ethylenediaminetetraacetic acid, pH 7.4) can be substituted for Standard Sodium Citrate (1× Standard Sodium Citrate is 0.15 M sodium chloride and 15 mM sodium citrate) in the hybridization and wash buffers; washes are performed for 15 minutes after hybridization is complete. It should be understood that the wash temperature and wash salt concentration can be adjusted as necessary to achieve a desired degree of stringency by applying the basic principles that govern hybridization reactions and duplex stability, as known to those skilled in the art and described further below (see, for example, Sambrook, J., E. F. Fritsch, and T. Maniatis (1989, Molecular Cloning: A Laboratory Manual, Cold Spring Harbor Laboratory Press, Cold Spring Harbor, N.Y.). When hybridizing a polynucleotide to a target polynucleotide of unknown sequence, the hybrid length is assumed to be that of the hybridizing polynucleotide. When polynucleotides of known sequence are hybridized, the hybrid length can be determined by aligning the sequences of the polynucleotides and identifying the region or regions of optimal sequence complementarity. The hybridization temperature for hybrids anticipated to be less than 50 base pairs in length should be 5 to 10° C. less than the melting temperature of the hybrid, where melting temperature is determined according to the following equations. For hybrids less than 18 base pairs in length, melting temperature (° C.)=2(number of A+T bases)+4(number of G+C bases). For hybrids above 18 base pairs in length, melting temperature (° C.)=81.5+16.6(log 10 [Na+])+0.41(% G+C)−(600/N), where N is the number of bases in the hybrid, and [Na+] is the concentration of sodium ions in the hybridization buffer ([Na+] for 1× Standard Sodium Citrate=0.165M). Typically, each such hybridizing polynucleotide has a length that is at least 25% (commonly at least 50%, 60%, or 70%, and most commonly at least 80%) of the length of a polynucleotide to which it hybridizes, and has at least 60% sequence identity (for example, at least 70%, 72%, 75%, 80%, 85%, 90%, 95%, 96%, 97%, 98%, 99% or 100%) with a polynucleotide to which it hybridizes.

As will be understood by the person skilled in the art, a linear DNA has two possible orientations: the 5'-to-3' direction and the 3'-to-5' direction. For example, if a reference sequence is positioned in the 5'-to-3' direction, and if a second sequence is positioned in the 5'-to-3' direction within the same polynucleotide molecule/strand, then the reference sequence and the second sequence are orientated in the same direction, or have the same orientation. Typically, a promoter sequence and a gene of interest under the regulation of the given promoter are positioned in the same orientation. However, with respect to the reference sequence positioned in the 5'-to-3' direction, if a second sequence is positioned in the 3'-to-5' direction within the same polynucleotide molecule/strand, then the reference sequence and the second sequence are orientated in anti-sense direction, or have anti-sense orientation. Two sequences having anti-sense orientations with respect to each other can be alternatively described as having the same orientation, if the reference sequence (5'-to-3' direction) and the reverse complementary sequence of the reference sequence (reference sequence positioned in the 5'-to-3') are positioned within the same polynucleotide molecule/strand. The sequences set forth herein are shown in the 5'-to-3' direction.

Recombinant constructs provided herein can be used to transform plants or plant cells in order to modulate protein expression and/or activity levels. A recombinant polynucleotide construct can comprise a polynucleotide encoding one or more polynucleotides as described herein, operably linked to a regulatory region suitable for expressing the polypeptide. Thus, a polynucleotide can comprise a coding sequence that encodes the polypeptide as described herein. Plants or plant cells in which protein expression and/or activity levels are modulated can include mutant, non-naturally occurring, transgenic, man-made or genetically engineered plants or plant cells. Suitably, the plant or plant cell comprises a genome that has been altered by the stable integration of recombinant DNA. Recombinant DNA includes DNA which has been genetically engineered and constructed outside of a cell and includes DNA containing naturally occurring DNA or cDNA or synthetic DNA. The plant can include a plant regenerated from an originally-transformed plant cell and progeny plants from later generations or crosses of a transformed plant. Suitably, the modification alters the expression or activity of the polynucleotide or the polypeptide described herein as compared to a control plant.

The polypeptide encoded by a recombinant polynucleotide can be a native polypeptide, or can be heterologous to the cell. In some cases, the recombinant construct contains a polynucleotide that modulates expression, operably linked to a regulatory region. Examples of suitable regulatory regions are described herein.

Vectors containing recombinant polynucleotide constructs such as those described herein are also provided. Suitable vector backbones include, for example, those routinely used in the art such as plasmids, viruses, artificial chromosomes, bacterial artificial chromosomes, yeast artificial chromosomes, or bacteriophage artificial chromosomes. Suitable expression vectors include, without limitation, plasmids and viral vectors derived from, for example, bacteriophage, baculoviruses, and retroviruses. Numerous vectors and expression systems are commercially available. The vectors can include, for example, origins of replication, scaffold attachment regions or markers. A marker gene can confer a selectable phenotype on a plant cell. For example, a marker can confer biocide resistance, such as resistance to an antibiotic (for example, kanamycin, G418, bleomycin, or hygromycin), or an herbicide (for example, glyphosate, chlorsulfuron or phosphinothricin). In addition, an expression vector can include a tag sequence designed to facilitate manipulation or detection (for example, purification or localization) of the expressed polypeptide. Tag sequences, such as luciferase, beta-glucuronidase, green fluorescent protein, glutathione S-transferase, polyhistidine, c-myc or hemagglutinin sequences typically are expressed as a fusion with the encoded polypeptide. Such tags can be inserted anywhere within the polypeptide, including at either the carboxyl or amino terminus.

A plant or plant cell can be transformed by having the recombinant polynucleotide integrated into its genome to become stably transformed. The plant or plant cell described herein can be stably transformed. Stably transformed cells typically retain the introduced polynucleotide with each cell division. A plant or plant cell can be transiently transformed such that the recombinant polynucleotide is not integrated into its genome. Transiently transformed cells typically lose all or some portion of the introduced recombinant polynucleotide with each cell division such that the introduced recombinant polynucleotide cannot be detected in daughter cells after a sufficient number of cell divisions. The use of genome editing is also contemplated herein.

A number of methods are available in the art for transforming a plant cell which are all encompassed herein, including biolistics, gene gun techniques, *Agrobacterium*-mediated transformation, viral vector-mediated transformation and electroporation. The *Agrobacterium* system for integration of foreign DNA into plant chromosomes has been extensively studied, modified, and exploited for plant genetic engineering. Naked recombinant DNA molecules comprising DNA sequences corresponding to the subject purified protein operably linked, in the sense or antisense orientation, to regulatory sequences are joined to appropriate T-DNA sequences by conventional methods. These are introduced into protoplasts by polyethylene glycol techniques or by electroporation techniques, both of which are standard. Alternatively, such vectors comprising recombinant DNA molecules encoding the subject purified protein are introduced into live *Agrobacterium* cells, which then transfer the DNA into the plant cells. Transformation by naked DNA without accompanying T-DNA vector sequences can be accomplished via fusion of protoplasts with DNA-containing liposomes or via electroporation. Naked DNA unaccompanied by T-DNA vector sequences can also be used to transform cells via inert, high velocity microprojectiles.

If a cell or cultured tissue is used as the recipient tissue for transformation, plants can be regenerated from transformed cultures if desired, by techniques known to those skilled in the art.

The choice of regulatory regions to be included in a recombinant construct depends upon several factors, including, but not limited to, efficiency, selectability, inducibility, desired expression level, and cell- or tissue-preferential expression. It is a routine matter for one of skill in the art to modulate the expression of a coding sequence by appropriately selecting and positioning regulatory regions relative to the coding sequence. Transcription of a polynucleotide can be modulated in a similar manner. Some suitable regulatory regions initiate transcription only, or predominantly, in certain cell types. Methods for identifying and characterizing regulatory regions in plant genomic DNA are known in the art.

Examples of promoters include tissue-specific promoters recognized by tissue-specific factors present in different tissues or cell types (for example, root-specific promoters, shoot-specific promoters, xylem-specific promoters), or present during different developmental stages, or present in response to different environmental conditions. Examples of promoters include constitutive promoters that can be activated in most cell types without requiring specific inducers. Examples of promoters for controlling RNAi polypeptide production include the cauliflower mosaic virus 35S (CaMV/35S), SSU, OCS, lib4, usp, STLS1, B33, nos or ubiquitin- or phaseolin-promoters. Persons skilled in the art are capable of generating multiple variations of recombinant promoters.

Tissue-specific promoters are transcriptional control elements that are only active in particular cells or tissues at specific times during plant development, such as in vegetative tissues or reproductive tissues. Tissue-specific expression can be advantageous, for example, when the expression of polynucleotides in certain tissues is preferred. Examples of tissue-specific promoters under developmental control include promoters that can initiate transcription only (or primarily only) in certain tissues, such as vegetative tissues, for example, roots or leaves, or reproductive tissues, such as fruit, ovules, seeds, pollen, pistols, flowers, or any embryonic tissue. Reproductive tissue-specific promoters may be, for example, anther-specific, ovule-specific, embryo-specific, endosperm-specific, integument-specific, seed and seed coat-specific, pollen-specific, petal-specific, sepal-specific, or combinations thereof.

Examples of leaf-specific promoters include pyruvate, orthophosphate dikinase (PPDK) promoter from C4 plant (maize), cab-m1Ca+2 promoter from maize, the *Arabidopsis thaliana* myb-related gene promoter (Atmyb5), the ribulose biphosphate carboxylase (RBCS) promoters (for example, the tomato RBCS 1, RBCS2 and RBCS3A genes expressed in leaves and light-grown seedlings, RBCS1 and RBCS2 expressed in developing tomato fruits or ribulose bisphosphate carboxylase promoter expressed almost exclusively in mesophyll cells in leaf blades and leaf sheaths at high levels).

Examples of senescence-specific promoters include a tomato promoter active during fruit ripening, senescence and abscission of leaves, a maize promoter of gene encoding a cysteine protease, the promoter of 82E4 and the promoter of SAG genes.

Anther-specific promoters are further examples. Root-preferred promoters known to persons skilled in the art may be selected. Seed-preferred promoters include both seed-specific promoters (those promoters active during seed development such as promoters of seed storage proteins) and seed-germinating promoters (those promoters active during seed germination). Such seed-preferred promoters include, but are not limited to, Cim1 (cytokinin-induced message); cZ19B1 (maize 19 kDa zein); milps (myo-inositol-1-phosphate synthase); mZE40-2, also known as Zm-40; nucic; and celA (cellulose synthase). Gama-zein is an endosperm-specific promoter. Glob-1 is an embryo-specific promoter. For dicots, seed-specific promoters include, but are not limited to, bean beta-phaseolin, napin, β-conglycinin, soybean lectin, cruciferin, and the like. For monocots, seed-specific promoters include, but are not limited to, a maize 15 kDa zein promoter, a 22 kDa zein promoter, a 27 kDa zein promoter, a g-zein promoter, a 27 kDa gamma-zein promoter (such as gzw64A promoter, see Genbank Accession number S78780), a waxy promoter, a shrunken 1 promoter, a shrunken 2 promoter, a globulin 1 promoter (see Genbank Accession number L22344), an Itp2 promoter, cim1 promoter, maize end1 and end2 promoters, nuc1 promoter, Zm40 promoter, eep1 and eep2; lec1 thioredoxin H promoter; mlip15 promoter, PCNA2 promoter; and the shrunken-2 promoter.

Examples of inducible promoters include promoters responsive to pathogen attack, anaerobic conditions, elevated temperature, light, drought, cold temperature, or high salt concentration. Pathogen-inducible promoters include those from pathogenesis-related proteins (PR proteins), which are induced following infection by a pathogen (for example, PR proteins, SAR proteins, beta-1,3-glucanase, chitinase).

In addition to plant promoters, other suitable promoters may be derived from bacterial origin for example, the octopine synthase promoter, the nopaline synthase promoter and other promoters derived from Ti plasmids), or may be derived from viral promoters (for example, 35S and 19S RNA promoters of cauliflower mosaic virus (CaMV), constitutive promoters of tobacco mosaic virus, cauliflower mosaic virus (CaMV) 19S and 35S promoters, or figwort mosaic virus 35S promoter). In certain embodiments, a Mirabilis Mosaic Virus (MMV) promoter is preferred. In certain embodiments, a 35S promoter is preferred.

In another aspect, there is provided an isolated polypeptide comprising, consisting or consisting essentially of a polypeptide sequence having at least 72% sequence identity to any of the polypeptide sequences described herein, including any of the polypeptides shown in the sequence listing. Suitably, the isolated polypeptide comprises, consists or consists essentially of a sequence having at least 75%, 76%, 77%, 78%, 79%, 80%, 85%, 87%, 88%, 89%, 90%, 91%, 92%, 93%, 94%, 95% 96%, 97%, 98%, 99%, 99.1%, 99.2%, 99.3%, 99.4%, 99.5%, 99.6%, 99.7%, 99.8%, 99.9% or 100% sequence identity thereto.

In one embodiment, the isolated polypeptide comprises, consists or consists essentially of a sequence having at least 72%, 75%, 76%, 77%, 78%, 79%, 80%, 85%, 87%, 88%, 89%, 90%, 91%, 92%, 93%, 94%, 95% 96%, 97%, 98%, 99%, 99.1%, 99.2%, 99.3%, 99.4%, 99.5%, 99.6%, 99.7%, 99.8%, 99.9% or 100% sequence identity to SEQ ID NO: 3 or SEQ ID NO:9 or SEQ ID NO:12 or SEQ ID NO:15 or SEQ ID NO:18 or SEQ ID NO:21.

In another embodiment, the isolated polypeptide comprises, consists or consists essentially of a sequence having at least 72%, 75%, 76%, 77%, 78%, 79%, 80%, 85%, 87%, 88%, 89%, 90%, 91%, 92%, 93%, 94%, 95% 96%, 97%, 98%, 99%, 99.1%, 99.2%, 99.3%, 99.4%, 99.5%, 99.6%, 99.7%, 99.8%, 99.9% or 100% sequence identity to SEQ ID NO:9 or SEQ ID NO:12 or SEQ ID NO:21.

In certain embodiments, the activity of a polypeptide comprising, consisting or consisting essentially of a sequence encoding Terminal Flower 1 protein and having at least 72% sequence identity to SEQ ID NO: 3 or SEQ ID NO:9 or SEQ ID NO:12 or SEQ ID NO:15 or SEQ ID NO:18 or SEQ ID NO:21 is modulated. In another embodiment, the activity of a polypeptide comprising, consisting or consisting essentially of a sequence encoding Terminal Flower 1 protein and having at least 72% sequence identity to SEQ ID NO:9 or SEQ ID NO:12 or SEQ ID NO:21 is modulated.

The polypeptide can include fragments of sequences comprising a sufficient or substantial degree of identity or similarity to function as Terminal Flower 1 protein. Fragments of the polypeptide(s) typically retain some or all of the activity of the full length sequence—such as at least about 95%, 96%, 97%, 98%, 99%, 99.1%, 99.2%, 99.3%, 99.4%, 99.5%, 99.6%, 99.7%, 99.8%, 99.9% or 100% of the activity.

As discussed herein, the polypeptides also include mutants produced by introducing any type of alterations (for example, one or more insertions, deletions, or substitutions of amino acids; changes in glycosylation states; changes that affect refolding or isomerizations, three-dimensional structures, or self-association states), provided that they still have some or all of their function or activity as a Terminal Flower 1 protein. Suitably, the function or activity as a Terminal Flower 1 protein is modulated, reduced or inhibited. Suitably, the function or activity as an Terminal Flower 1 protein is inhibited such that the Terminal Flower 1 protein activity is not detectable. Exemplary mutants are described herein.

Polypeptides include variants produced by introducing any type of alterations (for example, insertions, deletions, or substitutions of amino acids; changes in glycosylation states; changes that affect refolding or isomerizations, three-dimensional structures, or self-association states), which can be deliberately engineered or isolated naturally. The alteration can be one or more stop codons. The variant may have alterations which produce a silent change and result in a functionally equivalent protein. Deliberate amino acid substitutions may be made on the basis of similarity in polarity, charge, solubility, hydrophobicity, hydrophilicity and the amphipathic nature of the residues as long as the secondary binding activity of the substance is retained. For example, negatively charged amino acids include aspartic acid and glutamic acid; positively charged amino acids include lysine and arginine; and amino acids with uncharged polar head groups having similar hydrophilicity values include leucine, isoleucine, valine, glycine, alanine, asparagine, glutamine, serine, threonine, phenylalanine, and tyrosine. Conservative substitutions may be made, for example according to the Table below. Amino acids in the same block in the second column and preferably in the same line in the third column may be substituted for each other:

| | | |
|---|---|---|
| ALIPHATIC | Non-polar | Gly Ala Pro |
| | | Ile Leu Val |
| | Polar—uncharged | Cys Ser Thr Met |
| | | Asn Gly |
| | Polar—charged | Asp Glu |
| | | Lys Arg |
| AROMATIC | | His Phe TrpTyr |

The polypeptide may be a mature protein or an immature protein or a protein derived from an immature protein. Polypeptides may be in linear form or cyclized using known methods. Polypeptides typically comprise at least 10, at least 20, at least 30, or at least 40, or at least 50, or at least 100, or at least 200, or at least 300, or at least 400, or at least 500, or at least 600 contiguous amino acids.

A polypeptide encoded by SEQ ID NO: 3 or SEQ ID NO:9 or SEQ ID NO:12 or SEQ ID NO:15 or SEQ ID NO:18 or SEQ ID NO:21 that has 100% sequence identity thereto or a polypeptide comprising, consisting or consisting essentially of the sequence set forth in SEQ ID NO:9 or SEQ ID NO:12 or SEQ ID NO:15 or SEQ ID NO:21 is also disclosed.

A polypeptide may be prepared by culturing transformed or recombinant host cells under culture conditions suitable to express a polypeptide. The resulting expressed polypeptide may then be purified from such culture using known purification processes. The purification of the polypeptide may include an affinity column containing agents which will bind to the polypeptide; one or more column steps over such affinity resins; one or more steps involving hydrophobic interaction chromatography; or immunoaffinity chromatography. Alternatively, the polypeptide may also be expressed in a form that will facilitate purification. For example, it may be expressed as a fusion polypeptide, such as those of maltose binding polypeptide, glutathione-5-transferase, his-tag or thioredoxin. Kits for expression and purification of fusion polypeptides are commercially available. The polypeptide may be tagged with an epitope and subsequently purified by using a specific antibody directed to such epitope. One or more liquid chromatography steps—such as reverse-phase high performance liquid chromatography can be employed to further purify the polypeptide. Some or all of the foregoing purification steps, in various combinations, can be employed to provide a substantially homogeneous recombinant polypeptide. The polypeptide thus purified may be substantially free of other polypeptides and is defined herein as a “substantially purified polypeptide”; such purified polypeptides include polypeptides, fragments, variants, and the like. Expression, isolation, and purification of the polypeptides and fragments can be accomplished by any suitable technique, including but not limited to the methods described herein.

It is also possible to utilise an affinity column such as a monoclonal antibody generated against polypeptides, to affinity-purify expressed polypeptides. These polypeptides can be removed from an affinity column using conventional techniques, for example, in a high salt elution buffer and then dialyzed into a lower salt buffer for use or by changing pH or other components depending on the affinity matrix utilized, or be competitively removed using the naturally occurring substrate of the affinity moiety.

Isolated or substantially purified polynucleotides or protein compositions are disclosed. An “isolated” or “purified” polynucleotide or protein, or biologically active portion thereof, is substantially or essentially free from components that normally accompany or interact with the polynucleotide or protein as found in its naturally occurring environment. Thus, an isolated or purified polynucleotide or protein is substantially free of other cellular material or culture medium when produced by recombinant techniques, or substantially free of chemical precursors or other chemicals when chemically synthesized. Optimally, an “isolated” polynucleotide is free of sequences (optimally protein encoding sequences) that naturally flank the polynucleotide (for example, sequences located at the 5' and 3' ends of the polynucleotide) in the genomic DNA of the organism from which the polynucleotide is derived. For example, in various embodiments, the isolated polynucleotide can contain less than about 5 kb, 4 kb, 3 kb, 2 kb, 1 kb, 0.5 kb, or 0.1 kb of nucleotide sequence that naturally flank the polynucleotide in genomic DNA of the cell from which the polynucleotide is derived. A protein that is substantially free of cellular material includes preparations of protein having less than about 30%, 20%, 10%, 5%, or 1% (by dry weight) of contaminating protein.

A polypeptide may also be produced by known conventional chemical synthesis. Methods for constructing the polypeptides or fragments thereof by synthetic means are known to those skilled in the art. The synthetically-constructed polypeptide sequences, by virtue of sharing primary, secondary or tertiary structural or conformational characteristics with native polypeptides may possess biological properties in common therewith, including biological activity.

Differences in genetic background can be detected by phenotypic differences or by molecular biology techniques known in the art—such as nucleic acid sequencing, presence or absence of genetic markers (for example, microsatellite RNA markers).

Antibodies that are immunoreactive with the polypeptides described herein are also provided. The polypeptides, fragments, variants, fusion polypeptides, and the like, as set forth herein, can be employed as "immunogens" in producing antibodies immunoreactive therewith. Such antibodies may specifically bind to the polypeptide via the antigen-binding sites of the antibody. Specifically binding antibodies are those that will specifically recognize and bind with a polypeptide, homologues, and variants, but not with other molecules. In one embodiment, the antibodies are specific for polypeptides having an amino acid sequence as set forth herein and do not cross-react with other polypeptides.

More specifically, the polypeptides, fragment, variants, fusion polypeptides, and the like contain antigenic determinants or epitopes that elicit the formation of antibodies. These antigenic determinants or epitopes can be either linear or conformational (discontinuous). Linear epitopes are composed of a single section of amino acids of the polypeptide, while conformational or discontinuous epitopes are composed of amino acids sections from different regions of the polypeptide chain that are brought into close proximity upon polypeptide folding. Epitopes can be identified by any of the methods known in the art. Additionally, epitopes from the polypeptides can be used as research reagents, in assays, and to purify specific binding antibodies from substances such as polyclonal sera or supernatants from cultured hybridomas. Such epitopes or variants thereof can be produced using techniques known in the art such as solid-phase synthesis, chemical or enzymatic cleavage of a polypeptide, or using recombinant DNA technology.

Both polyclonal and monoclonal antibodies to the polypeptides can be prepared by conventional techniques. Hybridoma cell lines that produce monoclonal antibodies specific for the polypeptides are also contemplated herein. Such hybridomas can be produced and identified by conventional techniques. For the production of antibodies, various host animals may be immunized by injection with a polypeptide, fragment, variant, or mutants thereof. Such host animals may include, but are not limited to, rabbits, mice, and rats, to name a few. Various adjutants may be used to increase the immunological response. Depending on the host species, such adjuvants include, but are not limited to, Freund's (complete and incomplete), mineral gels such as aluminium hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*. The monoclonal antibodies can be recovered by conventional techniques. Such monoclonal antibodies may be of any immunoglobulin class including IgG, IgM, IgE, IgA, IgD, and any subclass thereof.

The antibodies can also be used in assays to detect the presence of the polypeptides or fragments, either in vitro or in vivo. The antibodies also can be employed in purifying polypeptides or fragments by immunoaffinity chromatography.

Fragments of polynucleotides described herein and polypeptides encoded thereby are also disclosed. Fragments of a polynucleotide may encode protein fragments that retain the biological activity of the native protein. Alternatively, fragments of a polynucleotide that are useful as hybridization probes or PCR primers generally do not encode fragment proteins retaining biological activity. Furthermore, fragments of the disclosed nucleotide sequences include those that can be assembled within recombinant constructs as discussed herein. Fragments of a polynucleotide sequence may range from at least about 21 nucleotides, about 22 nucleotides, about 23 nucleotides, about 25 nucleotides, about 50 nucleotides, about 75 nucleotides, about 100 nucleotides about 150 nucleotides, about 200 nucleotides, about 250 nucleotides, about 300 nucleotides, about 400 nucleotides, about 500 nucleotides, about 600 nucleotides, about 700 nucleotides, about 800 nucleotides, about 900 nucleotides, about 1000 nucleotides, about 1100 nucleotides, about 1200 nucleotides, about 1300 nucleotides, or about 1500 nucleotides, about 2000 nucleotides, about 3000 nucleotides, about 4000 nucleotides, about 5000 nucleotides, about 6000 nucleotides, about 7000 nucleotides, about 8000 nucleotides, about 9000 nucleotides, about 10000 nucleotides, about 15000 nucleotides, about 20000 nucleotides, and up to the full-length polynucleotide encoding the polypeptides described herein.

Fragments of a polypeptide sequence may range from at least about 25 amino acids, about 50 amino acids, about 75 amino acids, about 100 amino acids about 150 amino acids, about 200 amino acids, about 250 amino acids, about 300 amino acids, about 400 amino acids, about 500 amino acids, about 600 amino acids, or up to the full-length polypeptide described herein. Modulating the expression or activity of one or more TFL1 proteins or one more TFL1 nucleic acid sequences is advantageous for the reasons described herein. The expression of TFL1-2S (SEQ ID NO: 7 or 8) or TFL1-2T (SEQ ID NO: 10 or 11) or TFL1-4T (SEQ ID NO: 19 or 20) can be modulated separately in a plant such that the expression of only one of TFL1-2S (SEQ ID NO: 7 or 8) or TFL1-2T (SEQ ID NO: 10 or 11) or TFL1-4T (SEQ ID NO: 19 or 20) is modulated. The expression of two or more of TFL1-2S (SEQ ID NO: 7 or 8) or TFL1-2T (SEQ ID NO: 10 or 11) or TFL1-4T (SEQ ID NO: 19 or 20) can be modulated in a plant such that the expression of two or more of TFL1-2S (SEQ ID NO: 7 or 8) or TFL1-2T (SEQ ID NO: 10 or 11) or TFL1-4T (SEQ ID NO: 19 or 20) is modulated. For example, the expression of TFL1-2S (SEQ ID NO: 7 or 8) and TFL1-2T (SEQ ID NO: 10 or 11) can be modulated. For example, the expression of TFL1-2S (SEQ ID NO: 7 or 8) and TFL1-4T (SEQ ID NO: 19 or 20) can be modulated. For example, the expression of TFL1-2T (SEQ ID NO: 10 or 11) and TFL1-4T (SEQ ID NO: 19 or 20) can be modulated. For example, the expression of TFL1-2S (SEQ ID NO: 7 or 8) and TFL1-4T (SEQ ID NO: 19 or 20) can be modulated.

The activity of TFL1-2S (SEQ ID NO: 9) or TFL1-2T (SEQ ID NO: 12) or TFL1-4T (SEQ ID NO: 21) can be modulated separately in a plant such that the expression of only one of TFL1-2S (SEQ ID NO: 9) or TFL1-2T (SEQ ID NO: 12) or TFL1-4T (SEQ ID NO: 21) is modulated. The expression of two or more of TFL1-2S (SEQ ID NO: 9) or TFL1-2T (SEQ ID NO: 12) or TFL1-4T (SEQ ID NO: 21) can be modulated in a plant such that the expression of two or more of TFL1-2S (SEQ ID NO: 9) or TFL1-2T (SEQ ID NO: 12) or TFL1-4T (SEQ ID NO: 21) is modulated. For example, the expression of TFL1-2S (SEQ ID NO: 9) and TFL1-2T (SEQ ID NO: 12) can be modulated. For example, the expression of TFL1-2S (SEQ ID NO: 9) and TFL1-4T (SEQ ID NO: 21) can be modulated. For example, the expression of TFL1-2T (SEQ ID NO: 12) and TFL1-4T (SEQ ID NO: 21) can be modulated. For example, the expression of TFL1-2S (SEQ ID NO: 21) and TFL1-4T (SEQ ID NO: 21) can be modulated.

According to certain embodiments, modulating (for example, reducing) the expression of the Terminal Flower 1 protein can be carried out at the genomic and/or the transcript level using a variety of molecules that interfere with transcription and/or translation including, but not limited to, antisense, siRNA, Ribozyme, or DNAzyme molecules. Inserting one or more mutations to the at least one gene, including deletions, insertions, site specific mutations, zinc-finger nucleases and the like can be also used. According to other embodiments, expression can be inhibited at the protein level using antagonists, or enzymes that cleave the polypeptide and the like.

In one aspect, a mutant plant or part thereof comprising at least one mutation in (i) a polynucleotide sequence comprising, consisting or consisting essentially of a sequence having at least 72% sequence identity to SEQ ID NO:7 or SEQ ID NO:8 or SEQ ID NO:10 or SEQ ID NO:11 or SEQ ID NO:19 or SEQ ID NO:20; or (ii) a polypeptide encoded by the polynucleotide set forth in (i); or (iii) a polypeptide having at least 72% sequence identity to SEQ ID NO:9 or SEQ ID NO:12 or SEQ ID NO:21; or (iv) a construct, vector or expression vector comprising the isolated polynucleotide set forth in (i), wherein the at least one mutation reduces the expression or activity of the Terminal Flower 1 protein as compared to a control plant which does not comprise the at least one mutation is described. The plant or plant cell can therefore comprise one or more mutations in TFL1-2S (SEQ ID NO: 7 or 8) and/or TFL1-2T (SEQ ID NO: 10 or 11) and/or TFL1-4T (SEQ ID NO: 19 or 20) wherein said mutation results in reduced expression or reduced function of said gene or protein encoded thereby.

The expression or function of the mutant(s) may be modulated, inhibited or reduced. The mutant plant or plant cell can have one or more further mutations in one or more other genes or polypeptides. In certain embodiments, the mutants can have one or more further mutations in one or more other genes or polypeptides.

Said mutant plant or plant cell can be heterozygous or homozygous for the mutation(s). Said mutant plant or plant cell can be heterozygous for at least one mutation and homozygous for at least one different mutation. Suitably, the mutant plant or plant cell is homozygous for the mutation(s).

Exemplary mutants and mutations are described herein.

In one embodiment, the at least one mutation is selected from the group consisting of: a mutation at position T143 and/or G129 in SEQ ID NO: 9; or a mutation at position R120 and/or G129 and/or P131 in SEQ ID NO: 12; or a mutation at position P110 or H86 in SEQ ID NO: 21 or a combination of two or more thereof.

In one embodiment, the at least one mutation in SEQ ID NO: 9 is selected from mutations at positions: {T143,G129} {T143,H84} {G129,H84} {T143,G129,H84}.

In one embodiment, the at least one mutation in SEQ ID NO: 12 is selected from mutations at positions: {R120, G129} {R120,P131} {G129,P131}{R120,G129,P131} {R120,P131,D142}.

In one embodiment, the at least one mutation in SEQ ID NO: 12 is selected from mutations at positions: {P110,H86}.

In one embodiment, the at least one mutation is a mutation at position P131 in SEQ ID NO: 12, suitably wherein the mutation is P131S.

In one embodiment, the at least one mutation is a mutation at position P110 in SEQ ID NO: 21, suitably, wherein the mutation is P110L.

In one embodiment, the mutations are a mutation at position P131 in SEQ ID NO: 12, suitably wherein the mutation is P131S, and a mutation at position P110 in SEQ ID NO: 21, suitably, wherein the mutation is P110L.

All possible combinations of these mutations are disclosed, which includes any 2, 3, 4, 5, 6 or 7 mutations selected from positions T143 and G129 in SEQ ID NO: 9 and positions R120 and/or G129 and/or P131 in SEQ ID NO: 12 and positions P110 or H86 in SEQ ID NO: 21.

In one embodiment, the mutation is T143I in SEQ ID NO: 9. In one embodiment, the mutation is G129R in SEQ ID NO: 9. In one embodiment, the mutation is G129E in SEQ ID NO: 9. In one embodiment, the mutation is H84STOP in SEQ ID NO: 9. In one embodiment, the mutation is R1200 in SEQ ID NO: 12. In one embodiment, the mutation is G129E in SEQ ID NO: 12. In one embodiment, the mutation is P131S in SEQ ID NO: 12. In one embodiment, the mutation is P110L in SEQ ID NO: 21. In one embodiment, the mutation is H86STOP in SEQ ID NO: 21. All possible combinations of these mutations are disclosed, which includes any 2, 3, 4, 5, 6, 7, 8 or 9 mutations selected from T143I and/or G129R and/or G129E and/or H84STOP in SEQ ID NO: 9 and/or R1200 and/or G129E and/or P131S in SEQ ID NO: 12 and/or P110L and/or H86STOP in SEQ ID NO: 21.

In another aspect, there is provided a method for shortening time to flowering in a plant or in plant material derived from the plant, said method comprising introducing into the genome of said plant one or more mutations that reduce the expression of at least one TFL-1 gene, wherein said at least one TFL-1 gene encodes TFL1-2S (SEQ ID NO: 7 or 8), TFL1-2T (SEQ ID NO: 10 or 11) and TFL1-4T (SEQ ID NO: 19 or 20).

There is also provided a method for identifying a plant with shortened time to flowering, said method comprising screening a nucleic acid sample from a plant of interest for the presence of one or more mutations in TFL1-2S (SEQ ID NO: 7 or 8), TFL1-2T (SEQ ID NO: 10 or 11) and TFL1-4T (SEQ ID NO: 19 or 20).

There is also disclosed a plant or plant cell that is heterozygous or homozygous for one or more mutations in a gene encoding TFL1-2S (SEQ ID NO: 7 or 8), TFL1-2T (SEQ ID NO: 10 or 11) and TFL1-4T (SEQ ID NO: 19 or 20), wherein said mutation(s) results in reduced expression of the gene or reduced function of the protein encoded thereby.

In some embodiments, the favourable mutation(s) is introduced into a plant or plant cell using a mutagenesis approach, and the introduced mutation is identified or selected using methods known to those of skill in the art—such as Southern blot analysis, DNA sequencing, PCR analysis, or phenotypic analysis. Mutations that impact gene expression or that interfere with the function of the encoded protein can be determined using methods that are well known in the art. Insertional mutations in gene exons usually result in null-mutants. Mutations in conserved residues can be particularly effective in inhibiting or reducing the metabolic function of the encoded protein.

Methods for obtaining mutant polynucleotides and polypeptides are also disclosed. Any plant of interest, including a plant cell or plant material can be genetically modified by various methods known to induce mutagenesis, including site-directed mutagenesis, oligonucleotide-directed mutagenesis, chemically-induced mutagenesis, irradiation-induced mutagenesis, mutagenesis utilizing modified bases, mutagenesis utilizing gapped duplex DNA, double-strand break mutagenesis, mutagenesis utilizing repair-deficient host strains, mutagenesis by total gene synthesis, DNA shuffling and other equivalent methods.

Mutant polypeptide variants can be used to create mutant, non-naturally occurring or transgenic plants (for example, mutant, non-naturally occurring, transgenic, man-made or genetically engineered plants) or plant cells comprising one or more mutant polypeptide variants. Suitably, mutant polypeptide variants retain the activity of the unmutated polypeptide. The activity of the mutant polypeptide variant may be higher, lower or about the same as the unmutated polypeptide.

Mutations in the nucleotide sequences and polypeptides described herein can include man-made mutations or synthetic mutations or genetically engineered mutations. Mutations in the nucleotide sequences and polypeptides described herein can be mutations that are obtained or obtainable via a process which includes an in vitro or an in vivo manipulation step. Mutations in the nucleotide sequences and polypeptides described herein can be mutations that are obtained or obtainable via a process which includes intervention by man. By way of example, the process may include mutagenesis using exogenously added chemicals—such as mutagenic, teratogenic, or carcinogenic organic compounds, for example ethyl methanesulfonate (EMS), that produce random mutations in genetic material. By way of further example, the process may include one or more genetic engineering steps—such as one or more of the genetic engineering steps that are described herein or combinations thereof. By way of further example, the process may include one or more plant crossing steps.

The activity of one or more Terminal Flower 1 polypeptides in a plant is reduced or inhibited according to the present disclosure if the conversion activity is statistically lower than the conversion activity of the same Terminal Flower 1 polypeptide(s) in a plant that has not been modified to inhibit the conversion activity of that Terminal Flower 1 polypeptide and which has been cultured and harvested using the same protocols. The activity of a Terminal Flower 1 polypeptide in a plant is considered to be eliminated when it is not detectable by the assay methods described herein. Methods of determining the activity of a Terminal Flower 1 polypeptide are described herein.

Other than mutagenesis, compositions that can modulate the expression or the activity of one or more of the polynucleotides or polypeptides described herein include, but are not limited to, sequence-specific polynucleotides that can interfere with the transcription of one or more endogenous gene(s); sequence-specific polynucleotides that can interfere with the translation of RNA transcripts (for example, double-stranded RNAs, siRNAs, ribozymes); sequence-specific polypeptides that can interfere with the stability of one or more proteins; sequence-specific polynucleotides that can interfere with the enzymatic activity of one or more proteins or the binding activity of one or more proteins with respect to substrates or regulatory proteins; antibodies that exhibit specificity for one or more proteins; small molecule compounds that can interfere with the stability of one or more proteins or the enzymatic activity of one or more proteins or the binding activity of one or more proteins; zinc finger proteins that bind one or more polynucleotides; and meganucleases that have activity towards one or more polynucleotides. Gene editing technologies, genetic editing technologies and genome editing technologies are well known in the art.

One method of gene editing involves the use of transcription activator-like effector nucleases (TALENs) which induce double-strand breaks which cells can respond to with repair mechanisms. Non-homologous end joining reconnects DNA from either side of a double-strand break where there is very little or no sequence overlap for annealing. This repair mechanism induces errors in the genome via insertion or deletion, or chromosomal rearrangement. Any such errors may render the gene products coded at that location non-functional. Another method of gene editing involves the use of the bacterial CRISPR/Cas system. Bacteria and archaea exhibit chromosomal elements called clustered regularly interspaced short palindromic repeats (CRISPR) that are part of an adaptive immune system that protects against invading viral and plasmid DNA. In Type II CRISPR systems, CRISPR RNAs (crRNAs) function with trans-activating crRNA (tracrRNA) and CRISPR-associated (Cas) proteins to introduce double-stranded breaks in target DNA. Target cleavage by Cas9 requires base-pairing between the crRNA and tracrRNA as well as base pairing between the crRNA and the target DNA. Target recognition is facilitated by the presence of a short motif called a protospacer-adjacent motif (PAM) that conforms to the sequence NGG. This system can be harnessed for genome editing. Cas9 is normally programmed by a dual RNA consisting of the crRNA and tracrRNA. However, the core components of these RNAs can be combined into a single hybrid 'guide RNA' for Cas9 targeting. The use of a noncoding RNA guide to target DNA for site-specific cleavage promises to be significantly more straightforward than existing technologies—such as TALENs. Using the CRISPR/Cas strategy, retargeting the nuclease complex only requires introduction of a new RNA sequence and there is no need to reengineer the specificity of protein transcription factors. Antisense technology is another well-known method that can be used to modulate the expression of a polypeptide. A polynucleotide of the gene to be repressed is cloned and operably linked to a regulatory region and a transcription termination sequence so that the antisense strand of RNA is transcribed. The recombinant construct is then transformed into a plant cell and the antisense strand of RNA is produced. The polynucleotide need not be the entire sequence of the gene to be repressed, but typically will be substantially complementary to at least a portion of the sense strand of the gene to be repressed.

A polynucleotide may be transcribed into a ribozyme, or catalytic RNA, that affects expression of an mRNA. Ribozymes can be designed to specifically pair with virtually any target RNA and cleave the phosphodiester backbone at a specific location, thereby functionally inactivating the target RNA. Heterologous polynucleotides can encode ribozymes designed to cleave particular mRNA transcripts, thus preventing expression of a polypeptide. Hammerhead ribozymes are useful for destroying particular mRNAs, although various ribozymes that cleave mRNA at site-specific recognition sequences can be used. Hammerhead ribozymes cleave mRNAs at locations dictated by flanking regions that form complementary base pairs with the target mRNA. The sole requirement is that the target RNA contains a 5'-UG-3' nucleotide sequence. The construction and production of hammerhead ribozymes is known in the art. Hammerhead ribozyme sequences can be embedded in a stable RNA such as a transfer RNA (tRNA) to increase cleavage efficiency in vivo.

In one embodiment, the sequence-specific polynucleotide that can interfere with the translation of RNA transcript(s) is interfering RNA. RNA interference or RNA silencing is an evolutionarily conserved process by which specific mRNAs can be targeted for enzymatic degradation. A double-stranded RNA (double-stranded RNA) is introduced or produced by a cell (for example, double-stranded RNA virus, or interfering RNA polynucleotides) to initiate the interfering RNA pathway. The double-stranded RNA can be converted into multiple small interfering RNA duplexes of 21-23 bp length by RNases III, which are double-stranded RNA-specific endonucleases. The small interfering RNAs can be subsequently recognized by RNA-induced silencing complexes that promote the unwinding of small interfering RNA through an ATP-dependent process. The unwound antisense strand of the small interfering RNA guides the activated RNA-induced silencing complexes to the targeted mRNA comprising a sequence complementary to the small interfering RNA anti-sense strand. The targeted mRNA and the anti-sense strand can form an A-form helix, and the major groove of the A-form helix can be recognized by the activated RNA-induced silencing complexes. The target mRNA can be cleaved by activated RNA-induced silencing complexes at a single site defined by the binding site of the 5'-end of the small interfering RNA strand. The activated RNA-induced silencing complexes can be recycled to catalyze another cleavage event.

An example of a sense RNAi target sequence for TFL1-1S/T is set forth in SEQ ID NO: 22. An example of an anti-sense RNAi target sequence for TFL1-1S/T is set forth in SEQ ID NO: 23.

An example of a TFL1-1S/T RNAi construct is set forth in SEQ ID NO: 24.

An example of a sense RNAi target sequence for TFL1-1S is set forth in SEQ ID NO: 25. An example of an anti-sense RNAi target sequence for TFL1-1S is set forth in SEQ ID NO: 26.

An example of a sense RNAi target sequence for TFL1-1T is set forth in SEQ ID NO: 27. An example of an anti-sense RNAi target sequence for TFL1-1T is set forth in SEQ ID NO: 28.

An example of a sense RNAi target sequence for TFL1-2S/T is set forth in SEQ ID NO: 29. An example of an anti-sense RNAi target sequence for TFL1-2S/T is set forth in SEQ ID NO: 30.

An example of a TFL1-2S/T RNAi construct is set forth in SEQ ID NO: 31.

An example of a sense RNAi target sequence for TFL1-2S is set forth in SEQ ID NO: 32. An example of an anti-sense RNAi target sequence for TFL1-2S is set forth in SEQ ID NO: 33.

An example of a sense RNAi target sequence for TFL1-2T is set forth in SEQ ID NO: 34. An example of an anti-sense RNAi target sequence for TFL1-2T is set forth in SEQ ID NO: 35.

An example of a sense RNAi target sequence for TFL1-3T is set forth in SEQ ID NO: 36. An example of an anti-sense RNAi target sequence for TFL1-3T is set forth in SEQ ID NO: 37. An example of a TFL1-3T RNAi construct is set forth in SEQ ID NO: 38.

An example of a sense RNAi target sequence for TFL1-4T is set forth in SEQ ID NO: 39. An example of an anti-sense RNAi target sequence for TFL1-4T is set forth in SEQ ID NO: 40. An example of a TFL1-4T RNAi construct is set forth in SEQ ID NO: 41.

Sequences of between about 21 to 23 nucleotides in length for any of SEQ ID NOs: 22, 23, 25, 26, 27, 28, 29, 30, 32, 33, 34, 35, 36, 37, 39, 40 or 41 are disclosed.

Methods of gene silencing using these coding sequences and uses thereof are also contemplated.

Interfering RNA expression vectors may comprise interfering RNA constructs encoding interfering RNA polynucleotides that exhibit RNA interference activity by reducing the expression level of mRNAs, pre-mRNAs, or related RNA variants. The expression vectors may comprise a promoter positioned upstream and operably-linked to an interfering RNA construct, as further described herein. Interfering RNA expression vectors may comprise a suitable minimal core promoter, an interfering RNA construct of interest, an upstream (5') regulatory region, a downstream (3') regulatory region, including transcription termination and polyadenylation signals, and other sequences known to persons skilled in the art, such as various selection markers.

Examples of interfering RNA constructs are set forth in SEQ ID NOs: 24, 31, 38 and 41. In one embodiment, expression vector comprises a promoter—such as the strong constitutive MMV (Mirabilis Mosaic Virus) promoter—positioned upstream and operably-linked to an interfering RNA construct and a downstream (3') regulatory region—such as the 3' nos terminator sequence of the nopaline synthase gene of *Agrobacterium tumefaciens*.

The polynucleotides can be produced in various forms, including as double stranded structures (that is, a double-stranded RNA molecule comprising an antisense strand and a complementary sense strand), double-stranded hairpin-like structures, or single-stranded structures (that is, a ssRNA molecule comprising just an antisense strand). The structures may comprise a duplex, asymmetric duplex, hairpin or asymmetric hairpin secondary structure, having self-complementary sense and antisense strands. The double stranded interfering RNA can be enzymatically converted to double-stranded small interfering RNAs. One of the strands of the small interfering RNA duplex can anneal to a complementary sequence within the target mRNA and related RNA variants. The small interfering RNA/mRNA duplexes are recognized by RNA-induced silencing complexes that can cleave RNAs at multiple sites in a sequence-dependent manner, resulting in the degradation of the target mRNA and related RNA variants.

The double-stranded RNA molecules may include small interfering RNA molecules assembled from a single oligonucleotide in a stem-loop structure, wherein self-complementary sense and antisense regions of the small interfering RNA molecule are linked by means of a polynucleotide based or non-polynucleotide-based linker(s), as well as circular single-stranded RNA having two or more loop structures and a stem comprising self-complementary sense and antisense strands, wherein the circular RNA can be processed either in vivo or in vitro to generate an active small interfering RNA molecule capable of mediating interfering RNA.

The double-stranded RNA can comprise at least two sequences that are at least partially complementary to each other. A sense strand can comprise a first sequence and an antisense strand can comprise a second sequence. At least one of the sequences can comprise at least 10 contiguous nucleotides of TFL1 RNA. At least one of the sequences can comprise about 21 to 23 contiguous nucleotides of TFL1 RNA.

In one embodiment, the double-stranded RNA has a first sequence has at least about 10 contiguous nucleotides of TFL1, suitably about 21 to 23 contiguous nucleotides of TFL-1. The double-stranded RNA can have a second sequence. The double-stranded RNA can have a third sequence having a reverse complementary sequence of the first sequence, positioned in the same orientation as the first sequence. The second sequence can be positioned between the first sequence and the third sequence. The second sequence can be operably-linked to the first sequence and to the third sequence.

The first sequence can be selected from the group consisting of: SEQ ID NO:7 or SEQ ID NO:8 or SEQ ID NO:10 or SEQ ID NO:11 or SEQ ID NO:19 or SEQ ID NO:20 and/or wherein the third sequence is the reverse complement of the corresponding sequence to SEQ ID NO:7 or SEQ ID NO:8 or SEQ ID NO:10 or SEQ ID NO:11 or SEQ ID NO:19 or SEQ ID NO:20.

The first sequence can comprise or consist of SEQ ID NO: 22 and the third sequence can comprise or consist of SEQ ID NO: 23; or the first sequence can comprise or consist of SEQ ID NO: 25 and the third sequence can comprise or consist of SEQ ID NO: 26; or the first sequence can comprise or consist of SEQ ID NO: 27 and the third sequence can comprise or consist of SEQ ID NO: 28; or the first sequence can comprise or consist of SEQ ID NO: 29 and the third sequence can comprise or consist of SEQ ID NO: 30; or the first sequence can comprise or consist of SEQ ID NO: 32 and the third sequence can comprise or consist of SEQ ID NO: 33; or the first sequence can comprise or consist of SEQ ID NO: 34 and the third sequence can comprise or consist of SEQ ID NO: 35; or the first sequence can comprise or consist of SEQ ID NO: 36 and the third sequence can comprise or consist of SEQ ID NO: 37; or the first sequence can comprise or consist of SEQ ID NO: 39 and the third sequence can comprise or consist of SEQ ID NO: 40.

The double-stranded RNA can comprise or consist of the sequence selected from the group consisting of: SEQ ID NO: 24, SEQ ID NO: 35, SEQ ID NO: 31, SEQ ID NO: 38 and SEQ ID NO: 41.

The use of small hairpin RNA molecules is also contemplated. They comprise a specific antisense sequence in addition to the reverse complement (sense) sequence, typically separated by a spacer or loop sequence. Cleavage of the spacer or loop provides a single-stranded RNA molecule and its reverse complement, such that they may anneal to form a double-stranded RNA molecule (optionally with additional processing steps that may result in addition or removal of one, two, three or more nucleotides from the 3' end or the 5' end of either or both strands). The spacer can be of a sufficient length to permit the antisense and sense sequences to anneal and form a double-stranded structure (or stem) prior to cleavage of the spacer (and, optionally, subsequent processing steps that may result in addition or removal of one, two, three, four, or more nucleotides from the 3' end or the 5' end of either or both strands). The spacer sequence is typically an unrelated nucleotide sequence that is situated between two complementary nucleotide sequence regions which, when annealed into a double-stranded polynucleotide, comprise a small hairpin RNA. The spacer sequence generally comprises between about 3 and about 100 nucleotides.

Any RNA polynucleotide of interest can be produced by selecting a suitable sequence composition, loop size, and stem length for producing the hairpin duplex. Examplary DNA sequence of antisense and sense target RNAi sequences and constructs are shown in SEQ ID Nos: 22 to 41. A suitable range for designing stem lengths of a hairpin duplex, includes stem lengths of at least about 10, 11, 12, 13, 14, 15, 16, 17, 18, 19 or 20 nucleotides—such as about 14-30 nucleotides, about 30-50 nucleotides, about 50-100 nucleotides, about 100-150 nucleotides, about 150-200 nucleotides, about 200-300 nucleotides, about 300-400 nucleotides, about 400-500 nucleotides, about 500-600 nucleotides, and about 600-700 nucleotides. A suitable range for designing loop lengths of a hairpin duplex, includes loop lengths of about 4-25 nucleotides, about 25-50 nucleotides, or longer if the stem length of the hair duplex is substantial. In certain embodiments, a double-stranded RNA or ssRNA molecule is between about 15 and about 40 nucleotides in length. In another embodiment, the small interfering RNA molecule is a double-stranded RNA or ssRNA molecule between about 15 and about 35 nucleotides in length. In another embodiment, the small interfering RNA molecule is a double-stranded RNA or ssRNA molecule between about 17 and about 30 nucleotides in length. In another embodiment, the small interfering RNA molecule is a double-stranded RNA or ssRNA molecule between about 19 and about 25 nucleotides in length. In another embodiment, the small interfering RNA molecule is a double-stranded RNA or ssRNA molecule between about 21 to about 23 nucleotides in length. In certain embodiments, hairpin structures with duplexed regions longer than 21 nucleotides may promote effective small interfering RNA-directed silencing, regardless of loop sequence and length. Exemplary sequences used for RNA interference are set forth in SEQ ID NOs: 22 to 33.

The target mRNA sequence is typically between about 14 to about 50 nucleotides in length. The target mRNA can, therefore, be scanned for regions between about 14 and about 50 nucleotides in length that preferably meet one or more of the following criteria for a target sequence: an A+T/G+C ratio of between about 2:1 and about 1:2; an AA dinucleotide or a CA dinucleotide at the 5' end of the target sequence; a sequence of at least 10 consecutive nucleotides unique to the target mRNA (that is, the sequence is not present in other mRNA sequences from the same plant); and no "runs" of more than three consecutive guanine (G) nucleotides or more than three consecutive cytosine (C) nucleotides. These criteria can be assessed using various techniques known in the art, for example, computer programs such as BLAST can be used to search publicly available databases to determine whether the selected target sequence is unique to the target mRNA. Alternatively, a target sequence can be selected (and a small interfering RNA sequence designed) using computer software available commercially (for example, OligoEngine, Target Finder and the small interfering RNA Design Tool which are commercially available).

In one embodiment, target mRNA sequences are selected that are between about 14 and about 30 nucleotides in length that meet one or more of the above criteria. In another embodiment, target sequences are selected that are between about 16 and about 30 nucleotides in length that meet one or more of the above criteria. In a further embodiment, target sequences are selected that are between about 19 and about 30 nucleotides in length that meet one or more of the above criteria. In another embodiment, target sequences are selected that are between about 19 and about 25 nucleotides in length that meet one or more of the above criteria.

In an exemplary embodiment, the small interfering RNA molecules comprise a specific antisense sequence that is complementary to at least 12, 13, 14, 15, 16, 17, 18, 19, 20, 21, 22, 23, 24, 25, 26, 27, 28, 29, 30, or more contiguous nucleotides of any one of the polynucleotide sequences described herein.

The specific antisense sequence comprised by the small interfering RNA molecule can be identical or substantially identical to the complement of the target sequence. In one embodiment, the specific antisense sequence comprised by the small interfering RNA molecule is at least about 75%, 80%, 85%, 90%, 95%, 96%, 97%, 98%, 99% or 100% identical to the complement of the target mRNA sequence. Methods of determining sequence identity are known in the art and can be determined, for example, by using the BLASTN program of the University of Wisconsin Computer Group (GCG) software or provided on the NCBI website.

The specific antisense sequence of the small interfering RNA molecules may exhibit variability by differing (for example, by nucleotide substitution, including transition or transversion) at one, two, three, four or more nucleotides from the sequence of the target mRNA. When such nucleotide substitutions are present in the antisense strand of a double-stranded RNA molecule, the complementary nucleotide in the sense strand with which the substitute nucleotide would typically form hydrogen bond base-pairing may or may not be correspondingly substituted. Double-stranded RNA molecules, in which one or more nucleotide substitution occurs in the sense sequence, but not in the antisense strand, are also contemplated. When the antisense sequence of an small interfering RNA molecule comprises one or more mismatches between the nucleotide sequence of the small interfering RNA and the target nucleotide sequence, as described above, the mismatches may be found at the 3' terminus, the 5' terminus or in the central portion of the antisense sequence.

In another embodiment, the small interfering RNA molecules comprise a specific antisense sequence that is capable of selectively hybridizing under stringent conditions to a portion of a naturally occurring target gene or target mRNA. As known to those of ordinary skill in the art, variations in stringency of hybridization conditions may be achieved by altering the time, temperature or concentration of the solutions used for the hybridization and wash steps. Suitable conditions can also depend in part on the particular nucleotide sequences used, for example the sequence of the target mRNA or gene.

One method for inducing double stranded RNA-silencing in plants is transformation with a gene construct producing hairpin RNA (see Smith et al. (2000) *Nature,* 407, 319-320). Such constructs comprise inverted regions of the target gene sequence, separated by an appropriate spacer. The insertion of a functional plant intron region as a spacer fragment additionally increases the efficiency of the gene silencing induction, due to generation of an intron spliced hairpin RNA (Wesley et al. (2001) *Plant J.,* 27, 581-590). Suitably, the stem length is about 50 nucleotides to about 1 kilobases in length. Methods for producing intron spliced hairpin RNA are well described in the art (see for example, *Bioscience, Biotechnology, and Biochemistry* (2008) 72, 2, 615-617).

Interfering RNA molecules having a duplex or double-stranded structure, for example double-stranded RNA or small hairpin RNA, can have blunt ends, or can have 3' or 5' overhangs. As used herein, "overhang" refers to the unpaired nucleotide or nucleotides that protrude from a duplex structure when a 3'-terminus of one RNA strand extends beyond the 5'-terminus of the other strand (3' overhang), or vice versa (5' overhang). The nucleotides comprising the overhang can be ribonucleotides, deoxyribonucleotides or modified versions thereof. In one embodiment, at least one strand of the interfering RNA molecule has a 3' overhang from about 1 to about 6 nucleotides in length. In other embodiments, the 3' overhang is from about 1 to about 5 nucleotides, from about 1 to about 3 nucleotides and from about 2 to about 4 nucleotides in length.

When the interfering RNA molecule comprises a 3' overhang at one end of the molecule, the other end can be blunt-ended or have also an overhang (5' or 3'). When the interfering RNA molecule comprises an overhang at both ends of the molecule, the length of the overhangs may be the same or different. In one embodiment, the interfering RNA molecule comprises 3' overhangs of about 1 to about 3 nucleotides on both ends of the molecule. In a further embodiment, the interfering RNA molecule is a double-stranded RNA having a 3' overhang of 2 nucleotides at both ends of the molecule. In yet another embodiment, the nucleotides comprising the overhang of the interfering RNA are TT dinucleotides or UU dinucleotides.

When determining the percentage identity of the interfering RNA molecule comprising one or more overhangs to the target mRNA sequence, the overhang(s) may or may not be taken into account. For example, the nucleotides from a 3' overhang and up to 2 nucleotides from the 5'- or 3'-terminus of the double strand may be modified without significant loss of activity of the small interfering RNA molecule.

The interfering RNA molecules can comprise one or more 5' or 3'-cap structures. The interfering RNA molecule can comprise a cap structure at the 3'-end of the sense strand, the antisense strand, or both the sense and antisense strands; or at the 5'-end of the sense strand, the antisense strand, or both the sense and antisense strands of the interfering RNA molecule. Alternatively, the interfering RNA molecule can comprise a cap structure at both the 3'-end and 5'-end of the interfering RNA molecule. The term "cap structure" refers to a chemical modification incorporated at either terminus of an oligonucleotide, which protects the molecule from exonuclease degradation, and may also facilitate delivery or localisation within a cell.

Another modification applicable to interfering RNA molecules is the chemical linkage to the interfering RNA molecule of one or more moieties or conjugates which enhance the activity, cellular distribution, cellular uptake, bioavailability or stability of the interfering RNA molecule. The polynucleotides may be synthesized or modified by methods well established in the art. Chemical modifications may include, but are not limited to 2' modifications, introduction of non-natural bases, covalent attachment to a ligand, and replacement of phosphate linkages with thiophosphate linkages. In this embodiment, the integrity of the duplex structure is strengthened by at least one, and typically two, chemical linkages. Chemical linking may be achieved by any of a variety of well-known techniques, for example by introducing covalent, ionic or hydrogen bonds; hydrophobic interactions, van der Waals or stacking interactions; by means of metal-ion coordination, or through use of purine analogues.

The nucleotides at one or both of the two single strands may be modified to modulate the activation of cellular enzymes, such as, for example, without limitation, certain nucleases. Techniques for reducing or inhibiting the activation of cellular enzymes are known in the art including, but not limited to, 2'-amino modifications, 2'-fluoro modifications, 2'-alkyl modifications, uncharged backbone modifications, morpholino modifications, 2'-O-methyl modifications, and phosphoramidate. Thus, at least one 2'-hydroxyl group of the nucleotides on a double-stranded RNA is replaced by a chemical group. Also, at least one nucleotide may be modified to form a locked nucleotide. Such locked nucleotide contains a methylene or ethylene bridge that connects the 2'-oxygen of ribose with the 4'-carbon of ribose. Introduction of a locked nucleotide into an oligonucleotide improves the affinity for complementary sequences and increases the melting temperature by several degrees.

Ligands may be conjugated to an interfering RNA molecule, for example, to enhance its cellular absorption. In certain embodiments, a hydrophobic ligand is conjugated to the molecule to facilitate direct permeation of the cellular membrane. These approaches have been used to facilitate cell permeation of antisense oligonucleotides. In certain instances, conjugation of a cationic ligand to oligonucleotides often results in improved resistance to nucleases. Representative examples of cationic ligands include propylammonium and dimethylpropylammonium. Anti-sense oligonucleotides can retain their high binding affinity to mRNA when the cationic ligand is dispersed throughout the oligonucleotide.

The molecules and polynucleotides described herein may be prepared using well-known techniques of solid-phase synthesis. Any other means for such synthesis known in the art may additionally or alternatively be employed.

Various embodiments are directed to expression vectors comprising one or more of the polynucleotides or one or more interfering RNA constructs described herein. Exemplary constructs are shown in FIG. 21.

Various embodiments are directed to expression vectors comprising one or more polynucleotides or one or more interfering RNA constructs encoding one or more interfering RNA polynucleotides described herein that are capable of self-annealing to form a hairpin structure, in which the construct comprises (a) one or more of the polynucleotides described herein; (b) a second sequence encoding a spacer element that forms a loop of the hairpin structure; and (c) a third sequence comprising a reverse complementary sequence of the first sequence, positioned in the same orientation as the first sequence, wherein the second sequence is positioned between the first sequence and the third sequence, and the second sequence is operably-linked to the first sequence and to the third sequence.

The disclosed sequences can be utilised for constructing various polynucleotides that do not form hairpin structures. For example, a double-stranded RNA can be formed by (1) transcribing a first strand of the DNA by operably-linking to a first promoter, and (2) transcribing the reverse complementary sequence of the first strand of the DNA fragment by operably-linking to a second promoter. Each strand of the polynucleotide can be transcribed from the same expression vector, or from different expression vectors. The RNA duplex having RNA interference activity can be enzymatically converted to small interfering RNAs to modulate RNA levels.

Thus, various embodiments are directed to expression vectors comprising one or more polynucleotides or interfering RNA constructs described herein encoding interfering RNA polynucleotides capable of self-annealing, in which the construct comprises (a) one or more of the polynucleotides described herein; and (b) a second sequence comprising a complementary (for example, reverse complementary) sequence of the first sequence, positioned in the same orientation as the first sequence.

Various compositions and methods are provided for modulating the endogenous expression levels of one or more of the polypeptides described herein (or any combination thereof as described herein) by promoting co-suppression of gene expression. The phenomenon of co-suppression occurs as a result of introducing multiple copies of a transgene into a plant cell host. Integration of multiple copies of a transgene can result in modulated expression of the transgene and the targeted endogenous gene. The degree of co-suppression is dependent on the degree of sequence identity between the transgene and the targeted endogenous gene. The silencing of both the endogenous gene and the transgene can occur by extensive methylation of the silenced loci (that is, the endogenous promoter and endogenous gene of interest) that can preclude transcription. Alternatively, in some cases, co-suppression of the endogenous gene and the transgene can occur by post transcriptional gene silencing, in which transcripts can be produced but enhanced rates of degradation preclude accumulation of transcripts. The mechanism for co-suppression by post-transcriptional gene silencing is thought to resemble RNA interference, in that RNA seems to be both an important initiator and a target in these processes, and may be mediated at least in part by the same molecular machinery, possibly through RNA-guided degradation of mRNAs.

Co-suppression of nucleic acids can be achieved by integrating multiple copies of the nucleic acid or fragments thereof, as transgenes, into the genome of a plant of interest. The host plant can be transformed with an expression vector comprising a promoter operably-linked to the nucleic acid or fragments thereof. Various embodiments are directed to expression vectors for promoting co-suppression of endogenous genes comprising a promoter operably-linked to a polynucleotide.

Various embodiments are directed to methods for modulating the expression level of one or more of the polynucleotide(s) described herein (or any combination thereof as described herein) by integrating multiple copies of the polynucleotide(s) into a plant genome, comprising: transforming a plant cell host with an expression vector that comprises a promoter operably-linked to a polynucleotide.

Various compositions and methods are provided for modulating the endogenous gene expression level by modulating the translation of mRNA. A host plant cell can be transformed with an expression vector comprising: a promoter operably-linked to a polynucleotide, positioned in anti-sense orientation with respect to the promoter to enable the expression of RNA polynucleotides having a sequence complementary to a portion of mRNA.

Various expression vectors for modulating the translation of mRNA may comprise: a promoter operably-linked to a polynucleotide in which the sequence is positioned in anti-sense orientation with respect to the promoter. The lengths of anti-sense RNA polynucleotides can vary, and may be from about 15-20 nucleotides, about 20-30 nucleotides, about 30-50 nucleotides, about 50-75 nucleotides, about 75-100 nucleotides, about 100-150 nucleotides, about 150-200 nucleotides, and about 200-300 nucleotides.

Genes can also be targeted for inactivation by introducing transposons (for example, IS elements) into the genomes of plants of interest. These mobile genetic elements can be introduced by sexual cross-fertilization and insertion mutants can be screened for loss in protein activity. The disrupted gene in a parent plant can be introduced into other plants by crossing the parent plant with plant not subjected to transposon-induced mutagenesis by, for example, sexual cross-fertilization. Any standard breeding techniques known to persons skilled in the art can be utilized. In one embodiment, one or more genes can be inactivated by the insertion of one or more transposons. Mutations can result in homozygous disruption of one or more genes, in heterozygous disruption of one or more genes, or a combination of both homozygous and heterozygous disruptions if more than one gene is disrupted. Suitable transposable elements include retrotransposons, retroposons, and SINE-like elements. Such methods are known to persons skilled in the art.

Alternatively, genes can be targeted for inactivation by introducing ribozymes derived from a number of small circular RNAs that are capable of self-cleavage and replication in plants. These RNAs can replicate either alone (viroid RNAs) or with a helper virus (satellite RNAs). Examples of suitable RNAs include those derived from avocado sunblotch viroid and satellite RNAs derived from tobacco ringspot virus, lucerne transient streak virus, velvet tobacco mottle virus, *Solanum nodiflorum* mottle virus, and subterranean clover mottle virus. Various target RNA-specific ribozymes are known to persons skilled in the art.

As discussed herein, the expression of one or more polypeptides can be modulated by non-transgenic means—such as creating one or more mutations in one or more genes, as discussed herein. Methods that introduce a mutation randomly in a gene sequence can include chemical mutagenesis, EMS mutagenesis and radiation mutagenesis. Methods that introduce one or more targeted mutations into a cell include but are not limited to genome editing technology, particularly zinc finger nuclease-mediated mutagenesis and targeting induced local lesions in genomes (TILLING), homologous recombination, oligonucleotide-directed mutagenesis, and meganuclease-mediated mutagenesis. In one embodiment, TILLING is used. This is a mutagenesis technology that can be used to generate and/or identify polynucleotides encoding polypeptides with modified expression and/or activity. TILLING also allows selection of plants carrying such mutants. TILLING combines high-density mutagenesis with high-throughput screening methods. Methods for TILLING are well known in the art (see McCallum et al., (2000) *Nat Biotechnol* 18: 455-457 and Stemple (2004) *Nat Rev Genet* 5(2): 145-50).

Some non-limiting examples of mutations are deletions, insertions and missense mutations of at least one nucleotide, single nucleotide polymorphisms and a simple sequence repeat. After mutation, screening can be performed to identify mutations that create premature stop codons or otherwise non-functional genes. After mutation, screening can be performed to identify mutations that create functional genes that are capable of being expressed at elevated levels. Screening of mutants can be carried out by sequencing, or by the use of one or more probes or primers specific to the gene or protein. Specific mutations in polynucleotides can also be created that can result in modulated gene expression, modulated stability of mRNA, or modulated stability of protein. Such plants are referred to herein as "non-naturally occurring" or "mutant" plants. Typically, the mutant or non-naturally occurring plants will include at least a portion of foreign or synthetic or man-made nucleic acid (for example, DNA or RNA) that was not present in the plant before it was manipulated. The foreign nucleic acid may be a single nucleotide, two or more nucleotides, two or more contiguous nucleotides or two or more non-contiguous nucleotides—such as at least 10, 20, 30, 40, 50, 100, 200, 300, 400, 500, 600, 700, 800, 900, 1000, 1100, 1200, 1300, 1400 or 1500 or more contiguous or non-contiguous nucleotides.

The mutant or non-naturally occurring plants or plant cells can have any combination of one or more mutations in one or more genes which results in modulated protein levels. For example, the mutant or non-naturally occurring plants or plant cells may have a single mutation in a single gene; multiple mutations in a single gene; a single mutation in two or more or three or more or four or more genes; or multiple mutations in two or more or three or more or four or more genes. Examples of such mutations are described herein. By way of further example, the mutant or non-naturally occurring plants or plant cells may have one or more mutations in a specific portion of the gene(s)—such as in a region of the gene that encodes an active site of the protein or a portion thereof. By way of further example, the mutant or non-naturally occurring plants or plant cells may have one or more mutations in a region outside of one or more gene(s)—such as in a region upstream or downstream of the gene it regulates provided that they modulate the activity or expression of the gene(s). Upstream elements can include promoters, enhancers or transcription factors. Some elements—such as enhancers—can be positioned upstream or downstream of the gene it regulates. The element(s) need not be located near to the gene that it regulates since some elements have been found located several hundred thousand base pairs upstream or downstream of the gene that it regulates. The mutant or non-naturally occurring plants or plant cells may have one or more mutations located within the first 100 nucleotides of the gene(s), within the first 200 nucleotides of the gene(s), within the first 300 nucleotides of the gene(s), within the first 400 nucleotides of the gene(s), within the first 500 nucleotides of the gene(s), within the first 600 nucleotides of the gene(s), within the first 700 nucleotides of the gene(s), within the first 800 nucleotides of the gene(s), within the first 900 nucleotides of the gene(s), within the first 1000 nucleotides of the gene(s), within the first 1100 nucleotides of the gene(s), within the first 1200 nucleotides of the gene(s), within the first 1300 nucleotides of the gene(s), within the first 1400 nucleotides of the gene(s) or within the first 1500 nucleotides of the gene(s). The mutant or non-naturally occurring plants or plant cells may have one or more mutations located within the first, second, third, fourth, fifth, sixth, seventh, eighth, ninth, tenth, eleventh, twelfth, thirteenth, fourteenth or fifteenth set of 100 nucleotides of the gene(s) or combinations thereof. Mutant or non-naturally occurring plants or plant cells (for example, mutant, non-naturally occurring or transgenic plants or plant cells and the like, as described herein) comprising the mutant polypeptide variants are disclosed.

In one embodiment, seeds from plants are mutagenised and then grown into first generation mutant plants. The first generation plants are then allowed to self-pollinate and seeds from the first generation plant are grown into second generation plants, which are then screened for mutations in their loci. Though the mutagenized plant material can be screened for mutations, an advantage of screening the second generation plants is that all somatic mutations correspond to germline mutations. One of skill in the art would understand that a variety of plant materials, including but not limited to, seeds, pollen, plant tissue or plant cells, may be mutagenised in order to create the mutant plants. However, the type of plant material mutagenised may affect when the plant nucleic acid is screened for mutations. For example, when pollen is subjected to mutagenesis prior to pollination of a non-mutagenized plant the seeds resulting from that pollination are grown into first generation plants. Every cell of the first generation plants will contain mutations created in the pollen; thus these first generation plants may then be screened for mutations instead of waiting until the second generation.

Mutagens that create primarily point mutations and short deletions, insertions, transversions, and or transitions, including chemical mutagens or radiation, may be used to create the mutations. Mutagens include, but are not limited to, ethyl methanesulfonate, methylmethane sulfonate, N-ethyl-N-nitrosurea, triethylmelamine, N-methyl-N-nitrosourea, procarbazine, chlorambucil, cyclophosphamide, diethyl sulfate, acrylamide monomer, melphalan, nitrogen mustard, vincristine, dimethylnitrosamine, N-methyl-N'-nitro-Nitrosoguanidine, nitrosoguanidine, 2-aminopurine, 7,12 dimethyl-benz(a)anthracene, ethylene oxide, hexamethylphosphoramide, bisulfan, diepoxyalkanes (diepoxyoctane, diepoxybutane, and the like), 2-methoxy-6-chloro-9[3-(ethyl-2-chloro-ethyl)aminopropylamino]acridine di hydrochloride and formaldehyde.

Spontaneous mutations in the locus that may not have been directly caused by the mutagen are also contemplated provided that they result in the desired phenotype. Suitable mutagenic agents can also include, for example, ionising radiation—such as X-rays, gamma rays, fast neutron irradiation and UV radiation. Any method of plant nucleic acid preparation known to those of skill in the art may be used to prepare the plant nucleic acid for mutation screening.

Prepared nucleic acid from individual plants, plant cells, or plant material can optionally be pooled in order to expedite screening for mutations in the population of plants originating from the mutagenized plant tissue, cells or material. One or more subsequent generations of plants, plant cells or plant material can be screened. The size of the optionally pooled group is dependent upon the sensitivity of the screening method used.

After the nucleic acid samples are optionally pooled, they can be subjected to polynucleotide-specific amplification techniques, such as Polymerase Chain Reaction. Any one or more primers or probes specific to the gene or the sequences immediately adjacent to the gene may be utilized to amplify the sequences within the optionally pooled nucleic acid sample. Suitably, the one or more primers or probes are designed to amplify the regions of the locus where useful mutations are most likely to arise. Most preferably, the primer is designed to detect mutations within regions of the polynucleotide. Additionally, it is preferable for the primer(s) and probe(s) to avoid known polymorphic sites in order to ease screening for point mutations. To facilitate detection of amplification products, the one or more primers or probes may be labelled using any conventional labelling method. Primer(s) or probe(s) can be designed based upon the sequences described herein using methods that are well understood in the art.

To facilitate detection of amplification products, the primer(s) or probe(s) may be labelled using any conventional labelling method. These can be designed based upon the sequences described herein using methods that are well understood in the art. Polymorphisms may be identified by means known in the art and some have been described in the literature.

In a further aspect there is provided a method of preparing a mutant plant. The method involves providing at least one cell of a plant comprising a gene encoding a functional polynucleotide described herein (or any combination thereof as described herein). Next, the at least one cell of the plant is treated under conditions effective to modulate the activity of the polynucleotide(s) described herein. The at least one mutant plant cell is then propagated into a mutant plant, where the mutant plant has a modulated level of polypeptide(s) described (or any combination thereof as described herein) as compared to that of a control plant. In one embodiment of this method of making a mutant plant, the treating step involves subjecting the at least one cell to a chemical mutagenising agent as described above and under conditions effective to yield at least one mutant plant cell. In another embodiment of this method, the treating step involves subjecting the at least one cell to a radiation source under conditions effective to yield at least one mutant plant cell. The term "mutant plant" includes mutants plants in which the genotype is modified as compared to a control plant, suitably by means other than genetic engineering or genetic modification.

In certain embodiments, the mutant plant, mutant plant cell or mutant plant material may comprise one or more mutations that have occurred naturally in another plant, plant cell or plant material and confer a desired trait. This mutation can be incorporated (for example, introgressed) into another plant, plant cell or plant material (for example, a plant, plant cell or plant material with a different genetic background to the plant from which the mutation was derived) to create a mutation that is non-naturally occurring in that plant and to confer the trait thereto. Thus by way of example, a mutation that occurred naturally in a first plant may be introduced into a second plant—such as a second plant with a different genetic background to the first plant. The skilled person is therefore able to search for and identify a plant carrying naturally in its genome one or more mutant alleles of the genes described herein which confer a desired trait. In certain embodiments, one or more mutations in one allele is sufficient to shorten the time to flowering. The mutant allele(s) that occurs naturally can be transferred to the second plant by various methods including breeding, backcrossing and introgression to produce a lines, varieties or hybrids that have one or more mutations in the genes described herein. Plants showing a desired trait may be screened out of a pool of mutant plants. Suitably, the selection is carried out utilising the knowledge of the nucleotide sequences as described herein. Consequently, it is possible to screen for a genetic trait as compared to a control. Such a screening approach may involve the application of conventional nucleic acid amplification and/or hybridization techniques as discussed herein. Thus, a further aspect relates to a method for identifying a mutant plant with a shortened time to flowering as compared to a control plant comprising: (a) providing a sample from a plant to be screened; (b) determining if said sample comprises one or more mutations in one or more of the polynucleotides described herein; and (c) determining the speed of flowering of said plant.

In another aspect there is provided a method for preparing a mutant plant which has an shortened time to flowering as compared to a control plant comprising the steps of: (a) providing a sample from a first plant; (b) determining if said sample comprises one or more mutations in one or more of the polynucleotides described herein that result in shortened time to flowering; and (c) transferring the one or more mutations into a second plant. The mutation(s) can be transferred into the second plant using various methods that are known in the art—such as by genetic engineering, genetic manipulation, introgression, plant breeding, backcrossing and the like. In one embodiment, the first plant is a naturally occurring plant. In one embodiment, the second plant has a different genetic background to the first plant.

In another aspect there is provided a method for preparing a mutant plant which has shortened time to flowering as compared to a control plant comprising the steps of: (a) providing a sample from a first plant; (b) determining if said sample comprises one or more mutations in one or more of the polynucleotides described herein that results in shortened time to flowering; and (c) introgressing the one or more mutations from the first plant into a second plant. In one embodiment, the step of introgressing comprises plant breeding, optionally including backcrossing and the like. In one embodiment, the first plant is a naturally occurring plant. In one embodiment, the second plant has a different genetic background to the first plant. In one embodiment, the first plant is not a cultivar or an elite cultivar. In one embodiment, the second plant is a cultivar or an elite cultivar.

A further aspect relates to a mutant plant (including a cultivar or elite cultivar mutant plant) obtained or obtainable by the methods described herein. In certain embodiments, the "mutant plant" may have one or more mutations localised only to a specific region of the plant—such as within the sequence of the one or more polynucleotide(s) described herein. According to this embodiment, the remaining genomic sequence of the mutant plant will be the same or substantially the same as the plant prior to the mutagenesis.

In certain embodiments, the mutant plants may have one or more mutations localised in more than one region of the plant—such as within the sequence of one or more of the polynucleotides described herein and in one or more further regions of the genome. According to this embodiment, the remaining genomic sequence of the mutant plant will not be the same or will not be substantially the same as the plant prior to the mutagenesis. In certain embodiments, the mutant plants may not have one or more mutations in one or more, two or more, three or more, four or more or five or more exons of the polynucleotide(s) described herein; or may not have one or more mutations in one or more, two or more, three or more, four or more or five or more introns of the polynucleotide(s) described herein; or may not have one or more mutations in a promoter of the polynucleotide(s) described herein; or may not have one or more mutations in the 3' untranslated region of the polynucleotide(s) described herein; or may not have one or more mutations in the 5' untranslated region of the polynucleotide(s) described herein; or may not have one or more mutations in the coding region of the polynucleotide(s) described herein; or may not have one or more mutations in the non-coding region of the polynucleotide(s) described herein; or any combination of two or more, three or more, four or more, five or more; or six or more thereof parts thereof.

In a further aspect there is provided a method of identifying a plant, a plant cell or plant material comprising a mutation in a gene encoding a polynucleotide described herein comprising: (a) subjecting a plant, a plant cell or plant material to mutagenesis; (b) obtaining a nucleic acid sample from said plant, plant cell or plant material or descendants thereof; and (c) determining the nucleic acid sequence of the gene encoding a polynucleotide described herein or a variant or a fragment thereof, wherein a difference in said sequence is indicative of one or more mutations therein.

Zinc finger proteins can also be used to modulate the expression or the activity of one or more of the polynucleotides described herein. In various embodiments, a genomic DNA sequence comprising a part of or all of the coding sequence of the polynucleotide is modified by zinc finger nuclease-mediated mutagenesis. The genomic DNA sequence is searched for a unique site for zinc finger protein binding. Alternatively, the genomic DNA sequence is searched for two unique sites for zinc finger protein binding wherein both sites are on opposite strands and close together, for example, 1, 2, 3, 4, 5, 6 or more base pairs apart. Accordingly, zinc finger proteins that bind to polynucleotides are provided.

A zinc finger protein may be engineered to recognize a selected target site in a gene. A zinc finger protein can comprise any combination of motifs derived from natural zinc finger DNA-binding domains and non-natural zinc finger DNA-binding domains by truncation or expansion or a process of site-directed mutagenesis coupled to a selection method such as, but not limited to, phage display selection, bacterial two-hybrid selection or bacterial one-hybrid selection. The term "non-natural zinc finger DNA-binding domain" refers to a zinc finger DNA-binding domain that binds a three-base pair sequence within the target nucleic acid and that does not occur in the cell or organism comprising the nucleic acid which is to be modified. Methods for the design of zinc finger protein which binds specific nucleotide sequences which are unique to a target gene are known in the art.

A zinc finger nuclease may be constructed by making a fusion of a first polynucleotide coding for a zinc finger protein that binds to a polynucleotide, and a second polynucleotide coding for a non-specific endonuclease such as, but not limited to, those of a Type IIS endonuclease. A fusion protein between a zinc finger protein and the nuclease may comprise a spacer consisting of two base pairs or alternatively, the spacer can consist of three, four, five, six, seven or more base pairs. In various embodiments, a zinc finger nuclease introduces a double stranded break in a regulatory region, a coding region, or a non-coding region of a genomic DNA sequence of a polynucleotide and leads to a reduction of the level of expression of a polynucleotide, or a reduction in the activity of the protein encoded thereby. Cleavage by zinc finger nucleases frequently results in the deletion of DNA at the cleavage site following DNA repair by non-homologous end joining.

In other embodiments, a zinc finger protein may be selected to bind to a regulatory sequence of a polynucleotide. More specifically, the regulatory sequence may comprise a transcription initiation site, a start codon, a region of an exon, a boundary of an exon-intron, a terminator, or a stop codon. Accordingly, the disclosure provides a mutant, non-naturally occurring or transgenic plant or plant cells, produced by zinc finger nuclease-mediated mutagenesis in the vicinity of or within one or more polynucleotides described herein, and methods for making such a plant or plant cell by zinc finger nuclease-mediated mutagenesis. Methods for delivering zinc finger protein and zinc finger nuclease to a plant are similar to those described below for delivery of meganuclease.

In another aspect, methods for producing mutant, non-naturally occurring or transgenic or otherwise genetically-modified plants using meganucleases, such as I-CreI, are described. Naturally occurring meganucleases as well as recombinant meganucleases can be used to specifically cause a double-stranded break at a single site or at relatively few sites in the genomic DNA of a plant to allow for the disruption of one or more polynucleotides described herein. The meganuclease may be an engineered meganuclease with altered DNA-recognition properties. Meganuclease proteins can be delivered into plant cells by a variety of different mechanisms known in the art.

The disclosure also encompass the use of meganucleases to inactivate a polynucleotide(s) described herein (or any combination thereof as described herein) in a plant cell or plant. Particularly, the disclosure provides a method for inactivating a polynucleotide in a plant using a meganuclease comprising: a) providing a plant cell comprising a polynucleotide as described herein; (b) introducing a meganuclease or a construct encoding a meganuclease into said plant cell; and (c) allowing the meganuclease to substantially inactivate the polynucleotide(s)

Meganucleases can be used to cleave meganuclease recognition sites within the coding regions of a polynucleotide.

Such cleavage frequently results in the deletion of DNA at the meganuclease recognition site following mutagenic DNA repair by non-homologous end joining. Such mutations in the gene coding sequence are typically sufficient to inactivate the gene. This method to modify a plant cell involves, first, the delivery of a meganuclease expression cassette to a plant cell using a suitable transformation method. For highest efficiency, it is desirable to link the meganuclease expression cassette to a selectable marker and select for successfully transformed cells in the presence of a selection agent. This approach will result in the integration of the meganuclease expression cassette into the genome, however, which may not be desirable if the plant is likely to require regulatory approval. In such cases, the meganuclease expression cassette (and linked selectable marker gene) may be segregated away in subsequent plant generations using conventional breeding techniques. Alternatively, plant cells may be initially be transformed with a meganuclease expression cassette lacking a selectable marker and may be grown on media lacking a selection agent. Under such conditions, a fraction of the treated cells will acquire the meganuclease expression cassette and will express the engineered meganuclease transiently without integrating the meganuclease expression cassette into the genome. Because it does not account for transformation efficiency, this latter transformation procedure requires that a greater number of treated cells be screened to obtain the desired genome modification. The above approach can also be applied to modify a plant cell when using a zinc finger protein or zinc finger nuclease.

Following delivery of the meganuclease expression cassette, plant cells are grown, initially, under conditions that are typical for the particular transformation procedure that was used. This may mean growing transformed cells on media at temperatures below 26° C., frequently in the dark. Such standard conditions can be used for a period of time, preferably 1-4 days, to allow the plant cell to recover from the transformation process. At any point following this initial recovery period, growth temperature may be raised to stimulate the activity of the engineered meganuclease to cleave and mutate the meganuclease recognition site.

For certain applications, it may be desirable to precisely remove the polynucleotide from the genome of the plant. Such applications are possible using a pair of engineered meganucleases, each of which cleaves a meganuclease recognition site on either side of the intended deletion. TAL Effector Nucleases (TALENs) that are able to recognize and bind to a gene and introduce a double-strand break into the genome can also be used. Thus, in another aspect, methods for producing mutant, non-naturally occurring or transgenic or otherwise genetically-modified plants as described herein using TAL Effector Nucleases are contemplated.

Plants suitable for use in the present disclosure include, but are not limited to, monocotyledonous and dicotyledonous plants and plant cell systems, including species from one of the following families: Acanthaceae, Alliaceae, Alstroemeriaceae, Amaryllidaceae, Apocynaceae, Arecaceae, Asteraceae, Berberidaceae, Bixaceae, Brassicaceae, Bromeliaceae, Cannabaceae, Caryophyllaceae, Cephalotaxaceae, Chenopodiaceae, Colchicaceae, Cucurbitaceae, Dioscoreaceae, Ephedraceae, Erythroxylaceae, Euphorbiaceae, Fabaceae, Lamiaceae, Linaceae, Lycopodiaceae, Malvaceae, Melanthiaceae, Musaceae, Myrtaceae, Nyssaceae, Papaveraceae, Pinaceae, Plantaginaceae, Poaceae, Rosaceae, Rubiaceae, Salicaceae, Sapindaceae, Solanaceae, Taxaceae, Theaceae, or Vitaceae.

Suitable species may include members of the genera *Abelmoschus, Abies, Acer, Agrostis, Allium, Alstroemeria, Ananas, Andrographis, Andropogon, Artemisia, Arundo, Atropa, Berberis, Beta, Bixa, Brassica, Calendula, Camellia, Camptotheca, Cannabis, Capsicum, Carthamus, Catharanthus, Cephalotaxus, Chrysanthemum, Cinchona, Citrullus, Coffea, Colchicum, Coleus, Cucumis, Cucurbita, Cynodon, Datura, Dianthus, Digitalis, Dioscorea, Elaeis, Ephedra, Erianthus, Erythroxylum, Eucalyptus, Festuca, Fragaria, Galanthus, Glycine, Gossypium, Helianthus, Hevea, Hordeum, Hyoscyamus, Jatropha, Lactuca, Linum, Lolium, Lupinus, Lycopersicon, Lycopodium, Manihot, Medicago, Mentha, Miscanthus, Musa, Nicotiana, Oryza, Panicum, Papaver, Parthenium, Pennisetum, Petunia, Phalaris, Phleum, Pinus, Poa, Poinsettia, Populus, Rauwolfia, Ricinus, Rosa, Saccharum, Salix, Sanguinaria, Scopolia, Secale, Solanum, Sorghum, Spartina, Spinacea, Tanacetum, Taxus, Theobroma, Triticosecale, Triticum, Uniola, Veratrum, Vinca, Vitis*, and *Zea*.

Suitable species may include *Panicum* spp., *Sorghum* spp., *Miscanthus* spp., *Saccharum* spp., *Erianthus* spp., *Populus* spp., *Andropogon gerardii* (big bluestem), *Pennisetum purpureum* (elephant grass), *Phalaris arundinacea* (reed canarygrass), *Cynodon dactylon* (bermudagrass), *Festuca arundinacea* (tall fescue), *Spartina pectinata* (prairie cord-grass), *Medicago sativa* (alfalfa), *Arundo donax* (giant reed), *Secale cereale* (rye), *Salix* spp. (willow), *Eucalyptus* spp. (*eucalyptus*), *Triticosecale* (tritic wheat times rye), bamboo, *Helianthus annuus* (sunflower), *Carthamus tinctorius* (safflower), *Jatropha curcas* (*jatropha*), *Ricinus communis* (castor), *Elaeis guineensis* (palm), *Linum usitatissimum* (flax), *Brassica juncea, Beta vulgaris* (sugarbeet), *Manihot esculenta* (cassaya), *Lycopersicon esculentum* (tomato), *Lactuca sativa* (lettuce), *Musyclise alca* (banana), *Solanum tuberosum* (potato), *Brassica oleracea* (broccoli, cauliflower, Brussels sprouts), *Camellia sinensis* (tea), *Fragaria ananassa* (strawberry), *Theobroma cacao* (cocoa), *Coffea ycliseca* (coffee), *Vitis vinifera* (grape), *Ananas comosus* (pineapple), *Capsicum annum* (hot & sweet pepper), *Allium cepa* (onion), *Cucumis melo* (melon), *Cucumis sativus* (cucumber), *Cucurbita maxima* (squash), *Cucurbita moschata* (squash), *Spinacea oleracea* (spinach), *Citrullus lanatus* (watermelon), *Abelmoschus esculentus* (okra), *Solanum melongena* (eggplant), *Rosa* spp. (rose), *Dianthus caryophyllus* (carnation), *Petunia* spp. (*petunia*), *Poinsettia pulcherrima* (poinsettia), *Lupinus albus* (lupin), *Uniola paniculata* (oats), bentgrass (*Agrostis* spp.), *Populus tremuloides* (aspen), *Pinus* spp. (pine), *Abies* spp. (fir), *Acer* spp. (maple), *Hordeum vulgare* (barley), *Poa pratensis* (bluegrass), *Lolium* spp. (ryegrass) and *Phleum pratense* (timothy), *Panicum virgatum* (switchgrass), Sorghu52yclise52or (sorghum, sudangrass), *Miscanthus giganteus* (*miscanthus*), *Saccharum* sp. (energycane), *Populus balsamifera* (poplar), *Zea mays* (corn), *Glycine max* (soybean), *Brassica napus* (canola), *Triticum aestivum* (wheat), *Gossypium hirsutum* (cotton), *Oryza sativa* (rice), *Helianthus annuus* (sunflower), *Medicago sativa* (alfalfa), *Beta vulgaris* (sugarbeet), or *Pennisetum glaucum* (pearl millet).

Various embodiments are directed to mutant, non-naturally occurring or transgenic plants or plant cells modified to modulate gene expression levels thereby producing a plant or plant cell—such as a tobacco plant or tobacco plant cell—in which the expression level of a polypeptide is modulated within tissues of interest as compared to a control. The disclosed compositions and methods can be applied to any species of the genus *Nicotiana*, including *N. rustica* and *N. tabacum* (for example, LA B21, LN KY171, TI 1406, Basma, Galpao, Perique, Beinhart 1000-1, and Petico). Other species include *N. acaulis, N. acuminata, N.*

*africana, N. alata, N. ameghinoi, N. amplexicaulis, N. arentsii, N. attenuata, N. azambujae, N. benavidesii, N. benthamiana, N. bigelovii, N. bonariensis, N. cavicola, N. clevelandii, N. cordifolia, N. corymbosa, N. debneyi, N. excelsior, N. forgetiana, N. fragrans, N. glauca, N. glutinosa, N. goodspeedii, N. gossei, N. hybrid, N. ingulba, N. kawakamii, N. knightiana, N. langsdorffii, N. linearis, N. longiflora, N. maritima, N. megalosiphon, N. miersii, N. noctiflora, N. nudicaulis, N. obtusifolia, N. occidentalis, N. occidentalis* subsp. *hesperis, N. otophora, N. paniculata, N. pauciflora, N. petunioides, N. plumbaginifolia, N. quadrivalvis, N. raimondii, N. repanda, N. rosulata, N. rosulata* subsp. *ingulba, N. rotundifolia, N. setchellii, N. simulans, N. solanifolia, N. spegazzinii, N. stocktonii, N. suaveolens, N. sylvestris, N. thyrsiflora, N. tomentosa, N. tomentosiformis, N. trigonophylla, N. umbratica, N. undulata, N. velutina, N. wigandioides*, and *N. x sanderae.*

The use of tobacco cultivars and elite tobacco cultivars is also contemplated herein. The transgenic, non-naturally occurring or mutant plant may therefore be a tobacco variety or elite tobacco cultivar that comprises one or more transgenes, or one or more genetic mutations or a combination thereof. The genetic mutation(s) (for example, one or more polymorphisms) can be mutations that do not exist naturally in the individual tobacco variety or tobacco cultivar (for example, elite tobacco cultivar) or can be genetic mutation(s) that do occur naturally provided that the mutation does not occur naturally in the individual tobacco variety or tobacco cultivar (for example, elite tobacco cultivar).

Particularly useful *Nicotiana tabacum* varieties include Burley type, dark type, flue-cured type, and Oriental type tobaccos. Non-limiting examples of varieties or cultivars are: BD 64, CC 101, CC 200, CC 27, CC 301, CC 400, CC 500, CC 600, CC 700, CC 800, CC 900, Coker 176, Coker 319, Coker 371 Gold, Coker 48, CD 263, DF911, DT 538 LC Galpao tobacco, GL 26H, GL 350, GL 600, GL 737, GL 939, GL 973, HB 04P, HB 04P LC, HB3307PLC, Hybrid 403LC, Hybrid 404LC, Hybrid 501 LC, K 149, K 326, K 346, K 358, K394, K 399, K 730, KDH 959, KT 200, KT204LC, KY10, KY14, KY 160, KY 17, KY 171, KY 907, KY907LC, KY14xL8 LC, Little Crittenden, McNair 373, McNair 944, msKY 14xL8, Narrow Leaf Madole, Narrow Leaf Madole LC, NBH 98, N-126, N-777LC, N-7371LC, NC 100, NC 102, NC 2000, NC 291, NC 297, NC 299, NC 3, NC 4, NC 5, NC 6, NC7, NC 606, NC 71, NC 72, NC 810, NC BH 129, NC 2002, Neal Smith Madole, OXFORD 207, PD 7302 LC, PD 7309 LC, PD 7312 LC, 'Periqe' tobacco, PVH03, PVH09, PVH19, PVH50, PVH51, R 610, R 630, R 7-11, R 7-12, RG 17, RG 81, RG H51, RGH 4, RGH 51, RS 1410, Speight 168, Speight 172, Speight 179, Speight 210, Speight 220, Speight 225, Speight 227, Speight 234, Speight G-28, Speight G-70, Speight H-6, Speight H20, Speight NF3, TI 1406, TI 1269, TN 86, TN86LC, TN 90, TN 97, TN97LC, TN D94, TN D950, TR (Tom Rosson) Madole, VA 309, VA359, AA 37-1, B13P, Xanthi (Mitchell-Mor), Bel-W3, 79-615, Samsun Holmes NN, KTRDC number 2 Hybrid 49, Burley 21, KY8959, KY9, MD 609, PG01, PG04, P01, P02, P03, RG11, RG 8, VA509, AS44, Banket A1, Basma Drama B84/31, Basma I Zichna ZP4/B, Basma Xanthi BX 2A, Batek, Besuki Jember, C104, Coker 347, Criollo Misionero, Delcrest, Djebel 81, DVH 405, Galpão Comum, HBO4P, Hicks Broadleaf, Kabakulak Elassona, Kutsage E1, LA BU 21, NC 2326, NC 297, PVH 2110, Red Russian, Samsun, Saplak, Simmaba, Talgar 28, Wislica, Yayaldag, Prilep HC-72, Prilep P23, Prilep PB 156/1, Prilep P12-2/1, Yaka JK-48, Yaka JB 125/3, TI-1068, KDH-960, TI-1070, TW136, Basma, TKF 4028, L8, TKF 2002, GR141, *Basma xanthi*, GR149, GR153, Petit Havana. Low converter subvarieties of the above, even if not specifically identified herein, are also contemplated.

Embodiments are also directed to compositions and methods for producing mutant plants, non-naturally occurring plants, hybrid plants, or transgenic plants that have been modified to modulate the expression or activity of a polynucleotide(s) described herein (or any combination thereof as described herein). Various phenotypic characteristics such as degree of maturity, number of leaves per plant, stalk height, leaf insertion angle, leaf size (width and length), internode distance, and lamina-midrib ratio can be assessed by field observations.

One aspect relates to a seed of a mutant plant, a non-naturally occurring plant, a hybrid plant or a transgenic plant described herein. Preferably, the seed is a tobacco seed. A further aspect relates to pollen or an ovule of a mutant plant, a non-naturally occurring plant, a hybrid plant or a transgenic plant that is described herein. In addition, there is provided a mutant plant, a non-naturally occurring plant, a hybrid plant or a transgenic plant as described herein which further comprises a nucleic acid conferring male sterility.

Also provided is a tissue culture of regenerable cells of the mutant plant, non-naturally occurring plant, hybrid plant, or transgenic plant or a part thereof as described herein, which culture regenerates plants capable of expressing all the morphological and physiological characteristics of the parent. The regenerable cells include but are not limited to cells from leaves, pollen, embryos, cotyledons, hypocotyls, roots, root tips, anthers, flowers and a part thereof, ovules, shoots, stems, stalks, pith and capsules or callus or protoplasts derived therefrom.

A still further aspect, relates to a cured plant material—such as cured leaf or cured tobacco—derived or derivable from the mutant, non-naturally occurring or transgenic plant or cell. Embodiments are also directed to compositions and methods for producing mutant, non-naturally occurring or transgenic plants or plant cells that have been modified to modulate the expression or activity of the one or more of the polynucleotides or polypeptides described herein which can result in plants with shortened time to flowering.

In another aspect, there is provided a method for shortening time to flowering in a plant comprising: (i) modulating (eg. reducing) the expression or activity of an one or more of the polypeptides or polynucleotides described herein; (ii) measuring the speed of flowering of the mutant, non-naturally occurring or transgenic plant obtained in step (i); and (iii) identifying a mutant, non-naturally occurring or transgenic plant which has a shortened time to flowering in comparison to a control plant. Suitably, the plant is a tobacco plant.

A reduction in expression as compared to a control may be from about 5% to about 100%, or a reduction of at least 10%, at least 20%, at least 25%, at least 30%, at least 40%, at least 50%, at least 60%, at least 70%, at least 75%, at least 80%, at least 90%, at least 95%, at least 98%, or 100%, which includes a reduction in transcriptional activity or polynucleotide expression or polypeptide expression or a combination thereof.

A reduction in activity as compared to a control may be from about 5% to about 100%, or a reduction of at least 10%, at least 20%, at least 25%, at least 30%, at least 40%, at least 50%, at least 60%, at least 70%, at least 75%, at least 80%, at least 90%, at least 95%, at least 98%, or 100%.

Polynucleotides and recombinant constructs described herein can be used to modulate expression in a plant species of interest, suitably tobacco.

A number of polynucleotide based methods can be used to increase gene expression in plants and plant cells, for example. By way of example, a construct, vector or expression vector that is compatible with the plant to be transformed can be prepared which comprises the gene of interest together with an upstream promoter that is capable of overexpressing the gene in the plant or plant cell. Exemplary promoters are described herein. Following transformation and when grown under suitable conditions, the promoter can drive expression. In one exemplary embodiment, a vector carrying one or more polynucleotides described herein (or any combination thereof as described herein) is generated to overexpress the gene in a plant or plant cell. The vector carries a suitable promoter—such as the cauliflower mosaic virus CaMV 35S promoter—upstream of the transgene driving its constitutive expression in all tissues of the plant. The vector also carries an antibiotic resistance gene in order to confer selection of the transformed calli and cell lines.

Various embodiments are directed to methods for reducing the expression level of one or more polynucleotides described herein by integrating multiple copies of the polynucleotide into a plant genome, comprising: transforming a plant cell host with an expression vector that comprises a promoter operably-linked to one or more polynucleotides described herein. The polypeptide encoded by a recombinant polynucleotide can be a native polypeptide, or can be heterologous to the cell.

A plant carrying a mutant allele of one or more polynucleotides described herein (or any combination thereof as described herein) can be used in a plant breeding program to create useful lines, varieties and hybrids. In particular, the mutant allele is introgressed into the commercially important varieties described above. Thus, methods for breeding plants are provided, that comprise crossing a mutant plant, a non-naturally occurring plant or a transgenic plant as described herein with a plant comprising a different genetic identity. The method may further comprise crossing the progeny plant with another plant, and optionally repeating the crossing until a progeny with the desirable genetic traits or genetic background is obtained. One purpose served by such breeding methods is to introduce a desirable genetic trait into other varieties, breeding lines, hybrids or cultivars, particularly those that are of commercial interest. Another purpose is to facilitate stacking of genetic modifications of different genes in a single plant variety, lines, hybrids or cultivars. Intraspecific as well as interspecific matings are contemplated. The progeny plants that arise from such crosses, also referred to as breeding lines, are examples of non-naturally occurring plants of the disclosure.

In one embodiment, a method is provided for producing a non-naturally occurring plant comprising: (a) crossing a mutant or transgenic plant with a second plant to yield progeny tobacco seed; (b) growing the progeny seed, under plant growth conditions, to yield the non-naturally occurring plant. The method may further comprise: (c) crossing the previous generation of non-naturally occurring plant with itself or another plant to yield progeny seed; (d) growing the progeny seed of step (c) under plant growth conditions, to yield additional non-naturally occurring plants; and (e) repeating the crossing and growing steps of (c) and (d) multiple times to generate further generations of non-naturally occurring plants. The method may optionally comprise prior to step (a), a step of providing a parent plant which comprises a genetic identity that is characterized and that is not identical to the mutant or transgenic plant. In some embodiments, depending on the breeding program, the crossing and growing steps are repeated from 0 to 2 times, from 0 to 3 times, from 0 to 4 times, 0 to 5 times, from 0 to 6 times, from 0 to 7 times, from 0 to 8 times, from 0 to 9 times or from 0 to 10 times, in order to generate generations of non-naturally occurring plants. Backcrossing is an example of such a method wherein a progeny is crossed with one of its parents or another plant genetically similar to its parent, in order to obtain a progeny plant in the next generation that has a genetic identity which is closer to that of one of the parents. Techniques for plant breeding, particularly plant breeding, are well known and can be used in the methods of the disclosure. The disclosure further provides non-naturally occurring plants produced by these methods. Certain embodiments exclude the step of selecting a plant.

In some embodiments of the methods described herein, lines resulting from breeding and screening for variant genes are evaluated in the field using standard field procedures. Control genotypes including the original unmutagenized parent are included and entries are arranged in the field in a randomized complete block design or other appropriate field design. For tobacco, standard agronomic practices are used, for example, the tobacco is harvested, weighed, and sampled for chemical and other common testing before and during curing or drying. Statistical analyses of the data are performed to confirm the similarity of the selected lines to the parental line. Cytogenetic analyses of the selected plants are optionally performed to confirm the chromosome complement and chromosome pairing relationships.

DNA fingerprinting, single nucleotide polymorphism, microsatellite markers, or similar technologies may be used in a marker-assisted selection (MAS) breeding program to transfer or breed mutant alleles of a gene into other plants, as described herein. For example, a breeder can create segregating populations from hybridizations of a genotype containing a mutant allele with an agronomically desirable genotype. Plants in the F2 or backcross generations can be screened using a marker developed from a genomic sequence or a fragment thereof, using one of the techniques listed herein. Plants identified as possessing the mutant allele can be backcrossed or self-pollinated to create a second population to be screened. Depending on the expected inheritance pattern or the MAS technology used, it may be necessary to self-pollinate the selected plants before each cycle of backcrossing to aid identification of the desired individual plants. Backcrossing or other breeding procedure can be repeated until the desired phenotype of the recurrent parent is recovered.

In a breeding program, successful crosses yield F1 plants that are fertile. Selected F1 plants can be crossed with one of the parents, and the first backcross generation plants are self-pollinated to produce a population that is again screened for variant gene expression (for example, the null version of the gene). The process of backcrossing, self-pollination, and screening is repeated, for example, at least 4 times until the final screening produces a plant that is fertile and reasonably similar to the recurrent parent. This plant, if desired, is self-pollinated and the progeny are subsequently screened again to confirm that the plant exhibits variant gene expression. In some embodiments, a plant population in the F2 generation is screened for variant gene expression, for example, a plant is identified that fails to express a polypeptide due to the absence of the gene according to standard methods, for example, by using a PCR method with primers based upon the nucleotide sequence information for the polynucleotide(s) described herein (or any combination thereof as described herein).

Hybrid varieties can be produced by preventing self-pollination of female parent plants (that is, seed parents) of a first variety, permitting pollen from male parent plants of a second variety to fertilize the female parent plants, and allowing F1 hybrid seeds to form on the female plants. Self-pollination of female plants can be prevented by emasculating the flowers at an early stage of flower development. Alternatively, pollen formation can be prevented on the female parent plants using a form of male sterility. For example, male sterility can be produced by cytoplasmic male sterility (CMS), or transgenic male sterility wherein a transgene inhibits microsporogenesis and/or pollen formation, or self-incompatibility. Female parent plants containing CMS are particularly useful. In embodiments in which the female parent plants are CMS, pollen is harvested from male fertile plants and applied manually to the stigmas of CMS female parent plants, and the resulting F1 seed is harvested.

Varieties and lines described herein can be used to form single-cross F1 hybrids. In such embodiments, the plants of the parent varieties can be grown as substantially homogeneous adjoining populations to facilitate natural cross-pollination from the male parent plants to the female parent plants. The F1 seed formed on the female parent plants is selectively harvested by conventional means. One also can grow the two parent plant varieties in bulk and harvest a blend of F1 hybrid seed formed on the female parent and seed formed upon the male parent as the result of self-pollination. Alternatively, three-way crosses can be carried out wherein a single-cross F1 hybrid is used as a female parent and is crossed with a different male parent. As another alternative, double-cross hybrids can be created wherein the F1 progeny of two different single-crosses are themselves crossed.

A population of mutant, non-naturally occurring or transgenic plants can be screened or selected for those members of the population that have a desired trait or phenotype. The desired trait or phenotype can be a shortened time to flowering (for example, at least a 30% shortened time to flowering as compared to a wild-type plant) and optionally fewer leaves than the wild-type plant and optionally the same height as the wild-type plant.

For example, a population of progeny of a single transformation event can be screened for those plants having a desired level of expression or activity of the polypeptide(s) encoded thereby. Physical and biochemical methods can be used to identify expression or activity levels. These include Southern analysis or PCR amplification for detection of a polynucleotide; Northern blots, 51 RNase protection, primer-extension, or RT-PCR amplification for detecting RNA transcripts; enzymatic assays for detecting enzyme or ribozyme activity of polypeptides and polynucleotides; and protein gel electrophoresis, Western blots, immunoprecipitation, and enzyme-linked immunoassays to detect polypeptides. Other techniques such as in situ hybridization, enzyme staining, and immunostaining and enzyme assays also can be used to detect the presence or expression or activity of polypeptides or polynucleotides.

Mutant, non-naturally occurring or transgenic plant cells and plants are described herein comprising one or more recombinant polynucleotides, one or more polynucleotide constructs, one or more double-stranded RNAs, one or more conjugates or one or more vectors/expression vectors.

Without limitation, the plants described herein may be modified for other purposes either before or after the expression or activity has been modulated according to the present disclosure. One or more of the following genetic modifications can be present in the mutant, non-naturally occurring or transgenic plants. In one embodiment, one or more genes that are involved in the conversion of nitrogenous metabolic intermediates is modified resulting in plants (such as leaves) that when cured, produces lower levels of at least one tobacco-specific nitrosamine than control plants. Non-limiting examples of genes that can be modified include genes encoding an asparagine synthetase, such as CYP82E4, CYP82E5 and CYP82E10 which participate in the conversion of nicotine to nornicotine and are described in WO2006091194, WO2008070274, WO2009064771 and PCT/US2011/021088 and as described herein. In another embodiment, one or more genes that are involved in heavy metal uptake or heavy metal transport are modified resulting in plants or parts of plants (such as leaves) having a lower heavy metal content than control plants or parts thereof without the modification(s). Non-limiting examples include genes in the family of multidrug resistance associated proteins, the family of cation diffusion facilitators (CDF), the family of Zrt-, Irt-like proteins (ZIP), the family of cation exchangers (CAX), the family of copper transporters (COPT), the family of heavy-metal P-type ATPases (for example, HMAs, as described in WO2009074325), the family of homologs of natural resistance-associated macrophage proteins (NRAMP), and the family of ATP-binding cassette (ABC) transporters (for example, MRPs, as described in WO2012/028309, which participate in transport of heavy metals, such as cadmium. The term heavy metal as used herein includes transition metals. Examples of other modifications include herbicide tolerance, for example, glyphosate is an active ingredient of many broad spectrum herbicides. Glyphosate resistant transgenic plants have been developed by transferring the aroA gene (a glyphosate EPSP synthetase from *Salmonella typhimurium* and *E. coli*). Sulphonylurea resistant plants have been produced by transforming the mutant ALS (acetolactate synthetase) gene from *Arabidopsis*. OB protein of photosystem II from mutant *Amaranthus hybridus* has been transferred in to plants to produce atrazine resistant transgenic plants; and bromoxynil resistant transgenic plants have been produced by incorporating the bxn gene from the bacterium *Klebsiella pneumoniae*. Another exemplary modification results in plants that are resistant to insects. *Bacillus thuringiensis* (Bt) toxins can provide an effective way of delaying the emergence of Bt-resistant pests, as recently illustrated in broccoli where pyramided cry1Ac and cry1C Bt genes controlled diamondback moths resistant to either single protein and significantly delayed the evolution of resistant insects. Another exemplary modification results in plants that are resistant to diseases caused by pathogens (for example, viruses, bacteria, fungi). Plants expressing the Xa21 gene (resistance to bacterial blight) with plants expressing both a Bt fusion gene and a chitinase gene (resistance to yellow stem borer and tolerance to sheath) have been engineered. Another exemplary modification results in altered reproductive capability, such as male sterility. Another exemplary modification results in plants that are tolerant to abiotic stress (for example, drought, temperature, salinity), and tolerant transgenic plants have been produced by transferring acyl glycerol phosphate enzyme from *Arabidopsis*; genes coding mannitol dehydrogenase and sorbitol dehydrogenase which are involved in synthesis of mannitol and sorbitol improve drought resistance. Other exemplary modifications can result in plants with improved storage proteins and oils, plants with enhanced photosynthetic efficiency, plants with prolonged shelf life, plants with enhanced carbohydrate content, and plants resistant to fungi; plants encoding an enzyme involved in the biosynthesis of alkaloids. Transgenic plants in which the expression of S-adenosyl-L-methionine (SAM) and/or cystathionine gamma-synthase (CGS) has been modulated are also contemplated.

One or more such traits may be introgressed into the mutant, non-naturally occurring or transgenic plants from another cultivar or may be directly transformed into it. The introgression of the trait(s) into the mutant, non-naturally occurring or transgenic plants may be achieved by any method of plant breeding known in the art, for example, pedigree breeding, backcrossing, doubled-haploid breeding, and the like (see, Wernsman, E. A, and Rufty, R. C. 1987. Chapter Seventeen. Tobacco. Pages 669-698 In: *Cultivar Development. Crop Species*. W. H. Fehr (ed.), MacMillan Publishing Co, Inc., New York, N.Y. 761 pp.). Molecular biology-based techniques described above, in particular RFLP and microsatellite markers, can be used in such backcrosses to identify the progenies having the highest degree of genetic identity with the recurrent parent. This permits one to accelerate the production of varieties having at least 90%, preferably at least 95%, more preferably at least 99% genetic identity with the recurrent parent, yet more preferably genetically identical to the recurrent parent, and further comprising the trait(s) introgressed from the donor parent. Such determination of genetic identity can be based on molecular markers known in the art.

The last backcross generation can be selfed to give pure breeding progeny for the nucleic acid(s) being transferred. The resulting plants generally have essentially all of the morphological and physiological characteristics of the mutant, non-naturally occurring or transgenic plants, in addition to the transferred trait(s) (for example, one or more single gene traits). The exact backcrossing protocol will depend on the trait being altered to determine an appropriate testing protocol. Although backcrossing methods are simplified when the trait being transferred is a dominant allele, a recessive allele may also be transferred. In this instance, it may be necessary to introduce a test of the progeny to determine if the desired trait has been successfully transferred.

Various embodiments provide mutant plants, non-naturally occurring plants or transgenic plants, as well as biomass in which the expression level of a polynucleotide (or any combination thereof as described herein) is reduced to shorten time to flowering.

Various embodiments provide mutant plants, non-naturally occurring plants or transgenic plants, as well as biomass in which the activity of a polypeptide (or any combination thereof as described herein) is reduced to shorten time to flowering.

Parts of such plants, particularly tobacco plants, and more particularly the leaf lamina and midrib of tobacco plants, can be incorporated into or used in making various consumable products including but not limited to aerosol forming materials, aerosol forming devices, smoking articles, smokable articles, smokeless products, and tobacco products. Examples of aerosol forming materials include but are not limited to tobacco compositions, tobaccos, tobacco extract, cut tobacco, cut filler, cured or dried tobacco, expanded tobacco, homogenized tobacco, reconstituted tobacco, and pipe tobaccos. Smoking articles and smokable articles are types of aerosol forming devices. Examples of smoking articles or smokable articles include but are not limited to cigarettes, cigarillos, and cigars. Examples of smokeless products comprise chewing tobaccos, and snuffs. In certain aerosol forming devices, rather than combustion (or burning), a tobacco composition or another aerosol forming material is heated, for example, by one or more electrical heating elements or a carbon heat source to produce an aerosol. Typically in such heated smoking articles, an aerosol is generated by the transfer of heat from a heat source to a physically separate aerosol-forming substrate or material, which may be located within, around or downstream of the heat source. During smoking, volatile compounds are released from the aerosol-forming substrate by heat transfer from the heat source and entrained in air drawn through the smoking article. As the released compounds cool, they condense to form an aerosol that is inhaled by the user. Such devices include, for example, electrically heated aerosol-generating devices in which an aerosol is generated by the transfer of heat from of the aerosol-generating device to the aerosol-forming substrate of a heated smoking article. Suitably, during heating of the aerosol-forming substrate, combustion or burning of the tobacco does not occur. A suitable aerosol forming article is described in WO2013/098405 and comprises an aerosol-forming substrate for generating an inhalable aerosol when heated by an internal heating element of an aerosol-generating device. It can comprise an electrically heated aerosol-generating device comprising an internal heating element. It can further comprise, in a linear sequential arrangement, an aerosol-forming substrate, a support element located immediately downstream of the aerosol-forming substrate, an aerosol-cooling element located downstream of the support element, and an outer wrapper circumscribing the aerosol-forming substrate, the support element and the aerosol-cooling element. The support element can abut the aerosol-forming substrate. The aerosol-forming substrate is penetrable by the heating element of the aerosol-generating device.

As used herein, the term "combustion" refers to a redox chemical reaction where the reactant molecules, namely the fuel and the oxidant, mix and rearrange to become product molecules with the simultaneous release of heat. Combustion may be positively indicated by the presence of relevant amounts of nitrogen oxides in the gaseous products, not formed from the decomposition of nitrates present in the original reactant substrate, and the clear evidence of a simultaneous overall exothermic process. The evolution of relevant amounts of nitrogen oxides in the gaseous products for combustion may be determined by comparing the overall quantities of nitrogen oxides formed in the conditions of interest (for example, in air) and nitrogen oxides formed in the same conditions but in the absence of oxygen (for example, in a pure nitrogen or helium atmosphere). In another type of heated aerosol forming device, an aerosol is produced by the transfer of heat from a combustible fuel element or heat source to a physically separate aerosol forming material, which may be located within, around or downstream of the heat source. Smokeless tobacco products and various tobacco-containing aerosol forming materials may contain tobacco in any form, including as dried particles, shreds, granules, powders, or slurry, deposited on, mixed in, surrounded by, or otherwise combined with other ingredients in any format, such as flakes, films, tabs, foams, or beads. As used herein, the term 'smoke' is used to describe a type of aerosol that is produced by smoking articles, such as combustible cigarettes, or by combusting an aerosol forming material.

In certain embodiments, heating without combusting or burning the plant material is preferred.

In one embodiment, there is also provided cured plant material from the mutant, transgenic and non-naturally occurring tobacco plants described herein. Processes of curing green tobacco leaves are known by those having ordinary skill in the art and include without limitation air-curing, fire-curing, flue-curing and sun-curing. The process of curing green tobacco leaves depends on the type of tobacco harvested. For example, Burley and certain dark strains are usually air-cured, and pipe tobacco, chewing tobacco, and snuff are usually fire-cured.

In another embodiment, there is also provided dried plant material from the mutant, transgenic and non-naturally occurring plants described herein. Processes of drying leaves are known by those having ordinary skill in the art and include without limitation air-drying and sun-drying. The exact process of drying leaves depends on the type of plant that is harvested. Suitably, the plant material is dried after harvesting. Thus, the use of dried material and post-harvested dried material is contemplated herein.

In another embodiment, there is described tobacco products including tobacco-containing aerosol forming materials comprising plant material—such as leaves, preferably cured or dried leaves—from the mutant tobacco plants, transgenic tobacco plants or non-naturally occurring tobacco plants described herein. The tobacco products described herein can be a blended tobacco product which may further comprise unmodified tobacco.

The disclosure also provides methods for producing seeds comprising cultivating the mutant plant, non-naturally occurring plant, or transgenic plant described herein, and collecting seeds from the cultivated plants. Seeds from plants described herein can be conditioned and bagged in packaging material by means known in the art to form an article of manufacture. Packaging material such as paper and cloth are well known in the art. A package of seed can have a label, for example, a tag or label secured to the packaging material, a label printed on the package that describes the nature of the seeds therein.

Compositions, methods and kits for genotyping plants for identification, selection, or breeding can comprise a means of detecting the presence of a polynucleotide (or any combination thereof as described herein) in a sample of polynucleotide. Accordingly, a composition is described comprising one of more primers for specifically amplifying at least a portion of one or more of the polynucleotides and optionally one or more probes and optionally one or more reagents for conducting the amplification or detection.

Accordingly, gene specific oligonucleotide primers or probes comprising about 10 or more contiguous polynucleotides corresponding to the polynucleotide(s) described herein are disclosed. Said primers or probes may comprise or consist of about 15, 20, 25, 30, 40, 45 or 50 more contiguous polynucleotides that hybridise (for example, specifically hybridise) to the polynucleotide(s) described herein. In some embodiments, the primers or probes may comprise or consist of about 10 to 50 contiguous nucleotides, about 10 to 40 contiguous nucleotides, about 10 to 30 contiguous nucleotides or about 15 to 30 contiguous nucleotides that may be used in sequence-dependent methods of gene identification (for example, Southern hybridization) or isolation (for example, in situ hybridization of bacterial colonies or bacteriophage plaques) or gene detection (for example, as one or more amplification primers in nucleic acid amplification or detection). The one or more specific primers or probes can be designed and used to amplify or detect a part or all of the polynucleotide(s). By way of specific example, two primers may be used in a polymerase chain reaction protocol to amplify a nucleic acid fragment encoding a nucleic acid—such as DNA or RNA. The polymerase chain reaction may also be performed using one primer that is derived from a nucleic acid sequence and a second primer that hybridises to the sequence upstream or downstream of the nucleic acid sequence—such as a promoter sequence, the 3' end of the mRNA precursor or a sequence derived from a vector. Examples of thermal and isothermal techniques useful for in vitro amplification of polynucleotides are well known in the art. The sample may be or may be derived from a plant, a plant cell or plant material or a tobacco product made or derived from the plant, the plant cell or the plant material as described herein.

In a further aspect, there is also provided a method of detecting a polynucleotide(s) described herein (or any combination thereof as described herein) in a sample comprising the step of: (a) providing a sample comprising, or suspected of comprising, a polynucleotide; (b) contacting said sample with one of more primers or one or more probes for specifically detecting at least a portion of the polynucleotide(s); and (c) detecting the presence of an amplification product, wherein the presence of an amplification product is indicative of the presence of the polynucleotide(s) in the sample. In a further aspect, there is also provided the use of one of more primers or probes for specifically detecting at least a portion of the polynucleotide(s). Kits for detecting at least a portion of the polynucleotide(s) are also provided which comprise one of more primers or probes for specifically detecting at least a portion of the polynucleotide(s). The kit may comprise reagents for polynucleotide amplification—such as PCR—or reagents for probe hybridization-detection technology—such as Southern Blots, Northern Blots, in-situ hybridization, or microarray. The kit may comprise reagents for antibody binding-detection technology such as Western Blots, ELISAs, SELDI mass spectrometry or test strips. The kit may comprise reagents for DNA sequencing.

In some embodiments, a kit may comprise instructions for one or more of the methods described. The kits described may be useful for genetic identity determination, phylogenetic studies, genotyping, haplotyping, pedigree analysis or plant breeding particularly with co-dominant scoring.

The present disclosure also provides a method of genotyping a plant, a plant cell or plant material comprising a polynucleotide as described herein. Genotyping provides a means of distinguishing homologs of a chromosome pair and can be used to differentiate segregants in a plant population. Molecular marker methods can be used for phylogenetic studies, characterizing genetic relationships among crop varieties, identifying crosses or somatic hybrids, localizing chromosomal segments affecting monogenic traits, map based cloning, and the study of quantitative inheritance. The specific method of genotyping may employ any number of molecular marker analytic techniques including amplification fragment length polymorphisms (AFLPs). AFLPs are the product of allelic differences between amplification fragments caused by nucleotide sequence variability. Thus, the present disclosure further provides a means to follow segregation of one or more genes or nucleic acids as well as chromosomal sequences genetically linked to these genes or nucleic acids using such techniques as AFLP analysis.

In one embodiment, there is also provided cured or dried plant material from the mutant, transgenic and non-naturally occurring plants described herein. For example, processes of curing or drying tobacco leaves are known by those having skills in the field and include without limitation air-curing, fire-curing, flue-curing and sun-curing. The process of curing green tobacco leaves depends on the type of tobacco harvested as described herein.

In another embodiment, there is described tobacco products including tobacco products comprising plant material— such as leaves, suitably cured plant material—such as cured or dried leaves—from the mutant, transgenic and non-naturally occurring plants described herein or which are produced by the methods described herein. The tobacco products described herein may further comprise unmodified tobacco.

In another embodiment, there is described tobacco products comprising plant material, preferably leaves—such as cured or dried leaves, from the mutant, transgenic and non-naturally occurring plants described herein. For example, the plant material may be added to the inside or outside of the tobacco product and so upon burning a desirable aroma is released. The tobacco product according to this embodiment may even be an unmodified tobacco or a modified tobacco. The tobacco product according to this embodiment may even be derived from a mutant, transgenic or non-naturally occurring plant which has modifications in one or more genes other than the genes disclosed herein.

In a further aspect, there is provided a method of identifying a molecule that modulates activity or expression of a TFL1 polynucleotide or a TFL1 polypeptide. Exemplary molecules that can be used in such a method are described herein including antisense, siRNA, ribozyme molecules, DNAzyme molecules, TALENS, zinc finger nucleases and the like. The use of chemical compounds is also contemplated.

A mutant, non-naturally occurring or transgenic plant or part thereof having modulated (eg. reduced or increased) expression of the gene encoding Terminal Flower 1 (TFL1) or modulated (eg. reduced or increased) activity of the protein encoded by TFL1, said TFL1 is also described comprising, consisting or consisting essentially of: (i) a polynucleotide sequence comprising, consisting or consisting essentially of a sequence having at least 72% sequence identity to SEQ ID NO:7 or SEQ ID NO:8 or SEQ ID NO:10 or SEQ ID NO:11 or SEQ ID NO:19 or SEQ ID NO:20; or (ii) a polypeptide encoded by the polynucleotide set forth in (i); or (iii) a polypeptide having at least 72% sequence identity to SEQ ID NO:9 or SEQ ID NO:12 or SEQ ID NO:21; wherein the expression or activity of the polynucleotide or the polypeptide set forth in (i), (ii) or (iii) is modulated (eg. reduced or increased) as compared to a control plant in which the expression or activity of the polynucleotide or the polypeptide set forth in (i), (ii) or (iii) has not been modulated (eg. reduced or increased).

The modulated expression of the polynucleotide or the modulated activity of the polypeptide modulated the time to flowering as compared to the control plant, suitably, wherein the time to flowering time is modulated by at least 8% or at least 20%.

The increased expression of the polynucleotide or the increased activity of the polypeptide lengthens the time to flowering as compared to the control plant, suitably, wherein the time to flowering time is lengthened by at least 8% or at least 20%.

There is also disclosed a method of modulating (eg. increasing or decreasing) time to flowering in a plant comprising modifying the plant by modulating the expression of at least one TFL1 gene or the activity of at least one protein encoded thereby in said plant; suitably, wherein the method comprises (a) providing a plant or part thereof comprising: (i) a polynucleotide sequence comprising, consisting or consisting essentially of a sequence having at least 72% sequence identity to SEQ ID NO:7 or SEQ ID NO:8 or SEQ ID NO:10 or SEQ ID NO:11 or SEQ ID NO:19 or SEQ ID NO:20; or (ii) a polypeptide encoded by the polynucleotide set forth in (i); or (iii) a polypeptide having at least 72% sequence identity to SEQ ID NO:9 or SEQ ID NO:12 or SEQ ID NO:21; and (b) modulating (eg. increasing or decreasing) the expression of the TFL1 gene or the activity of the TFL1 protein in the plant; and (c) obtaining a plant with modulated time to flowering as compared to a control plant in which the expression of the TFL1 gene or the activity of the TFL1 protein has not been modulated.

Suitably, the expression of TFL1 or the activity of TFL1 is modulated by a method selected from the group consisting of: a) mutating the TFL1 gene in the plant; b) expressing an exogenous polynucleotide or polypeptide in the plant; and c) eliminating the TFL1 gene in the plant, or a combination of one or more thereof.

There is also disclosed a method of increasing time to flowering in a plant comprising modifying the plant by increasing the expression of at least one TFL1 gene or the activity of at least one protein encoded thereby in said plant; suitably, wherein the method comprises (a) providing a plant or part thereof comprising: (i) a polynucleotide sequence comprising, consisting or consisting essentially of a sequence having at least 72% sequence identity to SEQ ID NO:7 or SEQ ID NO:8 or SEQ ID NO:10 or SEQ ID NO:11 or SEQ ID NO:19 or SEQ ID NO:20; or (ii) a polypeptide encoded by the polynucleotide set forth in (i); or (iii) a polypeptide having at least 72% sequence identity to SEQ ID NO:9 or SEQ ID NO:12 or SEQ ID NO:21; and (b) increasing the expression of the TFL1 gene or the activity of the TFL1 protein in the plant; and (c) obtaining a plant with lengthened time to flowering as compared to a control plant in which the expression of the TFL1 gene or the activity of the TFL1 protein has not been modulated.

Suitably, the expression of TFL1 or the activity of TFL1 is increased by a method selected from the group consisting of: a) mutating the TFL1 gene in the plant; b) expressing an exogenous polynucleotide or polypeptide in the plant; and c) eliminating the TFL1 gene in the plant, or a combination of one or more thereof.

There is also described a method for producing plant material with modulated time to flowering as compared to a control plant, said method comprising: (a) providing the plant or the plant material described herein; (b) harvesting plant material from the plant; (c) optionally curing or drying the plant material for a period of time; and (d) obtaining plant material that has a modulated time to flowering as compared to the control plant.

There is also described a method for producing plant material with lengthened time to flowering as compared to a control plant, said method comprising: (a) providing the plant or the plant material described herein; (b) harvesting plant material from the plant; (c) optionally curing or drying the plant material for a period of time; and (d) obtaining plant material that has a lengthened time to flowering as compared to the control plant.

The invention is further described in the Examples below, which are provided to describe the invention in further detail. These examples, which set forth a preferred mode presently contemplated for carrying out the invention, are intended to illustrate and not to limit the invention.

EXAMPLES

Example 1—Identification of Tobacco TFL1 Genes

The TFL1 gene family is identified in tobacco and the identity of 7 tobacco TFL1 genes determined. They are named: TFL1-1S, TFL1-1T, TFL1-2S, TFL1-2T, TFL1-3T, TFL1-4T and TFL1-3S. The sequences of these genes are described herein.

Example 2—Analysis of TFL1 Expression Levels

To identify the active forms of TFL1 in vegetative leaf and root tissues, *N. tabacum* plants of three different varieties (Burley-TN90, Virginia-K326 and Oriental-BX_Basma Xanthi) are grown on bactoagar-MS magenta boxes and expression data (FPKM) calculated after isolation of RNA and the sequencing of the corresponding cDNA libraries (*Nat Commun*. (2014) 5: 3833). The data is shown in Table 1. TFL1 is mainly expressed in root tissues. The main TFL1 genes expressed in the roots under these conditions (vegetative state) are TFL1-2S, TFL1-2T, TFL1-3T and TFL1-4T. It can be seen that TFL1-4S transcripts are not identified in Virginia (K326), Burley (TN90) or Dark tobacco, whereas only very little RNA copies are found in the root of the oriental Basma Xanthi (BX). The reason why no transcripts are detected in K326 and TN90 is unclear but may derive from promoter disruption, since the 5' end of the 2 kB promoter in K326 and TN90 could not be identified.

To determine if the gene expression profiles are different in flowering plants, *N. tabacum* (cultivar TN90) is grown in the field and RNA isolated in immature flowers, lower stalk leaves, mid stalk leaves, upper stalk leaves, petals, roots, sepals and stem, just after the onset of the first flowers. The results are shown in FIG. 1. In these plants, TFL1-2T and TFL1-4T remained slightly expressed in the root, stem and immature flowers (FPKM values not exceeding 1.1).

Example 3—Genetic Manipulation of TFL1: TFL1-RNAi Tobacco Plants

Four specific DNA fragments are designed to silence the six expressed TFL1 copies (see SEQ ID NOs: 24, 27, 30 and 33) and cloned between the strong constitutive MMV (Mirabilis Mosaic Virus) promoter and the 3' nos terminator sequence of the nopaline synthase gene of *Agrobacterium tumefaciens* (*Plant Mol Biol*. (1999) 40: 771-82): (1) C100S3-MMVp-GW-pDONR221—TFL1-1 S/T; (2) C100S3-MMVp-GW-pDONR221—TFL1-2 S/T; (3) C100S3-MMVp-GW-pDONR221—TFL1-3 T; (4) C100S3-MMVp-GW-pDONR221—TFL1-4 T.

Figure 2:
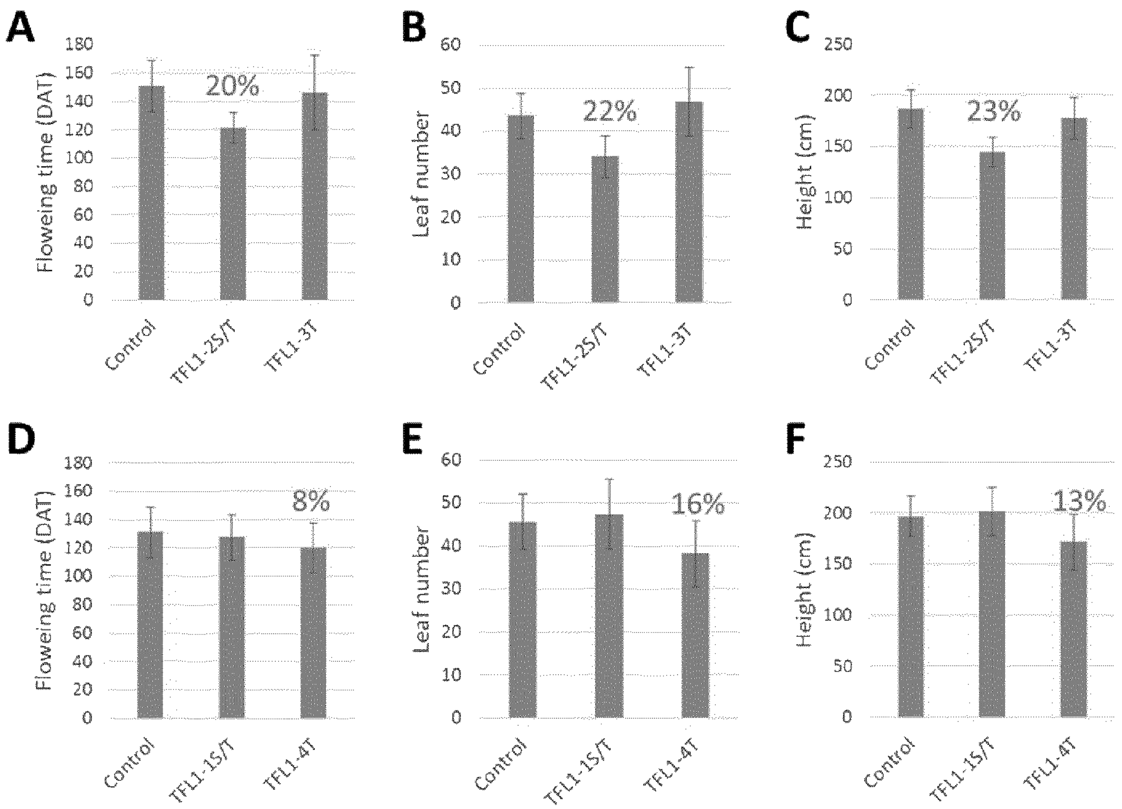
FIG. 2. Phenotypic analyses of TFL1-1S/T, TFL1-2S/T, TFL1-3T and TFL1-4T RNAi TO (20) and control (10) plants grown in the greenhouse under controlled conditions. Flowering time (days after transplantation, DAT) of the four transgenic lines is shown in A and D, Leaf numbers are shown in B and E, and height of the four lines are shown in C and F. Average values and standard deviations from each plant are shown.
Figure 3:
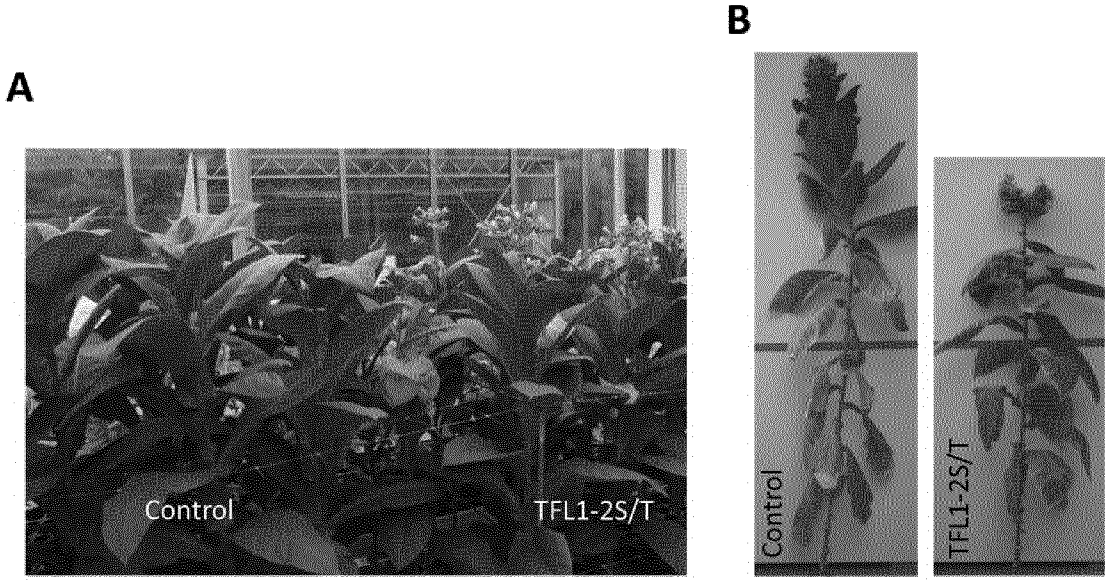
FIG. 3. Pictures of TFL1-2S/T RNAi plants in the greenhouse. Fast flowering of TFL1-2S/T RNAi lines compared to the control plants (Coltabaco 23RM), 117 days after pot transplantation (A), and after seed ball production, single plant comparison (B).

The dark tobacco variety is transformed with each of the four constructs using standard *Agrobacterium*-mediated transformation protocols (*Cold Spring Harb Symp Quant Biol*. (1985) 50: 433-437). From each construct, 20 independent TO plants are selected on kanamycin and then transferred into soil to a greenhouse compartment set up with 9 h of light (24° C.+/−3° C.) and 15 h of darkness (18° C.+/−3° C.) for the three first months then 15 h light and 9 h darkness. Control plants followed the same in vitro procedure (without the transformation step) and are also transferred simultaneously to the greenhouse. Plantlets are first cultivated in trays and transplanted to 5 It pots after 25 days. Plants are watered every day with a fertilization solution (Yara, Netherlands). Each plant from the four constructs and their respective controls are analysed phenotypically and data recorded as flower emergence after transplantation (DAT), height and leaf numbers (see FIG. 2 and Table 2). The data from TFL1-1S/T and TFL1-4T RNAi plants and their respective controls (FIG. 2A,B,C) have to be compared separately from the group of TFL1-2S/T and TFL1-3T (FIG. 2D,E,F), since the first set of plants were transplanted and cultivated in the greenhouse 3 weeks after the second set of plants. All plants were grown under the similar greenhouse conditions. The data showed that the TFL1-2S/T RNAi transgenic lines flowered significantly faster than control plants showing a 20% time reduction of flowering. In addition, the TFL1-2S/T RNAi line also exhibited significant height and leaf number reduction which is consistent with a shortened time to flowering (FIG. 2A, B, C). The data are statistically relevant for all measured parameters (P<0.001) and phenotypes were clearly visible in the greenhouse (FIG. 3). In addition, another TFL1 gene product, TFL1-4T, seems to play a role in regulating the flowering time. Indeed, 8% reduction of flowering time was observed, but not significantly compared to the control, the two other measured parameters, height (16% reduction compared to the control) and leaf numbers (13% reduction compared to the control), being statistically relevant.

The data collected from the RNAi plants in association with the expression data suggest that TFL1-1S and TFL1-1T are minor contributors in the regulation of flowering time and maintenance of the vegetative state of the plants.

In conclusion, the data indicate that the most effective TFL1 genes for the maintenance of the vegetative state in tobacco in the described growth conditions are: TFL1-2S, TFL1-2T >TFL1-4T >TFL1-3T >TFL1-1S, TFL1-1T. Therefore, silencing or knocking-out TFL1-2S and/or TFL1-2T and/or TFL1-4-T is likely a solution to shortening time to flowering.

Example 4—TFL1 Mutations to Shorten Time to Flowering

For tobacco breeding, an EMS population of a tobacco cultivar is screened for mutations in TFL1. All amino acid substitutions identified in TFL1-2S, TFL1-2T and TFL-4T are analysed for possible impact on protein function using the SIFT program (*Nucleic Acids Res*. (2003) 1; 31(13): 3812-4). A small SIFT score (<0.05) implies that an amino acid residue is likely not tolerated at the functional level. In TFL1-2S, TFL1-2T and TFL-4T seven mutations are identified with a SIFT score ratio below 0.05, as shown below:

| | |
|---|---|
| TFL1-2S_G129E | 0.0002 |
| TFL1-2S_G129R | 0.0002 |
| TFL1-2S_T143I | 0.0011 |
| TFL1-2T_R120C | 0 |
| TFL1-2T_P131S | 0.0007 |
| TFL1-2T_G129E | 0.0002 |
| TFL1-4T_P110L | 0 |

The SIFT score is used as a tool to facilitate the selection of mutations. In a greenhouse experiment, the mutations and combinations of mutations are tested and the speed of flowering is measured.

In TFL1-2S, TFL1-2T and TFL1-4T, the His88 motif is conserved at the position 84, 88 and 86, respectively. A mutation (for example, a missense mutation) at this amino acid position could disrupt the three dimensional structure of the transcription factor, thereby affecting binding properties on the promoter. Suitably, the mutation can be a stop mutation.

The Asp144 motif is conserved in TFL1-2S and TFL1-2T at position 138 and 142, respectively. It is replaced by a glutamate in TFL1-4T at position 139. Three mutations close to TFL1-2S (D138), TFL1-2T (D142), respectively, are identified close to this region and may affect the three dimensional structure of the transcription factor and thereby alter promotor binding.

Example 5—TFL1-2T-P131S Mutation

Figure 4:
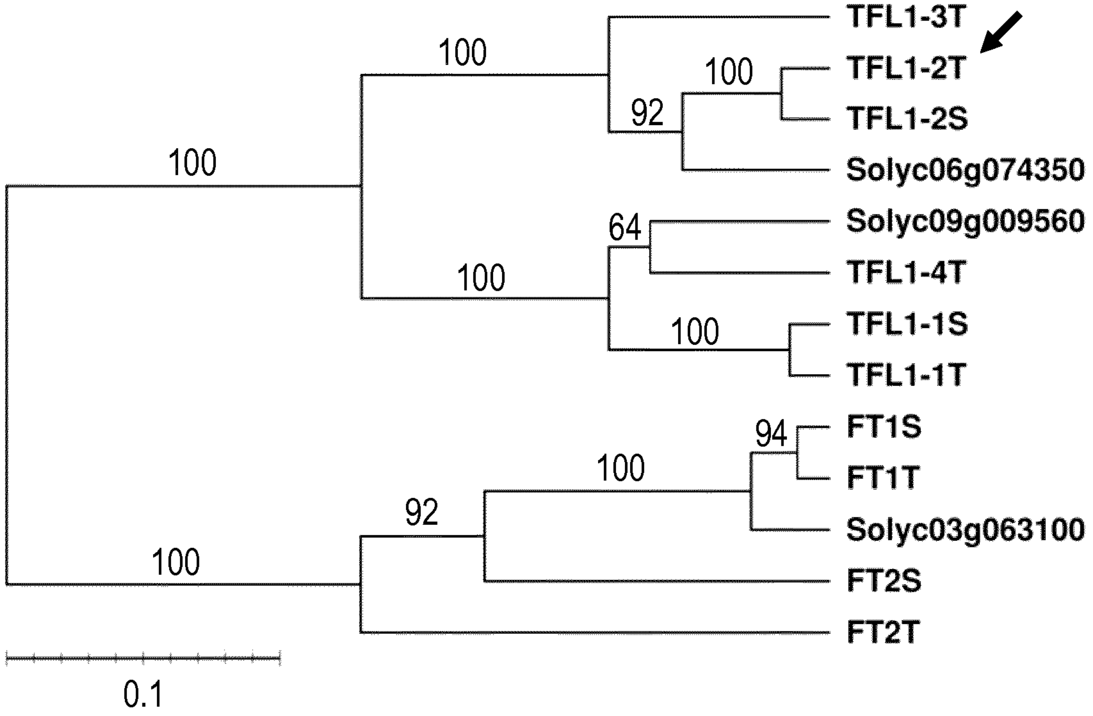
FIG. 4. Diagram illustrating the TFL1-2T-P131S mutation. Mutating codon CCT >Pro to TCT >Ser.
Figure 5:
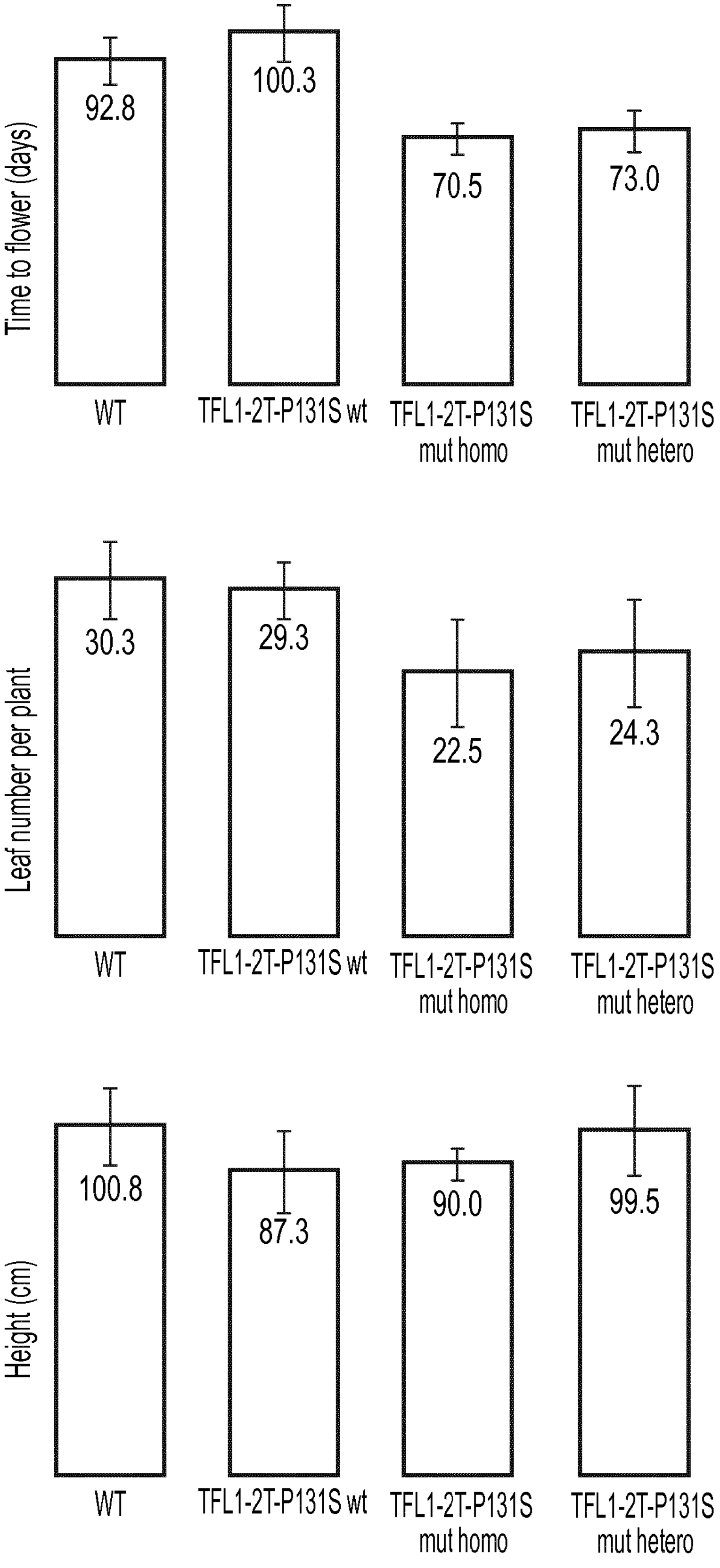
FIG. 5. A bar graph illustrating that TFL1-2T-P131S mutant plants are flowering approximately 30% faster in both homozygous plants (mutant in both alleles) and heterozygous plants (mutant in one allele). Mutant plants have less leaves but no impact on plant height is observed compared to wildtype tobacco plant. WT=*Nicotiana tabacum*; TFL1-2T-P131S wt=an out segregant of mutated plant with no mutation and considered an additional control plant in same phenotypic background as mutant plants; TFL1-2T-P131S mut homo=homozygous mutant plant; TFL1-2T-P131S mut hetero=heterozygous mutant plant. N=4.

A tobacco plant containing the TFL1-2T-P131S mutation (as shown in FIG. 4) is grown under greenhouse conditions. The flowering time, leaf number and height of the mutant plants are monitored against a wild-type plant. Tobacco plants containing this mutation flower 30% faster and have less leaves (6-7) when the TFL1-2T copy harbors the mutation P131S in both homozygotes and heterozygotes. No impact on plant height is seen. The mutant tobacco plant has a shortened time to flowering as compared to the wild-type plant.

Example 6—TFL1-4T-P110L Mutation

Figure 6:
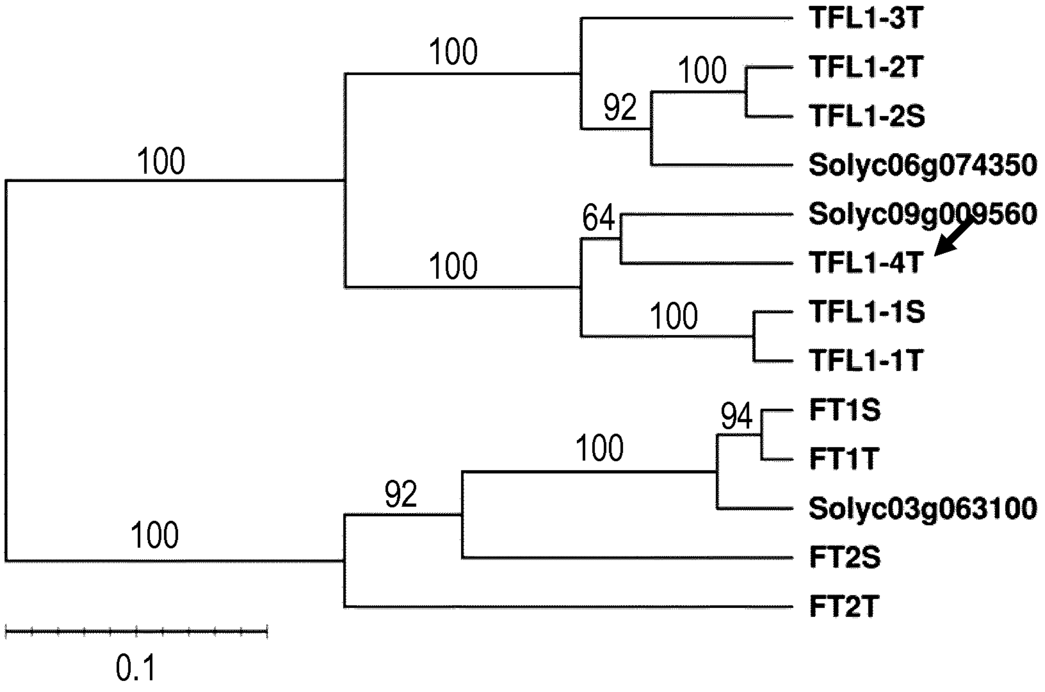
FIG. 6. Diagram illustrating the TFL1-4T-P110L mutation. Mutating codon CCA >Pro to CTA >Leu.
Figure 7:
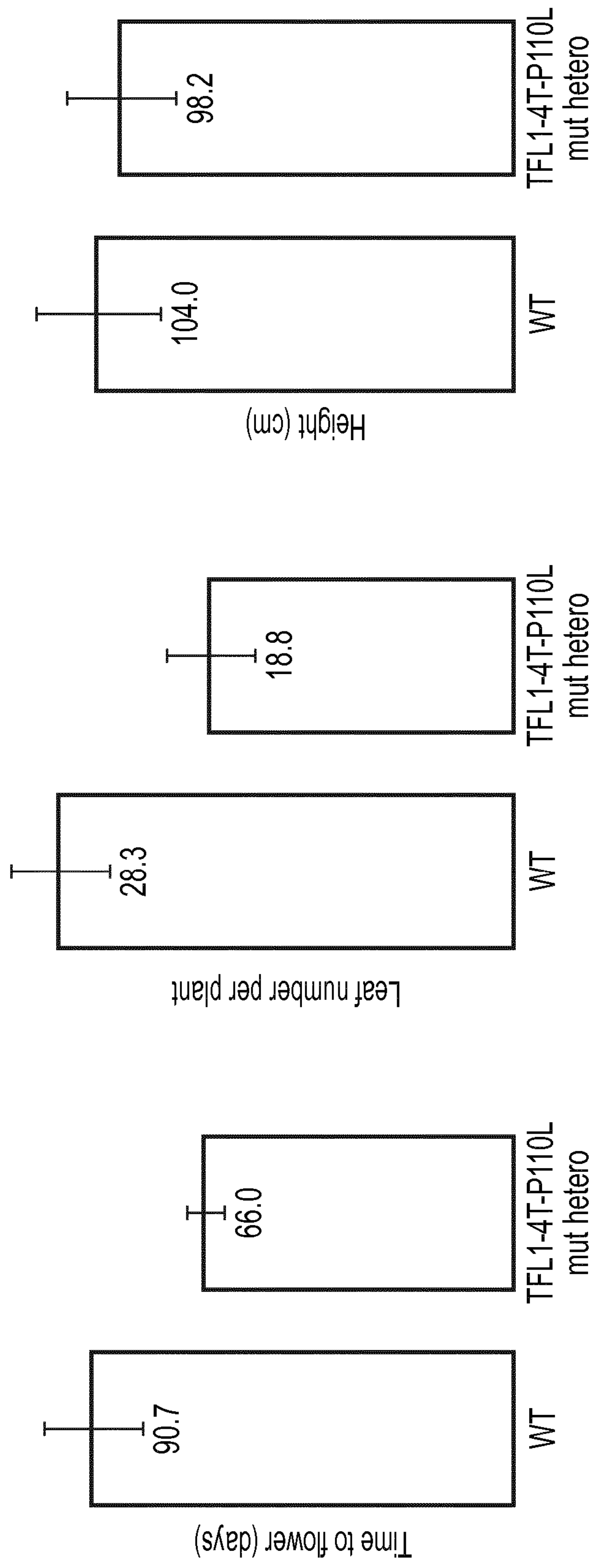
FIG. 7. A bar graph illustrating that TFL1-4T-P110L mutant plants are flowering approximately 30% faster in heterozygous plants (mutant in one allele). Mutant plants have less leaves but no impact on plant height is observed compared to wildtype tobacco plant. WT=*Nicotiana tabacum*; TFL1-4T-P110L mut hetero=heterozygous mutant plant. N=3.

A tobacco plant containing the TFL1-4T-P110L mutation (as shown in FIG. 6) is grown under greenhouse conditions. The flowering time, leaf number and height of the mutant plants are monitored against a wild-type plant. No homozygous plants are available for this mutant, but as observed for TFL1-2T-P131S, tobacco plants flower about 30% faster (for example, about 28% faster) and have less leaves (8-9) when TFL1-4T harbors the heterozygous mutation P110L. No impact on height is seen. The mutant tobacco plant has a shortened time to flowering as compared to the wild-type plant. The data suggest that only one allele is sufficient to drive faster flowering for both mutations TFL1-2T-P131S and TFL1-4T-P110L.

Any publication cited or described herein provides relevant information disclosed prior to the filing date of the present application. Statements herein are not to be construed as an admission that the inventors are not entitled to antedate such disclosures. All publications mentioned in the above specification are herein incorporated by reference. Various modifications and variations of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in cellular, molecular and plant biology or related fields are intended to be within the scope of the following claims.

TABLE 1

TFL1 expression data (FPKM) in vegetative (non-flowering) plants grown under bactoagar-MS conditions. No transcripts were detected in TN90 and K326 (no).

| | LEAF | | | ROOT | | |
|---|---|---|---|---|---|---|
| | TN90 | K326 | BX | TN90 | K326 | BX |
| TFL1-1_S | 0.00 | 0.00 | 0.00 | 0.00 | 0.29 | 0.00 |
| TFL1-1_T | 0.00 | 0.00 | 0.00 | 0.53 | 0.82 | 1.92 |
| TFL1-4_S | no | no | 0.01 | no | no | 0.32 |
| TFL1-4_T | 0.39 | 0.00 | 0.01 | 2.07 | 6.90 | 7.87 |
| TFL1-2_S | 0.05 | 0.01 | 0.03 | 7.23 | 14.97 | 23.78 |
| TFL1-2_T | 0.18 | 0.07 | 0.11 | 9.71 | 22.33 | 27.26 |
| TFL1-3_T | 0.01 | 0.00 | 0.01 | 6.24 | 15.32 | 25.89 |

TABLE 2

Statistical analyses of the data presented in FIG. 2 performed using the Welch Modified Two-Sample t-Test (Biometrika (1947) 34 (1-2): 28-35; BioMed Central Medical Research Methodology (2012) 12: 78)

| | Outcome | LL (95%) | UL (95%) | t-stat | p-value |
|---|---|---|---|---|---|
| | | A | | | |
| TFL1-2S/T vs CTR | DAT | −43.011 | 46.189 | −4.797 | 0.000 |
| TFL1-3T vs CTR | | −12.016 | 23.121 | 0.652 | 0.521 |
| TFL1-2S/T vs CTR | # of | −13.661 | −5.239 | −4.742 | 0.000 |
| TFL1-3T vs CTR | leaves | −1.796 | 8.296 | 1.325 | 0.197 |
| TFL1-2S/T vs CTR | Height | −56.350 | −27.850 | −6.303 | 0.000 |
| TFL1-3T vs CTR | | −24.103 | 6.703 | −1.179 | 0.252 |
| | | B | | | |
| TFL1-4T vs CTR | DAT | −30.022 | 8.232 | −1.307 | 0.227 |
| TFL1-1S/T vs CTR | | −5.086 | 32.975 | 1.696 | 0.129 |
| TFL1-4T vs CTR | # of | −13.197 | −1.614 | −2.682 | 0.115 |
| TFL1-1S/T vs CTR | leaves | −4.088 | 7.677 | 0.638 | 0.531 |
| TFL1-4T vs CTR | Height | −44.301 | −6.740 | −2.824 | 0.010 |
| TFL1-1S/T vs CTR | | −13.007 | 22.129 | 0.545 | 0.592 |

SEQUENCES

SEQ ID NO: 1 Genomic sequence of the *N. tabacum* TFL1-1S gene, including 2 kB before ATG (in bold)

```
tgtttattgtacattttgaactgcatcgagctgcacgattgacagatctagtctgcaacagagtactttggtttctaattatagta

atcctaacacctcagaaatttccaaaattggaattatgggtgcaaatcatctttatatatactctcaaatgacttctcagatctta

cggtcactaattgtctgtaaattaagtatggtggagttcactttatatactctgagcggtgtgcccatcctcctccatcagaatat

cacttaaaacaattaacgtactttataatctttccctattgtttacacacaatttaggaaagtttctaacaaagataagcccatat

ttcaagattagtgtcttaggattaccctaaatgaaaaaagcaatagattccctggcaatatgtttacttatattttgaatttttgc

aaaaaaaataaataaatgtgtgtcaacttgcttagttgggaccacatgcaaaaactaattcaaggatttcatctgataattttata

gtggagaggaaaaggcttggattaatttaagtacttattatgtagggcaaatatcacttttagcctgcggccaccatatttatatt

caagccgtaaaagtgtataaaatttgtatttttttatatataatatacggaaatgtgtgtatatatatatatatatatatatatat

atatatataagaaatataaaaaaaattggctattatttttcagagcagctatacaatatcattttccatatcaggtaagctgaaca

acaaatcatggaccaattcgaagagcaccagtcaggtgtgaaagagaactgacatgatagcataaaatacatatcactaactcctc

cacatctaagagcatacatttaatttcctatatggaagataagattaattagaaaagtgtttgataaagctaagatatgttagtac

cagtttgtagtatccagttgaaattttagtgtcaacttaaggataattttactatgattagaagacagttatacattcacaaagtt
```

-continued tctgaaaggaacttataagtcttctttttattgtacttacatttgtcaagtcatatatagtacatatgacccctcctaaaggaaaa gaaagtagggaaagtaccaagctagggcatatttaaaggaaaataaaatggcaattttaagatgttagagtaagggcaggggtagg ccaaagaagtattggggagaagtgattagacaagacatgccactgcttcacctaaccgcggacataactagcgataggaagatgtg gaggtcgagaattaaggttgtgagttgacaggtagttatgagtttactagtaatactagtactattcttgtattcttttattctta gtttttattactttgttatgtcactcgcttccattactagttatctgttgttattgcttgttgctttattttaccattttttta gccgagggtctatcaaaaacagtctctctgcctttataggataggggtaaggctgcgtacacactaccctttccagaccccacgta tgggattaatccgagtttgttgttgttgttgttgttgatgttgttgttgttgaaaaggaaacgtttataattaagtacatgtatta agatttcattattttcggggaagaatttcgaatgtatttaaaccataaaacgtcattctcctgcaagtatttttggtgatcaagat aagtatagttaaaaattgagcaatcttctttgcctacgatgtcctgtataaaactaacaaagaaaaaattcagtttatttttcagg ggtagggttactttttttttaaaaaatattctatttgaagttccataaaatcccatttttttatttgcaactatattgagtagatgt tccgagacagcaactataagtgaggctctatttcactgttcaaccaaaatctctcacaagctaagttccttgcaatccaaaagatc tctctctctctctctctctctaatggcaaggaatgtagagcctctagtagtagggagagtagtaggggatgttcttgattcattta gtcccacagttaaaatgacagtcacttacaacaataaacaagtttgcaatggccaagagctcttcccttctgcagtcactattaga cctagggttgaagttcaaggtggtgatatgagaactttcttcacattggtaacttttctaattttccttcaggttattaacttttc attgctatatagacatctttcaaacctgtctagaagattcttttcttgagctgagggttcggagacagcctctctatcccacacaa gataaggttaacgtctgcatataccttgccgtcccctgacaccacatatgggattatactgcgtatgttgttgttgttgtattgct atatagacatctttgataaatcactaatcatgcatgatattattcttcttattgtaggtcatcacagatcctgatgtacctggccc tagtgatccgtatctgagagaacatgttcactggtatgtactacattcaagaaaatctatggaaaaaaaataactagaagagatga gtccaaaagaaaggagattaattattgtttgatttgtatttttttatttgcattagattaagtcatgcaattacctagtaataaatt cgttataaggacatacacaaaaggtatgctcaacataattaaagaaagaaaagcataagcattatattcttatatgcaagctccca atctgattgtggcgaagctaagaatttcttcgggtgtttaaatttaaaagaagtgaaaaaaaatccgataaaaaatttatgtgtta tatacctctaaaacttaatattgtacctatatacatattgtaatttttcgacgaatgaccactcttattgcccatgctgccaatgc caatatgtaaaatacttcgccaatagacaaatatgtatcacattaattagttacctaaataggtaattatccataataagtgggac tcgtaacttgaaaaatatggttagtaatttgctacaacatgttaagatacagtgagaatgtaaatgtatatatgtcctttcacgcc gtcgtaagtttatataagttaaatctggttaacaatgtaggtcatcataacactcacaattgggaataataactcttaatcatact tctttacattcatatttgcaggatagtgactgatattccaggaactacagatgccacctttggtaaattggctattttggtttctt ttattaagctggtgtttgacatgctagaattaatgtactttaattttgagcaggaaaagagttggttagctatgagatcccaaggc ctaatattggaatacataggtttgtgtttgttctctttaagcagaaatgcagacaatcagtcagcccacctacttcaagggatcat ttcaacactcgcaactttgccaacgtaaatgaccttggtccgcctgtcgccgccgtcttcttcaatgcacaacgagagaccgccgc caggaggcgctaa SEQ ID NO: 2 Genomic sequence of the *N. tabacum* TFL1-1S gene
atggcaaggaatgtagagcctctagtagtagggagagtagtaggggatgttcttgattcatttagtcccacagttaaaatgacagt cacttacaacaataaacaagtttgcaatggccaagagctcttcccttctgcagtcactattagacctagggttgaagttcaaggtg gtgatatgagaactttcttcacattggtaacttttctaattttccttcaggttattaacttttcattgctatatagacatctttca aacctgtctagaagattcttttcttgagctgagggttcggagacagcctctctatcccacacaagataaggttaacgtctgcatat accttgccgtcccctgacaccacatatgggattatactgcgtatgttgttgttgttgtattgctatatagacatctttgataaatc actaatcatgcatgatattattcttcttattgtaggtcatcacagatcctgatgtacctggccctagtgatccgtatctgagagaa catgttcactggtatgtactacattcaagaaaatctatggaaaaaaaataactagaagagatgagtccaaaagaaaggagattaat tattgtttgatttgtatttttttatttgcattagattaagtcatgcaattacctagtaataaattcgttataaggacatacacaaaa ggtatgctcaacataattaaagaaagaaaagcataagcattatattcttatatgcaagctcccaatctgattgtggcgaagctaag aatttcttcgggtgtttaaatttaaaagaagtgaaaaaaaatccgataaaaaatttatgtgttatatacctctaaaacttaatatt -continued gtacctatatacatattgtaatttttcgacgaatgaccactcttattgcccatgctgccaatgccaatatgtaaaatacttcgcca atagacaaatatgtatcacattaattagttacctaaataggtaattatccataataagtgggactcgtaacttgaaaaatatggtt agtaatttgctacaacatgttaagatacagtgagaatgtaaatgtatatatgtcctttcacgccgtcgtaagtttatataagttaa atctggttaacaatgtaggtcatcataacactcacaattgggaataataactcttaatcatacttctttacattcatatttgcagg atagtgactgatattccaggaactacagatgccacctttggtaaattggctattttggtttcttttattaagctggtgtttgacat gctagaattaatgtactttaattttgagcaggaaaagagttggttagctatgagatcccaaggcctaatattggaatacataggtt tgtgtttgttctctttaagcagaaatgcagacaatcagtcagcccacctacttcaagggatcatttcaacactcgcaactttgcca acgtaaatgaccttggtccgcctgtcgccgccgtcttcttcaatgcacaacgagagaccgccgccaggaggcgctaa SEQ ID NO: 3 Amino acid sequence of the *N. tabacum* TFL1-1S gene derived from SEQ ID NO: 1 or SEQ ID NO: 2.

MARNVEPLVVGRVVGDVLDSFSPTVKMTVTYNNKQVCNGQELFPSAVTIRPRVEVQGGDMRTFFTLVITDPDVPGPSDPYLREHVH

WIVTDIPGTTDATFGKELVSYEIPRPNIGIHRFVFVLFKQKCRQSVSPPTSRDHFNTRNFANVNDLGPPVAAVFFNAQRETAARRR

SEQ ID NO: 4 Genomic sequence of the *N. tabacum* TFL1-1T gene, including 2 kB before ATG (in bold)

ttcgagtcgtgataagtgttttgcaaaaatataagataagactgcatgcgtacaatagactcttttggtccggcccttttctggac cctgcgcataacggaagcttagtgcacccggcaaccgtttttcaacgttccagatgcaagaatattataaggaggctttttgacac ttttaaatttaatctaatagagtttaagtttcatgcatcgactgtcaaaaaaatatttatataatcactaatacgataattacaag tgaaatgctatactaaacattaagtagtaacctaataaaacggtagctagctaatctactatatatcacgtagtattaaaattaca cttatgtaaaaatctttacggtgttaagaataacttaaaagcaatttagtaatacattaatgagtgaaaaaggtgaagaggaaacg tggtgtgttttgaactgcatcgagctgcacgattgacagagctagtctggaacagagtactttggtttctaattatagtaatccta acatctcagaaatttccataataggaattatgggtgcaaatcatctttatatatactctcaaattaatgacttctcagcaagtact gtcattgtctgtaaattaagtatggtggagttcactttatactctgagcagtgtgcccatcctcctccatcacttaaaacaattaa tgtactttataatctttccctattgtttacacacacaatttaggaaagtttttaacaaagacaagcccatgtttcaagatttgttt cttaggattaccctaaatgaaaaaagcaatagattccctggcaatttacttatattttgaattttttgcaaaaacaaaaagaaaaag tgacaacttgcttagttgggaccacatgcaaaaactaatttaaggaattcatctgatatttttatagtggagaggaaaagggctgg attaatttaaatattccttatttgccaaaattatttatattcgatagctgtaaaaatatataaaatttgtatatttgtttttgtat agtatacacggaaatgtatatatatacaagaaattaaaaaaaaactattattttcagagcagttatacaatattattttccctatc atgtaagcttagcttatcaacaaatcatggaccaattctaagagctccattcaggtgtgaaagagagctgacatgatagtataaaa tacacatcactaactcctccacatttgagagctatagattaatttcctatatggaagataagattaattagaaaagtgtttgaata agctaagatgtgttagtaccagtttgtaatatcaagctaaaattttagtgtcaatttaaggataattttactatgattagaagaca agttatcattcacaaatttctgaaaggaacttataagacttttatttttatttttttattgtacttacatttgtcaattaagtaca tgtgacccctcctaaaggaaaagaaagtagggaaattaaagtaccaagttagcgcatacttaaagccaaggtaagcaaaatggcaa ttttaaggtgttgtagaggaaacgtttataattaagtacacgtactaagatttcattattttcgtggaagaaatttagaatgtatt taaaccataaaacgtcattctcgtgcaagtatttttggtgatcaagataagtatagttaacgttgaacaatcttctttgcttacta tgtcttgtataaaactaacaaagaaaaattcagtttatttttcaggggtagggttactttttttaaaaaaaaatattctatttgaag ttccataagatcccattttttaatttgtaactatattgagtagatattccaagacagcaactataaatgaggatctatttcaccgtt caatcaaaatctctcacaagctaagttcctagcaatccaaaaaagatctctctctctctctctctctctctctctctctctctc tctctctctctctctctctctaatggcaaggaatgtagagcctctagttgtagggagagtagtaggggatgttcttgattcattca gtcccaaagttaaaatgacagtcacttacaacaataaacaagtttgcaatggccaagagctcttcccttctgcggtcaccattaga cctagggttgaggttcaaggtggtgatatgagaactttcttcacattggtaacttttctaaattctccttaaggttattaactttt catttctatatagacacatcgagggtcaacagagacaactctatctcacacaaggtaggggtaaggtattcgtataccctacccgg cccacatgtgagatcacactgaatatgttgttgttgtcgcatttaggggtgtacaaatgaaactgacaaactgcaccaatctgata -continued atccgagtcaaatcgagaaaaaatccgattatggtttggtttgatttggtttggtgatggaaaaaaccccgacatatttggttttg tttggttttaactaaaaaaagtcaaaccgaaaccaaaccaaccagacattatatgtgtagaaattttaaatatatttaatacataa aaatatttatggtagtgtaatttataaatatttcttaagatttttcatagtttatcttttaacgtattatttcaaacttgggctta taatttttggatgctccaataagttttatagtccataaatgttagtaactcaaataaatcctaaaccaaaatcaaatcaatactaa tgctaataaaagacattcaattcaattgtactatgaatgaaaatagtgttggatatatatttttatagtttttccacggtttagat aaaatgtataacttatttttctttgagtatggttagtcatgtaaataatcttattaatcataattttaaattatgtttatttttat tatggcttattaataatatttaatttttttgtgcaattttattatctttattgttgaatattttagtacaatgccacgactcatctc atatttatgttattttattgaaaaacacctcatatagttctgcctcattaggattaaaaaaatatttggagcacaaattttacttt ttgtgttatgaagactttatgaaaaaaaaataaaataaaaacccgaaaacccgaaacctcgagaaaaatcgagattaaaaatccga cttttattggtttggtttggtatttagatttaataacccgatacaattagtttggtttggtaattagaaaatccgaatcaaacccc taaccgtgtacacccctagtcgtattggtatatagacatctttgataaatcattaatcatgcatgatattcttcgatctccttatt gtaggtcatgacagaccctgatgttcctggccctagtgatccgtatctgagagaacatcttcactggtatgcactatattcaagaa aagctatggaaaaaaataactagatgagataggtaaaaaagaaaggagtttaatgattgtttgatttgcattaattatattaagtc atgccattatctagtaataaactggttataaggacatacacaaaaggtatggtcaacatataatcaaagaaagaaaagcataagca tccttatgcaagctgccaatgtcatgtaaaatacttcgctaatagacaaatatatattacattagttacctaaaagataggtatat aatcagtgggactcctaacttaaaaaataaggttagtaatctgctataacgatacactgagaatcgtcgtcgtcagtttataagtt aaaaattaatgtaggtcatcacaacactcacaaagagtgcctcaattgggaagagtatgttatatagttagaatttatgttacata tggaaccacagtactacagaaggataactcttaaacatacttctttaccatcatatttgcaggatagtgactgatattccaggaac aacagatgccacctttggtaagctcactattttggcattttcatttttccttcaatttcttttagtatatagctaggttggttttt gacatgctaattttgagcaggaaaagagttggttagctatgagatcccacggcctaatattggaatacataggtttgtgtttgttc tgtttaagcagaaatgcagacagtcagttagtccacatgatgtttccagagatcacttcaacactcgcaactttgccaacgtaaac gatcttggcccgcctgtcgccgccgtcttcttcaatgcacaacgagagaccgccgccaggagacgctaa SEQ ID NO: 5 Genomic sequence of the *N. tabacum* TFL1-1T gene atggcaaggaatgtagagcctctagttgtagggagagtagtaggggatgttcttgattcattcagtcccaaagttaaaatgacagt cacttacaacaataaacaagtttgcaatggccaagagctcttcccttctgcggtcaccattagacctagggttgaggttcaaggtg gtgatatgagaactttcttcacattggtaacttttctaaattctccttaaggttattaacttttcatttctatatagacacatcga gggtcaacagagacaactctatctcacacaaggtaggggtaaggtattcgtataccctacccggcccacatgtgagatcacactga atatgttgttgttgtcgcatttaggggtgtacaaatgaaactgacaaactgcaccaatctgataatccgagtcaaatcgagaaaaa atccgattatggtttggtttgatttggtttggtgatggaaaaaaccccgacatatttggttttgtttggttttaactaaaaaaagt caaaccgaaaccaaaccaaccagacattatatgtgtagaaattttaaatatatttaatacataaaaatatttatggtagtgtaatt tataaatatttcttaagatttttcatagtttatcttttaacgtattatttcaaacttgggcttataatttttggatgctccaataa gttttatagtccataaatgttagtaactcaaataaatcctaaaccaaaatcaaatcaatactaatgctaataaaagacattcaatt caattgtactatgaatgaaaatagtgttggatatatatttttatagtttttccacggtttagataaaatgtataacttatttttct ttgagtatggttagtcatgtaaataatcttattaatcataattttaaattatgtttatttttattatggcttattaataatattta atttttttgtgcaattttattatctttattgttgaatattttagtacaatgccacgactcatctcatatttatgttattttattgaa aaacacctcatatagttctgcctcattaggattaaaaaaatatttggagcacaaattttactttttgtgttatgaagactttatga aaaaaaaataaaataaaaacccgaaaacccgaaacctcgagaaaaatcgagattaaaaatccgacttttattggtttggtttggta tttagatttaataacccgatacaattagtttggtttggtaattagaaaatccgaatcaaacccctaaccgtgtacacccctagtcg tattggtatatagacatctttgataaatcattaatcatgcatgatattcttcgatctccttattgtaggtcatgacagaccctgat gttcctggccctagtgatccgtatctgagagaacatcttcactggtatgcactatattcaagaaaagctatggaaaaaaataacta gatgagataggtaaaaaagaaaggagtttaatgattgtttgatttgcattaattatattaagtcatgccattatctagtaataaac -continued tggttataaggacatacacaaaaggtatggtcaacatataatcaaagaaagaaaagcataagcatccttatgcaagctgccaatgt catgtaaaatacttcgctaatagacaaatatatattacattagttacctaaaagataggtatataatcagtgggactcctaactta aaaaataaggttagtaatctgctataacgatacactgagaatcgtcgtcgtcagtttataagttaaaaattaatgtaggtcatcac aacactcacaaagagtgcctcaattgggaagagtatgttatatagttagaatttatgttacatatggaaccacagtactacagaag gataactcttaaacatacttctttaccatcatatttgcaggatagtgactgatattccaggaacaacagatgccacctttggtaag ctcactattttggcattttcatttttccttcaatttcttttagtatatagctaggttggtttttgacatgctaattttgagcagga aaagagttggttagctatgagatcccacggcctaatattggaatacataggtttgtgtttgttctgtttaagcagaaatgcagaca gtcagttagtccacatgatgtttccagagatcacttcaacactcgcaactttgccaacgtaaacgatcttggcccgcctgtcgccg ccgtcttcttcaatgcacaacgagagaccgccgccaggagacgctaa SEQ ID NO: 6 Amino acid sequence of the *N. tabacum* TFL1-1T gene derived from
SEQ ID NO: 4 or SEQ ID NO: 5.
MARNVEPLVVGRVVGDVLDSFSPKVKMTVTYNNKQVCNGQELFPSAVTIRPRVEVQGGDMRTFFTLVMTDPDVPGPSDPYLREHLH WIVTDIPGTTDATFGKELVSYEIPRPNIGIHRFVFVLFKQKCRQSVSPHDVSRDHFNTRNFANVNDLGPPVAAVFFNAQRETAARR

R

SEQ ID NO: 7 Genomic sequence of the *N. tabacum* TFL1-2S gene, including 2 kB before
ATG (in bold)
catgaccttttagctactcttaactcttctgattgttctgctgtaacttgtccccttgagttaaatgtaaagttaaaggctaaaga aggggatcctctccctaatcctgaaaattatagaggcctcgttggtaagctaaatttcctcactcacactaggcctgacataagtt ttgttgtgcaacatcttagtcagttcatgcaacagccctgctttcctcacatgaaggcagctttgcacctgttgaggtatctcaga gacacttctaattttggcctcttatactcgaattctactgatctctctttgcaggcttattgtgatagtgattggggatcctgccc tgataactggagatttgtttctgatttctgtttattctttggtggcagtctcattgggtggaaatctaagaaacatgcagtggtct ctttatcttcggctgaagttgagtatagatctatgagcaaggctgtggctgaaattacttgggtgtgtaggcgtctatctgatctt ggggtctcttctgcttctcttgttcctctccattgtgacagtatctctgccattcacattgcctacaatcctgtcttctatgagcg gaccaaagacattgagttggattgccattttgaacgtaccaagcttgctgaaggtctcatcagtttatctcacatttccagtgctt ctcagctcgcgaatgtcttcatcaaacccctgtgtgggccttctcaccatcttcatattcgaaagttgggagttctctcaccctcc tacttgaggggggctgttgagataggctgaaatcagtgtggctcagacccaattattatttatttatgtacatcagattaggccc attagttagtctttagttagtcttttatttctttacatatattgggccatgtatacatacatagagacccgattttgtaatagtta gatgattcatttttcggttcttaatcaataagaaatatctcgaactttctctctatctctctttaaccctaaattcttcttcgttg aatctacgagaatgatgaacattaacattagaaaatgtagatttgatcaaatcttcttaatcttttgtttatcatcttttctaatt gttttgtatctgattgtatattagttaaccaccaaaattgctcaaacaatctggcttcaaatttatctaacgtttgaatatatata tatggttgaaacatgaaaaataaattttttgaagatgagatgaaaaataatttttgaaagttaaaattgtatttgaacacgtatttt acttgaaaagaatttgaaattttgtgagcagaaaacttaaaaaattactctaaaacttttttttgagatttgaggattttattttc aaaattttccataaaatggcttaaatctataagcaaaagatatttgaaaataattttttttttaaaaaagctctcaaattttacag ccaaacggaagcttaggataaaaaagggggaaatgggggagatgggtgggcaggttgggctgaagagaaatagacaacagtgcatt aacatgtcaaatcatctttatccctctttctaaaccttacaaggagtactttttatttttcttttttctttttttggccctaataaa aattaaaacacatattctctagctgctaagctataactttaactcattggcaccacgacgagtaggagaataacctttttgggctt ttcttttcttttctttggtcccctttttttgaactatcaatattttagtccaaacacacctgactctacagtgatctgatggccac tataaatattggctttttgcaactctcttctcaccaaaatacaaatcggttgaactcttcatatataatattcccactactattac tcttaactttaaatagatttcttatatatgggttcaaaaatgtctgatccccttgtgattggtagagtgattggggaagttgttga ttatttcactccaagtgttaagatgtctgttacttataacagcagcaagcatgtttataatgggcatgaactctttccttcctcag tcacctctaaacctagggttgaagttcatggaggtgatttgagatctttctttacaatggtacatactgcttccttcgattttcaa tacttttattaggggtggagcttagcggcggagccaagattttaactaaggggagtcaaaatataaataagtaagcacacaaaaaa atcaaggggggtcaacgtatagtatatacacataaaattaagaatttaacatatttataccgtgtaattttccagcgaaggggtgtc -continued aattgactctccttgccaatgagtggctccgccactggcggagctagagttctagttacggttcgttgtattgtgttaagaagtcc
acttatactgtcttttctagaatttagaattcataaattcaaaattatggctctgcccttaaatttatttttatacatttctatta
tatagtaaatcgtttatattgaccccttattttttcttttttaccttaattgacagatcatgatagacccagatgttcctggtccta
gtgatccatatctcagggaacacctacactggtaaagaaataagtttttttaattactaactcattcaattttatcgtcccttcttt
tccttgtttacttggagggaaaataatacgatctcatcgaaaagataaaaattcttcaggcttgttatctaaaaacttgttaaaaa
ataccgtaatgaaaagacatatgagtttgttattaggtatttgactaaatatgatcgatcatatggtgttcggacaagaaatattt
tgtgaaaaggtccgcatacttttaaaaaaagaaaatctgccttgactcttgagtttgtgcttctcgggaaaacaatttcttccttc
ttttttttttttttttggtttattgacctttacatattaaagacaccactgagacacatatctagaaaaattgtatttgggaacg
caaaagcaaagaaaacatgtgttattaatcttatgtcaatgccaccagcagctcaggaaaaatatggtcgatatattgtgatttgc
ttgcaaaaggagcaaagaagaaatcttttgataatgtttgttatgacgatgtacttaaagcaaataagttagaggtcgtttggtac
atgggataaggataataattttgggataaagtttaggattaactttatcttatatttggtttggagtattagctaaccgcgaggta
tttttcaaactaaaatagtgggattagctatcccatataaaaagtaggatagctaatcccatgggatatcccaccctatcggatag
taatagtccaataggagacaactctaatttgtacagacataatgtccagtcacaccttgtttttttgtcatgacacatattaagca
tgaataataatatttcgacaatcttgtagcatttgattagacttagcaaattataaatatgtccaataattggtcacattgttcta
ataattacttgtttcccttatcattatatatagtgcttcattcactaaacagaacccaaaaaaaaaaaaaaaaaaactgcaaaatg
gtcatatcatgtagtaacggaataaaaacgtactcagttttatgataaaatcaaagtgacatatttgtacgctttgatagttgaca
aatacctgaaaaaagaatttgaccatctttacaggattgtcacagacattccaggcactacagattgctcgtttggtatgtatctt
taacccaaatttcaagcttcgaaatagtaacagcttttgtttttaatatttatttgtcttaaatacatatttccttattataaa
tttcttcgcctagtggtaacgggatcaggtattgattcgtatttatttttttattgatcaacaaaaaaagagtacaaaagaaagaat
tgtttttctacacttagatttatatatatgcaatgtctagaaattaatgagtttacaaattcattgatgtgtatatctcacaatca
aatccaaaatactgatccaaaaatttttgatcagggaaagaaatagttggctatgaaatgccaaggccaaatattggaattcacagg
tttgtatttctgctgttcaagcagaagaagaggcaaacagtattgactgcacctctctccagggatcgatttaatacgcgtaaatt
cgcagaagaaaatgagcttgggtctcctgttgcagcagttttcttcaattgccagagggaaactgctgccagaaggcgttga SEQ ID NO: 8 Genomic sequence of the *N. tabacum* TFL1-2S gene
atgtctgttacttataacagcagcaagcatgtttataatgggcatgaactctttccttcctcagtcacctctaaacctagggttga
agttcatggaggtgatttgagatctttctttacaatggtacatactgcttccttcgattttcaatacttttattaggggtggagct
tagcggcggagccaagattttaactaaggggagtcaaaatataaataagtaagcacacaaaaaaatcaaggggggtcaacgtatagt
atatacacataaaattaagaatttaacatatttataccgtgtaattttccagcgaaggggtgtcaattgactctccttgccaatga
gtggctccgccactggcggagctagagttctagttacggttcgttgtattgtgttaagaagtccacttatactgtcttttctagaa
tttagaattcataaattcaaaattatggctctgcccttaaatttatttttatacatttctattatatagtaaatcgtttatattga
ccccttattttttcttttttaccttaattgacagatcatgatagacccagatgttcctggtcctagtgatccatatctcagggaaca
cctacactggtaaagaaataagtttttttaattactaactcattcaattttatcgtcccttcttttccttgtttacttggagggaaa
ataatacgatctcatcgaaaagataaaaattcttcaggcttgttatctaaaaacttgttaaaaaataccgtaatgaaaagacatat
gagtttgttattaggtatttgactaaatatgatcgatcatatggtgttcggacaagaaatattttgtgaaaaggtccgcatacttt
taaaaaaagaaaatctgccttgactcttgagtttgtgcttctcgggaaaacaatttcttccttcttttttttttttttttggttt
attgacctttacatattaaagacaccactgagacacatatctagaaaaattgtatttgggaacgcaaaagcaaagaaaacatgtgt
tattaatcttatgtcaatgccaccagcagctcaggaaaaatatggtcgatatattgtgatttgcttgcaaaaggagcaaagaagaa
atcttttgataatgtttgttatgacgatgtacttaaagcaaataagttagaggtcgtttggtacatgggataaggataataatttt
gggataaagtttaggattaactttatcttatatttggtttggagtattagctaaccgcgaggtatttttcaaactaaaatagtggg
attagctatcccatataaaaagtaggatagctaatcccatgggatatcccaccctatcggatagtaatagtccaataggagacaac
tctaatttgtacagacataatgtccagtcacaccttgtttttttgtcatgacacatattaagcatgaataataatatttcgacaat -continued cttgtagcatttgattagacttagcaaattataaatatgtccaataattggtcacattgttctaataattacttgtttcccttatc attatatatagtgcttcattcactaaacagaacccaaaaaaaaaaaaaaaaaaactgcaaaatggtcatatcatgtagtaacggaa taaaaacgtactcagttttatgataaaatcaaagtgacatatttgtacgctttgatagttgacaaatacctgaaaaaagaatttga ccatctttacaggattgtcacagacattccaggcactacagattgctcgtttggtatgtatctttaacccaaatttcaagcttcga aatagtaacagcttttgtttttaatattttatttgtcttaaatacatattttccttattataaatttcttcgcctagtggtaacgg gatcaggtattgattcgtatttattttttattgatcaacaaaaaaagagtacaaaagaaagaattgtttttctacacttagattta tatatatgcaatgtctagaaattaatgagtttacaaattcattgatgtgtatatctcacaatcaaatccaaaatactgatccaaaa attttgatcagggaaagaaatagttggctatgaaatgccaaggccaaatattggaattcacaggtttgtatttctgctgttcaagc agaagaagaggcaaacagtattgactgcacctctctccagggatcgatttaatacgcgtaaattcgcagaagaaaatgagcttggg tctcctgttgcagcagttttcttcaattgccagagggaaactgctgccagaaggcgttga SEQ ID NO: 9: Amino acid sequence of the *N. tabacum* TFL1-2S gene derived from SEQ ID NO: 7 or SEQ ID NO: 8
MSVTYNSSKHVYNGHELFPSSVTSKPRVEVHGGDLRSFFTMIMIDPDVPGPSDPYLREHLHWIVTDIPGTTDCSFGKEIVGYEMPR

PNIGIHRFVFLLFKQKKRQTVLTAPLSRDRFNTRKFAEENELGSPVAAVFFNCQRETAARRR

SEQ ID NO: 10: Genomic sequence of the *N. tabacum* TFL1-2T gene, including 2 kB before ATG (in bold)
agggcacgaccctaagaccttcttcatagctataaatagtgagctcaggtttcattgtaaatggaacgactattctggcaaactta tacaatattttatacaaaactcaattcaatcttatcttctgatttctagattctttttgtttttgtgcccgaaaaccttgttcctg gaattgttgcttctgttgtttcgtccatatcttaaggctaagtgttatataattcttcaattatttatttatttatttcaggttca aattaattcacttatctaaaaatcatgtataaatttaattgtaccattttacgggtgaacagtttggcgcccatcgtggggcctag ataaccgtgtaactaaaggacaaacgtcttttcgggaacttttctattttcaagaactcaaacccgagatttagacctctgaggga tctgatcatctcactacatcgctgagtggtagttgattccatatacgattaacctagtttacaactaaattaaattatgtgcatta atccaagcaactttgatgatcagctgatcaacctaacgtaagaaagcaattaatttagatgcatatattctacaaatggaaatta gtaggagcaagcaagttatgcaaaagaaaggaaaagagaaaacattagaagtaggccaaagaaagaagaaggaagaggaagcaatc agccactgttctagaatggaatatggagaaaaataataaattaaattcagatttctataagtagtaatcctcttctttctattacc ggttaaagctgcagaaattttcttttttcttgacatgacctgaccatagcttccaccattgtttgcaggctggtggtggagtccctt tataccctcatctctcctacctaagaaccataggattaggtgattcaagtttttatttttaacaaaaaaatgaaaaatttatgaagg aagttcaacttttttattaccttaaataaaaaaagaccttgatgctttaagtagctccaagacggtagctgcaaattccatctgcttt tcctttttaataaaataatgtactacctactatctgaaagtttaacttctatgattctgtaggttttgtaaaacacttgggggtat ttatattttataggggattgcaattagaggcagatacaatttggtttagttaaccaccgatattactcaaacaatttggctttaaa tctggttagtgtttggatatagatttggttgaaatttgaagaaaaaaaatgagtttttaaaaatgagatgaaaaataatttttgaa agttaaaattgtatttggacatgcattttatttgaaaagaatttgaagttttgtaagttaaaattttcaaaaacttcaaaaagtta tttttgagatttgaagattttattttcaaaatttgcattataatctataaacaaatagatactatttgagaacaaaatttaaaaaa taaagctttcaaacttatgacgaaagggaagcttaggataaaaagggggggaaatggcctgggagatgggtgggcaggttgggctga agagaaatagacaacagtgcattaacatgtcaaatcatctttatccctctttaaaaacattattaggagtacttctttttttcttg gggtgcaaaagcctaatacaagttaaaacacatattctctagctgctaagctataactttaactcattggtaccacgacgagtagg agaataaactttttgggcttttcttttcttttctttggttcccatttttttgaactatcaatattttagtccaaacacacctgactc tacagtgatctgatggccactataaatattggctttttgcagctccaaaatacaaatcggtcgaactcttcatatatattactctt aactttaaataaatagatttcttatatatgggttcaaaaatgtctgatccccttgtgattggtagagtgatagggggaagttgttga ttatttcactccaagtgttaagatgtctgttacttataacagcagcaagcatgtctataatggacatgaactctttccttcctcag tcacctctaaacctagggttgaagttcatggaggtgatttgagatctttctttacactggtacatactccttcgattttcactact tttaatttattaggggcgaagctagagttctagctacgggttcgttgtattaattgtgttaagaagtccacttaagctgtcttttt -continued tagaatttagaatccataaactcaaaatagtgactttgcttctaaattaattttttatgcatttctcttatatcgtgtatgtgaata ttgaccccttatttttttctttttaccttaattgacagatcatgatagacccagatgttcctggtcctagtgatccatatctcagg gaacatctacactggtaaagacatacgtttttttaattactaactcattcaattttatcgccccttcttttccttgtttacttggag ggaaaataatacgatctcgtcaagaagatcaaaaatcttcaggcttgttatttaggaacttgttcaaaaataccgttttgaaaaga acatatgagtttgttattaggtatttgactaaataggaacgatcatatggtgttcggacaagaaaatttttgtgaaaaggtccgca tactttaaaaaaaaaaaaaaaaaaaaaaatccgccttgactcttgagtttctgcttcttggaaaaaacatttcttcttttttttt ttgggtttttttgacctttatatattaattaaagacaccactgagacacttaattaaaaaattgtatatgggaacgcaaaaagaaaa aaaaacatgtgttattaatcttatgtcaatgccatcagcaactcaggaaaatacggtcgatatactgtgatttgcttgcgaaagga gcaaagaagaaatcttttgataatgtttgttatgacgatgcacttaacctaaaataagttaggggccgtttggtaaatgaaataag gataataatctcggaacaaagtttaggattaactttatcccatatttgatttggagtattagttaattgcgggataactttcaaat taaaatagtaggattagttatctcatatataaagtaaaatacctaatcccaataatataataggagacaactctaatttgcgtaga cataatgtccagtctcactttgtatatttgtcatgacgcatattaagcatgaatgataatatttcgacaatcttgtggcatttgat tacactcagcaaattataaatatgtccaataattgcattaataattacttgttcctcttatcattatagtgcctcattcactaaac cgaacccaaaagaacactgcaaaatggtcatatcatgtagtaacagaaaaaaaaaaacgtactcgattttatgataaaatcaaagtg acatatgtgtcgctttgataattgacaaatacctgaaaaaagaatttgaccatctttacaggattgtcacagacattccaggcact acagattgctcgtttggtatgtatctttaacccaaagttcaagctatgaaatagtaacagcttttctttttaatattttatttgtc ttaaatacatattttccttattataaatttattcgcctagtggtaacgggatcaggtattgattcgtatttaattttttattgttca acaaaaaagagtacaaaaagaaagaattgattttctacacttagatttatatgcaatatctagaaatcagaagatcagcaatgagt ttactaattcatcgatgtgtatatcgcacaatcaaatccaattactaataatactgatctaaaaatttcgatcagggagagaaata gttgggtatgaaatgccaaggccaaatattggaatccacaggtttgtatttctgctgttcaagcagaagaagaggcaaacattatt gagtgcacctctctccagggatcgatttaatacgcgcaaattctcagaagaaaatgagcttgggtctcctgttgcagcagctttct tcaattgccagagggaaaccgctgccagaaggcgttga SEQ ID NO: 11: Genomic sequence of the *N. tabacum* TFL1-2T gene
atgtctgttacttataacagcagcaagcatgtctataatggacatgaactctttccttcctcagtcacctctaaacctagggttga agttcatggaggtgatttgagatctttctttacactggtacatactccttcgattttcactacttttaatttattaggggcgaagc tagagttctagctacgggttcgttgtattaattgtgttaagaagtccacttaagctgtctttttttagaatttagaatccataaact caaaatagtgactttgcttctaaattaattttttatgcatttctcttatatcgtgtatgtgaatattgaccccttatttttttctttt ttaccttaattgacagatcatgatagacccagatgttcctggtcctagtgatccatatctcagggaacatctacactggtaaagac atacgtttttttaattactaactcattcaattttatcgccccttcttttccttgtttacttggagggaaaataatacgatctcgtca agaagatcaaaaatcttcaggcttgttatttaggaacttgttcaaaaataccgttttgaaaagaacatatgagtttgttattaggt atttgactaaataggaacgatcatatggtgttcggacaagaaaatttttgtgaaaaggtccgcatactttaaaaaaaaaaaaaaaa aaaaaaaatccgccttgactcttgagtttctgcttcttggaaaaaacatttcttcttttttttttttgggtttttttgacctttatat attaattaaagacaccactgagacacttaattaaaaaattgtatatgggaacgcaaaaagaaaaaaaaaacatgtgttattaatctt atgtcaatgccatcagcaactcaggaaaatacggtcgatatactgtgatttgcttgcgaaaggagcaaagaagaaatcttttgata atgtttgttatgacgatgcacttaacctaaaataagttaggggccgtttggtaaatgaaataaggataataatctcggaacaaagt ttaggattaactttatcccatatttgatttggagtattagttaattgcgggataactttcaaattaaaatagtaggattagttatc tcatatataaagtaaaatacctaatcccaataatataataggagacaactctaatttgcgtagacataatgtccagtctcactttg tatatttgtcatgacgcatattaagcatgaatgataatatttcgacaatcttgtggcatttgattacactcagcaaattataaata tgtccaataattgcattaataattacttgttcctcttatcattatagtgcctcattcactaaaccgaacccaaaagaacactgcaa aatggtcatatcatgtagtaacagaaaaaaaaaaacgtactcgattttatgataaaatcaaagtgacatatgtgtcgctttgataat tgacaaatacctgaaaaaagaatttgaccatctttacaggattgtcacagacattccaggcactacagattgctcgtttggtatgt -continued atctttaacccaaagttcaagctatgaaatagtaacagcttttcttttaatattttatttgtcttaaatacatattttccttatt ataaatttattcgcctagtggtaacgggatcaggtattgattcgtatttaatttttattgttcaacaaaaaagagtacaaaaagaa agaattgattttctacacttagatttatatgcaatatctagaaatcagaagatcagcaatgagtttactaattcatcgatgtgtat atcgcacaatcaaatccaattactaataatactgatctaaaaatttcgatcagggagagaaatagttgggtatgaaatgccaaggc caaatattggaatccacaggtttgtatttctgctgttcaagcagaagaagaggcaaacattattgagtgcacctctctccagggat cgatttaatacgcgcaaattctcagaagaaaatgagcttgggtctcctgttgcagcagctttcttcaattgccagagggaaaccgc tgccagaaggcgttga SEQ ID NO: 12: Amino acid sequence of the *N. tabacum* TFL1-2T gene derived from SEQ ID NO: 10 or SEQ ID NO: 11

MSVTYNSSKHVYNGHELFPSSVTSKPRVEVHGGDLRSFFTLIMIDPDVPGPSDPYLREHLHWIVTDIPGTTDCSFGREIVGYEMPR

PNIGIHRFVFLLFKQKKRQTLLSAPLSRDRFNTRKFSEENELGSPVAAAFFNCQRETAARRR

SEQ ID NO: 13: Genomic sequence of the *N. tabacum* TFL1-3T gene, including 2 kB before ATG tgaagttgtgtttggacatgcgttgtatttgagaaaaaattgaagttttgtgagaggaatttttttgaccccaaaactacataatt tgaattattatttaaaaaaaatgatcatattacatgaacaaacagtgttttcaatttatttttgaaaaaaacagccaaaatctagc caaatgggagctaagtgtatgatcaagattcatgtcccaaatggaaaagaatattaacaaaaaaaagggcagtaaagaagaggtgg ctacaataggatcgcgcaaaagaaagatggaaaaaagaggaacaggagggggaataagcagcacaagaagttattataagtcagc tcttccagaaaggaatatggagaaaagttaacctcaggtttctataaataggaatgtccaactttcatttactagtttaagctgca gaaattctctttttcttgacatgaccttttcaccatctttaatttggtgggctttgtggtggagtccctttataccataggctctc ctagaggatccataacattagattggtaaggttctaagtggactcacgatatgaaatttgtgatcgaacctataactcgtctgagt tactgaatttgtaataaaatatttatacatatttaataaattttctaatataaatacagaatctaaacaaaaactattgagttcat ccgtaccgatacctaatactctagctccaaccctgattctaatataatgaaaataaaaccacatctaggaagttcatgacctgttc ttaccttaaatgccaaaggccttaaacctttgatagcttgagaatagccaaacaagtatagattccatctactttaattttctttc tgattaagatatattgcaactcctgtaaatgcgcaaggagtcagctggttcttccccccatttctatatttttttagtatcactttct tttcttaattattccttcttacatttgaatctttttccatcagctagctgttttgatagtagtaaaaaatgcgaaggctcttcttac taatatttcaatgaccaatgaatttagatggagaagcaagttctattaaacgttcatgctagaaaataa caagtataatattt cat tttcattttatataacgctcttgtcttttcttgtctatttaaacaagaatcaatttaactctcttaatgacatgctctttagtcac agaaaaattataacaaattgaagacattagttattaatgttcttttcgcactaaaagtttttttaaaaatttttttatcttaaatgtt tgtgactaatcaaatatcatcatataaaattaatctgggaatatgacatttttcaatataactaatatggtgcaaattgcatacac tacgcaataaatttgtggttagggtcatatcattagcctgtcaaatcatctttatccctctttctctaaacgacttcttttctccc tttttttttcgcccctcaaacaaagcaaatagactattctctagctgctaattagctaaacaatgactttaactcgttgtgcccaga ggagaataacctttatctctcttctcttttctttgtttccatctttaatttagacttcttttttttggtttttttatcccatattcgg tatttattggagttcgattaaattcaaatttataataggaagtctcacattgagagtacgatgactccatactcaggattcgaatt tgagatctttagttaaagatgaaagaatatcattcaaccacaacttttgttggtcccatctttatatctatatgttcttactatat tttaatccatttcccacttccaatgatttaaagaagctataggataggtgcatttggaccactataaatataggttttgcagttct atgctccatacaaatatccagcaagaaactaaactatatatttactgagttactactaatagttttcactcaatctatttccactc tttctcctcttcattatattatatggctcaaatgacagatccccttgtgattagtagggtggttggagatgttgttgattatttct ctccaagtgttaagatgtgtgttatttataaccccagtaagcatgtctataatgggcatgaactctttccatcccttgttacctct aaacctaaggttgaagttcatggaggtgacatgagatccttctttacactggtaattaattcacactacttcaatagttttcttgt tcttatattttattatctatctatatatatataataaaggagcggcaaagccaccatataaatgacaaatgtaaactttttaggaca aaactccaaaaaaagttggagttttaaaattattttatatataaaataaataaataaataaataaataaactatcaattcaaattgg ggagtagtttcttactaatatgatagctatatctatatctatatctatctatatatgtaaaacatttatatgatgccaagtggcat aaccactgataagatttttaaatttgaatatgaatgaattttaaatgaagttctaacttcttaaaaataaaccctaatataggtta -continued ctatttttagtaatgattgaaattattattaaaatattttgttgaaaacaacatagagataaaatttgattattaaatttatgtat tacaacaataataattattgaaaatattgctaaaattttcatgaaaggattcacccataattattagtataatagaaaactaaaaa attattaagtctaaagttctagatctctatatttataaacgtataaactgttattttattttctgaaaaaagcaaaaatactgaag agaaaaatgataaaaatattttaaaatatgtaagtcatgtgcaaataataaagtgaacaaatgatgtagtagtatactgaataaga tatgtttttttgtcataaaataagtatatgcataactcatctcaataatttgctgactccatctgagtcaaaatatcttctaaatt caagcgaagataattatctatcgcattattttttatcattaatataaggcaagacgaatctatatctcatatgggactttttaaa tagatacatctttataaatgaaccactttatgagttttatcacgaattacaagtaagaataacttgaagattgaaagaatttttgg atttatttaattataatatattttttattcattttaaattaatttatattttcaaattatttgtagcaacctatataattatgatat ttgagtattatcttataagttatttgatgattgtcgtttgatttaattattgaactattactacaggggacataagatgataatta taattttgtagaaacatatgatctaatgtgctcaaataaattactatcatactttgatatgactaatattctttaataatttttgc gcatcgggcgggtactaatactagttcttaaaaaaagggtagcgcgatgcacaaagcattccgcattcacacaggatcctaggaat tgggtcgcaccccacagtctaccctaatgcaaacattagcgactactttcacggctcgaactcgtcacttatagatcatacagaga caaatttactgttgctccaagttccctttcttatttattattcttataatttctattcttatattgttataaattatttttttct ttttgatagatcatgactgaccctgatgttcctggtcctagcgatccatatcttagggagcacttacattggtatgtatcatacta tcatcaactttgaaagcttaaaacactgtaaagttgatgattcacaccaaagattttaatcgtcgtcgtgttacttccatataaat cagtatcgagaagtatgtggccatcactccatcaacgacaccaaaatgaaataaagagtccctatatcaatacaatataaattaat cttaaacatgaagttgactttaaattggataaattgtttccactactaagcttagcgtataaattagtcctttgactttcaatttt gtataataatgcgaagctttttttcttgtaaatgcaatttttgtccttgagggtttgcaacttctttttttaaggaaaaaaaaaaga ctaaagttgtgtgacactaaaaccaagagttagcttaatacttcatggacacacgttagcataaaacatataaccgatattcaaaa ttacaaaaaatgatagaatcataatttttgtttctatttaaaaaggaagtaagccaaattactactaacatagtggacttaaagggt attaatttttttgttattttaatgatatctgttcatgacttcttgactacttctactcctttatatcaatcaaattataatttactt cgtttgactatctaatttacagggtaattacagacattccaggcactacagattcctcgtttggtatggaataatattgtattcct tttttacttttctgcctagcatttctaaatagagtagtccgatacacgaaatatttcactttacgcaggatccagaaataaaggac cataccccaattgggtgtaatataagtagtcatgggcgcatgcagtattttagtgacgggtttaattgcactcataattttggacg cttagcataaagtagtagatatgtatccataacttcaaaaatataataggttcaatgttaaaaaatttcaaaagagatgaactcata gagtttaaatcatgatccgcctctgtaggcagtctaccctaatgaaagaatcagtggctgatttcacagttcaaaaccgtaaccta tgaatcacataaagccaactttaccatcgctccaagactcgccttcttctgcctaacattactactgctaataaagagaattttaa taaaactactaatgctaattattattctttgctaaaatcttcatcaggaaaagaagtggtgggctatgaaatgccaatgcctaaca ttggaatccataggtttgtgtttctgctcttcaagcagaagaagaggcaaacagtgagcgcaccattatccagggaccgattcaat acgcggaaatacgcagaagaaaatgagcttggctctccagttgctgctgttttcttcaactgccaaagggaaaccgcggccagaaa gcgttga SEQ ID NO: 14: Genomic sequence of the *N. tabacum* TFL1-3T gene
atggctcaaatgacagatccccttgtgattagtagggtggttggagatgttgttgattatttctctccaagtgttaagatgtgtgt tatttataaccccagtaagcatgtctataatgggcatgaactctttccatcccttgttacctctaaacctaaggttgaagttcatg gaggtgacatgagatccttctttacactggtaattaattcacactacttcaatagttttcttgttcttatattttattatctatct atatatatataataaaggagcggcaaagccaccatataaatgacaaatgtaaacttttaggacaaaactccaaaaaagttggagtt ttaaaattattttatatataaaataaataaataaataaataaataaactatcaattcaaattggggagtagtttcttactaatatg atagctatatctatatctatatctatctatatatgtaaaacatttatatgatgccaagtggcataaccactgataagatttttaaa tttgaatatgaatgaattttaaatgaagttctaacttcttaaaaataaaccctaatataggttactatttttagtaatgattgaaa ttattattaaaatattttgttgaaaacaacatagagataaaatttgattattaaatttatgtattacaacaataataattattgaa aatattgctaaaattttcatgaaaggattcacccataattattagtataatagaaaactaaaaaattattaagtctaaagttctag -continued atctctatatttataaacgtataaactgttattttattttctgaaaaaagcaaaaatactgaagagaaaaatgataaaaatatttt aaaatatgtaagtcatgtgcaaataataaagtgaacaaatgatgtagtagtatactgaataagatatgttttttgtcataaaata agtatatgcataactcatctcaataatttgctgactccatctgagtcaaaatatcttctaaattcaagcgaagataattatctatc gcattattttttatcattaatataaggcaagacgaatctatatctcatatgggactttttaaatagatacatctttataaatgaa ccactttatgagttttatcacgaattacaagtaagaataacttgaagattgaaagaatttttggatttatttaattataatatatt tttattcattttaaattaatttatattttcaaattatttgtagcaacctatataattatgatatttgagtattatcttataagtta tttgatgattgtcgtttgatttaattattgaactattactacaggggacataagatgataattataattttgtagaaacatatgat ctaatgtgctcaaataaattactatcatactttgatatgactaatattctttaataatttttgcgcatcgggcgggtactaatact agttcttaaaaaaagggtagcgcgatgcacaaagcattccgcattcacacaggatcctaggaattgggtcgcaccccacagtctac cctaatgcaaacattagcgactactttcacggctcgaactcgtcacttatagatcatacagagacaaatttactgttgctccaagt tccctttcttattttattattcttataatttctattcttatattgttataaattattttttttctttttgatagatcatgactgacc ctgatgttcctggtcctagcgatccatatcttagggagcacttacattggtatgtatcatactatcatcaactttgaaagcttaaa acactgtaaagttgatgattcacaccaaagattttaatcgtcgtcgtgttacttccatataaatcagtatcgagaagtatgtggcc atcactccatcaacgacaccaaaatgaaataaagagtccctatatcaatacaatataaattaatcttaaacatgaagttgacttta aattggataaattgtttccactactaagcttagcgtataaattagtcctttgactttcaattttgtataataatgcgaagcttttt ttcttgtaaatgcaatttttgtccttgagggtttgcaacttctttttaaggaaaaaaaaaagactaaagttgtgtgacactaaaa ccaagagttagcttaatacttcatggacacacgttagcataaaacatataaccgatattcaaaattacaaaaatgatagaatcata atttttgtttctatttaaaaaggaagtaagccaaattactactaacatagtggacttaaagggtattaatttttttgttattttaat gatatctgttcatgacttcttgactacttctactcctttatatcaatcaaattataatttacttcgtttgactatctaatttacag ggtaattacagacattccaggcactacagattcctcgtttggtatggaataatattgtattccttttttacttttctgcctagcat ttctaaatagagtagtccgatacacgaaatatttcactttacgcaggatccagaaataaaggaccataccccaattgggtgtaata taagtagtcatgggcgcatgcagtattttagtgacgggtttaattgcactcataattttggacgcttagcataaagtagtagatat gtatccataacttcaaaaatataataggttcaatgttaaaaatttcaaaagagatgaactcatagagtttaaatcatgatccgcct ctgtaggcagtctaccctaatgaaagaatcagtggctgatttcacagttcaaaaccgtaacctatgaatcacataaagccaacttt accatcgctccaagactcgccttcttctgcctaacattactactgctaataaagagaattttaataaaactactaatgctaattat tattctttgctaaaatcttcatcaggaaaagaagtggtgggctatgaaatgccaatgcctaacattggaatccataggtttgtgtt tctgctcttcaagcagaagaagaggcaaacagtgagcgcaccattatccagggaccgattcaatacgcggaaatacgcagaagaaa atgagcttggctctccagttgctgctgttttcttcaactgccaaagggaaaccgcggccagaaagcgttga SEQ ID NO: 15: Amino acid sequence of the *N. tabacum* TFL1-3T gene derived from SEQ ID NO: 13 or SEQ ID NO: 14

MAQMTDPLVISRVVGDVVDYFSPSVKMCVIYNPSKHVYNGHELFPSLVTSKPKVEVHGGDMRSFFTLIMTDPDVPGPSDPYLREHL

HWVITDIPGTTDSSFGKEVVGYEMPMPNIGIHRFVFLLFKQKKRQTVSAPLSRDRFNTRKYAEENELGSPVAAVFFNCQRETAARK

R

SEQ ID NO: 16: Genomic sequence of the *N. tabacum* TFL1-4S gene, including 2 kB before ATG (in bold)

ccttatgggttctcagcatttgggcaaaagtgatactttaagcaagtgaggaagtttttttaatgttggccggaaagatgcctgtgg gtgctgtttgggggaaaaaaacaaaagctcgggtaaattatcaatacccgagttggttcctttcgtttgccactggaccaactcct gattttgcttatatatgggttccaaactaaaaatacttatatatttaataaatttatcaatacaaatacaaggctcgggtaaaagt tattaggttctcggaaacccatacccgatactatggatccgcccctgcttatccctaccttgtgtgaggtagaaacgcttttgata aggttatttaaaagtaaaagaataagtttaatgtgacaatttgaatggttgagacaacatgccaaaagctaatttaagggatttta tttgacatttatatatgggagagaagaaaaagtattgcccagtatattattttaagctctacaaccaatcaagaatcaattcctag aatccattcaggtgtcaaagaatactgacatgatataataaaatacaatttatatcacatcagtatttgctttttcttgggagatt -continued agataaaaagagatcagaaatggagttttatggtactaggagaattcaaggatttactacttttgtggcacaacataagctcccaa tttttttaaggaatttataaaagttggttttctaagtacttacaattgtcaaatttacaagtcatttagtacataaaaagaaaccc aatgatgaggttcaggaaaaaaaaaaatcctatactgtgatttcctagttggcgttcggacataaaaattatgaaattccgaaaaa aaaaattgttttaagttgaaaatggtatgtgaaaattaaagttatatatggacataaatataatttggagctgttttgaatttt gtgagtgctttgaagtgaaattttctaaaaacagctttttggagtttttcaaattccggagttcaacttcaagcgaaaaattaaaa ttttcatgatcaaatgttgattccgaaaaaagtgaaaaaattcgaaaaaaagatttttttttttatggccaaacagacctaactag tttcattttagtcattaagggtagaattgaaagaattttaaattaaagtattttagatatataaaaataatgtactttttaaaac acacaaaaaaaggagtgccatatattaatttaatataaggatatatagtggatgcattcataactaacattaaccaaaagcattta ttgatcctattttgacaccattttattttaatacaattcataaatttcaagaatttgaatacattagcttaatctcacttaaattt tgaggtgatgcctgttctctttctagtcacaactttaatgtacattttatatgtcaaattaatacctgaatttgtaacccatcaaa tatcgccacataatatgaaacagtgaaaatatcttatattcctgtattttatgactaagacattaagtagctaacaacgatcgaaa aacattcctaataacaagcgaattacaactctgtcggataatcgtctgaaaccctaaaaagctactgaaatgatttcctactagta taattccgatgaaattttgttcgaaaattctataagaaatacacgtatttttagtagtgaaaaaagatttgttgtaatttttttag gtggggtggggtgatttggggagggttggggagtaggacctcaaaaacaaagaattttaatactttggagtttccttaggtcccat gttttatactttcttttattctccttcaccattatagctataacttagtacatatatatatatatatatatatatatatatata tatnatataaggtgtccatctgatcaagtatccaatacaaaccattcttaagtctttgaaaatttctcttttttttccttatctcta tctctgtctaattttctttattatggcaagaagtttagagcctctaattgttgggagagtagtaggagatgttcttgattcattta gtcctataatgaaaatgacaatatcatataacaacaaattagtgtgcaatggccatgaactccttccttctgttgtcactgctaga cctaaagttgaagttcaaggggagatttgagaactttcttcacattggtattttttttcttgatttctacttaatttccaagatca tcaagttcccattatttctttaaaaaaaaaaaaaagcagttcggtgcactaaactcccgctatgcgcggggttcggtgaagcaccga accataagggtctattgtacgcaaccttaccctgcatttatgcaagaggcttgctcaccattacaagttatattaatttaacatgt tatatataaccacaaaggctgtcgtgggatggtaaatatccttctatccttaatcagaagtttcgggttcaagttatagccctagg aatatagtcgtctttggtagggatcctttacccccaaaactttccgccgtgaatccagattagtaaacctcaaagcgggtatcggg cattggatgacaaaccaaaaaaacttcaacgtgttatagcatgttataacttattacagttaatttagttttccagtcgatactat attaaatagagtgcctgtaatttactttggagtgatttgattgttattttttcgcatcgtcagtacataaaacttatattaatttt cgaatatgtaggtcatgacagaccctgatgttcctggccctagtgatccttatctaagagagcatctccactggtatgccctaaac tcaatttttttttaaaaaaaaaaaaatagaaaatgagaaaaaaatatgtaaaaatctacaaatatgagaagatcatgattaattggaa ctatttttactgactatttgacaggatagtaactgacattccaggtaccactgatgctacttttggtaagttctctgtatcttctg caaaattacaagcacatgtgaagataaaagaagtttttctattattcacttattttgtctagctagttatatagaataattataag atcaacaattttgtatagtagtgaatgttggacttctaaagtcgaacatgtccacttgatgagtgtcacaaaaatgtagaaactaa acaatcgtttggacataaaaaaaaaaagtaagtttttttgagttaaattgaaaaagaaaatatttagaatttgaaattgtggatata catttaaattgaaaagcattgcagttttgtaaggaaaataaactttcatatacataaaaaagtgatttttttggaaactcatcttca agaatatttttaaaaatttccgtccaatgtataaccaaacattattttgaaaaagattaaaaaaaggaaaaactttaggaacaacg ggtcccaagataaatgtgtctagtcatataagattagataaattaggattttattatatttggtagaaggtgcaagaagcatatgt aaataataaattgagaagtcacttaagatattttgatcatgtcccacatcgataacaagaggtaccattctatatatgttaaatca tggtaagttaaagtattatatcacatattaaatggtgatataatagacctaaatcacatgaaacgaaattgtcccgaaaggtctat aaatttttgaaattcatgtagacgaagctaaaagtaggatacaataaaaaaaaaaattaaagatctatattggcgatactatttagt tgggattgcattttagttattctagtacatttactttaatctaattttttgctagctaggagtcttttaatcttattagaaatttac ataccaaaaaatttagagaacttgctaggacaattggtatttctttatataatattgtggaagttgtattagagtatgttgtttac attacactctttgagtgcgttccttctccgaactagctaatgcatgaacacgagatgccttctgcaccgtgctaccctattaatat ataaaaaaatggtagcccggtgcattaagctcccgctatgcgcgggttccgaaaaaggatcagaccacaagggtctatgtttgcaa -continued ccttacttgtatttctgcaagaaactgtttccacggctcgaacccatgatcttctggtcacatgacaataactttaccggttacac caaggttccccttcacgcgctgcccttttaatattgtctattaatatttcctactagagttatacacccctttgttattactcact cttagggtgattattaacatataatatgtttaatatttatactaaaaacaggacgagaattggttagctatgagattccaatgcca aatattggaatccataggtttgtatttgtacttttcaagcaaaaacgaagacaatcagttagctctcctacttcaagggatcactt caacactagaaattttgctgaagaaaatgatcttggccaacctgttgctgctgttttcttcaatgcacagcgagaaaccgccgcac gaagacgctaa SEQ ID NO: 17: Genomic sequence of the *N. tabacum* TFL1-4S gene
atggcaagaagtttagagcctctaattgttgggagagtagtaggagatgttcttgattcatttagtcctataatgaaaatgacaat atcatataacaacaaattagtgtgcaatggccatgaactccttccttctgttgtcactgctagacctaaagttgaagttcaagggg gagatttgagaactttcttcacattggtatttttttcttgatttctacttaatttccaagatcatcaagttcccattatttcttta aaaaaaaaaaaagcagttcggtgcactaaactcccgctatgcgcggggttcggtgaagcaccgaaccataagggtctattgtacgc aaccttaccctgcatttatgcaagaggcttgctcaccattacaagttatattaatttaacatgttatatataaccacaaaggctgt cgtgggatggtaaatatccttctatccttaatcagaagtttcgggttcaagttatagccctaggaatatagtcgtctttggtaggg atcctttaccccccaaaactttccgccgtgaatccagattagtaaacctcaaagcgggtatcgggcattggatgacaaaccaaaaaa acttcaacgtgttatagcatgttataacttattacagttaatttagttttccagtcgatactatattaaatagagtgcctgtaatt tactttggagtgatttgattgttatttttttcgcatcgtcagtacataaaacttatattaattttcgaatatgtaggtcatgacaga ccctgatgttcctggccctagtgatccttatctaagagagcatctccactggtatgccctaaactcaattttttttttaaaaaaaaa aaatagaaaatgagaaaaaatatgtaaaaatctacaaatatgagaagatcatgattaattggaactatttttactgactatttgac aggatagtaactgacattccaggtaccactgatgctacttttggtaagttctctgtatcttctgcaaaattacaagcacatgtgaa gataaaagaagtttttctattattcacttattttgtctagctagttatatagaataattataagatcaacaattttgtatagtagt gaatgttggacttctaaagtcgaacatgtccacttgatgagtgtcacaaaaatgtagaaactaaacaatcgtttggacataaaaaa aaaagtaagtttttttgagttaaattgaaaaagaaaatatttagaatttgaaattgtggatatacatttaaattgaaaagcattgc agttttgtaaggaaaataaactttcatatacataaaaaagtgatttttttggaaactcatcttcaagaatatttttaaaaatttccg tccaatgtataaccaaacattattttgaaaaagattaaaaaaaggaaaaactttaggaacaacgggtcccaagataaatgtgtcta gtcatataagattagataaattaggattttattatatttggtagaaggtgcaagaagcatatgtaaataataaattgagaagtcac ttaagatattttgatcatgtcccacatcgataacaagaggtaccattctatatatgttaaatcatggtaagttaaagtattatatc acatattaaatggtgatataatagacctaaatcacatgaaacgaaattgtcccgaaaggtctataaattttttgaaattcatgtaga cgaagctaaaagtaggatacaataaaaaaaaaaattaaagatctatattggcgatactatttagttgggattgcattttagttattc tagtacatttactttaatctaatttttgctagctaggagtcttttaatcttattagaaatttacataccaaaaaatttagagaact tgctaggacaattggtatttctttatataatattgtggaagttgtattagagtatgttgtttacattacactctttgagtgcgttc cttctccgaactagctaatgcatgaacacgagatgccttctgcaccgtgctaccctattaatatataaaaaaatggtagcccggtg cattaagctcccgctatgcgcgggttccgaaaaaggatcagaccacaagggtctatgtttgcaaccttacttgtatttctgcaaga aactgtttccacggctcgaacccatgatcttctggtcacatgacaataactttaccggttacaccaaggttccccttcacgcgctg cccttttaatattgtctattaatatttcctactagagttatacacccctttgttattactcactcttagggtgattattaacatat aatatgtttaatatttatactaaaaacaggacgagaattggttagctatgagattccaatgccaaatattggaatccataggtttg tatttgtacttttcaagcaaaaacgaagacaatcagttagctctcctacttcaagggatcacttcaacactagaaattttgctgaa gaaaatgatcttggccaacctgttgctgctgttttcttcaatgcacagcgagaaaccgccgcacgaagacgctaa -continued SEQ ID NO: 18: Amino acid sequence of the *N. tabacum* TFL1-4S gene derived from SEQ ID NO: 16 or SEQ ID NO: 17.
MARSLEPLIVGRVVGDVLDSFSPIMKMTISYNNKLVCNGHELLPSVVTARPKVEVQGGDLRTFFTLVMTDPDVPGPSDPYLREHLH WIVTDIPGTTDATFGRELVSYEIPMPNIGIHRFVFVLFKQKRRQSVSSPTSRDHFNTRNFAEENDLGQPVAAVFFNAQRETAARRR SEQ ID NO: 19: Genomic sequence of the *N. tabacum* TFL1-4T gene, including 2 kB before ATG (in bold)
atccccagaggcggatctaggatttgaaccttatgggttctcagcatttgggcaaaagtgatactttaagcaagtgaggaagtttt ttaatgttggccggaaagatgcctgtgggtgctgtttgggggaaaaaaacaaaagctcgggtaaattatcaatacccgagttggtt cctttcgtttgccactggaccaactcctgattttgcttatatatgggttccaaactaaaaatacttatatatttaataaatttatc aatacaaatacaaggctcgggtaaaagttattaggttctcggaaacccatacccgatactatggatccgcccctgcttatccctac cttgtgtgaggtagaaacgcttttgataaggttatttaaaagtaaaagaataagtttaatgtgacaatttgaatggttgagacaac atgccaaaagctaatttaagggattttatttgacatttatatatgggagagaagaaaaagtattgcccagtatattattttaagct ctacaaccaatcaagaatcaattcctagaatccattcaggtgtcaaagaatactgacatgatataataaaatacaatttatatcac atcagtatttgctttttcttgggagattagataaaaagagatcagaaatggagttttatggtactaggagaattcaaggatttact acttttgtggcacaacataagctcccaatttttttaaggaatttataaaagttggttttctaagtacttacaattgtcaaatttac aagtcatttagtacataaaaagaaacccaatgatgaggttcaggaaaaaaaaaaaatcctatactgtgatttcctagttggcgttc ggacataaaaattatgaaattccgaaaaaaaaaattgttttaagttgaaaatggtatgtgaaaattaaagttatatatggacataa atataatttggagctgtttttgaatttttgtgagtgctttgaagtgaaattttctaaaaacagctttttggagtttttcaaattcc ggagttcaacttcaagcgaaaaattaaaattttcatgatcaaatgttgattccgaaaaaagtgaaaaaattcgaaaaaaaagatttt ttttttatggccaaacagacctaactagtttcattttagtcattaagggtagaattgaaagaattttaaattaaagtatttttag atatataaaaataatgtacttttttaaaacacacaaaaaaaggagtgccatatattaatttaatataaggatatatagtggatgcat tcataactaacattaaccaaaagcatttattgatcctattttgacaccattttattttaatacaattcataaatttcaagaatttg aatacattagcttaatctcacttaaattttgaggtgatgcctgttctctttctagtcacaactttaatgtacattttatatgtcaa attaatacctgaatttgtaacccatcaaatatcgccacataatatgaaacagtgaaaatatcttatattcctgtattttatgacta agacattaagtagctaacaacgatcgaaaaacattcctaataacaagcgaattacaactctgtcggataatcgtctgaaaccctaa aaagctactgaaatgatttcctactagtataattccgatgaaattttgttcgaaaattctataagaaatacacgtatttttagtag tgaaaaaagatttgttgtaatttttttaggtggggtggggtgatttggggagggttggggagtaggacctcaaaaacaaagaattt taatactttggagtttccttaggtcccatgttttatactttcttttattctccttcaccattatagctataacttagtacatatat atatatggtggccctctgatccaatgtaaaatgcaaaccattcttaagatctttgaaatttctctcttttttttctttatctctat ctctgtctaattctctctattatggcaagaagtttggagcctctaatagttgggagagtagtaggagatgttcttgattcatttag tcctatagtgaaaatgacaattacttataacaacaaattagtgtgcaatggtcatgaattctttccttctattgtcacttctagac ctaaggttgaagttcaaggaggagatttgagaactttcttcacactggtaatttttcttgatttttttccttaattccaagatcatc aagttccatttatttctttacaagttatattaatttaaccctttataatcaccaaaggctggcgtgggttgctaagtaaccttcca tcgttaatcagatgtttcgggttcgagctagccctgggattacaatcgtttttttgtaggaagcgctttaaccccccaaaatttttca gcacgaacccggattagtaaacctcaaaactcgtgccaaatactagatgacaaaccaaaagagttttcaacctgttataacatatg ttacttgttacaattattagttttccggtcaatagtatattatgtaattttctttgaagtgacttgattgttatttttttcacatta tcagtgcataaaacttatactattattttttaatatgtaggtcatgacagaccctgatgttcccggccctagtgatccttatctac gagagcatctccactggtacactctctataatagtttcatttgttccgaattttcttggctgttatataaaaaatatattataaca tagcatgaaaattggttccacaaaaacttaatttttatagtgaataattgttatatattgatattgttatagagaggtctgtctat atgccctaaactcaatgaaaaaaaaatagaaaatgagaaaaaaatatgtaaaatctacaaatatgagaagatcatttttagttgaaac tatccttatatactactgaatatttagctggcaaataaaattgacagtgttttactgattgtttgacaggatagtaactgacattc caggtaccactgatgctacttttggtaagttttattagtttcttctgcaagattacaagcacatgtgaagaagatacaagatgttt -continued ttccattactcacttattttgtcttgctaataattatatagaacaattgtaagatcaacagtgttatataatagtgaatgttggac ttctaaagtcgaacatgtccacatgatgagcgtcacaaaaatgcagatacgagctcgtttggattgacttaaaaaatgtggttttt cagcaaaaataacttttaagccaaaaaacaataagttagggttgtccaccttttgcttttggcttaatttaagcattttaaaatt tattttaagcaatttttgacttagccaaacaccgaaaaaagctaaaagaaacttaaaagctgatttgactagcttaaaagtaaatc caaacaccctctaactaagcatttggacataaaaaaaatatgtcattttgaaaaaagtagttcttttgagttaagtcaaaaaaga atatataaaatttgaaattgtatttagacatgcatttcacttgaaaattattagagttttatgagaaaaatgaacttttagatgaa aaagtggtttttggaaactcatcttcaagaatttttccaaaacttcagtccaatcgtataaccaaacattattttgataaaaacat cgaaaataaaaataaatctatggagaaacgggtcccaagataaatgtgtctagtcatataagattattcaaaattaagaatttatc acatttgtaaaagatgtaagtagcatatgtaaatgataaaatgagaagtcacttgagatgttttgatcatgtcctacgtcgatctt cagaggtaccattccgtatacgtgattggtaagtaaaggtattaaaaagagacataatggacctaaattacgtgaaacgaaattgt cttgaaaagtctttcaaatttttgaaatccatgtagacgaatcgaaaagtagggcacaatgaaatatgatcaaaggtttataatgg tgatacaagttagttgggattacgttttagttatgccagtatatttactttaatctaatattttcttggagtttttaatcttatt agaaatttacttaccaaaaatttagagaacttgctagaacaatataattgataattcttcatatatattgtcttcgagctgtagaa acagccactaatgtttgcattaggatatgttgtctacatcacacttattgtgtgttgccctcaccggaccctgcatgaacgtatga tgccttatgcaccgcgcccctttaatattatttattaattaatatttcctgctagagttatactcctttgttattactcattctt aggttgatgattaacttataatatgcttaatctttatactaaaaataggaagagaattggttagctatgagattccaaggccaaat attggaatccataggtttgtatttgtacttttcaagcaaagacgaagacaatcagttagccctcctacttcaagggaaaacttcaa cactagaaattttgccgaagaaaatgatcttagccaacctgttgctgctgttttcttcaatgcacagcgagaaaccgccgcgcgaa gacgctaa SEQ ID NO: 20: Genomic sequence of the *N. tabacum* TFL1-4T gene
atggcaagaagtttggagcctctaatagttgggagagtagtaggagatgttcttgattcatttagtcctatagtgaaaatgacaat tacttataacaacaaattagtgtgcaatggtcatgaattctttccttctattgtcacttctagacctaaggttgaagttcaaggag gagatttgagaactttcttcacactggtaatttttcttgatttttttccttaattccaagatcatcaagttccatttatttctttac aagttatattaatttaaccctttataatcaccaaaggctggcgtgggttgctaagtaaccttccatcgttaatcagatgtttcggg ttcgagctagccctgggattacaatcgtttttttgtaggaagcgctttaacccccaaaattttcagcacgaacccggattagtaaa cctcaaaactcgtgccaaatactagatgacaaaccaaaagagttttcaacctgttataacatatgttacttgttacaattattagt tttccggtcaatagtatattatgtaattttctttgaagtgacttgattgttatttttttcacattatcagtgcataaaacttatact attatttttaatatgtaggtcatgacagaccctgatgttcccggccctagtgatccttatctacgagagcatctccactggtaca ctctctataatagtttcatttgttccgaattttcttggctgttatataaaaaatatattataacatagcatgaaaattggttccac aaaaacttaatttttatagtgaataattgttatatattgatattgttatagagaggtctgtctatatgccctaaactcaatgaaaa aaaatagaaaatgagaaaaaaatatgtaaaatctacaaatatgagaagatcatttttagttgaaactatccttatatactactgaat atttagctggcaaataaaattgacagtgttttactgattgtttgacaggatagtaactgacattccaggtaccactgatgctactt ttggtaagttttattagtttcttctgcaagattacaagcacatgtgaagaagatacaagatgtttttccattactcacttattttg tcttgctaataattatatagaacaattgtaagatcaacagtgttatataatagtgaatgttggacttctaaagtcgaacatgtcca catgatgagcgtcacaaaaatgcagatacgagctcgtttggattgacttaaaaaatgtggtttttcagcaaaaataacttttaagc caaaaaacaataagttagggttgtccaccttttgcttttggcttaatttaagcattttaaaatttattttaagcaatttttgact tagccaaacaccgaaaaaagctaaaagaaacttaaaagctgatttgactagcttaaaagtaaatccaaacaccctctaactaagca tttggacataaaaaaaatatgtcattttgaaaaaagtagttcttttgagttaagtcaaaaaagaatatataaaatttgaaattgt atttagacatgcatttcacttgaaaattattagagttttatgagaaaaatgaacttttagatgaaaaagtggtttttggaaactca tcttcaagaatttttccaaaacttcagtccaatcgtataaccaaacattattttgataaaaacatcgaaaataaaaataaatctat ggagaaacgggtcccaagataaatgtgtctagtcatataagattattcaaaattaagaatttatcacatttgtaaaagatgtaagt -continued agcatatgtaaatgataaaatgagaagtcacttgagatgttttgatcatgtcctacgtcgatcttcagaggtaccattccgtatac gtgattggtaagtaaaggtattaaaaagagacataatggacctaaattacgtgaaacgaaattgtcttgaaaagtctttcaaattt ttgaaatccatgtagacgaatcgaaaagtagggcacaatgaaatatgatcaaaggtttataatggtgatacaagttagttgggatt acgttttagttatgccagtatatttactttaatctaatattttcttggagtttttttaatcttattagaaatttacttaccaaaaat ttagagaacttgctagaacaatataattgataattcttcatatatattgtcttcgagctgtagaaacagccactaatgtttgcatt aggatatgttgtctacatcacacttattgtgtgttgccctcaccggaccctgcatgaacgtatgatgccttatgcaccgcgcccct tttaatattatttattaattaatatttcctgctagagttatactcctttgttattactcattcttaggttgatgattaacttataa tatgcttaatctttatactaaaaatagaagagaattggttagctatgagattccaaggccaaatattggaatccataggtttgta tttgtacttttcaagcaaagacgaagacaatcagttagccctcctacttcaagggaaaacttcaacactagaaattttgccgaaga aaatgatcttagccaacctgttgctgctgttttcttcaatgcacagcgagaaaccgccgcgcgaagacgctaa SEQ ID NO: 21: Amino acid sequence of the *N. tabacum* TFL1-4T gene derived from SEQ ID NO: 19 or SEQ ID NO: 20.
MARSLEPLIVGRVVGDVLDSFSPIVKMTITYNNKLVCNGHEFFPSIVTSRPKVEVQGGDLRTFFTLVMTDPDVPGPSDPYLREHLH WIVTDIPGTTDATFGRELVSYEIPRPNIGIHRFVFVLFKQRRRQSVSPPTSRENFNTRNFAEENDLSQPVAAVFFNAQRETAARRR SEQ ID NO: 22: DNA sequence of *N. tabacum* TFL1-1S/T sense RNAi target sequence
agttaaaatgacagtcacttacaacaataaacaagtttgcaatggccaagagctcttc SEQ ID NO: 23: DNA sequence of *N. tabacum* TFL1-1S/T antisense RNAi target sequence
Gaagagctcttggccattgcaaacttgtttattgttgtaagtgactgtcattttaact SEQ ID NO: 24: DNA sequence of an *N. tabacum* TFL1-1S/T RNAi construct
Ggtaccacaagtttgtacaaaaaagcaggctaagcttgtcgaccatggagttaaaatgacagtcacttacaacaataaacaagttt gcaatggccaagagctcttctggtaacctttaatgtttaaccgttcacatttctaatatttacttatttgtaacatgtcgtcacgt gttagtttcattctttttatgaaccaaacatgcatgcaaagatatttttagatatttggacggcgagtgagatttgaaactaggac cgtttgcctgatacaatattaaaatatgtaaccattttatgtacaagtttaaactgttgatagtagcatatttttttacttttattt aagtatactatattccaacaggtaagttaacgaagagctcttggccattgcaaacttgtttattgttgtaagtgactgtcatttta actggcgcgcccgggcaattgacccagctttcttgtacaaagtggtgagctc SEQ ID NO: 25: DNA sequence of *N. tabacum* TFL1-1S sense RNAi target sequence
tgcagtcactattagacctagggttgaagttcaaggtggtgatatgagaactttcttcacattggtcatcacagatcctgatgtac ct SEQ ID NO: 26: DNA sequence of *N. tabacum* TFL1-1S antisense RNAi target sequence
aggtacatcaggatctgtgatgaccaatgtgaagaaagttctcatatcaccaccttgaacttcaaccctaggtctaatagtgactg ca SEQ ID NO: 27: DNA sequence of *N. tabacum* TFL1-1T sense RNAi target sequence
tgcggtcaccattagacctagggttgaggttcaaggtggtgatatgagaactttcttcacattggtcatgacagaccctgatgttc ct SEQ ID NO: 28: DNA sequence of *N. tabacum* TFL1-1T antisense RNAi target sequence
aggaacatcagggtctgtcatgaccaatgtgaagaaagttctcatatcaccaccttgaacctcaaccctaggtctaatggtgaccg ca SEQ ID NO: 29: DNA sequence of *N. tabacum* TFL1-25/T sense target RNAi sequence
catgaactctttccttcctcagtcacctctaaacctagggttgaagttcatggaggtgatttgagatctttctttaca SEQ ID NO: 30: DNA sequence of *N. tabacum* TFL1-25/T antisense target RNAi sequence
tgtaaagaaagatctcaaatcacctccatgaacttcaaccctaggtttagaggtgactgaggaaggaaagagttcatg SEQ ID NO: 31: DNA sequence of an *N. tabacum* TFL1-25/T RNAi construct
ggtaccacaagtttgtacaaaaaagcaggctaagcttgtcgaccatggcatgaactctttccttcctcagtcacctctaaacctag ggttgaagttcatggaggtgatttgagatctttctttacatggtaacctttaatgtttaaccgttcacatttctaatatttactta tttgtaacatgtcgtcacgtgttagtttcattctttttatgaaccaaacatgcatgcaaagatatttttagatatttggacggcga gtgagatttgaaactaggaccgtttgcctgatacaatattaaaatatgtaaccattttatgtacaagtttaaactgttgatagtag catatttttttacttttatttaagtatactatattccaacaggtaagttaactgtaaagaaagatctcaaatcacctccatgaactt -continued caaccctaggtttagaggtgactgaggaaggaaagagttcatgggcgcgcccgggcaattgacccagctttcttgtacaaagtggt gagctc SEQ ID NO: 32: DNA sequence of *N. tabacum* TFL1-25 sense target RNAi sequence
gaaagaaatagttggctatgaaatgccaaggccaaatattggaattcacaggtttgtatttctgctgttcaagcagaagaagaggc aaacagtattgactgcacctctctccagggatcga SEQ ID NO: 33: DNA sequence of *N. tabacum* TFL1-2S antisense target RNAi sequence
tcgatccctggagagaggtgcagtcaatactgtttgcctcttcttctgcttgaacagcagaaatacaaacctgtgaattccaatat ttggccttggcatttcatagccaactatttctttc SEQ ID NO: 34: DNA sequence of *N. tabacum* TFL1-2T sense target RNAi sequence
gagagaaatagttgggtatgaaatgccaaggccaaatattggaatccacagcagctttcttcaattgccagagggaaaccgctgcc agaaggcgttgaagaagatgttta SEQ ID NO: 35: DNA sequence of *N. tabacum* TFL1-2T antisense target RNAi sequence
taaacatcttcttcaacgccttctggcagcggtttccctctggcaattgaagaaagctgctgtggattccaatatttggccttggc atttcatacccaactatttctctc SEQ ID NO: 36: DNA sequence of *N. tabacum* TFL1-3T sense target RNAi sequence
atggctcaaatgacagatccccttgtgattagtagggtggttggagatgttgttgattatttctctccaagtgttaagatgtgtgt tatttataaccccagtaagcatgtctataatgggcatgaactctttccatcc SEQ ID NO: 37: DNA sequence of *N. tabacum* TFL1-3T antisense target RNAi sequence
ggatggaaagagttcatgcccattatagacatgcttactggggttataaataacacacatcttaacacttggagagaaataatcaa caacatctccaaccaccctactaatcacaaggggatctgtcatttgagccat SEQ ID NO: 38: DNA sequence of an *N. tabacum* TFL1-3T RNAi construct
ggtaccacaagtttgtacaaaaaagcaggctaagcttgtcgaccatggatggctcaaatgacagatccccttgtgattagtagggt ggttggagatgttgttgattatttctctccaagtgttaagatgtgtgttatttataaccccagtaagcatgtctataatgggcatg aactctttccatcctggtaacctttaatgtttaaccgttcacatttctaatatttacttatttgtaacatgtcgtcacgtgttagt ttcattctttttatgaaccaaacatgcatgcaaagatatttttagatatttggacggcgagtgagatttgaaactaggaccgtttg cctgatacaatattaaaatatgtaaccattttatgtacaagtttaaactgttgatagtagcatatttttttacttttatttaagtat actatattccaacaggtaagttaacggatggaaagagttcatgcccattatagacatgcttactggggttataaataacacacatc ttaacacttggagagaaataatcaacaacatctccaaccaccctactaatcacaaggggatctgtcatttgagccatggcgcgccc gggcaattgacccagctttcttgtacaaagtggtgagctc SEQ ID NO: 39: DNA sequence of *N. tabacum* TFL1-4T sense target RNAi sequence
tagtcctatagtgaaaatgacaattacttataacaacaaattagtgtgcaatggtcatgaattctttccttctattgtcacttcta gacctaa SEQ ID NO: 40: DNA sequence of *N. tabacum* TFL1-4T antisense target RNAi sequence
ttaggtctagaagtgacaatagaaggaaagaattcatgaccattgcacactaatttgttgttataagtaattgtcattttcactat aggacta SEQ ID NO: 41: DNA sequence of an *N. tabacum* TFL1-4T RNAi construct
Ggtaccacaagtttgtacaaaaaagcaggctaagcttgtcgaccatggtagtcctatagtgaaaatgacaattacttataacaaca aattagtgtgcaatggtcatgaattctttccttctattgtcacttctagacctaatggtaacctttaatgtttaaccgttcacatt tctaatatttacttatttgtaacatgtcgtcacgtgttagtttcattctttttatgaaccaaacatgcatgcaaagatatttttag atatttggacggcgagtgagatttgaaactaggaccgtttgcctgatacaatattaaaatatgtaaccattttatgtacaagttta aactgttgatagtagcatatttttttacttttatttaagtatactatattccaacaggtaagttaacttaggtctagaagtgacaat agaaggaaagaattcatgaccattgcacactaatttgttgttataagtaattgtcattttcactataggactaggcgcgcccgggc aattgacccagctttcttgtacaaagtggtgagctc

The invention claimed is:

1. A mutant, non-naturally occurring or transgenic *Nicotiana* plant or part thereof comprising at least one mutation at:

position T143 or G129 in SEQ ID NO: 9;

position R120 or G129 or P131 in SEQ ID NO: 12; or position P110 or H86 in SEQ ID NO: 21.

2. The mutant, non-naturally occurring or transgenic *Nicotiana* plant or part thereof of claim 1, wherein the at least one mutation is at position T143 in SEQ ID NO: 9.

3. The mutant, non-naturally occurring or transgenic *Nicotiana* plant or part thereof of claim 2, wherein the at least one mutation is T143I.

4. The mutant, non-naturally occurring or transgenic *Nicotiana* plant or part thereof of claim 1, wherein the at least one mutation is at position G129 in SEQ ID NO: 9.

5. The mutant, non-naturally occurring or transgenic *Nicotiana* plant or part thereof of claim 4, wherein the at least one mutation is G129R.

6. The mutant, non-naturally occurring or transgenic *Nicotiana* plant or part thereof of claim 4, wherein the at least one mutation is G129E.

7. The mutant, non-naturally occurring or transgenic *Nicotiana* plant or part thereof of claim 1, wherein the at least one mutation is at position R120 in SEQ ID NO: 12.

8. The mutant, non-naturally occurring or transgenic *Nicotiana* plant or part thereof of claim 7, wherein the at least one mutation is R120C.

9. The mutant, non-naturally occurring or transgenic *Nicotiana* plant or part thereof of claim 1, wherein the at least one mutation is at position G129 in SEQ ID NO: 12.

10. The mutant, non-naturally occurring or transgenic *Nicotiana* plant or part thereof of claim 9, wherein the at least one mutation is G129E.

11. The mutant, non-naturally occurring or transgenic *Nicotiana* plant or part thereof of claim 1, wherein the at least one mutation is at position P110 in SEQ ID NO: 21.

12. The mutant, non-naturally occurring or transgenic *Nicotiana* plant or part thereof of claim 11, wherein the at least one mutation is P110L.

13. The mutant, non-naturally occurring or transgenic *Nicotiana* plant or part thereof of claim 1, wherein the at least one mutation is at position H86 in SEQ ID NO: 21.

14. The mutant, non-naturally occurring or transgenic *Nicotiana* plant or part thereof of claim 13, wherein the at least one mutation is H86STOP.

15. Plant material derived from the mutant, non-naturally occurring or transgenic *Nicotiana* plant of claim 1; or a *Nicotiana* plant product comprising at least a part of the mutant, non-naturally occurring or transgenic *Nicotiana* plant of claim 1 or said *Nicotiana* plant material, wherein said plant material comprises the at least one mutation at: position T143 or G129 in SEQ ID NO: 9; position R120 or G129 or P131 in SEQ ID NO: 12; or position P110 or H86 in SEQ ID NO: 21.

16. The mutant, non-naturally occurring or transgenic *Nicotiana* plant or part thereof according to claim 1, wherein the plant is *Nicotiana tabacum.*

17. A mutant, non-naturally occurring or transgenic *Nicotiana* plant or part thereof comprising at least one mutation at position P131 in SEQ ID NO: 12.

18. The mutant, non-naturally occurring or transgenic *Nicotiana* plant or part thereof of claim 17, wherein the at least one mutation is P131S.

19. Plant material derived from the mutant, non-naturally occurring or transgenic *Nicotiana* plant of claim 17; or a *Nicotiana* plant product comprising at least a part of the mutant, non-naturally occurring or transgenic *Nicotiana* plant of claim 17 or said *Nicotiana* plant material, wherein said plant material comprises the at least one mutation at position P131 in SEQ ID NO: 12.

20. The mutant, non-naturally occurring or transgenic *Nicotiana* plant or part thereof according to claim 17, wherein the plant is *Nicotiana tabacum.*

* * * * *

SEQUENCE LISTING

<160> NUMBER OF SEQ ID NOS: 57

<210> SEQ ID NO 1
<211> LENGTH: 3539
<212> TYPE: DNA
<213> ORGANISM: Nicotiana tabacum

<400> SEQUENCE: 1
tgtttattgt acattttgaa ctgcatcgag ctgcacgatt gacagatcta gtctgcaaca 60
gagtactttg gtttctaatt atagtaatcc taacacctca gaaatttcca aaattggaat 120
tatgggtgca aatcatcttt atatatactc tcaaatgact tctcagatct tacggtcact 180
aattgtctgt aaattaagta tggtggagtt cactttatat actctgagcg gtgtgcccat 240
cctcctccat cagaatatca cttaaaacaa ttaacgtact ttataatctt tccctattgt 300
ttacacacaa tttaggaaag tttctaacaa agataagccc atatttcaag attagtgtct 360
taggattacc ctaaatgaaa aaagcaatag attccctggc aatatgttta cttatatttt 420
gaatttttgc aaaaaaaata aataaatgtg tgtcaacttg cttagttggg accacatgca 480
aaaactaatt caaggatttc atctgataat tttatagtgg agaggaaaag gcttggatta 540
atttaagtac ttattatgta gggcaaatat cacttttagc ctgcggccac catatttata 600
ttcaagccgt aaaagtgtat aaaatttgta ttttttata tataatatac ggaaatgtgt 660
gtatatatat atatatatat atatatatat atatataaga aatataaaaa aaattggcta 720
ttatttttca gagcagctat acaatatcat tttccatatc aggtaagctg aacaacaaat 780
catggaccaa ttcgaagagc accagtcagg tgtgaaagag aactgacatg atagcataaa 840
atacatatca ctaactcctc cacatctaag agcatacatt taatttccta tatggaagat 900
aagattaatt agaaaagtgt ttgataaagc taagatatgt tagtaccagt ttgtagtatc 960
cagttgaaat tttagtgtca acttaaggat aattttacta tgattagaag acagttatac 1020
attcacaaag tttctgaaag gaacttataa gtcttctttt tattgtactt acatttgtca 1080
agtcatatat agtacatatg acccctccta aaggaaaaga aagtagggaa agtaccaagc 1140
tagggcatat ttaaaggaaa ataaaatggc aattttaaga tgttagagta agggcagggg 1200
taggccaaag aagtattggg gagaagtgat tagacaagac atgccactgc ttcacctaac 1260
cgcggacata actagcgata ggaagatgtg gaggtcgaga attaaggttg tgagttgaca 1320
ggtagttatg agtttactag taatactagt actattcttg tattctttta ttcttagttt 1380
tttattactt tgttatgtca ctcgcttcca ttactagtta tctgttgtta ttgcttgttg 1440
ctttattttt accatttttt tagccgaggg tctatcaaaa acagtctctc tgcctttata 1500
ggataggggt aaggctgcgt acacactacc ctttccagac cccacgtatg ggattaatcc 1560
gagtttgttg ttgttgttgt tgttgatgtt gttgttgttg aaaaggaaac gtttataatt 1620
aagtacatgt attaagattt cattattttc ggggaagaat ttcgaatgta tttaaaccat 1680
aaaacgtcat tctcctgcaa gtatttttgg tgatcaagat aagtatagtt aaaaattgag 1740
caatcttctt tgcctacgat gtcctgtata aaactaacaa agaaaaaatt cagtttattt 1800
ttcaggggta gggttacttt ttttttaaaa aatattctat ttgaagttcc ataaaatccc 1860 atttttttatt tgcaactata ttgagtagat gttccgagac agcaactata agtgaggctc 1920
tatttcactg ttcaaccaaa atctctcaca agctaagttc cttgcaatcc aaaagatctc 1980
tctctctctc tctctctcta atggcaagga atgtagagcc tctagtagta gggagagtag 2040
taggggatgt tcttgattca tttagtccca cagttaaaat gacagtcact tacaacaata 2100

```
aacaagtttg caatggccaa gagctcttcc cttctgcagt cactattaga cctagggttg   2160

aagttcaagg tggtgatatg agaactttct tcacattggt aacttttcta attttccttc   2220

aggttattaa cttttcattg ctatatagac atctttcaaa cctgtctaga agattctttt   2280

cttgagctga gggttcggag acagcctctc tatcccacac aagataaggt taacgtctgc   2340

atataccttg ccgtcccctg acaccacata tgggattata ctgcgtatgt tgttgttgtt   2400

gtattgctat atagacatct ttgataaatc actaatcatg catgatatta ttcttcttat   2460

tgtaggtcat cacagatcct gatgtacctg gccctagtga tccgtatctg agagaacatg   2520

ttcactggta tgtactacat tcaagaaaat ctatggaaaa aaaataacta gaagagatga   2580

gtccaaaaga aaggagatta attattgttt gatttgtatt ttttatttgc attagattaa   2640

gtcatgcaat tacctagtaa taaattcgtt ataaggacat acacaaaagg tatgctcaac   2700

ataattaaag aaagaaaagc ataagcatta tattcttata tgcaagctcc caatctgatt   2760

gtggcgaagc taagaatttc ttcgggtgtt taaatttaaa agaagtgaaa aaaaatccga   2820

taaaaaattt atgtgttata tacctctaaa acttaatatt gtacctatat acatattgta   2880

atttttcgac gaatgaccac tcttattgcc catgctgcca atgccaatat gtaaaatact   2940

tcgccaatag acaaatatgt atcacattaa ttagttacct aaataggtaa ttatccataa   3000

taagtgggac tcgtaacttg aaaaatatgg ttagtaattt gctacaacat gttaagatac   3060

agtgagaatg taaatgtata tatgtccttt cacgccgtcg taagtttata taagttaaat   3120

ctggttaaca atgtaggtca tcataacact cacaattggg aataataact cttaatcata   3180

cttctttaca ttcatatttg caggatagtg actgatattc caggaactac agatgccacc   3240

tttggtaaat tggctatttt ggtttctttt attaagctgg tgtttgacat gctagaatta   3300

atgtacttta attttgagca ggaaaagagt tggttagcta tgagatccca aggcctaata   3360

ttggaataca taggtttgtg tttgttctct ttaagcagaa atgcagacaa tcagtcagcc   3420

cacctacttc aagggatcat ttcaacactc gcaactttgc caacgtaaat gaccttggtc   3480

cgcctgtcgc cgccgtcttc ttcaatgcac aacgagagac cgccgccagg aggcgctaa    3539
```

<210> SEQ ID NO 2
<211> LENGTH: 1539
<212> TYPE: DNA
<213> ORGANISM: Nicotiana tabacum

<400> SEQUENCE: 2

```
atggcaagga atgtagagcc tctagtagta gggagagtag taggggatgt tcttgattca     60

tttagtccca cagttaaaat gacagtcact tacaacaata aacaagtttg caatggccaa    120

gagctcttcc cttctgcagt cactattaga cctagggttg aagttcaagg tggtgatatg    180

agaactttct tcacattggt aacttttcta attttccttc aggttattaa cttttcattg    240

ctatatagac atctttcaaa cctgtctaga agattctttt cttgagctga gggttcggag    300

acagcctctc tatcccacac aagataaggt taacgtctgc atataccttg ccgtcccctg    360

acaccacata tgggattata ctgcgtatgt tgttgttgtt gtattgctat atagacatct    420

ttgataaatc actaatcatg catgatatta ttcttcttat tgtaggtcat cacagatcct    480

gatgtacctg gccctagtga tccgtatctg agagaacatg ttcactggta tgtactacat    540

tcaagaaaat ctatggaaaa aaaataacta gaagagatga gtccaaaaga aaggagatta    600

attattgttt gatttgtatt ttttatttgc attagattaa gtcatgcaat tacctagtaa    660
```

-continued

```
taaattcgtt ataaggacat acacaaaagg tatgctcaac ataattaaag aaagaaaagc    720

ataagcatta tattcttata tgcaagctcc caatctgatt gtggcgaagc taagaatttc    780

ttcgggtgtt taaatttaaa agaagtgaaa aaaaatccga taaaaaattt atgtgttata    840

tacctctaaa acttaatatt gtacctatat acatattgta atttttcgac gaatgaccac    900

tcttattgcc catgctgcca atgccaatat gtaaaatact tcgccaatag acaaatatgt    960

atcacattaa ttagttacct aaataggtaa ttatccataa taagtgggac tcgtaacttg   1020

aaaaatatgg ttagtaattt gctacaacat gttaagatac agtgagaatg taaatgtata   1080

tatgtccttt cacgccgtcg taagtttata taagttaaat ctggttaaca atgtaggtca   1140

tcataacact cacaattggg aataataact cttaatcata cttctttaca ttcatatttg   1200

caggatagtg actgatattc caggaactac agatgccacc tttggtaaat tggctatttt   1260

ggtttctttt attaagctgg tgtttgacat gctagaatta atgtacttta attttgagca   1320

ggaaaagagt tggttagcta tgagatccca aggcctaata ttggaataca taggtttgtg   1380

tttgttctct ttaagcagaa atgcagacaa tcagtcagcc cacctacttc aagggatcat   1440

ttcaacactc gcaactttgc caacgtaaat gaccttggtc cgcctgtcgc cgccgtcttc   1500

ttcaatgcac aacgagagac cgccgccagg aggcgctaa                          1539
```

<210> SEQ ID NO 3
<211> LENGTH: 172
<212> TYPE: PRT
<213> ORGANISM: Nicotiana tabacum

<400> SEQUENCE: 3

```
Met Ala Arg Asn Val Glu Pro Leu Val Val Gly Arg Val Val Gly Asp
1               5                   10                  15

Val Leu Asp Ser Phe Ser Pro Thr Val Lys Met Thr Val Thr Tyr Asn
            20                  25                  30

Asn Lys Gln Val Cys Asn Gly Gln Glu Leu Phe Pro Ser Ala Val Thr
        35                  40                  45

Ile Arg Pro Arg Val Glu Val Gln Gly Gly Asp Met Arg Thr Phe Phe
    50                  55                  60

Thr Leu Val Ile Thr Asp Pro Asp Val Pro Gly Pro Ser Asp Pro Tyr
65                  70                  75                  80

Leu Arg Glu His Val His Trp Ile Val Thr Asp Ile Pro Gly Thr Thr
                85                  90                  95

Asp Ala Thr Phe Gly Lys Glu Leu Val Ser Tyr Glu Ile Pro Arg Pro
            100                 105                 110

Asn Ile Gly Ile His Arg Phe Val Phe Val Leu Phe Lys Gln Lys Cys
        115                 120                 125

Arg Gln Ser Val Ser Pro Pro Thr Ser Arg Asp His Phe Asn Thr Arg
    130                 135                 140

Asn Phe Ala Asn Val Asn Asp Leu Gly Pro Pro Val Ala Ala Val Phe
145                 150                 155                 160

Phe Asn Ala Gln Arg Glu Thr Ala Ala Arg Arg Arg
                165                 170
```

<210> SEQ ID NO 4
<211> LENGTH: 4283
<212> TYPE: DNA
<213> ORGANISM: Nicotiana tabacum

<400> SEQUENCE: 4

-continued

```
ttcgagtcgt gataagtgtt ttgcaaaaat ataagataag actgcatgcg tacaatagac     60
tcttttggtc cggccctttt ctggaccctg cgcataacgg aagcttagtg cacccggcaa    120
ccgtttttca acgttccaga tgcaagaata ttataaggag gctttttgac acttttaaat    180
ttaatctaat agagtttaag tttcatgcat cgactgtcaa aaaaatattt atataatcac    240
taatacgata attacaagtg aaatgctata ctaaacatta agtagtaacc taataaaacg    300
gtagctagct aatctactat atatcacgta gtattaaaat tacacttatg taaaaatctt    360
tacggtgtta agaataactt aaaagcaatt tagtaataca ttaatgagtg aaaaaggtga    420
agaggaaacg tggtgtgttt tgaactgcat cgagctgcac gattgacaga gctagtctgg    480
aacagagtac tttggtttct aattatagta atcctaacat ctcagaaatt tccataatag    540
gaattatggg tgcaaatcat ctttatatat actctcaaat taatgacttc tcagcaagta    600
ctgtcattgt ctgtaaatta agtatggtgg agttcacttt atactctgag cagtgtgccc    660
atcctcctcc atcacttaaa acaattaatg tactttataa tctttcccta ttgtttacac    720
acacaattta ggaaagtttt taacaaagac aagcccatgt ttcaagattt gtttcttagg    780
attaccctaa atgaaaaaag caatagattc cctggcaatt tacttatatt ttgaattttt    840
gcaaaaacaa aaagaaaaag tgacaacttg cttagttggg accacatgca aaaactaatt    900
taaggaattc atctgatatt tttatagtgg agaggaaaag ggctggatta atttaaatat    960
tccttatttg ccaaaattat ttatattcga tagctgtaaa aatatataaa atttgtatat   1020
ttgtttttgt atagtataca cggaaatgta tatatataca agaaattaaa aaaaaactat   1080
tattttcaga gcagttatac aatattattt tccctatcat gtaagcttag cttatcaaca   1140
aatcatggac caattctaag agctccattc aggtgtgaaa gagagctgac atgatagtat   1200
aaaatacaca tcactaactc ctccacattt gagagctata gattaatttc ctatatggaa   1260
gataagatta attagaaaag tgtttgaata agctaagatg tgttagtacc agtttgtaat   1320
atcaagctaa aattttagtg tcaatttaag gataatttta ctatgattag aagacaagtt   1380
atcattcaca aatttctgaa aggaacttat aagacttttt atttttattt tttattgtac   1440
ttacatttgt caattaagta catgtgaccc ctcctaaagg aaaagaaagt agggaaatta   1500
aagtaccaag ttagcgcata cttaaagcca aggtaagcaa aatggcaatt ttaaggtgtt   1560
gtagaggaaa cgtttataat taagtacacg tactaagatt tcattatttt cgtggaagaa   1620
atttagaatg tatttaaacc ataaaacgtc attctcgtgc aagtattttt ggtgatcaag   1680
ataagtatag ttaacgttga acaatcttct ttgcttacta tgtcttgtat aaaactaaca   1740
aagaaaaatt cagtttattt ttcaggggta gggttacttt tttaaaaaaa aatattctat   1800
ttgaagttcc ataagatccc atttttaatt tgtaactata ttgagtagat attccaagac   1860
agcaactata aatgaggatc tatttcaccg ttcaatcaaa atctctcaca agctaagttc   1920
ctagcaatcc aaaaaagatc tctctctctc tctctctctc tctctctctc tctctctctc   1980
tctctctctc tctctctcta atggcaagga atgtagagcc tctagttgta gggagagtag   2040
taggggatgt tcttgattca ttcagtccca aagttaaaat gacagtcact tacaacaata   2100
aacaagtttg caatggccaa gagctcttcc cttctgcggt caccattaga cctagggttg   2160
aggttcaagg tggtgatatg agaactttct tcacattggt aacttttcta aattctcctt   2220
aaggttatta acttttcatt tctatataga cacatcgagg gtcaacagag acaactctat   2280
ctcacacaag gtaggggtaa ggtattcgta taccctaccc ggcccacatg tgagatcaca   2340
ctgaatatgt tgttgttgtc gcatttaggg gtgtacaaat gaaactgaca aactgcacca   2400
```

-continued atctgataat ccgagtcaaa tcgagaaaaa atccgattat ggtttggttt gatttggttt 2460
ggtgatggaa aaaaccccga catatttggt tttgtttggt tttaactaaa aaaagtcaaa 2520
ccgaaaccaa accaaccaga cattatatgt gtagaaattt taaatatatt taatacataa 2580
aaatatttat ggtagtgtaa tttataaata tttcttaaga tttttcatag tttatctttt 2640
aacgtattat ttcaaacttg ggcttataat ttttggatgc tccaataagt tttatagtcc 2700
ataaatgtta gtaactcaaa taaatcctaa accaaaatca aatcaatact aatgctaata 2760
aaagacattc aattcaattg tactatgaat gaaaatagtg ttggatatat atttttatag 2820
tttttccacg gtttagataa aatgtataac ttatttttct ttgagtatgg ttagtcatgt 2880
aaataatctt attaatcata attttaaatt atgtttattt ttattatggc ttattaataa 2940
tatttaattt tttgtgcaat tttattatct ttattgttga atattttagt acaatgccac 3000
gactcatctc atatttatgt tattttattg aaaaacacct catatagttc tgcctcatta 3060
ggattaaaaa aatatttgga gcacaaattt tactttttgt gttatgaaga ctttatgaaa 3120
aaaaaataaa ataaaaaccc gaaaacccga aacctcgaga aaaatcgaga ttaaaaatcc 3180
gacttttatt ggtttggttt ggtatttaga tttaataacc cgatacaatt agtttggttt 3240
ggtaattaga aaatccgaat caaaccccta accgtgtaca cccctagtcg tattggtata 3300
tagacatctt tgataaatca ttaatcatgc atgatattct tcgatctcct tattgtaggt 3360
catgacagac cctgatgttc ctggccctag tgatccgtat ctgagagaac atcttcactg 3420
gtatgcacta tattcaagaa aagctatgga aaaaaataac tagatgagat aggtaaaaaa 3480
gaaaggagtt taatgattgt ttgatttgca ttaattatat taagtcatgc cattatctag 3540
taataaactg gttataagga catacacaaa aggtatggtc aacatataat caaagaaaga 3600
aaagcataag catccttatg caagctgcca atgtcatgta aaatacttcg ctaatagaca 3660
aatatatatt acattagtta cctaaaagat aggtatataa tcagtgggac tcctaactta 3720
aaaaataagg ttagtaatct gctataacga tacactgaga atcgtcgtcg tcagtttata 3780
agttaaaaat taatgtaggt catcacaaca ctcacaaaga gtgcctcaat tgggaagagt 3840
atgttatata gttagaattt atgttacata tggaaccaca gtactacaga aggataactc 3900
ttaaacatac ttctttacca tcatatttgc aggatagtga ctgatattcc aggaacaaca 3960
gatgccacct ttggtaagct cactattttg gcattttcat ttttccttca atttctttta 4020
gtatatagct aggttggttt ttgacatgct aattttgagc aggaaaagag ttggttagct 4080
atgagatccc acggcctaat attggaatac ataggtttgt gtttgttctg tttaagcaga 4140
aatgcagaca gtcagttagt ccacatgatg tttccagaga tcacttcaac actcgcaact 4200
ttgccaacgt aaacgatctt ggcccgcctg tcgccgccgt cttcttcaat gcacaacgag 4260
agaccgccgc caggagacgc taa 4283

<210> SEQ ID NO 5
<211> LENGTH: 2283
<212> TYPE: DNA
<213> ORGANISM: Nicotiana tabacum

<400> SEQUENCE: 5
atggcaagga atgtagagcc tctagttgta gggagagtag taggggatgt tcttgattca 60
ttcagtccca aagttaaaat gacagtcact tacaacaata aacaagtttg caatggccaa 120
gagctcttcc cttctgcggt caccattaga cctagggttg aggttcaagg tggtgatatg 180

-continued

```
agaactttct tcacattggt aacttttcta aattctcctt aaggttatta acttttcatt    240

tctatataga cacatcgagg gtcaacagag acaactctat ctcacacaag gtaggggtaa    300

ggtattcgta taccctaccc ggcccacatg tgagatcaca ctgaatatgt tgttgttgtc    360

gcatttaggg gtgtacaaat gaaactgaca aactgcacca atctgataat ccgagtcaaa    420

tcgagaaaaa atccgattat ggtttggttt gatttggttt ggtgatggaa aaaaccccga    480

catatttggt tttgtttggt tttaactaaa aaaagtcaaa ccgaaaccaa accaaccaga    540

cattatatgt gtagaaattt taaatatatt taatacataa aaatatttat ggtagtgtaa    600

tttataaata tttcttaaga tttttcatag tttatctttt aacgtattat ttcaaacttg    660

ggcttataat ttttggatgc tccaataagt tttatagtcc ataaatgtta gtaactcaaa    720

taaatcctaa accaaaatca aatcaatact aatgctaata aaagacattc aattcaattg    780

tactatgaat gaaaatagtg ttggatatat atttttatag tttttccacg gtttagataa    840

aatgtataac ttatttttct ttgagtatgg ttagtcatgt aaataatctt attaatcata    900

atttaaatt atgtttattt ttattatggc ttattaataa tatttaattt tttgtgcaat    960

tttattatct ttattgttga atattttagt acaatgccac gactcatctc atatttatgt   1020

tattttattg aaaaacacct catatagttc tgcctcatta ggattaaaaa aatatttgga   1080

gcacaaattt tactttttgt gttatgaaga ctttatgaaa aaaaaataaa ataaaaaccc   1140

gaaaacccga aacctcgaga aaaatcgaga ttaaaaatcc gacttttatt ggtttggttt   1200

ggtatttaga tttaataacc cgatacaatt agtttggttt ggtaattaga aaatccgaat   1260

caaaccccta accgtgtaca cccctagtcg tattggtata tagacatctt tgataaatca   1320

ttaatcatgc atgatattct tcgatctcct tattgtaggt catgacagac cctgatgttc   1380

ctggccctag tgatccgtat ctgagagaac atcttcactg gtatgcacta tattcaagaa   1440

aagctatgga aaaaaataac tagatgagat aggtaaaaaa gaaaggagtt taatgattgt   1500

ttgatttgca ttaattatat taagtcatgc cattatctag taataaactg gttataagga   1560

catacacaaa aggtatggtc aacatataat caaagaaaga aaagcataag catccttatg   1620

caagctgcca atgtcatgta aaatacttcg ctaatagaca aatatatatt acattagtta   1680

cctaaaagat aggtatataa tcagtgggac tcctaactta aaaaataagg ttagtaatct   1740

gctataacga tacactgaga atcgtcgtcg tcagtttata agttaaaaat taatgtaggt   1800

catcacaaca ctcacaaaga gtgcctcaat tgggaagagt atgttatata gttagaattt   1860

atgttacata tggaaccaca gtactacaga aggataactc ttaaacatac ttctttacca   1920

tcatatttgc aggatagtga ctgatattcc aggaacaaca gatgccacct ttggtaagct   1980

cactattttg gcattttcat ttttccttca atttctttta gtatatagct aggttggttt   2040

ttgacatgct aattttgagc aggaaaagag ttggttagct atgagatccc acggcctaat   2100

attggaatac ataggtttgt gtttgttctg tttaagcaga aatgcagaca gtcagttagt   2160

ccacatgatg tttccagaga tcacttcaac actcgcaact ttgccaacgt aaacgatctt   2220

ggcccgcctg tcgccgccgt cttcttcaat gcacaacgag agaccgccgc caggagacgc   2280

taa                                                                 2283
```

<210> SEQ ID NO 6
<211> LENGTH: 173
<212> TYPE: PRT
<213> ORGANISM: Nicotiana tabacum

<400> SEQUENCE: 6

```
Met Ala Arg Asn Val Glu Pro Leu Val Val Gly Arg Val Val Gly Asp
1               5                   10                  15

Val Leu Asp Ser Phe Ser Pro Lys Val Lys Met Thr Val Thr Tyr Asn
            20                  25                  30

Asn Lys Gln Val Cys Asn Gly Gln Glu Leu Phe Pro Ser Ala Val Thr
        35                  40                  45

Ile Arg Pro Arg Val Glu Val Gln Gly Gly Asp Met Arg Thr Phe Phe
    50                  55                  60

Thr Leu Val Met Thr Asp Pro Asp Val Pro Gly Pro Ser Asp Pro Tyr
65                  70                  75                  80

Leu Arg Glu His Leu His Trp Ile Val Thr Asp Ile Pro Gly Thr Thr
                85                  90                  95

Asp Ala Thr Phe Gly Lys Glu Leu Val Ser Tyr Glu Ile Pro Arg Pro
            100                 105                 110

Asn Ile Gly Ile His Arg Phe Val Phe Val Leu Phe Lys Gln Lys Cys
        115                 120                 125

Arg Gln Ser Val Ser Pro His Asp Val Ser Arg Asp His Phe Asn Thr
    130                 135                 140

Arg Asn Phe Ala Asn Val Asn Asp Leu Gly Pro Pro Val Ala Ala Val
145                 150                 155                 160

Phe Phe Asn Ala Gln Arg Glu Thr Ala Ala Arg Arg Arg
                165                 170


<210> SEQ ID NO 7
<211> LENGTH: 4296
<212> TYPE: DNA
<213> ORGANISM: Nicotiana tabacum

<400> SEQUENCE: 7

catgaccttt tagctactct taactcttct gattgttctg ctgtaacttg tccccttgag     60

ttaaatgtaa agttaaaggc taaagaaggg gatcctctcc ctaatcctga aaattataga    120

ggcctcgttg gtaagctaaa tttcctcact cacactaggc ctgacataag ttttgttgtg    180

caacatctta gtcagttcat gcaacagccc tgctttcctc acatgaaggc agctttgcac    240

ctgttgaggt atctcagaga cacttctaat tttggcctct tatactcgaa ttctactgat    300

ctctctttgc aggcttattg tgatagtgat tggggatcct gccctgataa ctggagattt    360

gtttctgatt tctgtttatt ctttggtggc agtctcattg ggtggaaatc taagaaacat    420

gcagtggtct ctttatcttc ggctgaagtt gagtatagat ctatgagcaa ggctgtggct    480

gaaattactt gggtgtgtag gcgtctatct gatcttgggg tctcttctgc ttctcttgtt    540

cctctccatt gtgacagtat ctctgccatt cacattgcct acaatcctgt cttctatgag    600

cggaccaaag acattgagtt ggattgccat tttgaacgta ccaagcttgc tgaaggtctc    660

atcagtttat ctcacatttc cagtgcttct cagctcgcga atgtcttcat caaacccctg    720

tgtgggcctt ctcaccatct tcatattcga aagttgggag ttctctcacc ctcctacttg    780

aggggggggct gttgagatag gctgaaatca gtgtggctca gacccaatta ttatttattt    840

atgtacatca gattaggccc attagttagt ctttagttag tcttttattt ctttacatat    900

attgggccat gtatacatac atagagaccc gattttgtaa tagttagatg attcattttt    960

cggttcttaa tcaataagaa atatctcgaa ctttctctct atctctcttt aaccctaaat   1020

tcttcttcgt tgaatctacg agaatgatga acattaacat tagaaaatgt agatttgatc   1080

aaatcttctt aatcttttgt ttatcatctt ttctaattgt tttgtatctg attgtatatt   1140
```

agttaaccac caaaattgct caaacaatct ggcttcaaat ttatctaacg tttgaatata 1200
tatatatggt tgaaacatga aaaataaatt tttgaagatg agatgaaaaa taatttttga 1260
aagttaaaat tgtatttgaa cacgtatttt acttgaaaag aatttgaaat tttgtgagca 1320
gaaaacttaa aaaattactc taaaactttt ttttgagatt tgaggatttt attttcaaaa 1380
ttttccataa aatggcttaa atctataagc aaaagatatt tgaaaataat ttttttttta 1440
aaaaagctct caaattttac agccaaacgg aagcttagga taaaaaaggg ggaaatgggg 1500
gagatgggtg ggcaggttgg gctgaagaga aatagacaac agtgcattaa catgtcaaat 1560
catctttatc cctctttcta aaccttacaa ggagtacttt ttattttctt ttttcttttt 1620
ttggccctaa taaaaattaa aacacatatt ctctagctgc taagctataa ctttaactca 1680
ttggcaccac gacgagtagg agaataacct ttttgggctt ttcttttctt ttctttggtc 1740
cccttttttt gaactatcaa tattttagtc caaacacacc tgactctaca gtgatctgat 1800
ggccactata aatattggct ttttgcaact ctcttctcac caaaatacaa atcggttgaa 1860
ctcttcatat ataatattcc cactactatt actcttaact ttaaatagat ttcttatata 1920
tgggttcaaa aatgtctgat ccccttgtga ttggtagagt gattggggaa gttgttgatt 1980
atttcactcc aagtgttaag atgtctgtta cttataacag cagcaagcat gtttataatg 2040
ggcatgaact ctttccttcc tcagtcacct ctaaacctag ggttgaagtt catggaggtg 2100
atttgagatc tttctttaca atggtacata ctgcttcctt cgattttcaa tacttttatt 2160
aggggtggag cttagcggcg gagccaagat tttaactaag gggagtcaaa atataaataa 2220
gtaagcacac aaaaaaatca agggggtcaa cgtatagtat atacacataa aattaagaat 2280
ttaacatatt tataccgtgt aattttccag cgaaggggtg tcaattgact ctccttgcca 2340
atgagtggct ccgccactgg cggagctaga gttctagtta cggttcgttg tattgtgtta 2400
agaagtccac ttatactgtc ttttctagaa tttagaattc ataaattcaa aattatggct 2460
ctgcccttaa atttattttt atacatttct attatatagt aaatcgttta tattgacccc 2520
ttatttttct tttttacctt aattgacaga tcatgataga cccagatgtt cctggtccta 2580
gtgatccata tctcagggaa cacctacact ggtaaagaaa taagtttttt aattactaac 2640
tcattcaatt ttatcgtccc ttcttttcct tgtttacttg gagggaaaat aatacgatct 2700
catcgaaaag ataaaaattc ttcaggcttg ttatctaaaa acttgttaaa aaataccgta 2760
atgaaaagac atatgagttt gttattaggt atttgactaa atatgatcga tcatatggtg 2820
ttcggacaag aaatattttg tgaaaaggtc cgcatacttt taaaaaaaga aaatctgcct 2880
tgactcttga gtttgtgctt ctcgggaaaa caatttcttc cttctttttt tttttttttt 2940
tggtttattg acctttacat attaaagaca ccactgagac acatatctag aaaaattgta 3000
tttgggaacg caaaagcaaa gaaaacatgt gttattaatc ttatgtcaat gccaccagca 3060
gctcaggaaa aatatggtcg atatattgtg atttgcttgc aaaaggagca aagaagaaat 3120
cttttgataa tgtttgttat gacgatgtac ttaaagcaaa taagttagag gtcgtttggt 3180
acatgggata aggataataa ttttgggata aagtttagga ttaactttat cttatatttg 3240
gtttggagta ttagctaacc gcgaggtatt tttcaaacta aaatagtggg attagctatc 3300
ccatataaaa agtaggatag ctaatcccat gggatatccc accctatcgg atagtaatag 3360
tccaatagga gacaactcta atttgtacag acataatgtc cagtcacacc ttgttttttt 3420
gtcatgacac atattaagca tgaataataa tatttcgaca atcttgtagc atttgattag 3480

-continued acttagcaaa ttataaatat gtccaataat tggtcacatt gttctaataa ttacttgttt 3540
cccttatcat tatatatagt gcttcattca ctaaacagaa cccaaaaaaa aaaaaaaaaa 3600
aactgcaaaa tggtcatatc atgtagtaac ggaataaaaa cgtactcagt tttatgataa 3660
aatcaaagtg acatatttgt acgctttgat agttgacaaa tacctgaaaa aagaatttga 3720
ccatctttac aggattgtca cagacattcc aggcactaca gattgctcgt ttggtatgta 3780
tctttaaccc aaatttcaag cttcgaaata gtaacagctt ttgtttttaa tattttattt 3840
gtcttaaata catattttcc ttattataaa tttcttcgcc tagtggtaac gggatcaggt 3900
attgattcgt atttattttt tattgatcaa caaaaaaaga gtacaaaaga aagaattgtt 3960
tttctacact tagatttata tatatgcaat gtctagaaat taatgagttt acaaattcat 4020
tgatgtgtat atctcacaat caaatccaaa atactgatcc aaaaattttg atcagggaaa 4080
gaaatagttg gctatgaaat gccaaggcca aatattggaa ttcacaggtt tgtatttctg 4140
ctgttcaagc agaagaagag gcaaacagta ttgactgcac ctctctccag ggatcgattt 4200
aatacgcgta aattcgcaga agaaaatgag cttgggtctc ctgttgcagc agttttcttc 4260
aattgccaga gggaaactgc tgccagaagg cgttga 4296

<210> SEQ ID NO 8
<211> LENGTH: 2296
<212> TYPE: DNA
<213> ORGANISM: Nicotiana tabacum

<400> SEQUENCE: 8
atgtctgtta cttataacag cagcaagcat gtttataatg ggcatgaact ctttccttcc 60
tcagtcacct ctaaacctag ggttgaagtt catggaggtg atttgagatc tttctttaca 120
atggtacata ctgcttcctt cgattttcaa tacttttatt aggggtggag cttagcggcg 180
gagccaagat tttaactaag gggagtcaaa atataaataa gtaagcacac aaaaaaatca 240
agggggtcaa cgtatagtat atacacataa aattaagaat ttaacatatt tataccgtgt 300
aattttccag cgaaggggtg tcaattgact ctccttgcca atgagtggct ccgccactgg 360
cggagctaga gttctagtta cggttcgttg tattgtgtta agaagtccac ttatactgtc 420
ttttctagaa tttagaattc ataaattcaa aattatggct ctgcccttaa atttattttt 480
atacatttct attatatagt aaatcgttta tattgacccc ttatttttct tttttacctt 540
aattgacaga tcatgataga cccagatgtt cctggtccta gtgatccata tctcagggaa 600
cacctacact ggtaaagaaa taagtttttt aattactaac tcattcaatt tttatcgtccc 660 ttcttttcct tgtttacttg gagggaaaat aatacgatct catcgaaaag ataaaaattc 720
ttcaggcttg ttatctaaaa acttgttaaa aaataccgta atgaaaagac atatgagttt 780
gttattaggt atttgactaa atatgatcga tcatatggtg ttcggacaag aaatattttg 840
tgaaaaggtc cgcatacttt taaaaaaaga aaatctgcct tgactcttga gtttgtgctt 900
ctcgggaaaa caatttcttc cttctttttt tttttttttt tggtttattg acctttacat 960
attaaagaca ccactgagac acatatctag aaaaattgta tttgggaacg caaaagcaaa 1020
gaaaacatgt gttattaatc ttatgtcaat gccaccagca gctcaggaaa aatatggtcg 1080
atatattgtg atttgcttgc aaaaggagca aagaagaaat cttttgataa tgtttgttat 1140
gacgatgtac ttaaagcaaa taagttagag gtcgtttggt acatgggata aggataataa 1200
ttttgggata aagtttagga ttaactttat cttatatttg gtttggagta ttagctaacc 1260
gcgaggtatt tttcaaacta aaatagtggg attagctatc ccatataaaa agtaggatag 1320

```
ctaatcccat gggatatccc accctatcgg atagtaatag tccaatagga gacaactcta   1380

atttgtacag acataatgtc cagtcacacc ttgttttttt gtcatgacac atattaagca   1440

tgaataataa tatttcgaca atcttgtagc atttgattag acttagcaaa ttataaatat   1500

gtccaataat tggtcacatt gttctaataa ttacttgttt cccttatcat tatatatagt   1560

gcttcattca ctaaacagaa cccaaaaaaa aaaaaaaaaa aactgcaaaa tggtcatatc   1620

atgtagtaac ggaataaaaa cgtactcagt tttatgataa aatcaaagtg acatatttgt   1680

acgctttgat agttgacaaa tacctgaaaa aagaatttga ccatctttac aggattgtca   1740

cagacattcc aggcactaca gattgctcgt ttggtatgta tctttaaccc aaatttcaag   1800

cttcgaaata gtaacagctt ttgtttttaa tattttattt gtcttaaata catattttcc   1860

ttattataaa tttcttcgcc tagtggtaac gggatcaggt attgattcgt atttattttt   1920

tattgatcaa caaaaaaaga gtacaaaaga aagaattgtt tttctacact tagatttata   1980

tatatgcaat gtctagaaat taatgagttt acaaattcat tgatgtgtat atctcacaat   2040

caaatccaaa atactgatcc aaaaattttg atcagggaaa gaaatagttg gctatgaaat   2100

gccaaggcca aatattggaa ttcacaggtt tgtatttctg ctgttcaagc agaagaagag   2160

gcaaacagta ttgactgcac ctctctccag ggatcgattt aatacgcgta aattcgcaga   2220

agaaaatgag cttgggtctc ctgttgcagc agttttcttc aattgccaga gggaaactgc   2280

tgccagaagg cgttga                                                   2296

<210> SEQ ID NO 9
<211> LENGTH: 148
<212> TYPE: PRT
<213> ORGANISM: Nicotiana tabacum

<400> SEQUENCE: 9

Met Ser Val Thr Tyr Asn Ser Ser Lys His Val Tyr Asn Gly His Glu
1               5                   10                  15

Leu Phe Pro Ser Ser Val Thr Ser Lys Pro Arg Val Glu Val His Gly
            20                  25                  30

Gly Asp Leu Arg Ser Phe Phe Thr Met Ile Met Ile Asp Pro Asp Val
        35                  40                  45

Pro Gly Pro Ser Asp Pro Tyr Leu Arg Glu His Leu His Trp Ile Val
    50                  55                  60

Thr Asp Ile Pro Gly Thr Thr Asp Cys Ser Phe Gly Lys Glu Ile Val
65                  70                  75                  80

Gly Tyr Glu Met Pro Arg Pro Asn Ile Gly Ile His Arg Phe Val Phe
                85                  90                  95

Leu Leu Phe Lys Gln Lys Lys Arg Gln Thr Val Leu Thr Ala Pro Leu
            100                 105                 110

Ser Arg Asp Arg Phe Asn Thr Arg Lys Phe Ala Glu Glu Asn Glu Leu
        115                 120                 125

Gly Ser Pro Val Ala Ala Val Phe Phe Asn Cys Gln Arg Glu Thr Ala
    130                 135                 140

Ala Arg Arg Arg
145


<210> SEQ ID NO 10
<211> LENGTH: 4080
<212> TYPE: DNA
<213> ORGANISM: Nicotiana tabacum
```

<400> SEQUENCE: 10

```
agggcacgac cctaagacct tcttcatagc tataaatagt gagctcaggt ttcattgtaa     60
atggaacgac tattctggca aacttataca atattttata caaaactcaa ttcaatctta    120
tcttctgatt tctagattct ttttgttttt gtgcccgaaa accttgttcc tggaattgtt    180
gcttctgttg tttcgtccat atcttaaggc taagtgttat ataattcttc aattatttat    240
ttatttattt caggttcaaa ttaattcact tatctaaaaa tcatgtataa atttaattgt    300
accattttac gggtgaacag tttggcgccc atcgtggggc ctagataacc gtgtaactaa    360
aggacaaacg tcttttcggg aacttttcta ttttcaagaa ctcaaacccg agatttagac    420
ctctgaggga tctgatcatc tcactacatc gctgagtggt agttgattcc atatacgatt    480
aacctagttt acaactaaat taaattatgt gcattaatcc aagcaacttt tgatgatcag    540
ctgatcaacc taacgtaaga aagcaattaa tttagatgca tatattctac aaatggaaat    600
tagtaggagc aagcaagtta tgcaaaagaa aggaaaagag aaaacattag aagtaggcca    660
aagaaagaag aaggaagagg aagcaatcag ccactgttct agaatggaat atggagaaaa    720
ataataaatt aaattcagat ttctataagt agtaatcctc ttctttctat taccggttaa    780
agctgcagaa attttctttt tcttgacatg acctgaccat agcttccacc attgtttgca    840
ggctggtggt ggagtccctt tataccctca tctctcctac ctaagaacca taggattagg    900
tgattcaagt ttttattttt aacaaaaaat gaaaaattta tgaaggaagt tcaacttttt    960
attaccttaa ataaaaaaga ccttgatgct ttaagtagct ccaagacggt agctgcaaat   1020
tccatctgct tttccttttt aataaaataa tgtactacct actatctgaa agtttaactt   1080
ctatgattct gtaggttttg taaaacactt gggggtattt atattttata ggggattgca   1140
attagaggca gatacaattt ggtttagtta accaccgata ttactcaaac aatttggctt   1200
taaatctggt tagtgtttgg atatagattt ggttgaaatt tgaagaaaaa aaatgagttt   1260
ttaaaaatga gatgaaaaat aatttttgaa agttaaaatt gtatttggac atgcatttta   1320
tttgaaaaga atttgaagtt ttgtaagtta aaattttcaa aaacttcaaa aagttatttt   1380
tgagatttga agattttatt ttcaaaattt gcattataat ctataaacaa atagatacta   1440
tttgagaaca aaatttaaaa aataaagctt tcaaacttat gacgaaaggg aagcttagga   1500
taaaaagggg ggaaatggcc tgggagatgg gtgggcaggt tgggctgaag agaaatagac   1560
aacagtgcat taacatgtca aatcatcttt atccctcttt aaaaacatta ttaggagtac   1620
ttcttttttt cttggggtgc aaaagcctaa tacaagttaa aacacatatt ctctagctgc   1680
taagctataa ctttaactca ttggtaccac gacgagtagg agaataaact ttttgggctt   1740
ttcttttctt ttctttggtt cccatttttt gaactatcaa tattttagtc caaacacacc   1800
tgactctaca gtgatctgat ggccactata aatattggct ttttgcagct ccaaaataca   1860
aatcggtcga actcttcata tatattactc ttaactttaa ataaatagat ttcttatata   1920
tgggttcaaa aatgtctgat ccccttgtga ttggtagagt gataggggaa gttgttgatt   1980
atttcactcc aagtgttaag atgtctgtta cttataacag cagcaagcat gtctataatg   2040
gacatgaact ctttccttcc tcagtcacct ctaaacctag ggttgaagtt catggaggtg   2100
atttgagatc tttctttaca ctggtacata ctccttcgat tttcactact tttaatttat   2160
taggggcgaa gctagagttc tagctacggg ttcgttgtat taattgtgtt aagaagtcca   2220
cttaagctgt ctttttttaga atttagaatc cataaactca aaatagtgac tttgcttcta   2280
aattaatttt tatgcatttc tcttatatcg tgtatgtgaa tattgacccc ttattttttc   2340
```

```
tttttacct taattgacag atcatgatag acccagatgt tcctggtcct agtgatccat   2400
atctcaggga acatctacac tggtaaagac atacgttttt taattactaa ctcattcaat   2460
tttatcgccc cttcttttcc ttgtttactt ggagggaaaa taatacgatc tcgtcaagaa   2520
gatcaaaaat cttcaggctt gttatttagg aacttgttca aaaataccgt tttgaaaaga   2580
acatatgagt ttgttattag gtatttgact aaataggaac gatcatatgg tgttcggaca   2640
agaaaatttt tgtgaaaagg tccgcatact ttaaaaaaaa aaaaaaaaaa aaaaaatccg   2700
ccttgactct tgagtttctg cttcttggaa aaaacatttc ttcttttttt ttttgggttt   2760
tttgaccttt atatattaat taaagacacc actgagacac ttaattaaaa aattgtatat   2820
gggaacgcaa aaagaaaaaa aaacatgtgt tattaatctt atgtcaatgc catcagcaac   2880
tcaggaaaat acggtcgata tactgtgatt tgcttgcgaa aggagcaaag aagaaatctt   2940
ttgataatgt ttgttatgac gatgcactta acctaaaata agttaggggc cgtttggtaa   3000
atgaaataag gataataatc tcggaacaaa gtttaggatt aactttatcc catatttgat   3060
ttggagtatt agttaattgc gggataactt tcaaattaaa atagtaggat tagttatctc   3120
atatataaag taaaatacct aatcccaata atataatagg agacaactct aatttgcgta   3180
gacataatgt ccagtctcac tttgtatatt tgtcatgacg catattaagc atgaatgata   3240
atatttcgac aatcttgtgg catttgatta cactcagcaa attataaata tgtccaataa   3300
ttgcattaat aattacttgt tcctcttatc attatagtgc ctcattcact aaaccgaacc   3360
caaaagaaca ctgcaaaatg gtcatatcat gtagtaacag aaaaaaaaaa cgtactcgat   3420
tttatgataa aatcaaagtg acatatgtgt cgctttgata attgacaaat acctgaaaaa   3480
agaatttgac catctttaca ggattgtcac agacattcca ggcactacag attgctcgtt   3540
tggtatgtat ctttaaccca aagttcaagc tatgaaatag taacagcttt tctttttaat   3600
attttatttg tcttaaatac atattttcct tattataaat ttattcgcct agtggtaacg   3660
ggatcaggta ttgattcgta tttaattttt attgttcaac aaaaaagagt acaaaaagaa   3720
agaattgatt ttctacactt agatttatat gcaatatcta gaaatcagaa gatcagcaat   3780
gagtttacta attcatcgat gtgtatatcg cacaatcaaa tccaattact aataatactg   3840
atctaaaaat ttcgatcagg gagagaaata gttgggtatg aaatgccaag gccaaatatt   3900
ggaatccaca ggtttgtatt tctgctgttc aagcagaaga agaggcaaac attattgagt   3960
gcacctctct ccagggatcg atttaatacg cgcaaattct cagaagaaaa tgagcttggg   4020
tctcctgttg cagcagcttt cttcaattgc cagagggaaa ccgctgccag aaggcgttga   4080
```

<210> SEQ ID NO 11
<211> LENGTH: 2080
<212> TYPE: DNA
<213> ORGANISM: Nicotiana tabacum

<400> SEQUENCE: 11

```
atgtctgtta cttataacag cagcaagcat gtctataatg gacatgaact ctttccttcc     60
tcagtcacct ctaaacctag ggttgaagtt catggaggtg atttgagatc tttctttaca    120
ctggtacata ctccttcgat tttcactact tttaatttat taggggcgaa gctagagttc    180
tagctacggg ttcgttgtat taattgtgtt aagaagtcca cttaagctgt cttttttaga    240
atttagaatc cataaactca aaatagtgac tttgcttcta aattaatttt tatgcatttc    300
tcttatatcg tgtatgtgaa tattgacccc ttattttttc tttttacct taattgacag    360
```

```
atcatgatag acccagatgt tcctggtcct agtgatccat atctcaggga acatctacac    420

tggtaaagac atacgttttt taattactaa ctcattcaat tttatcgccc cttcttttcc    480

ttgtttactt ggagggaaaa taatacgatc tcgtcaagaa gatcaaaaat cttcaggctt    540

gttatttagg aacttgttca aaaataccgt tttgaaaaga acatatgagt ttgttattag    600

gtatttgact aaataggaac gatcatatgg tgttcggaca agaaaatttt tgtgaaaagg    660

tccgcatact ttaaaaaaaa aaaaaaaaaa aaaaaatccg ccttgactct tgagtttctg    720

cttcttggaa aaaacatttc ttcttttttt ttttgggttt tttgaccttt atatattaat    780

taaagacacc actgagacac ttaattaaaa aattgtatat gggaacgcaa aaagaaaaaa    840

aaacatgtgt tattaatctt atgtcaatgc catcagcaac tcaggaaaat acggtcgata    900

tactgtgatt tgcttgcgaa aggagcaaag aagaaatctt ttgataatgt ttgttatgac    960

gatgcactta acctaaaata agttaggggc cgtttggtaa atgaaataag gataataatc   1020

tcggaacaaa gtttaggatt aactttatcc catatttgat ttggagtatt agttaattgc   1080

gggataactt tcaaattaaa atagtaggat tagttatctc atatataaag taaaatacct   1140

aatcccaata atataatagg agacaactct aatttgcgta gacataatgt ccagtctcac   1200

tttgtatatt tgtcatgacg catattaagc atgaatgata atatttcgac aatcttgtgg   1260

catttgatta cactcagcaa attataaata tgtccaataa ttgcattaat aattacttgt   1320

tcctcttatc attatagtgc ctcattcact aaaccgaacc caaaagaaca ctgcaaaatg   1380

gtcatatcat gtagtaacag aaaaaaaaaa cgtactcgat tttatgataa aatcaaagtg   1440

acatatgtgt cgctttgata attgacaaat acctgaaaaa agaatttgac catctttaca   1500

ggattgtcac agacattcca ggcactacag attgctcgtt tggtatgtat ctttaaccca   1560

aagttcaagc tatgaaatag taacagcttt tctttttaat attttatttg tcttaaatac   1620

atattttcct tattataaat ttattcgcct agtggtaacg ggatcaggta ttgattcgta   1680

tttaattttt attgttcaac aaaaaagagt acaaaaagaa agaattgatt ttctacactt   1740

agatttatat gcaatatcta gaaatcagaa gatcagcaat gagtttacta attcatcgat   1800

gtgtatatcg cacaatcaaa tccaattact aataatactg atctaaaaat ttcgatcagg   1860

gagagaaata gttgggtatg aaatgccaag gccaaatatt ggaatccaca ggtttgtatt   1920

tctgctgttc aagcagaaga agaggcaaac attattgagt gcacctctct ccagggatcg   1980

atttaatacg cgcaaattct cagaagaaaa tgagcttggg tctcctgttg cagcagcttt   2040

cttcaattgc cagagggaaa ccgctgccag aaggcgttga                         2080
```

```
<210> SEQ ID NO 12
<211> LENGTH: 148
<212> TYPE: PRT
<213> ORGANISM: Nicotiana tabacum

<400> SEQUENCE: 12

Met Ser Val Thr Tyr Asn Ser Ser Lys His Val Tyr Asn Gly His Glu
1               5                   10                  15

Leu Phe Pro Ser Ser Val Thr Ser Lys Pro Arg Val Glu Val His Gly
            20                  25                  30

Gly Asp Leu Arg Ser Phe Phe Thr Leu Ile Met Ile Asp Pro Asp Val
        35                  40                  45

Pro Gly Pro Ser Asp Pro Tyr Leu Arg Glu His Leu His Trp Ile Val
    50                  55                  60

Thr Asp Ile Pro Gly Thr Thr Asp Cys Ser Phe Gly Arg Glu Ile Val
```

-continued

```
65                  70                  75                  80

Gly Tyr Glu Met Pro Arg Pro Asn Ile Gly Ile His Arg Phe Val Phe
                85                  90                  95

Leu Leu Phe Lys Gln Lys Lys Arg Gln Thr Leu Leu Ser Ala Pro Leu
            100                 105                 110

Ser Arg Asp Arg Phe Asn Thr Arg Lys Phe Ser Glu Glu Asn Glu Leu
        115                 120                 125

Gly Ser Pro Val Ala Ala Ala Phe Phe Asn Cys Gln Arg Glu Thr Ala
    130                 135                 140

Ala Arg Arg Arg
145


<210> SEQ ID NO 13
<211> LENGTH: 5167
<212> TYPE: DNA
<213> ORGANISM: Nicotiana tabacum

<400> SEQUENCE: 13

tgaagttgtg tttggacatg cgttgtattt gagaaaaaat tgaagttttg tgagaggaat     60

ttttttgacc ccaaaactac ataatttgaa ttattattta aaaaaaatga tcatattaca    120

tgaacaaaca gtgttttcaa tttatttttg aaaaaaacag ccaaaatcta gccaaatggg    180

agctaagtgt atgatcaaga ttcatgtccc aaatggaaaa gaatattaac aaaaaaaagg    240

gcagtaaaga agaggtggct acaataggat cgcgcaaaag aaagatggaa aaaagaggaa    300

caggaggggg gaataagcag cacaagaagt tattataagt cagctcttcc agaaaggaat    360

atggagaaaa gttaacctca ggtttctata aataggaatg tccaactttc atttactagt    420

ttaagctgca gaaattctct ttttcttgac atgacctttt caccatcttt aatttggtgg    480

gctttgtggt ggagtccctt tataccatag gctctcctag aggatccata acattagatt    540

ggtaaggttc taagtggact cacgatatga aatttgtgat cgaacctata actcgtctga    600

gttactgaat ttgtaataaa atatttatac atatttaata aattttctaa tataaataca    660

gaatctaaac aaaaactatt gagttcatcc gtaccgatac ctaatactct agctccaacc    720

ctgattctaa tataatgaaa ataaaaccac atctaggaag ttcatgacct gttcttacct    780

taaatgccaa aggccttaaa cctttgatag cttgagaata gccaaacaag tatagattcc    840

atctacttta attttctttc tgattaagat atattgcaac tcctgtaaat gcgcaaggag    900

tcagctggtt cttcccccat ttctatattt tttagtatca ctttcttttc ttaattattc    960

cttcttacat ttgaatcttt ttccatcagc tagctgtttt gatagtagta aaaatgcgaa   1020

ggctcttctt actaatattt caatgaccaa tgaatttaga tggagaagca agttctatta   1080

aacgttcatg ctagaaaata acaagtataa tatttcattt tcattttata taacgctctt   1140

gtcttttctt gtctatttaa acaagaatca atttaactct cttaatgaca tgctctttag   1200

tcacagaaaa attataacaa attgaagaca ttagttatta atgttctttt cgcactaaaa   1260

gtttttttaaa aatttttttat cttaaatgtt tgtgactaat caaatatcat catataaaat   1320

taatctggga atatgacatt tttcaatata actaatatgg tgcaaattgc atacactacg   1380

caataaattt gtggttaggg tcatatcatt agcctgtcaa atcatcttta tccctctttc   1440

tctaaacgac ttcttttctc ccttttttttt cgcccctcaa acaaagcaaa tagactattc   1500

tctagctgct aattagctaa acaatgactt taactcgttg tgcccagagg agaataacct   1560

ttatctctct tctcttttct ttgtttccat ctttaattta gacttctttt tttggttttt   1620
```

```
tatcccatat tcggtattta ttggagttcg attaaattca aatttataat aggaagtctc   1680
acattgagag tacgatgact ccatactcag gattcgaatt tgagatcttt agttaaagat   1740
gaaagaatat cattcaacca caacttttgt tggtcccatc tttatatcta tatgttctta   1800
ctatatttta atccatttcc cacttccaat gatttaaaga agctatagga taggtgcatt   1860
tggaccacta taaatatagg ttttgcagtt ctatgctcca tacaaatatc cagcaagaaa   1920
ctaaactata tatttactga gttactacta atagttttca ctcaatctat ttccactctt   1980
tctcctcttc attatattat atggctcaaa tgacagatcc ccttgtgatt agtagggtgg   2040
ttggagatgt tgttgattat ttctctccaa gtgttaagat gtgtgttatt tataacccca   2100
gtaagcatgt ctataatggg catgaactct ttccatccct tgttacctct aaacctaagg   2160
ttgaagttca tggaggtgac atgagatcct tctttacact ggtaattaat tcacactact   2220
tcaatagttt tcttgttctt atattttatt atctatctat atatatataa taaaggagcg   2280
gcaaagccac catataaatg acaaatgtaa acttttagga caaaactcca aaaaagttgg   2340
agttttaaaa ttattttata tataaaataa ataaataaat aaataaataa actatcaatt   2400
caaattgggg agtagtttct tactaatatg atagctatat ctatatctat atctatctat   2460
atatgtaaaa catttatatg atgccaagtg gcataaccac tgataagatt tttaaatttg   2520
aatatgaatg aattttaaat gaagttctaa cttcttaaaa ataaacccta atataggtta   2580
ctatttttag taatgattga aattattatt aaaatatttt gttgaaaaca acatagagat   2640
aaaatttgat tattaaattt atgtattaca acaataataa ttattgaaaa tattgctaaa   2700
attttcatga aaggattcac ccataattat tagtataata gaaaactaaa aaattattaa   2760
gtctaaagtt ctagatctct atatttataa acgtataaac tgttatttta ttttctgaaa   2820
aaagcaaaaa tactgaagag aaaaatgata aaaatatttt aaaatatgta agtcatgtgc   2880
aaataataaa gtgaacaaat gatgtagtag tatactgaat aagatatgtt tttttgtcat   2940
aaaataagta tatgcataac tcatctcaat aatttgctga ctccatctga gtcaaaatat   3000
cttctaaatt caagcgaaga taattatcta tcgcattatt tttttatcat taatataagg   3060
caagacgaat ctatatctca tatgggactt tttaaataga tacatcttta taaatgaacc   3120
actttatgag ttttatcacg aattacaagt aagaataact tgaagattga aagaattttt   3180
ggatttattt aattataata tatttttatt cattttaaat taatttatat tttcaaatta   3240
tttgtagcaa cctatataat tatgatattt gagtattatc ttataagtta tttgatgatt   3300
gtcgtttgat ttaattattg aactattact acaggggaca taagatgata attataattt   3360
tgtagaaaca tatgatctaa tgtgctcaaa taaattacta tcatactttg atatgactaa   3420
tattctttaa taatttttgc gcatcgggcg ggtactaata ctagttctta aaaaaagggt   3480
agcgcgatgc acaaagcatt ccgcattcac acaggatcct aggaattggg tcgcacccca   3540
cagtctaccc taatgcaaac attagcgact actttcacgg ctcgaactcg tcacttatag   3600
atcatacaga gacaaattta ctgttgctcc aagttccctt tcttatttta ttattcttat   3660
aatttctatt cttatattgt tataaattat tttttctttt ttgatagatc atgactgacc   3720
ctgatgttcc tggtcctagc gatccatatc ttagggagca cttacattgg tatgtatcat   3780
actatcatca actttgaaag cttaaaacac tgtaaagttg atgattcaca ccaaagattt   3840
taatcgtcgt cgtgttactt ccatataaat cagtatcgag aagtatgtgg ccatcactcc   3900
atcaacgaca ccaaaatgaa ataaagagtc cctatatcaa tacaatataa attaatctta   3960
aacatgaagt tgactttaaa ttggataaat tgtttccact actaagctta gcgtataaat   4020
```

```
tagtcctttg actttcaatt ttgtataata atgcgaagct ttttttcttg taaatgcaat   4080
ttttgtcctt gagggtttgc aacttctttt ttaaggaaaa aaaaaagact aaagttgtgt   4140
gacactaaaa ccaagagtta gcttaatact tcatggacac acgttagcat aaaacatata   4200
accgatattc aaaattacaa aaatgataga atcataattt ttgtttctat ttaaaaagga   4260
agtaagccaa attactacta acatagtgga cttaaagggt attaattttt tgttatttta   4320
atgatatctg ttcatgactt cttgactact tctactcctt tatatcaatc aaattataat   4380
ttacttcgtt tgactatcta atttacaggg taattacaga cattccaggc actacagatt   4440
cctcgtttgg tatggaataa tattgtattc ctttttttact tttctgccta gcatttctaa   4500
atagagtagt ccgatacacg aaatatttca ctttacgcag gatccagaaa taaaggacca   4560
taccccaatt gggtgtaata taagtagtca tgggcgcatg cagtatttta gtgacgggtt   4620
taattgcact cataatttttg gacgcttagc ataaagtagt agatatgtat ccataacttc   4680
aaaaatataa taggttcaat gttaaaaatt tcaaaagaga tgaactcata gagtttaaat   4740
catgatccgc ctctgtaggc agtctaccct aatgaaagaa tcagtggctg atttcacagt   4800
tcaaaaccgt aacctatgaa tcacataaag ccaactttac catcgctcca agactcgcct   4860
tcttctgcct aacattacta ctgctaataa agagaatttt aataaaacta ctaatgctaa   4920
ttattattct ttgctaaaat cttcatcagg aaaagaagtg gtgggctatg aaatgccaat   4980
gcctaacatt ggaatccata ggtttgtgtt tctgctcttc aagcagaaga agaggcaaac   5040
agtgagcgca ccattatcca gggaccgatt caatacgcgg aaatacgcag aagaaaatga   5100
gcttggctct ccagttgctg ctgttttctt caactgccaa agggaaaccg cggccagaaa   5160
gcgttga                                                             5167
```

<210> SEQ ID NO 14
<211> LENGTH: 3167
<212> TYPE: DNA
<213> ORGANISM: Nicotiana tabacum

<400> SEQUENCE: 14

```
atggctcaaa tgacagatcc ccttgtgatt agtagggtgg ttggagatgt tgttgattat     60
ttctctccaa gtgttaagat gtgtgttatt tataacccca gtaagcatgt ctataatggg    120
catgaactct ttccatccct tgttacctct aaacctaagg ttgaagttca tggaggtgac    180
atgagatcct tctttacact ggtaattaat tcacactact tcaatagttt tcttgttctt    240
atattttatt atctatctat atatatataa taaaggagcg gcaaagccac catataaatg    300
acaaatgtaa acttttagga caaaactcca aaaaagttgg agttttaaaa ttattttata    360
tataaaataa ataaataaat aaataaataa actatcaatt caaattgggg agtagtttct    420
tactaatatg atagctatat ctatatctat atctatctat atatgtaaaa catttatatg    480
atgccaagtg gcataaccac tgataagatt tttaaatttg aatatgaatg aattttaaat    540
gaagttctaa cttcttaaaa ataaacccta atataggtta ctatttttag taatgattga    600
aattattatt aaaatatttt gttgaaaaca acatagagat aaaatttgat tattaaattt    660
atgtattaca acaataataa ttattgaaaa tattgctaaa attttcatga aaggattcac    720
ccataattat tagtataata gaaaactaaa aaattattaa gtctaaagtt ctagatctct    780
atatttataa acgtataaac tgttatttta ttttctgaaa aaagcaaaaa tactgaagag    840
aaaaatgata aaaatatttt aaaatatgta agtcatgtgc aaataataaa gtgaacaaat    900
```

```
gatgtagtag tatactgaat aagatatgtt tttttgtcat aaaataagta tatgcataac    960
tcatctcaat aatttgctga ctccatctga gtcaaaatat cttctaaatt caagcgaaga   1020
taattatcta tcgcattatt tttttatcat taatataagg caagacgaat ctatatctca   1080
tatgggactt tttaaataga tacatcttta taaatgaacc actttatgag ttttatcacg   1140
aattacaagt aagaataact tgaagattga aagaattttt ggatttattt aattataata   1200
tatttttatt cattttaaat taatttatat tttcaaatta tttgtagcaa cctatataat   1260
tatgatattt gagtattatc ttataagtta tttgatgatt gtcgtttgat ttaattattg   1320
aactattact acaggggaca taagatgata attataattt tgtagaaaca tatgatctaa   1380
tgtgctcaaa taaattacta tcatactttg atatgactaa tattctttaa taatttttgc   1440
gcatcgggcg ggtactaata ctagttctta aaaaaagggt agcgcgatgc acaaagcatt   1500
ccgcattcac acaggatcct aggaattggg tcgcacccca cagtctaccc taatgcaaac   1560
attagcgact actttcacgg ctcgaactcg tcacttatag atcatacaga gacaaattta   1620
ctgttgctcc aagttccctt tcttatttta ttattcttat aatttctatt cttatattgt   1680
tataaattat tttttctttt ttgatagatc atgactgacc ctgatgttcc tggtcctagc   1740
gatccatatc ttagggagca cttacattgg tatgtatcat actatcatca actttgaaag   1800
cttaaaacac tgtaaagttg atgattcaca ccaaagattt taatcgtcgt cgtgttactt   1860
ccatataaat cagtatcgag aagtatgtgg ccatcactcc atcaacgaca ccaaaatgaa   1920
ataaagagtc cctatatcaa tacaatataa attaatctta aacatgaagt tgactttaaa   1980
ttggataaat tgtttccact actaagctta gcgtataaat tagtcctttg actttcaatt   2040
ttgtataata atgcgaagct tttttcttg taaatgcaat ttttgtcctt gagggtttgc   2100
aacttctttt ttaaggaaaa aaaaaagact aaagttgtgt gacactaaaa ccaagagtta   2160
gcttaatact tcatggacac acgttagcat aaaacatata accgatattc aaaattacaa   2220
aaatgataga atcataattt ttgtttctat ttaaaaagga agtaagccaa attactacta   2280
acatagtgga cttaaagggt attaattttt tgttatttta atgatatctg ttcatgactt   2340
cttgactact tctactcctt tatatcaatc aaattataat ttacttcgtt tgactatcta   2400
atttacaggg taattacaga cattccaggc actacagatt cctcgtttgg tatggaataa   2460
tattgtattc cttttttact tttctgccta gcatttctaa atagagtagt ccgatacacg   2520
aaatatttca ctttacgcag gatccagaaa taaaggacca taccccaatt gggtgtaata   2580
taagtagtca tgggcgcatg cagtatttta gtgacgggtt taattgcact cataattttg   2640
gacgcttagc ataaagtagt agatatgtat ccataacttc aaaaatataa taggttcaat   2700
gttaaaaatt tcaaaagaga tgaactcata gagtttaaat catgatccgc ctctgtaggc   2760
agtctaccct aatgaaagaa tcagtggctg atttcacagt tcaaaaccgt aacctatgaa   2820
tcacataaag ccaactttac catcgctcca agactcgcct tcttctgcct aacattacta   2880
ctgctaataa agagaatttt aataaaacta ctaatgctaa ttattattct ttgctaaaat   2940
cttcatcagg aaaagaagtg gtgggctatg aaatgccaat gcctaacatt ggaatccata   3000
ggtttgtgtt tctgctcttc aagcagaaga agaggcaaac agtgagcgca ccattatcca   3060
gggaccgatt caatacgcgg aaatacgcag aagaaaatga gcttggctct ccagttgctg   3120
ctgttttctt caactgccaa agggaaaccg cggccagaaa gcgttga                 3167
```

<210> SEQ ID NO 15
<211> LENGTH: 173

-continued

<212> TYPE: PRT
<213> ORGANISM: Nicotiana tabacum

<400> SEQUENCE: 15

```
Met Ala Gln Met Thr Asp Pro Leu Val Ile Ser Arg Val Val Gly Asp
1               5                   10                  15

Val Val Asp Tyr Phe Ser Pro Ser Val Lys Met Cys Val Ile Tyr Asn
            20                  25                  30

Pro Ser Lys His Val Tyr Asn Gly His Glu Leu Phe Pro Ser Leu Val
        35                  40                  45

Thr Ser Lys Pro Lys Val Glu Val His Gly Gly Asp Met Arg Ser Phe
    50                  55                  60

Phe Thr Leu Ile Met Thr Asp Pro Asp Val Pro Gly Pro Ser Asp Pro
65                  70                  75                  80

Tyr Leu Arg Glu His Leu His Trp Val Ile Thr Asp Ile Pro Gly Thr
                85                  90                  95

Thr Asp Ser Ser Phe Gly Lys Glu Val Val Gly Tyr Glu Met Pro Met
            100                 105                 110

Pro Asn Ile Gly Ile His Arg Phe Val Phe Leu Leu Phe Lys Gln Lys
        115                 120                 125

Lys Arg Gln Thr Val Ser Ala Pro Leu Ser Arg Asp Arg Phe Asn Thr
    130                 135                 140

Arg Lys Tyr Ala Glu Glu Asn Glu Leu Gly Ser Pro Val Ala Ala Val
145                 150                 155                 160

Phe Phe Asn Cys Gln Arg Glu Thr Ala Ala Arg Lys Arg
                165                 170
```

<210> SEQ ID NO 16
<211> LENGTH: 4569
<212> TYPE: DNA
<213> ORGANISM: Nicotiana tabacum
<220> FEATURE:
<221> NAME/KEY: misc_feature
<222> LOCATION: (1896)..(1896)
<223> OTHER INFORMATION: n is a, c, g, or t

<400> SEQUENCE: 16

```
ccttatgggt tctcagcatt tgggcaaaag tgatacttta agcaagtgag gaagtttttt     60

aatgttggcc ggaaagatgc ctgtgggtgc tgtttggggg aaaaaaacaa aagctcgggt    120

aaattatcaa tacccgagtt ggttcctttc gtttgccact ggaccaactc ctgattttgc    180

ttatatatgg gttccaaact aaaaatactt atatatttaa taaatttatc aatacaaata    240

caaggctcgg gtaaaagtta ttaggttctc ggaaacccat acccgatact atggatccgc    300

ccctgcttat ccctaccttg tgtgaggtag aaacgctttt gataaggtta tttaaaagta    360

aaagaataag tttaatgtga caatttgaat ggttgagaca acatgccaaa agctaattta    420

agggatttta tttgacattt atatatggga gagaagaaaa agtattgccc agtatattat    480

tttaagctct acaaccaatc aagaatcaat tcctagaatc cattcaggtg tcaaagaata    540

ctgacatgat ataataaaat acaatttata tcacatcagt atttgctttt tcttgggaga    600

ttagataaaa agagatcaga aatggagttt tatggtacta ggagaattca aggatttact    660

acttttgtgg cacaacataa gctcccaatt tttttaagga atttataaaa gttggttttc    720

taagtactta caattgtcaa atttacaagt catttagtac ataaaaagaa acccaatgat    780

gaggttcagg aaaaaaaaaa atcctatact gtgatttcct agttggcgtt cggacataaa    840

aattatgaaa ttccgaaaaa aaaaattgtt ttaagttgaa aatggtatgt gaaaattaaa    900
```

```
gttatatatg gacataaata taatttggag ctgtttttga atttttgtga gtgctttgaa    960
gtgaaatttt ctaaaaacag ctttttggag tttttcaaat tccggagttc aacttcaagc   1020
gaaaaattaa aattttcatg atcaaatgtt gattccgaaa aaagtgaaaa aattcgaaaa   1080
aaagattttt tttttatgg ccaaacagac ctaactagtt tcattttagt cattaagggt   1140
agaattgaaa gaattttaaa ttaaagtatt tttagatata taaaaataat gtacttttta   1200
aaacacacaa aaaaaggagt gccatatatt aatttaatat aaggatatat agtggatgca   1260
ttcataacta acattaacca aaagcattta ttgatcctat tttgacacca ttttatttta   1320
atacaattca taaatttcaa gaatttgaat acattagctt aatctcactt aaattttgag   1380
gtgatgcctg ttctctttct agtcacaact ttaatgtaca ttttatatgt caaattaata   1440
cctgaatttg taacccatca aatatcgcca cataatatga aacagtgaaa atatcttata   1500
ttcctgtatt ttatgactaa gacattaagt agctaacaac gatcgaaaaa cattcctaat   1560
aacaagcgaa ttacaactct gtcggataat cgtctgaaac cctaaaaagc tactgaaatg   1620
atttcctact agtataattc cgatgaaatt ttgttcgaaa attctataag aaatacacgt   1680
atttttagta gtgaaaaaag atttgttgta attttttag gtggggtggg gtgatttggg   1740
gagggttggg gagtaggacc tcaaaaacaa agaattttaa tactttggag tttccttagg   1800
tcccatgttt tatactttct tttattctcc ttcaccatta tagctataac ttagtacata   1860
tatatatata tatatatata tatatatata tatatnatat aaggtgtcca tctgatcaag   1920
tatccaatac aaaccattct taagtctttg aaaatttctc tttttttcct tatctctatc   1980
tctgtctaat tttctttatt atggcaagaa gtttagagcc tctaattgtt gggagagtag   2040
taggagatgt tcttgattca tttagtccta taatgaaaat gacaatatca tataacaaca   2100
aattagtgtg caatggccat gaactccttc cttctgttgt cactgctaga cctaaagttg   2160
aagttcaagg gggagatttg agaactttct tcacattggt attttttct tgatttctac   2220
ttaatttcca agatcatcaa gttcccatta tttctttaaa aaaaaaaaaa gcagttcggt   2280
gcactaaact cccgctatgc gcggggttcg gtgaagcacc gaaccataag ggtctattgt   2340
acgcaacctt accctgcatt tatgcaagag gcttgctcac cattacaagt tatattaatt   2400
taacatgtta tatataacca caaaggctgt cgtgggatgg taaatatcct tctatcctta   2460
atcagaagtt tcgggttcaa gttatagccc taggaatata gtcgtctttg gtagggatcc   2520
tttacccca aaactttccg ccgtgaatcc agattagtaa acctcaaagc gggtatcggg   2580
cattggatga caaaccaaaa aaacttcaac gtgttatagc atgttataac ttattacagt   2640
taatttagtt ttccagtcga tactatatta aatagagtgc ctgtaattta ctttggagtg   2700
atttgattgt tattttttcg catcgtcagt acataaaact tatattaatt ttcgaatatg   2760
taggtcatga cagaccctga tgttcctggc cctagtgatc cttatctaag agagcatctc   2820
cactggtatg ccctaaactc aatttttttt taaaaaaaaa aaatagaaaa tgagaaaaaa   2880
tatgtaaaaa tctacaaata tgagaagatc atgattaatt ggaactattt ttactgacta   2940
tttgacagga tagtaactga cattccaggt accactgatg ctacttttgg taagttctct   3000
gtatcttctg caaaattaca agcacatgtg aagataaaag aagtttttct attattcact   3060
tattttgtct agctagttat atagaataat tataagatca acaattttgt atagtagtga   3120
atgttggact tctaaagtcg aacatgtcca cttgatgagt gtcacaaaaa tgtagaaact   3180
aaacaatcgt ttggacataa aaaaaaaagt aagttttttt gagttaaatt gaaaaagaaa   3240
```

-continued

```
atatttagaa tttgaaattg tggatataca tttaaattga aaagcattgc agttttgtaa   3300
ggaaaataaa ctttcatata cataaaaaag tgatttttttg gaaactcatc ttcaagaata   3360
tttttaaaaa tttccgtcca atgtataacc aaacattatt ttgaaaaaga ttaaaaaaag   3420
gaaaaacttt aggaacaacg ggtcccaaga taaatgtgtc tagtcatata agattagata   3480
aattaggatt ttattatatt tggtagaagg tgcaagaagc atatgtaaat aataaattga   3540
gaagtcactt aagatatttt gatcatgtcc cacatcgata acaagaggta ccattctata   3600
tatgttaaat catggtaagt taaagtatta tatcacatat taaatggtga tataatagac   3660
ctaaatcaca tgaaacgaaa ttgtcccgaa aggtctataa atttttgaaa ttcatgtaga   3720
cgaagctaaa agtaggatac aataaaaaaa aaattaaaga tctatattgg cgatactatt   3780
tagttgggat tgcattttag ttattctagt acatttactt taatctaatt tttgctagct   3840
aggagtcttt taatcttatt agaaatttac ataccaaaaa atttagagaa cttgctagga   3900
caattggtat ttctttatat aatattgtgg aagttgtatt agagtatgtt gtttacatta   3960
cactctttga gtgcgttcct tctccgaact agctaatgca tgaacacgag atgccttctg   4020
caccgtgcta ccctattaat atataaaaaa atggtagccc ggtgcattaa gctcccgcta   4080
tgcgcgggtt ccgaaaaagg atcagaccac aagggtctat gtttgcaacc ttacttgtat   4140
ttctgcaaga aactgtttcc acggctcgaa cccatgatct tctggtcaca tgacaataac   4200
tttaccggtt acaccaaggt tccccttcac gcgctgccct tttaatattg tctattaata   4260
tttcctacta gagttataca cccctttgtt attactcact cttagggtga ttattaacat   4320
ataatatgtt taatatttat actaaaaaca ggacgagaat tggttagcta tgagattcca   4380
atgccaaata ttggaatcca taggtttgta tttgtacttt tcaagcaaaa acgaagacaa   4440
tcagttagct ctcctacttc aagggatcac ttcaacacta gaaattttgc tgaagaaaat   4500
gatcttggcc aacctgttgc tgctgttttc ttcaatgcac agcgagaaac cgccgcacga   4560
agacgctaa                                                          4569
```

<210> SEQ ID NO 17
<211> LENGTH: 2569
<212> TYPE: DNA
<213> ORGANISM: Nicotiana tabacum

<400> SEQUENCE: 17

```
atggcaagaa gtttagagcc tctaattgtt gggagagtag taggagatgt tcttgattca     60
tttagtccta taatgaaaat gacaatatca tataacaaca aattagtgtg caatggccat    120
gaactccttc cttctgttgt cactgctaga cctaaagttg aagttcaagg gggagatttg    180
agaactttct tcacattggt attttttttct tgatttctac ttaatttcca agatcatcaa    240
gttcccatta tttctttaaa aaaaaaaaaa gcagttcggt gcactaaact cccgctatgc    300
gcggggttcg gtgaagcacc gaaccataag ggtctattgt acgcaacctt accctgcatt    360
tatgcaagag gcttgctcac cattacaagt tatattaatt taacatgtta tatataacca    420
caaaggctgt cgtgggatgg taaatatcct tctatcctta atcagaagtt tcgggttcaa    480
gttatagccc taggaatata gtcgtctttg gtagggatcc tttacccccca aaactttccg    540
ccgtgaatcc agattagtaa acctcaaagc gggtatcggg cattggatga caaaccaaaa    600
aaacttcaac gtgttatagc atgttataac ttattacagt taatttagtt ttccagtcga    660
tactatatta aatagagtgc ctgtaattta ctttggagtg atttgattgt tattttttcg    720
catcgtcagt acataaaact tatattaatt ttcgaatatg taggtcatga cagaccctga    780
```

```
tgttcctggc cctagtgatc cttatctaag agagcatctc cactggtatg ccctaaactc    840

aatttttttt taaaaaaaaa aaatagaaaa tgagaaaaaa tatgtaaaaa tctacaaata    900

tgagaagatc atgattaatt ggaactattt ttactgacta tttgacagga tagtaactga    960

cattccaggt accactgatg ctacttttgg taagttctct gtatcttctg caaaattaca   1020

agcacatgtg aagataaaag aagtttttct attattcact tattttgtct agctagttat   1080

atagaataat tataagatca acaattttgt atagtagtga atgttggact tctaaagtcg   1140

aacatgtcca cttgatgagt gtcacaaaaa tgtagaaact aaacaatcgt ttggacataa   1200

aaaaaaaagt aagttttttt gagttaaatt gaaaaagaaa atatttagaa tttgaaattg   1260

tggatataca tttaaattga aaagcattgc agttttgtaa ggaaaataaa ctttcatata   1320

cataaaaaag tgatttttttg gaaactcatc ttcaagaata tttttaaaaa tttccgtcca   1380

atgtataacc aaacattatt ttgaaaaaga ttaaaaaaag gaaaaacttt aggaacaacg   1440

ggtcccaaga taaatgtgtc tagtcatata agattagata aattaggatt ttattatatt   1500

tggtagaagg tgcaagaagc atatgtaaat aataaattga gaagtcactt aagatatttt   1560

gatcatgtcc cacatcgata acaagaggta ccattctata tatgttaaat catggtaagt   1620

taaagtatta tatcacatat taaatggtga tataatagac ctaaatcaca tgaaacgaaa   1680

ttgtcccgaa aggtctataa atttttgaaa ttcatgtaga cgaagctaaa agtaggatac   1740

aataaaaaaa aaattaaaga tctatattgg cgatactatt tagttgggat tgcattttag   1800

ttattctagt acatttactt taatctaatt tttgctagct aggagtcttt taatcttatt   1860

agaaatttac ataccaaaaa atttagagaa cttgctagga caattggtat ttctttatat   1920

aatattgtgg aagttgtatt agagtatgtt gtttacatta cactctttga gtgcgttcct   1980

tctccgaact agctaatgca tgaacacgag atgccttctg caccgtgcta ccctattaat   2040

atataaaaaa atggtagccc ggtgcattaa gctcccgcta tgcgcgggtt ccgaaaaagg   2100

atcagaccac aagggtctat gtttgcaacc ttacttgtat ttctgcaaga aactgtttcc   2160

acggctcgaa cccatgatct tctggtcaca tgacaataac tttaccggtt acaccaaggt   2220

tccccttcac gcgctgccct tttaatattg tctattaata tttcctacta gagttataca   2280

ccccttttgtt attactcact cttagggtga ttattaacat ataatatgtt taatatttat   2340

actaaaaaca ggacgagaat tggttagcta tgagattcca atgccaaata ttggaatcca   2400

taggtttgta tttgtacttt tcaagcaaaa acgaagacaa tcagttagct ctcctacttc   2460

aagggatcac ttcaacacta gaaattttgc tgaagaaaat gatcttggcc aacctgttgc   2520

tgctgttttc ttcaatgcac agcgagaaac cgccgcacga agacgctaa                2569
```

<210> SEQ ID NO 18
<211> LENGTH: 172
<212> TYPE: PRT
<213> ORGANISM: Nicotiana tabacum

<400> SEQUENCE: 18

```
Met Ala Arg Ser Leu Glu Pro Leu Ile Val Gly Arg Val Val Gly Asp
1               5                   10                  15

Val Leu Asp Ser Phe Ser Pro Ile Met Lys Met Thr Ile Ser Tyr Asn
            20                  25                  30

Asn Lys Leu Val Cys Asn Gly His Glu Leu Leu Pro Ser Val Val Thr
        35                  40                  45

Ala Arg Pro Lys Val Glu Val Gln Gly Gly Asp Leu Arg Thr Phe Phe
```

```
    50                  55                  60

Thr Leu Val Met Thr Asp Pro Asp Val Pro Gly Pro Ser Asp Pro Tyr
65                  70                  75                  80

Leu Arg Glu His Leu His Trp Ile Val Thr Asp Ile Pro Gly Thr Thr
                85                  90                  95

Asp Ala Thr Phe Gly Arg Glu Leu Val Ser Tyr Glu Ile Pro Met Pro
            100                 105                 110

Asn Ile Gly Ile His Arg Phe Val Phe Val Leu Phe Lys Gln Lys Arg
        115                 120                 125

Arg Gln Ser Val Ser Ser Pro Thr Ser Arg Asp His Phe Asn Thr Arg
    130                 135                 140

Asn Phe Ala Glu Glu Asn Asp Leu Gly Gln Pro Val Ala Ala Val Phe
145                 150                 155                 160

Phe Asn Ala Gln Arg Glu Thr Ala Ala Arg Arg Arg
                165                 170


<210> SEQ ID NO 19
<211> LENGTH: 4652
<212> TYPE: DNA
<213> ORGANISM: Nicotiana tabacum

<400> SEQUENCE: 19

atccccagag gcggatctag gatttgaacc ttatgggttc tcagcatttg ggcaaaagtg     60

atactttaag caagtgagga agttttttaa tgttggccgg aaagatgcct gtgggtgctg    120

tttgggggaa aaaaacaaaa gctcgggtaa attatcaata cccgagttgg ttcctttcgt    180

ttgccactgg accaactcct gattttgctt atatatgggt tccaaactaa aaatacttat    240

atatttaata aatttatcaa tacaaataca aggctcgggt aaaagttatt aggttctcgg    300

aaacccatac ccgatactat ggatccgccc ctgcttatcc ctaccttgtg tgaggtagaa    360

acgcttttga taaggttatt taaaagtaaa agaataagtt taatgtgaca atttgaatgg    420

ttgagacaac atgccaaaag ctaatttaag ggattttatt tgacatttat atatgggaga    480

gaagaaaaag tattgcccag tatattattt taagctctac aaccaatcaa gaatcaattc    540

ctagaatcca ttcaggtgtc aaagaatact gacatgatat aataaaatac aatttatatc    600

acatcagtat ttgctttttc ttgggagatt agataaaaag agatcagaaa tggagtttta    660

tggtactagg agaattcaag gatttactac ttttgtggca caacataagc tcccaatttt    720

tttaaggaat ttataaaagt tggttttcta agtacttaca attgtcaaat ttacaagtca    780

tttagtacat aaaaagaaac ccaatgatga ggttcaggaa aaaaaaaaaa tcctatactg    840

tgatttccta gttggcgttc ggacataaaa attatgaaat tccgaaaaaa aaaattgttt    900

taagttgaaa atggtatgtg aaaattaaag ttatatatgg acataaatat aatttggagc    960

tgtttttgaa tttttgtgag tgctttgaag tgaaattttc taaaaacagc tttttggagt   1020

ttttcaaatt ccggagttca acttcaagcg aaaaattaaa attttcatga tcaaatgttg   1080

attccgaaaa aagtgaaaaa attcgaaaaa aagatttttt tttttatggc caaacagacc   1140

taactagttt cattttagtc attaagggta gaattgaaag aattttaaat taaagtattt   1200

ttagatatat aaaaataatg tactttttaa aacacacaaa aaaaggagtg ccatatatta   1260

atttaatata aggatatata gtggatgcat tcataactaa cattaaccaa aagcatttat   1320

tgatcctatt ttgacaccat tttattttaa tacaattcat aaatttcaag aatttgaata   1380

cattagctta atctcactta aattttgagg tgatgcctgt tctctttcta gtcacaactt   1440
```

-continued

```
taatgtacat tttatatgtc aaattaatac ctgaatttgt aacccatcaa atatcgccac   1500
ataatatgaa acagtgaaaa tatcttatat tcctgtattt tatgactaag acattaagta   1560
gctaacaacg atcgaaaaac attcctaata acaagcgaat tacaactctg tcggataatc   1620
gtctgaaacc ctaaaaagct actgaaatga tttcctacta gtataattcc gatgaaattt   1680
tgttcgaaaa ttctataaga aatacacgta tttttagtag tgaaaaaaga tttgttgtaa   1740
ttttttttagg tggggtgggg tgatttgggg agggttgggg agtaggacct caaaaacaaa   1800
gaattttaat actttggagt ttccttaggt cccatgtttt atactttctt ttattctcct   1860
tcaccattat agctataact tagtacatat atatatatgg tggccctctg atccaatgta   1920
aaatgcaaac cattcttaag atctttgaaa tttctctctt ttttttcttt atctctatct   1980
ctgtctaatt ctctctatta tggcaagaag tttggagcct ctaatagttg ggagagtagt   2040
aggagatgtt cttgattcat ttagtcctat agtgaaaatg acaattactt ataacaacaa   2100
attagtgtgc aatggtcatg aattctttcc ttctattgtc acttctagac ctaaggttga   2160
agttcaagga ggagatttga gaactttctt cacactggta atttttcttg atttttttcct   2220
taattccaag atcatcaagt tccatttatt tctttacaag ttatattaat ttaacccttt   2280
ataatcacca aaggctggcg tgggttgcta agtaaccttc catcgttaat cagatgtttc   2340
gggttcgagc tagccctggg attacaatcg tttttgtag gaagcgcttt aaccccccaaa   2400
atttttcagc acgaacccgg attagtaaac ctcaaaactc gtgccaaata ctagatgaca   2460
aaccaaaaga gttttcaacc tgttataaca tatgttactt gttacaatta ttagttttcc   2520
ggtcaatagt atattatgta atttctttg aagtgacttg attgttattt tttcacatta   2580
tcagtgcata aaacttatac tattattttt taatatgtag gtcatgacag accctgatgt   2640
tcccggccct agtgatcctt atctacgaga gcatctccac tggtacactc tctataatag   2700
tttcatttgt tccgaatttt cttggctgtt atataaaaaa tatattataa catagcatga   2760
aaattggttc cacaaaaact taatttttat agtgaataat tgttatatat tgatattgtt   2820
atagagaggt ctgtctatat gccctaaact caatgaaaaa aaatagaaaa tgagaaaaaa   2880
tatgtaaaat ctacaaatat gagaagatca tttttagttg aaactatcct tatatactac   2940
tgaatattta gctggcaaat aaaattgaca gtgttttact gattgtttga caggatagta   3000
actgacattc caggtaccac tgatgctact tttggtaagt tttattagtt tcttctgcaa   3060
gattacaagc acatgtgaag aagatacaag atgtttttcc attactcact tattttgtct   3120
tgctaataat tatatagaac aattgtaaga tcaacagtgt tatataatag tgaatgttgg   3180
acttctaaag tcgaacatgt ccacatgatg agcgtcacaa aaatgcagat acgagctcgt   3240
ttggattgac ttaaaaaatg tggtttttca gcaaaaataa cttttaagcc aaaaaacaat   3300
aagttagggt tgtccacctt tttgcttttg gcttaattta agcattttaa aatttatttt   3360
aagcaatttt tgacttagcc aaacaccgaa aaaagctaaa agaaacttaa aagctgattt   3420
gactagctta aaagtaaatc caaacaccct ctaactaagc atttggacat aaaaaaaata   3480
tgtcattttt gaaaaaagta gttcttttga gttaagtcaa aaaagaatat ataaaatttg   3540
aaattgtatt tagacatgca tttcacttga aaattattag agttttatga gaaaaatgaa   3600
cttttagatg aaaaagtggt ttttggaaac tcatcttcaa gaatttttcc aaaacttcag   3660
tccaatcgta taaccaaaca ttattttgat aaaaacatcg aaaataaaaa taaatctatg   3720
gagaaacggg tcccaagata aatgtgtcta gtcatataag attattcaaa attaagaatt   3780
tatcacattt gtaaaagatg taagtagcat atgtaaatga taaaatgaga agtcacttga   3840
```

gatgttttga tcatgtccta cgtcgatctt cagaggtacc attccgtata cgtgattggt 3900
aagtaaaggt attaaaaaga gacataatgg acctaaatta cgtgaaacga aattgtcttg 3960
aaaagtcttt caaatttttg aaatccatgt agacgaatcg aaaagtaggg cacaatgaaa 4020
tatgatcaaa ggtttataat ggtgatacaa gttagttggg attacgtttt agttatgcca 4080
gtatatttac tttaatctaa tattttcttg gagtttttta atcttattag aaatttactt 4140
accaaaaatt tagagaactt gctagaacaa tataattgat aattcttcat atatattgtc 4200
ttcgagctgt agaaacagcc actaatgttt gcattaggat atgttgtcta catcacactt 4260
attgtgtgtt gccctcaccg gaccctgcat gaacgtatga tgccttatgc accgcgcccc 4320
ttttaatatt atttattaat taatatttcc tgctagagtt atactccttt gttattactc 4380
attcttaggt tgatgattaa cttataatat gcttaatctt tatactaaaa ataggaagag 4440
aattggttag ctatgagatt ccaaggccaa atattggaat ccataggttt gtatttgtac 4500
ttttcaagca aagacgaaga caatcagtta gccctcctac ttcaagggaa aacttcaaca 4560
ctagaaattt tgccgaagaa aatgatctta gccaacctgt tgctgctgtt ttcttcaatg 4620
cacagcgaga aaccgccgcg cgaagacgct aa 4652

<210> SEQ ID NO 20
<211> LENGTH: 2653
<212> TYPE: DNA
<213> ORGANISM: Nicotiana tabacum

<400> SEQUENCE: 20
atggcaagaa gtttggagcc tctaatagtt gggagagtag taggagatgt tcttgattca 60
tttagtccta tagtgaaaat gacaattact tataacaaca aattagtgtg caatggtcat 120
gaattctttc cttctattgt cacttctaga cctaaggttg aagttcaagg aggagatttg 180
agaactttct tcacactggt aatttttctt gatttttttcc ttaattccaa gatcatcaag 240
ttccatttat ttctttacaa gttatattaa tttaaccctt tataatcacc aaaggctggc 300
gtgggttgct aagtaacctt ccatcgttaa tcagatgttt cgggttcgag ctagccctgg 360
gattacaatc gtttttgta ggaagcgctt taacccccaa aatttttcag cacgaacccg 420
gattagtaaa cctcaaaact cgtgccaaat actagatgac aaaccaaaag agttttcaac 480
ctgttataac atatgttact tgttacaatt attagtttc cggtcaatag tatattatgt 540
aattttcttt gaagtgactt gattgttatt ttttcacatt atcagtgcat aaaacttata 600
ctattatttt ttaatatgta ggtcatgaca gaccctgatg ttcccggccc tagtgatcct 660
tatctacgag agcatctcca ctggtacact ctctataata gtttcatttg ttccgaattt 720
tcttggctgt tatataaaaa atatattata acatagcatg aaaattggtt ccacaaaaac 780
ttaattttta tagtgaataa ttgttatata ttgatattgt tatagagagg tctgtctata 840
tgccctaaac tcaatgaaaa aaaatagaaa atgagaaaaa atatgtaaaa tctacaaata 900
tgagaagatc atttttagtt gaaactatcc ttatatacta ctgaatattt agctggcaaa 960
taaaattgac agtgttttac tgattgtttg acaggatagt aactgacatt ccaggtacca 1020
ctgatgctac ttttggtaag ttttattagt ttcttctgca agattacaag cacatgtgaa 1080
gaagatacaa gatgttttc cattactcac ttattttgtc ttgctaataa ttatatagaa 1140
caattgtaag atcaacagtg ttatataata gtgaatgttg gacttctaaa gtcgaacatg 1200
tccacatgat gagcgtcaca aaaatgcaga tacgagctcg tttggattga cttaaaaaat 1260

```
gtggttttc agcaaaaata acttttaagc caaaaaacaa taagttaggg ttgtccacct   1320
ttttgctttt ggcttaattt aagcatttta aaatttattt taagcaattt ttgacttagc   1380
caaacaccga aaaaagctaa aagaaactta aaagctgatt tgactagctt aaaagtaaat   1440
ccaaacaccc tctaactaag catttggaca taaaaaaaat atgtcatttt tgaaaaaagt   1500
agttcttttg agttaagtca aaaaagaata tataaaattt gaaattgtat ttagacatgc   1560
atttcacttg aaaattatta gagttttatg agaaaaatga acttttagat gaaaaagtgg   1620
tttttggaaa ctcatcttca agaatttttc caaaacttca gtccaatcgt ataaccaaac   1680
attattttga taaaaacatc gaaaataaaa ataaatctat ggagaaacgg gtcccaagat   1740
aaatgtgtct agtcatataa gattattcaa aattaagaat ttatcacatt tgtaaaagat   1800
gtaagtagca tatgtaaatg ataaaatgag aagtcacttg agatgttttg atcatgtcct   1860
acgtcgatct tcagaggtac cattccgtat acgtgattgg taagtaaagg tattaaaaag   1920
agacataatg gacctaaatt acgtgaaacg aaattgtctt gaaaagtctt tcaaattttt   1980
gaaatccatg tagacgaatc gaaaagtagg gcacaatgaa atatgatcaa aggtttataa   2040
tggtgataca agttagttgg gattacgttt tagttatgcc agtatattta ctttaatcta   2100
atattttctt ggagtttttt aatcttatta gaaatttact taccaaaaat ttagagaact   2160
tgctagaaca atataattga taattcttca tatatattgt cttcgagctg tagaaacagc   2220
cactaatgtt tgcattagga tatgttgtct acatcacact tattgtgtgt tgccctcacc   2280
ggaccctgca tgaacgtatg atgccttatg caccgcgccc cttttaatat tatttattaa   2340
ttaatatttc ctgctagagt tatactcctt tgttattact cattcttagg ttgatgatta   2400
acttataata tgcttaatct ttatactaaa aataggaaga gaattggtta gctatgagat   2460
tccaaggcca aatattggaa tccataggtt tgtatttgta cttttcaagc aaagacgaag   2520
acaatcagtt agccctccta cttcaaggga aaacttcaac actagaaatt ttgccgaaga   2580
aaatgatctt agccaacctg ttgctgctgt tttcttcaat gcacagcgag aaaccgccgc   2640
gcgaagacgc taa                                                      2653
```

```
<210> SEQ ID NO 21
<211> LENGTH: 172
<212> TYPE: PRT
<213> ORGANISM: Nicotiana tabacum

<400> SEQUENCE: 21

Met Ala Arg Ser Leu Glu Pro Leu Ile Val Gly Arg Val Val Gly Asp
1               5                   10                  15

Val Leu Asp Ser Phe Ser Pro Ile Val Lys Met Thr Ile Thr Tyr Asn
            20                  25                  30

Asn Lys Leu Val Cys Asn Gly His Glu Phe Phe Pro Ser Ile Val Thr
        35                  40                  45

Ser Arg Pro Lys Val Glu Val Gln Gly Gly Asp Leu Arg Thr Phe Phe
    50                  55                  60

Thr Leu Val Met Thr Asp Pro Asp Val Pro Gly Pro Ser Asp Pro Tyr
65                  70                  75                  80

Leu Arg Glu His Leu His Trp Ile Val Thr Asp Ile Pro Gly Thr Thr
                85                  90                  95

Asp Ala Thr Phe Gly Arg Glu Leu Val Ser Tyr Glu Ile Pro Arg Pro
            100                 105                 110

Asn Ile Gly Ile His Arg Phe Val Phe Val Leu Phe Lys Gln Arg Arg
        115                 120                 125
```

```
Arg Gln Ser Val Ser Pro Pro Thr Ser Arg Glu Asn Phe Asn Thr Arg
    130                 135                 140

Asn Phe Ala Glu Glu Asn Asp Leu Ser Gln Pro Val Ala Ala Val Phe
145                 150                 155                 160

Phe Asn Ala Gln Arg Glu Thr Ala Ala Arg Arg Arg
                165                 170


<210> SEQ ID NO 22
<211> LENGTH: 58
<212> TYPE: DNA
<213> ORGANISM: Nicotiana tabacum

<400> SEQUENCE: 22

agttaaaatg acagtcactt acaacaataa acaagtttgc aatggccaag agctcttc       58


<210> SEQ ID NO 23
<211> LENGTH: 58
<212> TYPE: DNA
<213> ORGANISM: Nicotiana tabacum

<400> SEQUENCE: 23

gaagagctct tggccattgc aaacttgttt attgttgtaa gtgactgtca ttttaact       58


<210> SEQ ID NO 24
<211> LENGTH: 482
<212> TYPE: DNA
<213> ORGANISM: Nicotiana tabacum

<400> SEQUENCE: 24

ggtaccacaa gtttgtacaa aaaagcaggc taagcttgtc gaccatggag ttaaaatgac     60

agtcacttac aacaataaac aagtttgcaa tggccaagag ctcttctggt aacctttaat    120

gtttaaccgt tcacatttct aatatttact tatttgtaac atgtcgtcac gtgttagttt    180

cattcttttt atgaaccaaa catgcatgca aagatatttt tagatatttg gacggcgagt    240

gagatttgaa actaggaccg tttgcctgat acaatattaa aatatgtaac cattttatgt    300

acaagtttaa actgttgata gtagcatatt ttttactttt atttaagtat actatattcc    360

aacaggtaag ttaacgaaga gctcttggcc attgcaaact tgtttattgt tgtaagtgac    420

tgtcatttta actggcgcgc ccgggcaatt gacccagctt tcttgtacaa agtggtgagc    480

tc                                                                   482


<210> SEQ ID NO 25
<211> LENGTH: 88
<212> TYPE: DNA
<213> ORGANISM: Nicotiana tabacum

<400> SEQUENCE: 25

tgcagtcact attagaccta gggttgaagt tcaaggtggt gatatgagaa ctttcttcac     60

attggtcatc acagatcctg atgtacct                                        88


<210> SEQ ID NO 26
<211> LENGTH: 88
<212> TYPE: DNA
<213> ORGANISM: Nicotiana tabacum

<400> SEQUENCE: 26

aggtacatca ggatctgtga tgaccaatgt gaagaaagtt ctcatatcac caccttgaac     60

ttcaacccta ggtctaatag tgactgca                                        88
```

<210> SEQ ID NO 27
<211> LENGTH: 88
<212> TYPE: DNA
<213> ORGANISM: Nicotiana tabacum

<400> SEQUENCE: 27
tgcggtcacc attagaccta gggttgaggt tcaaggtggt gatatgagaa ctttcttcac 60
attggtcatg acagaccctg atgttcct 88

<210> SEQ ID NO 28
<211> LENGTH: 88
<212> TYPE: DNA
<213> ORGANISM: Nicotiana tabacum

<400> SEQUENCE: 28
aggaacatca gggtctgtca tgaccaatgt gaagaaagtt ctcatatcac caccttgaac 60
ctcaacccta ggtctaatgg tgaccgca 88

<210> SEQ ID NO 29
<211> LENGTH: 78
<212> TYPE: DNA
<213> ORGANISM: Nicotiana tabacum

<400> SEQUENCE: 29
catgaactct ttccttcctc agtcacctct aaacctaggg ttgaagttca tggaggtgat 60
ttgagatctt tctttaca 78

<210> SEQ ID NO 30
<211> LENGTH: 78
<212> TYPE: DNA
<213> ORGANISM: Nicotiana tabacum

<400> SEQUENCE: 30
tgtaaagaaa gatctcaaat cacctccatg aacttcaacc ctaggtttag aggtgactga 60
ggaaggaaag agttcatg 78

<210> SEQ ID NO 31
<211> LENGTH: 522
<212> TYPE: DNA
<213> ORGANISM: Nicotiana tabacum

<400> SEQUENCE: 31
ggtaccacaa gtttgtacaa aaaagcaggc taagcttgtc gaccatggca tgaactcttt 60
ccttcctcag tcacctctaa acctagggtt gaagttcatg gaggtgattt gagatctttc 120
tttacatggt aacctttaat gtttaaccgt tcacatttct aatatttact tatttgtaac 180
atgtcgtcac gtgttagttt cattcttttt atgaaccaaa catgcatgca aagatatttt 240
tagatatttg gacggcgagt gagatttgaa actaggaccg tttgcctgat acaatattaa 300
aatatgtaac cattttatgt acaagtttaa actgttgata gtagcatatt ttttactttt 360
atttaagtat actatattcc aacaggtaag ttaactgtaa agaaagatct caaatcacct 420
ccatgaactt caaccctagg tttagaggtg actgaggaag gaaagagttc atgggcgcgc 480
ccgggcaatt gacccagctt tcttgtacaa agtggtgagc tc 522

<210> SEQ ID NO 32
<211> LENGTH: 121
<212> TYPE: DNA

<213> ORGANISM: Nicotiana tabacum

<400> SEQUENCE: 32

```
gaaagaaata gttggctatg aaatgccaag gccaaatatt ggaattcaca ggtttgtatt    60
tctgctgttc aagcagaaga agaggcaaac agtattgact gcacctctct ccagggatcg   120
a                                                                   121
```

<210> SEQ ID NO 33
<211> LENGTH: 121
<212> TYPE: DNA
<213> ORGANISM: Nicotiana tabacum

<400> SEQUENCE: 33

```
tcgatccctg gagagaggtg cagtcaatac tgtttgcctc ttcttctgct tgaacagcag    60
aaatacaaac ctgtgaattc caatatttgg ccttggcatt tcatagccaa ctatttcttt   120
c                                                                   121
```

<210> SEQ ID NO 34
<211> LENGTH: 110
<212> TYPE: DNA
<213> ORGANISM: Nicotiana tabacum

<400> SEQUENCE: 34

```
gagagaaata gttgggtatg aaatgccaag gccaaatatt ggaatccaca gcagctttct    60
tcaattgcca gagggaaacc gctgccagaa ggcgttgaag aagatgttta              110
```

<210> SEQ ID NO 35
<211> LENGTH: 110
<212> TYPE: DNA
<213> ORGANISM: Nicotiana tabacum

<400> SEQUENCE: 35

```
taaacatctt cttcaacgcc ttctggcagc ggtttccctc tggcaattga agaaagctgc    60
tgtggattcc aatatttggc cttggcattt catacccaac tatttctctc              110
```

<210> SEQ ID NO 36
<211> LENGTH: 138
<212> TYPE: DNA
<213> ORGANISM: Nicotiana tabacum

<400> SEQUENCE: 36

```
atggctcaaa tgacagatcc ccttgtgatt agtagggtgg ttggagatgt tgttgattat    60
ttctctccaa gtgttaagat gtgtgttatt tataacccca gtaagcatgt ctataatggg   120
catgaactct ttccatcc                                                 138
```

<210> SEQ ID NO 37
<211> LENGTH: 138
<212> TYPE: DNA
<213> ORGANISM: Nicotiana tabacum

<400> SEQUENCE: 37

```
ggatggaaag agttcatgcc cattatagac atgcttactg gggttataaa taacacacat    60
cttaacactt ggagagaaat aatcaacaac atctccaacc accctactaa tcacaagggg   120
atctgtcatt tgagccat                                                 138
```

<210> SEQ ID NO 38
<211> LENGTH: 642

<212> TYPE: DNA
<213> ORGANISM: Nicotiana tabacum

<400> SEQUENCE: 38
ggtaccacaa gtttgtacaa aaaagcaggc taagcttgtc gaccatggat ggctcaaatg 60
acagatcccc ttgtgattag tagggtggtt ggagatgttg ttgattattt ctctccaagt 120
gttaagatgt gtgttattta taaccccagt aagcatgtct ataatgggca tgaactcttt 180
ccatcctggt aacctttaat gtttaaccgt tcacatttct aatatttact tatttgtaac 240
atgtcgtcac gtgttagttt cattcttttt atgaaccaaa catgcatgca aagatatttt 300
tagatatttg gacggcgagt gagatttgaa actaggaccg tttgcctgat acaatattaa 360
aatatgtaac cattttatgt acaagtttaa actgttgata gtagcatatt ttttactttt 420
atttaagtat actatattcc aacaggtaag ttaacggatg gaaagagttc atgcccatta 480
tagacatgct tactggggtt ataaataaca cacatcttaa cacttggaga gaaataatca 540
acaacatctc caaccaccct actaatcaca aggggatctg tcatttgagc catggcgcgc 600
ccgggcaatt gacccagctt tcttgtacaa agtggtgagc tc 642

<210> SEQ ID NO 39
<211> LENGTH: 93
<212> TYPE: DNA
<213> ORGANISM: Nicotiana tabacum

<400> SEQUENCE: 39
tagtcctata gtgaaaatga caattactta taacaacaaa ttagtgtgca atggtcatga 60
attctttcct tctattgtca cttctagacc taa 93

<210> SEQ ID NO 40
<211> LENGTH: 93
<212> TYPE: DNA
<213> ORGANISM: Nicotiana tabacum

<400> SEQUENCE: 40
ttaggtctag aagtgacaat agaaggaaag aattcatgac cattgcacac taatttgttg 60
ttataagtaa ttgtcatttt cactatagga cta 93

<210> SEQ ID NO 41
<211> LENGTH: 552
<212> TYPE: DNA
<213> ORGANISM: Nicotiana tabacum

<400> SEQUENCE: 41
ggtaccacaa gtttgtacaa aaaagcaggc taagcttgtc gaccatggta gtcctatagt 60
gaaaatgaca attacttata acaacaaatt agtgtgcaat ggtcatgaat tctttccttc 120
tattgtcact tctagaccta atggtaacct ttaatgttta accgttcaca tttctaatat 180
ttacttattt gtaacatgtc gtcacgtgtt agtttcattc tttttatgaa ccaaacatgc 240
atgcaaagat atttttagat atttggacgg cgagtgagat ttgaaactag gaccgtttgc 300
ctgatacaat attaaaatat gtaaccattt tatgtacaag tttaaactgt tgatagtagc 360 atattttttta cttttattta agtatactat attccaacag gtaagttaac ttaggtctag 420
aagtgacaat agaaggaaag aattcatgac cattgcacac taatttgttg ttataagtaa 480
ttgtcatttt cactatagga ctaggcgcgc ccgggcaatt gacccagctt tcttgtacaa 540
agtggtgagc tc 552

-continued

<210> SEQ ID NO 42
<211> LENGTH: 41
<212> TYPE: PRT
<213> ORGANISM: Nicotiana tabacum

<400> SEQUENCE: 42

```
Met Ser Val Thr Tyr Asn Ser Ser Lys His Val Tyr Asn Gly His Glu
1               5                   10                  15

Leu Phe Pro Ser Ser Val Thr Ser Lys Pro Arg Val Glu Val His Gly
            20                  25                  30

Gly Asp Leu Arg Ser Phe Phe Thr Leu
        35                  40
```

<210> SEQ ID NO 43
<211> LENGTH: 125
<212> TYPE: DNA
<213> ORGANISM: Nicotiana tabacum

<400> SEQUENCE: 43

```
atgtctgtta cttataacag cagcaagcat gtctataatg gacatgaact ctttccttcc     60

tcagtcacct ctaaacctag ggttgaagtt catggaggtg atttgagatc tttctttaca    120

ctggt                                                                125
```

<210> SEQ ID NO 44
<211> LENGTH: 20
<212> TYPE: PRT
<213> ORGANISM: Nicotiana tabacum

<400> SEQUENCE: 44

```
Ile Met Ile Asp Pro Asp Val Pro Gly Pro Ser Asp Pro Tyr Leu Arg
1               5                   10                  15

Glu His Leu His
            20
```

<210> SEQ ID NO 45
<211> LENGTH: 66
<212> TYPE: DNA
<213> ORGANISM: Nicotiana tabacum

<400> SEQUENCE: 45

```
agatcatgat agacccagat gttcctggtc ctagtgatcc atatctcagg gaacatctac     60

actggt                                                                66
```

<210> SEQ ID NO 46
<211> LENGTH: 13
<212> TYPE: PRT
<213> ORGANISM: Nicotiana tabacum

<400> SEQUENCE: 46

```
Ile Val Thr Asp Ile Pro Gly Thr Thr Asp Cys Ser Phe
1               5                   10
```

<210> SEQ ID NO 47
<211> LENGTH: 45
<212> TYPE: DNA
<213> ORGANISM: Nicotiana tabacum

<400> SEQUENCE: 47

```
aggattgtca cagacattcc aggcactaca gattgctcgt ttggt                     45
```

<210> SEQ ID NO 48
<211> LENGTH: 72
<212> TYPE: PRT
<213> ORGANISM: Nicotiana tabacum

<400> SEQUENCE: 48

```
Arg Glu Ile Val Gly Tyr Glu Met Pro Arg Pro Asn Ile Gly Ile His
1               5                   10                  15

Arg Phe Val Phe Leu Leu Phe Lys Gln Lys Lys Arg Gln Thr Leu Leu
            20                  25                  30

Ser Ala Pro Leu Ser Arg Asp Arg Phe Asn Thr Arg Lys Phe Ser Glu
        35                  40                  45

Glu Asn Glu Leu Gly Ser Pro Val Ala Ala Ala Phe Phe Asn Cys Gln
    50                  55                  60

Arg Glu Thr Ala Ala Arg Arg Arg
65                  70
```

<210> SEQ ID NO 49
<211> LENGTH: 220
<212> TYPE: DNA
<213> ORGANISM: Nicotiana tabacum

<400> SEQUENCE: 49

```
agggagagaa atagttgggt atgaaatgcc aaggccaaat attggaatcc acaggtttgt      60

atttctgctg ttcaagcaga agaagaggca aacattattg agtgcacctc tctccaggga     120

tcgatttaat acgcgcaaat tctcagaaga aaatgagctt gggtctcctg ttgcagcagc     180

tttcttcaat tgccagaggg aaaccgctgc cagaaggcgt                           220
```

<210> SEQ ID NO 50
<211> LENGTH: 66
<212> TYPE: PRT
<213> ORGANISM: Nicotiana tabacum

<400> SEQUENCE: 50

```
Met Ala Arg Ser Leu Glu Pro Leu Ile Val Gly Arg Val Val Gly Asp
1               5                   10                  15

Val Leu Asp Ser Phe Ser Pro Ile Val Lys Met Thr Ile Thr Tyr Asn
            20                  25                  30

Asn Lys Leu Val Cys Asn Gly His Glu Phe Phe Pro Ser Ile Val Thr
        35                  40                  45

Ser Arg Pro Lys Val Glu Val Gln Gly Gly Asp Leu Arg Thr Phe Phe
    50                  55                  60

Thr Leu
65
```

<210> SEQ ID NO 51
<211> LENGTH: 200
<212> TYPE: DNA
<213> ORGANISM: Nicotiana tabacum

<400> SEQUENCE: 51

```
atggcaagaa gtttggagcc tctaatagtt gggagagtag taggagatgt tcttgattca      60

tttagtccta tagtgaaaat gacaattact tataacaaca aattagtgtg caatggtcat     120

gaattctttc cttctattgt cacttctaga cctaaggttg aagttcaagg aggagatttg     180

agaactttct tcacactggt                                                 200
```

<210> SEQ ID NO 52

<211> LENGTH: 20
<212> TYPE: PRT
<213> ORGANISM: Nicotiana tabacum

<400> SEQUENCE: 52

Val Met Thr Asp Pro Asp Val Pro Gly Pro Ser Asp Pro Tyr Leu Arg
1 5 10 15

Glu His Leu His
20

<210> SEQ ID NO 53
<211> LENGTH: 66
<212> TYPE: DNA
<213> ORGANISM: Nicotiana tabacum

<400> SEQUENCE: 53
aggtcatgac agaccctgat gttcccggcc ctagtgatcc ttatctacga gagcatctcc 60
actggt 66

<210> SEQ ID NO 54
<211> LENGTH: 13
<212> TYPE: PRT
<213> ORGANISM: Nicotiana tabacum

<400> SEQUENCE: 54

Ile Val Thr Asp Ile Pro Gly Thr Thr Asp Ala Thr Phe
1 5 10

<210> SEQ ID NO 55
<211> LENGTH: 45
<212> TYPE: DNA
<213> ORGANISM: Nicotiana tabacum

<400> SEQUENCE: 55
aggatagtaa ctgacattcc aggtaccact gatgctactt ttggt 45

<210> SEQ ID NO 56
<211> LENGTH: 71
<212> TYPE: PRT
<213> ORGANISM: Nicotiana tabacum

<400> SEQUENCE: 56

Arg Glu Leu Val Ser Tyr Glu Ile Pro Arg Pro Asn Ile Gly Ile His
1 5 10 15

Arg Phe Val Phe Val Leu Phe Lys Gln Arg Arg Arg Gln Ser Val Ser
20 25 30

Pro Pro Thr Ser Arg Glu Asn Phe Asn Thr Arg Asn Phe Ala Glu Glu
35 40 45

Asn Asp Leu Ser Gln Pro Val Ala Ala Val Phe Phe Asn Ala Gln Arg
50 55 60

Glu Thr Ala Ala Arg Arg Arg
65 70

<210> SEQ ID NO 57
<211> LENGTH: 217
<212> TYPE: DNA
<213> ORGANISM: Nicotiana tabacum

<400> SEQUENCE: 57
aggaagagaa ttggttagct atgagattcc aaggccaaat attggaatcc ataggtttgt 60
atttgtactt ttcaagcaaa gacgaagaca atcagttagc cctcctactt caagggaaaa 120

-continued

```
cttcaacact agaaattttg ccgaagaaaa tgatcttagc caacctgttg ctgctgtttt    180

cttcaatgca cagcgagaaa ccgccgcgcg aagacgc                             217
```